(12) United States Patent
Du et al.

(10) Patent No.: US 10,730,951 B2
(45) Date of Patent: *Aug. 4, 2020

(54) ANTI-OX40 ANTIBODIES AND METHODS OF USE

(71) Applicant: Genentech, Inc., South San Francisco, CA (US)

(72) Inventors: Changchun Du, South San Francisco, CA (US); Jeong Kim, San Francisco, CA (US); Jing Zhu, Moraga, CA (US); Jack Bevers, III, San Mateo, CA (US); Kevin Walsh, Walnut Creek, CA (US); Patricia De Almeida, Pleasant Hill, CA (US); James Andya, Millbrae, CA (US); Ye Shen, Daly City, CA (US)

(73) Assignee: Genentech, Inc., South San Francisco, CA (US)

( * ) Notice: Subject to any disclaimer, the term of this patent is extended or adjusted under 35 U.S.C. 154(b) by 108 days.

This patent is subject to a terminal disclaimer.

(21) Appl. No.: 15/951,082

(22) Filed: Apr. 11, 2018

(65) Prior Publication Data

US 2018/0230227 A1 Aug. 16, 2018

Related U.S. Application Data

(62) Division of application No. 14/673,792, filed on Mar. 30, 2015, now Pat. No. 9,975,957.

(60) Provisional application No. 62/113,345, filed on Feb. 6, 2015, provisional application No. 62/080,171, filed on Nov. 14, 2014, provisional application No. 62/073,873, filed on Oct. 31, 2014, provisional application No. 61/989,448, filed on May 6, 2014, provisional application No. 61/973,193, filed on Mar. 31, 2014.

(51) Int. Cl.
| | | |
|---|---|---|
| *C12N 5/10* | (2006.01) |
| *C12N 15/63* | (2006.01) |
| *C12N 15/70* | (2006.01) |
| *C12N 15/79* | (2006.01) |
| *C07K 16/28* | (2006.01) |
| *C07K 16/30* | (2006.01) |
| *C07K 16/22* | (2006.01) |
| *A61K 47/68* | (2017.01) |
| *A61K 39/395* | (2006.01) |
| *A61K 45/06* | (2006.01) |
| *A61K 39/00* | (2006.01) |
| *C12N 15/64* | (2006.01) |
| *A61K 48/00* | (2006.01) |

(52) U.S. Cl.
CPC ...... *C07K 16/2878* (2013.01); *A61K 39/3955* (2013.01); *A61K 39/39558* (2013.01); *A61K 45/06* (2013.01); *A61K 47/6803* (2017.08); *A61K 47/6849* (2017.08); *C07K 16/22* (2013.01); *C07K 16/30* (2013.01); *C07K 16/303* (2013.01); *C07K 16/3015* (2013.01); *C07K 16/3023* (2013.01); *C07K 16/3038* (2013.01); *C07K 16/3046* (2013.01); *C07K 16/3069* (2013.01); *A61K 48/00* (2013.01); *A61K 2039/505* (2013.01); *A61K 2039/507* (2013.01); *C07K 2317/21* (2013.01); *C07K 2317/24* (2013.01); *C07K 2317/51* (2013.01); *C07K 2317/515* (2013.01); *C07K 2317/56* (2013.01); *C07K 2317/71* (2013.01); *C07K 2317/732* (2013.01); *C07K 2317/75* (2013.01); *C07K 2317/76* (2013.01); *C07K 2317/92* (2013.01); *C12N 5/10* (2013.01); *C12N 15/63* (2013.01); *C12N 15/64* (2013.01); *C12N 15/70* (2013.01); *C12N 15/79* (2013.01); *C12N 2800/00* (2013.01)

(58) Field of Classification Search
CPC ........ C07K 16/28; C12N 15/00; C12N 15/09; C12N 15/63; C12N 2800/00
See application file for complete search history.

(56) References Cited

U.S. PATENT DOCUMENTS

| | | |
|---|---|---|
| 4,016,043 A | 4/1977 | Schuurs et al. |
| 4,018,653 A | 4/1977 | Mennen |
| 4,275,149 A | 6/1981 | Litman et al. |
| 4,318,980 A | 3/1982 | Boguslaski et al. |
| RE30,985 E | 6/1982 | Cartaya |
| 4,419,446 A | 12/1983 | Howley et al. |
| 4,424,279 A | 1/1984 | Bohn et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,683,195 A | 7/1987 | Mullis et al. |
| 4,737,456 A | 4/1988 | Weng et al. |
| 4,767,704 A | 8/1988 | Cleveland et al. |
| 4,816,567 A | 3/1989 | Cabilly et al. |
| 4,892,538 A | 1/1990 | Aebischer et al. |
| 4,927,762 A | 5/1990 | Darfler |

(Continued)

FOREIGN PATENT DOCUMENTS

| | | |
|---|---|---|
| CN | 102203132 A | 9/2011 |
| EP | 0 073 657 A1 | 3/1983 |

(Continued)

OTHER PUBLICATIONS

Paul, Fundamental Immunology, 3rd Edition, 1993, pp. 292-295.*

(Continued)

*Primary Examiner* — Hong Sang
(74) *Attorney, Agent, or Firm* — Morrison & Foerster LLP

(57) ABSTRACT

The invention provides anti-OX40 antibodies and methods of using the same.

7 Claims, 39 Drawing Sheets

Specification includes a Sequence Listing.

(56) References Cited

U.S. PATENT DOCUMENTS

| | | |
|---|---|---|
| 4,943,533 A | 7/1990 | Mendelsohn et al. |
| 4,965,199 A | 10/1990 | Capon et al. |
| 5,122,469 A | 6/1992 | Mather et al. |
| 5,208,020 A | 5/1993 | Chari et al. |
| 5,212,290 A | 5/1993 | Vogelstein et al. |
| 5,283,187 A | 2/1994 | Aebischer et al. |
| 5,416,064 A | 5/1995 | Chari et al. |
| 5,457,105 A | 10/1995 | Barker |
| 5,475,001 A | 12/1995 | Barker |
| 5,500,362 A | 3/1996 | Robinson et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,591,828 A | 1/1997 | Bosslet et al. |
| 5,616,582 A | 4/1997 | Barker |
| 5,624,821 A | 4/1997 | Winter et al. |
| 5,625,126 A | 4/1997 | Lonberg et al. |
| 5,631,144 A | 5/1997 | Lemoine et al. |
| 5,633,425 A | 5/1997 | Lonberg et al. |
| 5,635,483 A | 6/1997 | Pettit et al. |
| 5,641,870 A | 6/1997 | Rinderknecht et al. |
| 5,648,237 A | 7/1997 | Carter |
| 5,648,260 A | 7/1997 | Winter et al. |
| 5,654,307 A | 8/1997 | Bridges et al. |
| 5,661,016 A | 8/1997 | Lonberg et al. |
| 5,679,683 A | 10/1997 | Bridges et al. |
| 5,712,374 A | 1/1998 | Kuntsmann et al. |
| 5,714,586 A | 2/1998 | Kuntsmann et al. |
| 5,731,168 A | 3/1998 | Carter et al. |
| 5,739,116 A | 4/1998 | Hamann et al. |
| 5,747,498 A | 5/1998 | Schnur et al. |
| 5,750,373 A | 5/1998 | Garrard et al. |
| 5,760,041 A | 6/1998 | Wissner et al. |
| 5,767,285 A | 6/1998 | Hamann et al. |
| 5,770,429 A | 6/1998 | Lonberg et al. |
| 5,770,599 A | 6/1998 | Gibson |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,789,199 A | 8/1998 | Joly et al. |
| 5,804,396 A | 9/1998 | Plowman |
| 5,807,706 A | 9/1998 | Carter et al. |
| 5,821,332 A | 10/1998 | Godfrey et al. |
| 5,821,333 A | 10/1998 | Carter et al. |
| 5,821,337 A | 10/1998 | Carter et al. |
| 5,840,523 A | 11/1998 | Simmons et al. |
| 5,866,572 A | 2/1999 | Barker et al. |
| 5,869,046 A | 2/1999 | Presta et al. |
| 5,877,296 A | 3/1999 | Hamann et al. |
| 5,891,996 A | 4/1999 | Mateo de Acosta del Rio et al. |
| 5,959,177 A | 9/1999 | Hein et al. |
| 6,002,008 A | 12/1999 | Wissner et al. |
| 6,040,498 A | 3/2000 | Stomp et al. |
| 6,054,297 A | 4/2000 | Carter et al. |
| 6,075,181 A | 6/2000 | Kucherlapati et al. |
| 6,084,095 A | 7/2000 | Bridges et al. |
| 6,107,045 A * | 8/2000 | Koren .......... C07K 16/18 435/7.1 |
| 6,140,332 A | 10/2000 | Traxler et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,235,883 B1 | 5/2001 | Jakobovits et al. |
| 6,248,516 B1 | 6/2001 | Winter et al. |
| 6,265,410 B1 | 7/2001 | Bridges et al. |
| 6,267,958 B1 | 7/2001 | Andya et al. |
| 6,277,962 B1 | 8/2001 | Godfrey et al. |
| 6,344,455 B1 | 2/2002 | Bridges et al. |
| 6,344,459 B1 | 2/2002 | Bridges et al. |
| 6,391,874 B1 | 5/2002 | Cockerill et al. |
| 6,399,602 B1 | 6/2002 | Barker et al. |
| 6,417,429 B1 | 7/2002 | Hein et al. |
| 6,420,548 B1 | 7/2002 | Vezina et al. |
| 6,455,534 B2 | 9/2002 | Bridges et al. |
| 6,521,620 B1 | 2/2003 | Bridges et al. |
| 6,582,959 B2 | 6/2003 | Kim |
| 6,596,726 B1 | 7/2003 | Bridges et al. |
| 6,602,684 B1 | 8/2003 | Umana et al. |
| 6,602,863 B1 | 8/2003 | Bridges et al. |
| 6,630,579 B2 | 10/2003 | Chari et al. |
| 6,703,020 B1 | 3/2004 | Thorpe et al. |
| 6,713,484 B2 | 3/2004 | Bridges et al. |
| 6,737,056 B1 | 5/2004 | Presta |
| 6,884,879 B1 | 4/2005 | Baca et al. |
| 6,919,436 B2 | 7/2005 | Lihme et al. |
| 6,946,292 B2 | 9/2005 | Kanda et al. |
| 6,982,321 B2 | 1/2006 | Winter |
| 7,041,870 B2 | 5/2006 | Tomizuka et al. |
| 7,060,269 B1 | 6/2006 | Baca et al. |
| 7,078,492 B2 | 7/2006 | Pirofski et al. |
| 7,087,409 B2 | 8/2006 | Barbas, III et al. |
| 7,125,978 B1 | 10/2006 | Vezina et al. |
| 7,153,507 B2 | 12/2006 | Van de Winkel et al. |
| 7,189,826 B2 | 3/2007 | Rodman |
| 7,332,581 B2 | 2/2008 | Presta |
| 7,364,733 B2 | 4/2008 | Godfrey et al. |
| 7,371,826 B2 | 5/2008 | Presta |
| 7,498,298 B2 | 3/2009 | Doronina et al. |
| 7,504,256 B1 | 3/2009 | Ogawa et al. |
| 7,521,541 B2 | 4/2009 | Eigenbrot et al. |
| 7,527,791 B2 | 5/2009 | Adams et al. |
| 7,550,140 B2 | 6/2009 | Bakker et al. |
| 7,642,228 B2 | 1/2010 | Carter et al. |
| 7,695,936 B2 | 4/2010 | Carter et al. |
| 7,696,175 B2 | 4/2010 | Epstein et al. |
| 7,959,925 B2 | 6/2011 | Weinberg et al. |
| 7,960,515 B2 | 6/2011 | Min et al. |
| 8,133,983 B2 | 3/2012 | Bakker et al. |
| 8,216,805 B2 | 7/2012 | Carter et al. |
| 8,217,149 B2 | 7/2012 | Irving et al. |
| 8,236,930 B2 | 8/2012 | Min et al. |
| 8,283,450 B2 | 10/2012 | Kato et al. |
| 8,313,913 B2 | 11/2012 | Nakamura et al. |
| 8,614,295 B2 | 12/2013 | Lawson et al. |
| 8,748,585 B2 | 6/2014 | Attinger et al. |
| 8,945,867 B2 | 2/2015 | Ogawa et al. |
| 9,006,399 B2 | 4/2015 | Liu et al. |
| 9,028,824 B2 | 5/2015 | Min et al. |
| 9,163,085 B2 | 10/2015 | Liu et al. |
| 9,975,957 B2 | 5/2018 | Du et al. |
| 2001/0044522 A1 | 11/2001 | Godfrey et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2003/0190317 A1 | 10/2003 | Baca et al. |
| 2003/0203409 A1 | 10/2003 | Kim |
| 2003/0206899 A1 | 11/2003 | Ferrara et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2004/0136995 A1 | 7/2004 | Godfrey et al. |
| 2005/0014934 A1 | 1/2005 | Hinton et al. |
| 2005/0026229 A1 | 2/2005 | Reiter et al. |
| 2005/0031613 A1 | 2/2005 | Nakamura et al. |
| 2005/0079574 A1 | 4/2005 | Bond |
| 2005/0100546 A1 | 5/2005 | Jakobovits et al. |
| 2005/0112126 A1 | 5/2005 | Baca et al. |
| 2005/0119455 A1 | 6/2005 | Fuh et al. |
| 2005/0123546 A1 | 6/2005 | Umana et al. |
| 2005/0176122 A1 | 8/2005 | Lihme et al. |
| 2005/0186208 A1 | 8/2005 | Fyfe et al. |
| 2005/0260186 A1 | 11/2005 | Bookbinder et al. |
| 2005/0266000 A1 | 12/2005 | Bond et al. |
| 2005/0287149 A1 | 12/2005 | Keler et al. |
| 2006/0025576 A1 | 2/2006 | Miller et al. |
| 2006/0059575 A1 | 3/2006 | Kusunoki et al. |
| 2006/0088523 A1 | 4/2006 | Andya et al. |
| 2006/0093600 A1 | 5/2006 | Bedian et al. |
| 2006/0104968 A1 | 5/2006 | Bookbinder et al. |

(56) References Cited

U.S. PATENT DOCUMENTS

| | | | |
|---|---|---|---|
| 2006/0183887 A1 | 8/2006 | Jakobovits et al. |
| 2006/0258841 A1 | 11/2006 | Michl et al. |
| 2006/0280728 A1 | 12/2006 | Weinberg et al. |
| 2006/0281072 A1 | 12/2006 | Bakker et al. |
| 2007/0061900 A1 | 3/2007 | Murphy et al. |
| 2007/0077247 A1 | 4/2007 | Godfrey et al. |
| 2007/0117126 A1 | 5/2007 | Sidhu et al. |
| 2007/0134759 A1 | 6/2007 | Nishiya et al. |
| 2007/0160598 A1 | 7/2007 | Dennis et al. |
| 2007/0166303 A1 | 7/2007 | Hanai et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2008/0241884 A1 | 10/2008 | Shitara et al. |
| 2009/0002360 A1 | 1/2009 | Chen et al. |
| 2010/0196359 A1* | 8/2010 | Kato ................. C07K 16/2878 424/133.1 |
| 2010/0203056 A1 | 8/2010 | Irving et al. |
| 2011/0236388 A1 | 9/2011 | Baehner et al. |
| 2012/0128687 A1 | 5/2012 | Adler et al. |
| 2013/0034559 A1 | 2/2013 | Queva et al. |
| 2013/0045200 A1 | 2/2013 | Irving et al. |
| 2013/0045201 A1 | 2/2013 | Irving et al. |
| 2013/0045202 A1 | 2/2013 | Irving et al. |
| 2013/0089553 A1 | 4/2013 | Carter et al. |
| 2013/0280275 A1* | 10/2013 | Liu .................... C07K 16/2878 424/173.1 |
| 2013/0330344 A1 | 12/2013 | Lawson et al. |
| 2014/0044703 A1 | 2/2014 | Kato et al. |
| 2014/0065135 A1 | 3/2014 | Irving et al. |
| 2014/0294824 A1 | 10/2014 | Attinger et al. |
| 2014/0377284 A1 | 12/2014 | Simons et al. |
| 2015/0098942 A1 | 4/2015 | Curti et al. |
| 2015/0132288 A1 | 5/2015 | Simons et al. |
| 2015/0174268 A1 | 6/2015 | Li |
| 2015/0190506 A1 | 7/2015 | Cheung et al. |
| 2015/0218279 A1 | 8/2015 | Min et al. |
| 2015/0307617 A1 | 10/2015 | Du et al. |
| 2015/0307620 A1 | 10/2015 | Vella et al. |
| 2015/0315281 A1 | 11/2015 | Liu et al. |
| 2015/0322119 A1 | 11/2015 | Engelhardt et al. |
| 2016/0068604 A1 | 3/2016 | Liu et al. |
| 2016/0108123 A1 | 4/2016 | Freeman et al. |
| 2016/0137740 A1 | 5/2016 | Hammond et al. |
| 2016/0152720 A1 | 6/2016 | Kim et al. |
| 2016/0160290 A1 | 6/2016 | Huseni |
| 2016/0161485 A1 | 6/2016 | Chu et al. |
| 2016/0166685 A1 | 6/2016 | Cheung et al. |
| 2016/0355597 A1 | 12/2016 | Rhee et al. |
| 2017/0000885 A1 | 1/2017 | Rhee et al. |
| 2017/0008971 A1 | 1/2017 | Dennis et al. |
| 2017/0015755 A1 | 1/2017 | Harm et al. |
| 2017/0073386 A1 | 3/2017 | Stewart et al. |
| 2017/0290913 A1 | 10/2017 | Cheung et al. |
| 2018/0022813 A1 | 1/2018 | Lazar et al. |
| 2018/0057598 A1 | 3/2018 | Lazar et al. |
| 2018/0303936 A1 | 10/2018 | Cheung et al. |
| 2019/0062444 A1 | 2/2019 | Walsh |

FOREIGN PATENT DOCUMENTS

| | | |
|---|---|---|
| EP | 0 244 234 A2 | 11/1987 |
| EP | 0 402 226 A1 | 12/1990 |
| EP | 0 404 097 A2 | 12/1990 |
| EP | 0 425 235 A2 | 5/1991 |
| EP | 0 183 070 B1 | 10/1991 |
| EP | 0 308 936 A2 | 7/1994 |
| EP | 0 308 936 A3 | 7/1994 |
| EP | 0 308 936 B1 | 7/1994 |
| EP | 0 659 439 A2 | 6/1995 |
| EP | 0 666 868 A1 | 8/1995 |
| EP | 0 672 141 A1 | 9/1995 |
| WO | WO-1987/00195 A1 | 1/1987 |
| WO | WO-1989/06692 A1 | 7/1989 |
| WO | WO-1990/03430 A1 | 4/1990 |
| WO | WO-1990/13646 A1 | 11/1990 |
| WO | WO-1991/00360 A1 | 1/1991 |
| WO | WO-1991/10741 A1 | 7/1991 |
| WO | WO-1992/20373 A1 | 11/1992 |
| WO | WO-1993/01161 A1 | 1/1993 |
| WO | WO-1993/08829 A1 | 5/1993 |
| WO | WO-1993/16185 A1 | 8/1993 |
| WO | WO-1993/25673 A1 | 12/1993 |
| WO | WO-1994/04690 A1 | 3/1994 |
| WO | WO-1994/10202 A1 | 5/1994 |
| WO | WO-1994/11026 A1 | 5/1994 |
| WO | WO-1994/29351 A2 | 12/1994 |
| WO | WO-1994/29351 A3 | 12/1994 |
| WO | WO-1995/12673 A1 | 5/1995 |
| WO | WO-1995/21251 A1 | 8/1995 |
| WO | WO-1995/27062 A1 | 10/1995 |
| WO | WO-1996/03397 A1 | 2/1996 |
| WO | WO-1996/07321 A1 | 3/1996 |
| WO | WO-1996/27011 A1 | 9/1996 |
| WO | WO-1996/30046 A1 | 10/1996 |
| WO | WO-1996/30347 A1 | 10/1996 |
| WO | WO-1996/33735 A1 | 10/1996 |
| WO | WO-1996/33978 A1 | 10/1996 |
| WO | WO-1996/33979 A1 | 10/1996 |
| WO | WO-1996/33980 A1 | 10/1996 |
| WO | WO-1996/34096 A1 | 10/1996 |
| WO | WO-1996/40210 A1 | 12/1996 |
| WO | WO-1997/30087 A1 | 8/1997 |
| WO | WO-1997/38983 A1 | 10/1997 |
| WO | WO-1997/44453 A1 | 11/1997 |
| WO | WO-1998/14451 A1 | 4/1998 |
| WO | WO-1998/24893 A2 | 6/1998 |
| WO | WO-1998/43960 A1 | 10/1998 |
| WO | WO-1998/45332 A2 | 10/1998 |
| WO | WO-1998/45332 A3 | 10/1998 |
| WO | WO-1998/50038 A1 | 11/1998 |
| WO | WO-1998/50433 A2 | 11/1998 |
| WO | WO-1998/50433 A3 | 11/1998 |
| WO | WO-1998/58964 A1 | 12/1998 |
| WO | WO-1999/06378 A1 | 2/1999 |
| WO | WO-1999/06396 A1 | 2/1999 |
| WO | WO-1999/09016 A1 | 2/1999 |
| WO | WO-1999/22764 A1 | 5/1999 |
| WO | WO-1999/24037 A1 | 5/1999 |
| WO | WO-1999/42585 A1 | 8/1999 |
| WO | WO-1999/51642 A1 | 10/1999 |
| WO | WO-2000/42072 A2 | 7/2000 |
| WO | WO-2000/42072 A3 | 7/2000 |
| WO | WO-2000/61739 A1 | 10/2000 |
| WO | WO-2001/29246 A1 | 4/2001 |
| WO | WO-2002/31140 A1 | 4/2002 |
| WO | WO-2003/011878 A2 | 2/2003 |
| WO | WO-2003/011878 A3 | 2/2003 |
| WO | WO-2003/084570 A1 | 10/2003 |
| WO | WO-2003/085107 A1 | 10/2003 |
| WO | WO-2003/085119 A1 | 10/2003 |
| WO | WO-2003/106498 A2 | 12/2003 |
| WO | WO-2003/106498 A3 | 12/2003 |
| WO | WO-2004/056312 A2 | 7/2004 |
| WO | WO-2004/056312 A3 | 7/2004 |
| WO | WO-2004/092219 A2 | 10/2004 |
| WO | WO-2004/092219 A3 | 10/2004 |
| WO | WO-2005/012359 A2 | 2/2005 |
| WO | WO-2005/012359 A3 | 2/2005 |
| WO | WO-2005/035586 A1 | 4/2005 |
| WO | WO-2005/035778 A1 | 4/2005 |
| WO | WO-2005/044853 A2 | 5/2005 |
| WO | WO-2005/044853 A3 | 5/2005 |
| WO | WO-2005/053742 A1 | 6/2005 |
| WO | WO-2005/100402 A1 | 10/2005 |
| WO | WO-2006/029879 A2 | 3/2006 |
| WO | WO-2006/029879 A3 | 3/2006 |
| WO | WO-2006/044908 A2 | 4/2006 |
| WO | WO-2006/044908 A3 | 4/2006 |
| WO | WO-2006/121168 A1 | 11/2006 |
| WO | WO-2006/121810 A2 | 11/2006 |
| WO | WO-2006/121810 A3 | 11/2006 |
| WO | WO-2007/005874 A2 | 1/2007 |

(56) References Cited

FOREIGN PATENT DOCUMENTS

| WO | WO-2007/005874 A3 | 1/2007 |
|---|---|---|
| WO | WO-2007/062245 A2 | 5/2007 |
| WO | WO-2007/062245 A3 | 5/2007 |
| WO | WO-2008/051424 A2 | 5/2008 |
| WO | WO-2008/051424 A3 | 5/2008 |
| WO | WO-2008/077546 A1 | 7/2008 |
| WO | WO-2009/079335 A1 | 6/2009 |
| WO | WO-2009/089004 A1 | 7/2009 |
| WO | WO-2009/101611 A1 | 8/2009 |
| WO | WO-2009/114335 A2 | 9/2009 |
| WO | WO-2009/114335 A3 | 9/2009 |
| WO | WO-2010/005958 A2 | 1/2010 |
| WO | WO-2010/005958 A3 | 1/2010 |
| WO | WO-2010/027423 A2 | 3/2010 |
| WO | WO-2010/027423 A3 | 3/2010 |
| WO | WO-2010/027827 A2 | 3/2010 |
| WO | WO-2010/027827 A3 | 3/2010 |
| WO | WO-2010/077634 A1 | 7/2010 |
| WO | WO-2010/096418 A2 | 8/2010 |
| WO | WO-2010/096418 A3 | 8/2010 |
| WO | WO-2011/066342 A2 | 6/2011 |
| WO | WO-2011/066342 A3 | 6/2011 |
| WO | WO-2011/066389 A1 | 6/2011 |
| WO | WO-2011/071871 A1 | 6/2011 |
| WO | WO-2012/027328 A2 | 3/2012 |
| WO | WO-2012/027328 A3 | 3/2012 |
| WO | WO-2013/008171 A1 | 1/2013 |
| WO | WO-2013/019906 A1 | 2/2013 |
| WO | WO-2013/028231 A1 | 2/2013 |
| WO | WO-2013/038191 A2 | 3/2013 |
| WO | WO-2013/038191 A3 | 3/2013 |
| WO | WO-2013/068563 A2 | 5/2013 |
| WO | WO-2013/068563 A3 | 5/2013 |
| WO | WO-2013/119202 A1 | 8/2013 |
| WO | WO-2014/012479 A1 | 1/2014 |
| WO | WO-2014/089113 A1 | 6/2014 |
| WO | WO-2014/148895 A1 | 9/2014 |
| WO | WO-2015/095418 A1 | 6/2015 |
| WO | WO-2015/095423 A2 | 6/2015 |
| WO | WO-2015/095423 A3 | 6/2015 |
| WO | WO-2015/112900 A1 | 7/2015 |
| WO | WO-2015/120198 A1 | 8/2015 |
| WO | WO-2015/135558 A1 | 9/2015 |
| WO | WO-2015/153513 A1 | 10/2015 |
| WO | WO-2015/153514 A1 | 10/2015 |
| WO | WO-2015/153857 A1 | 10/2015 |
| WO | WO-2016/004875 A1 | 1/2016 |
| WO | WO-2016/004876 A1 | 1/2016 |
| WO | WO-2016/034085 A1 | 3/2016 |
| WO | WO-2016/040892 A1 | 3/2016 |
| WO | WO-2016/054555 A2 | 4/2016 |
| WO | WO-2016/054555 A3 | 4/2016 |
| WO | WO-2016/057667 A1 | 4/2016 |
| WO | WO-2016/057841 A1 | 4/2016 |
| WO | WO-2016/061142 A1 | 4/2016 |
| WO | WO-2016/073282 A1 | 5/2016 |
| WO | WO-2016/073378 A1 | 5/2016 |
| WO | WO-2016/073380 A1 | 5/2016 |
| WO | WO-2016/075174 A1 | 5/2016 |
| WO | WO-2016/081384 A1 | 5/2016 |
| WO | WO-2016/092419 A1 | 6/2016 |
| WO | WO-2016/100882 A1 | 6/2016 |
| WO | WO-2016/164480 A1 | 10/2016 |
| WO | WO-2016/196228 A1 | 12/2016 |
| WO | WO-2017/021791 A1 | 2/2017 |
| WO | WO-2017/178869 A1 | 10/2017 |

OTHER PUBLICATIONS

Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Overbeek , "Factors affecting transgenic animal production," Transgenic animal technology, 1994, pp. 96-98.*
Wall, Theriogenology, 1996, vol. 45, pp. 57-68.*
Houdebine, J. Biotech. 1994, vol. 34, pp. 269-287.*
Kappell, Current Opinions in Biotechnology, 1992, vol. 3, pp. 548-553.*
Liu et al., Methods Mol Biol. 2013, 1027: 1-17.*
Abcam catalog No. ab76000, retrieved Aug. 13, 2015 from http://www.abcam.com/cd134—ox40-antibody-epr17y-ab76000.html, last visited Aug. 13, 2015, 3 pages.
Abcam catalog No. ab76130, retrieved Aug. 13, 2015 from http://www.abcam.com/cd134—ox40-antibody-ep1168y-ab76130.html, last visited Aug. 13, 2015, 3 pages.
Abcam catalog No. ab80677, retrieved Aug. 13, 2015 from <http://www.abcam.com/cd134-- ox40-antibody-ap-mab0833-ab80677.html>, last visited Aug. 13, 2015, 3 pages.
AbD Serotec catalog No. MCA2568GA, retrieved Aug. 13, 2015 from <http://www.labome.com/product/AbD-Serotec-Bio-Rad/MCA2568GA.html>, last visited Aug. 13, 2015, 2 pages.
Achen et al. "Vascular Endothelial Growth Factor D (VEGF-D) Is a Ligand for the Tyrosine Kinases VEGF Receptor 2 (Flk1) and VEGF Receptor 3 (Flt4)," *Proc. Natl. Acad. Sci. USA* 95:548-553, (Jan. 1998).
Aguirre et al. "Activated Kras and Ink4a/Arf Deficiency Cooperate to Produce Metastatic Pancreatic Ductal Adenocarcinoma," *Genes Dev.* 17(24):3112-3126, (2003).
Ahmadzadeh et al. "Tumor Antigen-Specific CD8 T Cells Infiltrating the Tumor Express High Levels of PD-1 and Are Functionally Impaired," *Blood* 114(8):1537-1544, (2009).
Almagro et al. "Humanization of Antibodies," *Front. Biosci.* 13:1619-1633, (Jan. 1, 2008).
Al-Shamkhani et al. "OX40 Is Differentially Expressed on Activated Rat and Mouse T Cells and Is the Sole Receptor for the OX40 Ligand," *Eur. J. Immunol.* 26:1695-1699, (1996).
Anderson, W.F. "Human Gene Therapy," *Science* 256:808-813, (May 8, 1992).
Baca et al. "Antibody Humanization Using Monovalent Phage Display," *J. Biol. Chem.* 272(16):10678-10684, (Apr. 18, 1997).
Barnes et al. "Methods for Growth of Cultured Cells in Serum-Free Medium," *Anal. Biochem.* 102:255-270, (1980).
Bd Biosciences catalog No. 340420, retrieved Aug. 13, 2015 from http://www.bdbiosciences.com/ptProduct.jsp?ccn=340420, last visited Aug. 13, 2015, 1 page.
Bd Biosciences catalog No. 554848, retrieved Aug. 13, 2015 from <http://www.bdbiosciences.com/ptProduct.jsp?ccn=554848>, last visited Aug. 13, 2015, 1 page.
Bd Biosciences catalog No. 555836, retrieved Aug. 13, 2015 from <http://www.bdbiosciences.com/us/applications/research/t-cell-immunology/regulatory-t-cells/surface-markers/human/purified-mouse-anti-human-cd134-act35-also-known-as-ber-act35/p/555836>, last visited Aug. 13, 2015, 1 page.
Bd Biosciences catalog No. 562181, retrieved Aug. 13, 2015 from <http://www.bdbiosciences.com/ptProduct.jsp?ccn=562181>, last visited Aug. 13, 2015, 1 page.
Blazar et al. "Ligation of OX40 (CD134) Regulates Graft-Versus-Host Disease (GVHD) and Graft Rejection in Allogeneic Bone Marrow Transplant Recipients," *Blood* 101(9):3741-3748, (May 1, 2003, e-pub. Jan. 9, 2003).
Boerner et al. "Production of Antigen-Specific Human Monoclonal Antibodies From In Vitro—Primed Human Splenocytes," *J. Immunol.* 147(1):86-95, (Jul. 1, 1991).
Brennan et al. "Preparation of Bispecific Antibodies by Chemical Recombination of Monoclonal Immunoglobulin $G_1$ Fragments," *Science* 229:81-83, (Jul. 5, 1985).
Bretscher et al. "A Theory of Self-Nonself Discrimination," *Science* 169:1042-1049, (1970).
Bretscher et al. "A Two-Step, Two-Signal Model for the Primary Activation of Precursor Helper T Cells," *Proc. Natl. Acad. Sci. USA* 96:185-190, (Jan. 1999).

(56) References Cited

OTHER PUBLICATIONS

Bruggemann et al. "Comparison of the Effector Functions of Human Immunoglobulins Using a Matched Set of Chimeric Antibodies," *J. Exp. Med.* 166:1351-1361, (Nov. 1, 1987).
Bruggemann et al. "Designer Mice: the Production of Human Antibody Repertoires in Transgenic Animals," *Year in Immunol.* 7:33-40, (1993).
Bulliard et al. "OX40 Engagement Depletes Intratumoral Tregs Via Activating FcγRs, Leading to Antitumor Efficacy," *Immunol. Cell Biol.* 92:475-480, (2014, e-pub. Apr. 15, 2014).
Burocchi et al. "Intratumor OX40 Stimulation Inhibits IRF1 Expression and IL-10 Production by Treg Cells While Enhancing CD40L Expression by Effector Memory T Cells," *Eur. J. Immunol.* 41:3615-3626, (2011).
Capel et al. "Heterogeneity of Human IgG Fc Receptors," *Immunomethods* 4:25-34, (1994).
Carter et al. "High Level *Escherichia Coli* Expression and Production of a Bivalent Humanized Antibody Fragment," *Biotech.* 10:163-167, (Feb. 1992).
Carter et al. "Humanization of an Anti-p185$^{HER2}$ Antibody for Human Cancer Therapy," *Proc. Natl. Acad. Sci. USA* 89:4285-4289, (May 1992).
Cha, E. "S49. Clinical Activity and Development of Biomarkers for an Engineered Anti PDL1 Antibody MPDL3280A," *Journal for Immunotherapy of Cancer*, 2(Suppl 2), I21, (Mar. 12, 2014).
Champe et al. "Monoclonal Antibodies That Block the Activity of Leukocyte Function—Associated Antigen 1 Recognize Three Discrete Epitopes in the Inserted Domain of CD11a," *J. Biol. Chem.* 270(3):1388-1394, (Jan. 20, 1995).
Chari, R.V. et al. "Immunoconjugates Containing Novel Maytansinoids: Promising Anticancer Drugs," *Cancer Res.* 52:127-131, (Jan. 1, 1992).
Chen et al. "Selection and Analysis of an Optimized Anti-VEGF Antibody: Crystal Structure of an Affinity-Matured Fab in Complex With Antigen," *J. Mol. Biol.* 293:865-881, (1999).
Chothia et al. "Acetylcholinesterase: The Structure of Crystals of a Globular Form From Electric Eel," *J. Mol. Biol.* 97:55-60, (1975).
Chothia et al. "Canonical Structures for the Hypervariable Regions of Immunoglobulins," *J. Mol. Biol.* 196:901-917, (1987).
Chowdhury, P.S. "Engineering Hot Spots for Affinity Enhancement of Antibodies," *Methods Mol. Biol.* 207:179-196, (2003).
Clackson et al. "Making Antibody Fragments Using Phage Display Libraries," *Nature* 352:624-628, (Aug. 15, 1991).
Clark-Lewis et al. "Structure-Function Relationship Between the Human Chemokine Receptor CXCR3 and Its Ligands," *J. Biol. Chem.* 278(1):289-295, (Jan. 3, 2003).
ClinicalTrials.gov (2015). "Identifier NCT00889954: Her2 and TGFBeta CTLs in treatment of Her2 positive malignancy (HERCREEM)," located at <http://www.clinicaltrials.gov/ct2/show/study/NCT00889954>, last visited on Jul. 10, 2015, four pages.
Clynes, R., et al. "Fc Receptors Are Required in Passive and Active Immunity to Melanoma," *Proc. Natl. Acad. Sci. USA* 95:652-656, (Jan. 1998).
Cole, S.P.C. et al. "The EBV-Hybridoma Technique and its Application to Human Lung Cancer," in *Monoclonal Antibodies and Cancer Therapy*, Alan R. Liss. pp. 77-96, (1985).
Cragg, M.S., et al. "Complement-Mediated Lysis by Anti-CD20 mAb Correlates With Segregation Into Lipid Rafts," *Blood* 101(3):1045-1052, (Feb. 1, 2003, e-pub. Sep. 19, 2002).
Cragg et al. "Antibody Specificity Controls In Vivo Effector Mechanisms of Anti-CD20 Reagents," *Blood* 103:2738-2743, (Apr. 1, 2004, e-pub. Oct. 9, 2003).
Cronin et al. "Measurement of Gene Expression in Archival Paraffin-Embedded Tissues," *Am. J. Pathol.* 164:35-42, (Jan. 2004).
Cunningham et al. "High-Resolution Epitope Mapping of hGH-receptor Interactions by Alanine-Scanning Mutagenesis," *Science* 244:1081-1085, (Jun. 2, 1989).
Curti et al. "OX40 Is a Potent Immune-Stimulating Target in Late-Stage Cancer Patients," *Cancer Res.* 73:7189-7198, (2013, e-pub. Oct. 31, 2013).

Daeron. "Fc Receptor Biology," *Annu. Rev. Immunol.* 15:203-234, (1997).
Dall'acqua et al. "Antibody Humanization by Framework Shuffling," *Methods* 36:43-60, (2005).
Dankort et al. "A New Mouse Model to Explore the Initiation, Progression, and Therapy of BRAF$^{V600E}$-Induced Lung Tumors," *Genes Dev.* 21:379-384, (2007).
Database Accession No. NM_001504, "*Home sapiens* Chemokine (C-X-C Motif) Receptor 3 (CXCR3), Transcript Variant 1, mRNA," located at <http://www.ncbi.nlm.nih.gov/nuccore/NM_001504>, last visited Aug. 13, 2015, 5 pages.
Database Accession No. NM_014009, "*Home sapiens* Forkhead Box P3 (FOXP3), Transcript Variant 1, mRNA," located at <http://www.ncbi.nlm.nih.gov/nuccore/NM_014009>, last visited Aug. 13, 2015, 5 pages.
Database Accession No. NM_172213, "*Home sapiens* CD8b Molecule (CD8B), Transcript Variant 2, mRNA," located at <http://www.ncbi.nlm.nih.gov/nuccore/NM_172213>, last visited Aug. 13, 2015, 4 pages.
De Haas et al. "Fcγ Receptors of Phagocytes," *J. Lab. Clin. Med.* 126:330-341, (1995).
De Vries et al. "The fms-Like Tyrosine Kinase, a Receptor for Vascular Endothelial Growth Factor," *Science* 255:989-991, (Feb. 21, 1992).
Dubowchik et al. "Doxorubicin Immunoconjugates Containing Bivalent, Lysosomally-Cleavable Dipeptide Linkages," *Bioorg. & Med. Chem. Letters* 12:1529-1532, (2002).
Duncan et al. "The Binding Site for C1q on IgG," *Nature* 332:738-740, (Apr. 1988).
Durkop et al. "Expression of the Human OX40 (hOX40) Antigen in Normal and Neoplastic Tissues," *Br. J. Haematol.* 91(4):927-931, (Dec. 1995).
Eisenhauer et al. "New response Evaluation Criteria in Solid Tumours: Revised RECIST Guideline (Version 1.1)," *Eur. J. Cancer* 45:228-247, (2009).
Epitomics catalog No. 2359-1, located at <http://www.labome.com/product/Epitomics/2359- 1.html>, last visited Aug. 13, 2015, 2 pages.
Even et al. "Serum-Free Hybridoma Culture: Ethical, Scientific and Safety Considerations," *Trends in Biotech.* 24(3):105-108, (Mar. 2006, e-pub. Jan. 19, 2006).
Fellouse et al. "Synthetic Antibodies From a Four-Amino-Acid Code: A Dominant Role for Tyrosine in Antigen Recognition," *Proc. Natl. Acad. Sci. USA* 101(34):12467-12472, (Aug. 24, 2004).
Ferrara et al. "Vascular Endothelial Growth Factor. The Trigger for Neovascularization in the Eye," *Lab. Invest.* 72(6):615-618, (1995).
Ferrara et al. "The Biology of Vascular Endothelial Growth Factor," *Endo. Rev.* 18(1):4-25, (1997).
Ferrara et al. "Clinical Applications of Angiogenic Growth Factors and Their Inhibitors," *Nature Med.* 5(12):1359-1364, (Dec. 1999).
Ferrara et al. "Modulation of Therapeutic Antibody Effector Functions by Glycosylation Engineering: Influence of Golgi Enzyme Localization Domain and Co-Expression of Heterologous β1, 4-N-Acetylglucosaminyltransferase III and Golgi α-Mannosidase II," *Biotech. And Bioengin.* 93(5):851-861, (2006, e-pub. Jan. 24, 2006).
Fishwild et al. "High-Avidity Human IgGk Monoclonal Antibodies From a Novel Strain of Minilocus Transgenic Mice," *Nature Biotech.* 14:845-851, (Jul. 1996).
Flatman et al. "Process Analytics for Purification of Monoclonal Antibodies," *J. Chrom. B.* 848:79-87, (2007, e-pub. Dec. 11, 2006).
Fleer et al. "Stable Multicopy Vectors for High-Level Secretion of Recombinant Human Serum Albumin by *Kluyveromyces* Yeasts," *Biotech.* 9:968-975, (Oct. 1991).
Flutter et al. "Enforced Co-Stimulation and Co-Inhibitory Blockade Synergize to Enhance the Functions of Exhausted CTL,"Abstract 1911 *Blood*, 118(21):833-834, (2011).
Foell et al. "T Cell Costimulatory and Inhibitory Receptors As Therapeutic Targets for Inducing Anti-Tumor Immunity," *Curr. Cancer Drug Targets* 7:55-70, (2007).
Franek. "Oligopeptides As Tools for Improving Productivity of Hybridoma Cell Cultures," in *Trends in Monoclonal Antibody Research*, Simmons (Ed), Nova Science Publishers, Inc., Nova Biomedical Books, New York, pp. 111-122. (2005).

(56) References Cited

OTHER PUBLICATIONS

Garcia-Rodriguez et al. "L-627, a Novel Carbapenem: In-Vitro Activity Against Anaerobes," *J. Antimicrob. Chemothera.* 33:183-186, (1994).
Gazzano-Santoro et al. "A Non-Radioactive Complement-Dependent Cytotoxicity Assay for Anti-CD20 Monoclonal Antibody," *J. Immunol. Methods* 202:163-171, (1997).
Genentech, Inc. "View of NCT02410512 on May 29, 2015" ClinicalTrials.gov Archive May 29, 2015 Retrieved from the Internet: <URL:https://clinicaltrials.gov/archive/NCT02410512/2015 05 29 retrieved on-2016-08-01> the whole document, last visited on May 22, 2017, 4 pages.
Gerngross, T.U. "Advances in the Production of human Therapeutic Proteins in Yeasts and Filamentous Fungi," *Nat. Biotech.* 22(11):1409-1414, (Nov. 2004, e-pub. Nov. 4, 2004).
Ghetie et al. "FcRn: the MHC Class I-Related Receptor That Is More Than an IgG Transporter," *Immunol. Today* 18(12):592-598, (Dec. 1997).
Goding. *Monoclonal Antibodies: Principles and Practice Academic Press* pp. 59-103, (1983).
Graham, F.L., et al. "Characteristics of a Human Cell Line Transformed by DNA From Human Adenovirus Type 5," *J. Gen. Virol.* 36:59-74, (1977).
Griffiths, A.D. et al. "Human Anti-Self Antibodies With High Specificity From Phage Display Libraries," *EMBO J.* 12(2):725-734, (1993).
Groom et al. "CXCR3 in T Cell Function," *Exp. Cell. Res.* 317:620-631, (Mar. 10, 2011), 21 pages.
Gruber et al. "Efficient Tumor Cell Lysis Mediated by a Bispecific Single Chain Antibody Expressed in *Escherichia coli*," *J. Immunol.* 152:5368-5374, (1994).
Guo et al. "PD-1 Blockade and OX40 Triggering Synergistically Protects Against Tumor Growth in a Murine Model of Ovarian Cancer," *PloS One* 9(2):e89350, (Feb. 27, 2014), 10 pages.
Guss et al. "Structure of the IgG-Binding Regions of Streptococcal Protein G," *EMBO J.* 5(7):1567-1575, (1986).
Guyer, R.L., et al. "Immunoglobulin Binding by Mouse Intestinal Epithelial Cell Receptors," *J. Immunol.* 117(2):587-593, (Aug. 1976).
Ham et al. "Media and Growth Requirements," *Meth. Enz.* 58:44-93, (1979).
Hamers-Casterman et al. "Naturally Occurring Antibodies Devoid of Light Chains," *Nature* 363:446-448, (Jun. 3, 1993).
Harris. "Therapeutic Monoclonals," *Soc. Transactions* 23:1035-1038, (Jul. 1995).
Hellstrom et al. "Strong Antitumor Activities of IgG3 Antibodies to a Human Melanoma-Associated Ganglioside," *Proc. Natl. Acad. Sci. USA* 82:1499-1502, (Mar. 1985).
Hellstrom et al. "Antitumor Effects of L6, an IgG2a Antibody That Reacts With Most Human Carcinomas," *Proc. Natl. Acad. Sci. USA* 83:7059-7063, (Sep. 1986).
Herbst et al. "Predictive Correlates of Response to the Anti-PD-L1 Antibody MPDL3280A in Cancer Patients," *Nature* 515:563-567, (Nov. 27, 2014).
Hinman, L.M., et al. "Preparation and Characterization of Monoclonal Antibody Conjugates of the Calicheamicins: A Novel and Potent Family of Antitumor Antibiotics," *Cancer Res.* 53:3336-3342, (Jul. 15, 1993).
Hinton et al. "Engineered Human IgG antibodies With Longer Serum Half-Lives in Primates," *J. Biol. Chem.* 279(8):6213-6216, (Feb. 20, 2004).
Hirschhorn-Cymerman et al. "OX40 Engagement and Chemotherapy Combination Provides Potent Antitumor Immunity With Concomitant Regulatory T Cell Apoptosis," *J. Exp. Med.* 206:1103-1116, (May 4, 2009).
Holliger, P., et al. "Diabodies: Small Bivalent and Bispecific Antibody Fragments," *Proc. Natl. Acad. Sci. USA* 90:6444-6448, (Jul. 1993).
Hongo et al. "Development and Characterization of Murine Monoclonal Antibodies to the Latency-Associated Peptide of Transforming Growth Factor $\beta_1$," *Hybridoma* 14(3):253-260, (1995).

Hoogenboom et al. "By-passing Immunisation. Human Antibodies From Synthetic Repertoires of Germline $V_H$ Gene Segments Rearranged In Vitro," *J. Mol. Biol.* 227:381-388, (1992).
Hoogenboom et al. "Overview of Antibody Phage-Display Technology and Its Applications," *Methods Mol. Biol.* 178:1-37, (2002).
Hosida et al. "Produce of Human OX40 Antibody and Its Immunohistochemistry and Western Blot," *Acta Histochem. Cytochem.* 28(5):491, Abstract P-19, (1995).
Houck et al. "The Vascular Endothelial Growth Factor Family: Identification of a Fourth Molecular Species and Characterization of Alternative Splicing of RNA," *Mol. Endocrin.* 5:1806-1814, (1991).
Huang et al. "Identification of B7-H1 As a Novel Mediator of the Innate Immune/Proinflammatory Response As Well As a possible Myeloid Cell Prognostic Biomarker in Sepsis," *J Immunol.* 192(3):1091-1099, (Feb. 1, 2014, e-pub. Dec. 30, 2013).
Hudson et al. "Engineered Antibodies," *Nat. Med.* 9(1):129-134, (Jan. 2003).
Hurle et al. "Protein Engineering Techniques for Antibody Humanization," *Curr. Op. Biotech.* 5:428-433, (1994).
Hurwitz et al. "Bevacizumab Plus Irinotecan, Fluorouracil, and Leucovorin for Metastatic Colorectal Cancer," *N. Engl. J. Med.* 350(23):2335-2342, (Jun. 3, 2004).
Huseni, M. et al.: "T Cell-Mediated Cancer Immunotherapy Through OX40 Agonism (Abstract 128)," *European Journal of Cancer* 50(Suppl 6):45 (Nov. 19, 2014).
Idusogie et al. "Mapping of the C1q Binding Site on Rituxan, a Chimeric Antibody With a Human IgG1 Fc," *J. Immunol.* 164:4178-4184, (2000).
Imura et al. "The Human OX40/gp34 System Directly Mediates Adhesion of Activated T Cells to Vascular Endothelial Cells," *J. Exp. Med.* 183:2185-2195, (May 1, 1996).
Jackson et al. "Analysis of Lung Tumor Initiation and Progression Using Conditional Expression of Oncogenic K-ras," *Genes Dev.* 15(24):3243-3248, (Dec. 2001), 9 pages.
Jakobovits et al. "Germ-Line Transmission and Expression of a Human-Derived Yeast Artificial Chromosome," *Nature* 362:255-258, (Mar. 18, 1993).
Jakobovits et al. "Analysis of Homozygous Mutant Chimeric Mice: Deletion of the Immunoglobulin Heavy-Chain Joining Region Blocks B-cell development and antibody production," *Proc. Natl. Acad. Sci. USA* 90:2551-2555, (Mar. 1993).
Jeffrey, S.C., et al. "Dipeptide-Based Highly Potent Doxorubicin Antibody Conjugates," *Bioorg. Med. Chem. Lett.* 16:358-362, (2006, e-pub. Nov. 3, 2005).
Jeltsch et al. "Hyperplasia of Lymphatic Vessels in VEGF-C Transgenic Mice," *Science* 276:1423-1425, (May 30, 1997).
Jenkins et al. "Antigen Presentation by Chemically Modified Splenocytes Induces Antigen-Specific T Cell Unresponsiveness In Vitro and In Vivo," *J. Exp. Med.* 165:302-319, (Feb. 1987).
Johns et al. "Identification of the Epitope for the Epidermal Growth Factor Receptor-Specific Monoclonal Antibody 806 Reveals That It Preferentially Recognizes an Untethered Form of the Receptor," *J. Biol. Chem.* 279(29):30375-30384, (Jul. 16, 2004).
Johnson, G. et al. "The Kabat Database and a Bioinformatics Example," in *Methods in Molecular Biology* 248:1-25 Lo, ed., Human Press, Totowa, NJ, (2003).
Jones et al. "Proteinase Mutants of *Saccharomyces cerevisiae*," *Genetics* 85:23-33, (Jan. 1977).
Jones et al. "Replacing the Complementarity—Determining Regions in a Human Antibody With Those From a Mouse," *Nature* 321:522-525, (May 29, 1986).
Joukov et al. "A Novel Vascular Endothelial Growth Factor, VEGF-C, Is a Ligand for the Flt4 (VEGFR-3) and KDR (VEGFR-2) receptor Tyrosine Kinases," *Embo J.* 15(7):1751, (1996).
Kaleeba et al. "The OX-40 Receptor Provides a Potent Co-Stimulatory Signal Capable of Inducing Encephalitogenicity in Myelin-Specific CD4+ T Cells," *Int. Immunol.* 10(4):453-461, (1998).
Kam, N.W. et al. "Carbon Nanotubes As Multifunctional Biological Transporters and Near-Infrared Agents for Selective Cancer Cell Destruction," *Proc. Natl. Acad. Sci. USA* 102(33):11600-11605, (Aug. 16, 2005).

(56) References Cited

OTHER PUBLICATIONS

Kanda, Y. et al. "Comparison of Cell Lines for Stable Production of Fucose-Negative Antibodies With Enhanced ADCC," *Biotechnol. Bioeng.* 94:680-688, (2006, e-pub. Apr. 11, 2006).

Kashmiri et al. "SDR Grafting—A New Approach to Antibody Humanization," *Methods* 36:25-34, (2005).

Keir et al. "PD-1 and Its Ligands in Tolerance and Immunity," *Annu. Rev. Immunol.* 26:677-704, (2008, e-pub. Jan. 2, 2008).

Kim, J.K. et al. "Localization of the Site of the Murine IgG1 Molecule That Is Involved in Binding to the Murine Intestinal Fc Receptor," *J. Immunol.* 24:2429-2434, (1994).

Kim, J.M. "Abstract DDT01-02: Unleashing Anti-Tumor Immunity Through Anti-OX40 Monotherapy and in Combination with Anti-PD-L1," *Proceedings: AACR 106th Annual Meeting* (Apr. 18-22, 2015) 4 pages.

King, H.D. et al. "Monoclonal Antibody Conjugates of Doxorubicin Prepared With Branched Peptide Linkers: Inhibition of Aggregation by Methoxytriethyleneglycol Chains," *J. Med. Chem.* 45:4336-4343, (2002).

Kjaergaard et al. "Therapeutic Efficacy of OX-40 receptor Antibody Depends on Tumor Immunogenicity and Anatomic Site of Tumor Growth," *Cancer Res.* 60:5514-5521, (Oct. 1, 2000).

Kjaergaard et al. "Augmentation Versus Inhibition: Effects of Conjunctional OX-40 Receptor Monoclonal Antibody and IL-2 Treatment on Adoptive Immunotherapy of Advanced Tumor," *J. Immunol.* 167:6669-6677, (2001).

Klagsbrun et al. "Regulators of Angiogenesis," *Annu. Rev. Physiol.* 53:217-239, (1991).

Klimka et al. "Human Anti-CD30 Recombinant Antibodies by Guided Phage Antibody Selection Using Cell Panning," *Br. J. Cancer* 83:252-260, (2000).

Kohler et al. "Continuous Cultures of Fused Cells Secreting Antibody of Predefined Specificity," *Nature* 256:495-497, (Aug. 7, 1975).

Kostelny et al. "Formation of a Bispecific Antibody by the Use of Leucine Zippers," *J. Immunol.* 148(5):1547-1553, (Mar. 1, 1992).

Kozbor. "A Human Hybrid Myeloma for Production of human Monoclonal Antibodies," *J. Immunol.* 133(6):3001-3005, (Dec. 1984).

Kratz, F. et al. "Prodrugs of Anthracyclines in Cancer Chemotherapy," *Current Med. Chem.* 13: 477-523, (2006).

Lafferty et al. "A New Analysis of Allogeneic Interactions," *Aust. J. Exp. Biol. Med. Sci.* 53:27-42, (1975).

Lee et al. "Vascular Endothelial Growth Factor-Related Protein: A Ligand and Specific Activator of the Tyrosine Kinase Receptor Flt4," *Proc. Natl. Acad. Sci. USA* 93:1988-1992, (Mar. 1996).

Lee et al. "Generation of Primary Tumors With Flp Recombinase in FRT-Flanked p53 Mice," *Dis. Model Mech.* 5:397-402, (May 2012, e-pub. Dec. 22, 2011), 12 pages.

Lee, C.V. et al. "Bivalent Antibody Phage Display Mimics Natural Immunoglobulin," *J. Immunol. Methods* 284:119-132, (2004).

Lee, C.V. et al. "High Affinity Human Antibodies From Phage Displayed Synthetic Fab Libraries With a Single Framework Scaffold," *J. Mol. Biol.* 340:1073-1093, (2004).

Lenschow et al. "CD28/B7 System of T Cell Costimulation," *Ann. Rev. Immunol.* 14:233-258, (1996).

Leung et al. "Vascular Endothelial Growth Factor Is a Secreted Angiogenic Mitogen," *Science* 246:1306-1309, (1989).

Li et al. "The Effect of Anti-Human CD134 Monoclonal Antibody on Phytohemagglutinin-Induced mRNA Expression of Perforin in Peripheral Blood Mononuclear Cells," *Cell Mol. Immunol.* 2(6):467-471, (Dec. 2005).

Li, H. et al. "Optimization of Humanized IgGs in Glycoengineered *Pichia pastoris*," *Nat. Biotech.* 24(2):210-215, (Feb. 2006, e-pub. Jan. 22, 2006).

Li, J. et al. "Human Antibodies for Immunotherapy Development Generated Via a Human B Cell Hybridoma Technology," *Proc. Natl. Acad. Sci. USA* 103(10):3557-3562, (Mar. 7, 2006).

Linch, S.N. et al. "OX40 Agonists and Combination Immunotherapy: Putting the Pedal to the Metal," *Frontiers in Oncology* 5(34):1-14 (Feb. 16, 2015).

Lindmark et al. "Binding of Immunoglobulins to Protein A and Immunoglobulin Levels in Mammalian Sera," *J. Immunol. Meth.* 62:1-13, (1983).

Lode, H.N., et al. "Targeted Therapy With a Novel Enediyene Antibiotic Calicheamicin $\theta^I{}_1$ Effectively Suppresses Growth and Dissemination of Liver Metastases in a Syngeneic Model of Murine Neuroblastoma," *Cancer Res.* 58:2925-2928, (Jul. 15, 1998).

Lonberg et al. "Antigen-Specific Human Antibodies From Mice Comprising Four Distinct Genetic Modifications," *Nature* 368:856-859, (Apr. 28, 1994).

Lonberg et al. "Human Antibodies From Transgenic Mice," *Intern. Rev. Immunol.* 13:65-93, (1995).

Lonberg. "Human Antibodies From Transgenic Animals," *Nat. Biotech.* 23(9):1117-1125, (Sep. 2005, e-pub. Sep. 7, 2005).

Lonberg. "Fully Human Antibodies From Transgenic Mouse and Phage Display Platforms," *Curr. Opin. Immunol.* 20:450-459, (2008, e-pub. Jul. 21, 2008).

Ma et al. "A Two-Gene Expression Ratio Predicts Clinical Outcome in Breast Cancer Patients Treated With Tamoxifen," *Cancer Cell* 5:607-616, (Jun. 2004).

Ma et al. "The Expression and the Regulatory Role of OX40 and 4-1BB Heterodimer in Activated Human T Cells," *Blood* 106(6):2002-2010, (2005, e-pub. Jun. 7, 2005).

Maccallum et al. "Antibody-Antigen Interactions: Contact Analysis and Binding Site Topography," *J. Mol. Biol.* 262:732-745, (1996).

Marks et al. "By-passing immunization. Human Antibodies From V-Gene Libraries Displayed on Phage," *J. Mol. Biol.* 222:581-597, (1991).

Marks et al. "By-Passing Immunization: Building High Affinity Human Antibodies by Chain Shuffling,"*Bio/Technology* 10:779-783, (Jul. 1992).

Marks et al. "Selection of Human Antibodies From Phage Display Libraries, " *Methods in Molecular Biology* 248:161-175, (2004).

Martinez-Navio et al. "Neutralizing Capacity of Monoclonal Antibodies That Recognize Peptide Sequences Underlying the Carbohydrates on gp41 of Simian Immunodeficiency Virus," *J. Virol.* 86(23):12484-12493, (Dec. 2012).

Mather, J.P. "Establishment and Characterization of Two Distinct Mouse Testicular Epithelial Cell Lines, " *Biol. Reprod.* 23:243-252, (1980).

Mather, J.P. et al. "Culture of Testicular Cells in Hormone-Supplemented Serum-Free Medium,"*Annals N.Y. Acad. Sci.* 383:44-68, (1982).

Matthews et al. "A Receptor Tyrosine Kinase cDNA Isolated From a Population of Enriched Primitive Hematopoietic Cells and Exhibiting Close Genetic Linkage to C-Kit," *Proc. Natl. Acad. Sci. USA* 88:9026-9030, (Oct. 1991).

Mccafferty, J. et al. "Phage Antibodies: Filamentous Phage Displaying Antibody Variable Domains," *Nature* 348:552-554, (Dec. 6, 1990).

Melero et al. "Clinical Development of Immunostimulatory Monoclonal Antibodies and Opportunities for Combination," *Clinical Cancer Res.* 19:997-1008, (2013).

Melero, I. et al. "Agonist Antibodies to TNFR Molecules That Costimulate T and NK Cells," *Clin. Cancer Res.* 19(5):1044-1053 (Mar. 1, 2013), 20 pages.

Meng et al. "Predictive biomarkers in PD-1/PD-L1 checkpoint blockade immunotherapy," *Cancer Treat Rev.* 41(10):868-876. (Dec. 2015).

Meyer et al. "A Novel Vascular Endothelial Growth Factor Encoded by Orf Virus, VEGF-E, Mediates Angiogenesis Via Signalling Through VEGFR-2 (KDR) But Not VEGFR-1 (Flt-1) Receptor Tyrosine Kinases," *Embo J.* 18(2):363-374, (1999).

Milstein. "Hybrid Hybridomas and Their Use in Immunohistochemistry," *Nature* 305:537-540, (Oct. 6, 1983).

Morales-Kastresana et al. "Combined Immunostimulatory Monoclonal Antibodies Extend Survival in an Aggressive Transgenic Hepatocellular Carcinoma Mouse Model," *Clinical Cancer Res.* 19(22):6151-6162, (2013, e-pub. Sep. 12, 2013).

(56) References Cited

OTHER PUBLICATIONS

Morales-Kastresana, A. et al. "Therapeutic Activity of a Combination of Immunostimulatory Monoclonal Antibodies (Anti-B7-H1, CD137 and OX40) on a c-myc-Driven Spontaneous Transgenic Model of Hepatcellular Carcinoma," *J. For Immunotherapy of Cancer* 1(Suppl. 1):7, (Nov. 7, 2013) 1 page.
Morimoto et al. "Single-Step Purification of F(ab')2 fragments of Mouse Monoclonal Antibodies (Immunoglobulins G1) by Hydrophobic Interaction High Performance Liquid Chromatography Using TSKgel Phenyl-5PW," *J. Biochem. And Biophysical Methods* 24:107-117, (1992).
Morrison et al. "Chimeric Human Antibody Molecules: Mouse Antigen-Binding Domains With Human Constant Region Domains," *Proc. Natl. Acad. Sci. USA* 81:6851-6855, (Nov. 1984).
Morrison et al. "Success in Specification," *Nature* 368:812-813, (Apr. 28, 1994).
Muller et al. "VEGF and the Fab Fragment of a Humanized Neutralizing Antibody: Crystal Structure of the Complex at 2.4 a Resolution and Mutational Analysis of the Interface," *Structure* 6(9):1153-1167, (1998).
Mullis et al. "Specific Enzymatic Amplification of DNA in Vitro: The Polymerase Chain Reaction," *Cold Spring Harbor Symp. Quant. Biol.* 51(Pt. 1):263-273, (1986).
Munson et al. "Ligand: A Versatile Computerized Approach for Characterization of Ligand-Binding Systems," *Anal. Biochem.* 107:220-239, (1980).
Nagy, A., et al., "Stability of Cytotoxic Luteinizing Hormone-Releasing Hormone Conjugate (AN-152) Containing Doxorubicin 14-O-Hemiglutarate in Mouse and Human Serum In Vitro: Implications for the Design of Preclinical Studies," *Proc. Natl. Acad. Sci. USA* 97(2):829-834, (Jan. 18, 2000).
Neuberger. "Generating High-Avidity Human Mabs in Mice," *Nature Biotech.* 14:826, (Jul. 1996).
Ni. "Research Progress and Future Perspectives in Antibodomics and Antibodomic Drugs," *Xiandai Mianyixue* 26(4):265-268, (Oct. 23, 2006). (Abstract Only).
Nicolaou et al. "Calicheamicin $\theta^I_1$ :A Rationally Designed Molecule With Extremely Potent and Selective DNA Cleaving Properties and apoptosis Inducing Activity," *Angew Chem. Intl. Ed. Engl.* 33(2):183-186, (1994).
Ogawa et al. "A Novel Type of Vascular Endothelial Growth Factor, VEGF-E (NZ-7 VEGF), Preferentially Utilizes KDR/Flk-1 Receptor and Carries a Potent Mitotic Activity Without Heparin-Binding Domain," *J. Biol. Chem.* 273(47):31273-31281, (Nov. 20, 1998).
Okazaki, A. et al. "Fucose Depletion From Human IgG1 Oligosaccharide Enhances Binding Enthalpy and Association Rate Between IgG1 and FcγRIIIa," *J. Mol. Biol.* 336:1239-1249, (2004).
Okazaki et al. "PD-1 and PD-1 ligands: From Discovery to Clinical Application," *Intern. Immun.* 19(7):813-824, (2007).
Osbourn et al. "From Rodent Reagents to Human Therapeutics Using Antibody Guided Selection," *Methods* 36:61-68, (2005).
Padlan et al. "A Possible Procedure for Reducing the Immunogenicity of Antibody Variable Domains While Preserving Their Ligand-Binding Properties," *Mol. Immunol.* 28(4/5):489-498, (1991).
Petkova, S.B. et al. "Enhanced Half-Life of Genetically Engineered Human IgG1 Antibodies in a Humanized FcRn Mouse Model: Potential Application in Humorally Mediated Autoimmune Disease," *Int. Immunol.* 18(12):1759-1769, (2006).
Pluckthun, A. "Antibodies from *Escherichia coli*," *The Pharmacology of Monoclonal Antibodies, vol. 113* Rosenburg and Moore eds. Springer-Verlag, New York pp. 269-315, (1994).
Popkov et al. "Human/mouse Cross-Reactive Anti-VEGF Receptor 2 Recombinant Antibodies Selected From an Immune b9 Allotype Rabbit Antibody Library," *J. Immunol. Meth.* 288:149-164, (2004, e-pub. Apr. 28, 2004).
Portolano et al. "Lack of Promiscuity in Autoantigen-Specific H and L Chain Combinations As Revealed by Human H and L Chain 'Roulette'," *J. Immunol.* 150(3):880-887, (Feb. 1, 1993).
Powles et al. "MPDL3280A (Anti-PD-L1) Treatment Leads to Clinical Activity in Metastatic Bladder Cancer," *Nature* 515:558-562, (Nov. 27, 2014).
Prell, R. et al. "Nonclinical Safety Assessment of a Humanized Anti-OX40 Agonist Antibody, MOXR0916 (Abstract 424)," *European Journal of Cancer* 50(Suppl. 6):136, (Nov. 20, 2014).
Presta et al. "Antibody Engineering," *Curr. Op. Struct. Biol.* 2:593-596, (1992).
Presta et al. "Humanization of an Antibody Directed Against IgE" *J. Immunol.* 151(5):2623-2632, (Sep. 1, 1993).
Presta et al. "Humanization of an Anti-Vascular Endothelial Growth Factor Monoclonal Antibody for the Therapy of Solid Tumors and Other Disorders," *Cancer Res.* 57:4593-4599, (Oct. 15, 1997).
Qian et al. "Active Vaccination With Dickkopf-1 Induces Protective and Therapeutic Antitumor Immunity in Murine Multiple Myeloma," *Blood* 119(1):161-169, (Jan. 5, 2011, e-pub. Nov. 2, 2011).
Queen et al. "A Humanized Antibody That Binds to the Interleukin 2 Receptor," *Proc. Natl. Acad. Sci. USA* 86:10029-10033, (Dec. 1989).
R&D Systems catalog No. MAB3388, retrieved Aug. 13, 2015 from https://www.rndsystems.com/products/human-ox40-tnfrsf4-antibody-443318_mab3388, last visited Aug. 13, 2015.
Rabinovich et al. "Immunosuppressive Strategies That Are Mediated by Tumor Cells," *Annual Rev. Immunol.* 25:267-296, (2007), 34 pages.
Ravetch et al. "Fc Receptors," *Annu. Rev. Immunol.* 9:457-492, (1991).
Redmond et al. "Defects in the Acquisition of CD8 T Cell Effector Function After Priming With Tumor or Soluble Antigen Can Be Overcome by the Addition of an OX40 Agonist," *J. Immunol.* 179:7244-7253, (2007).
Redmond et al. "Targeting OX40 and OX40L for the Treatment of Autoimmunity and Cancer," *Crit. Rev. Immunol.* 27:415-436, (2007).
Reyes et al. "Expression of Human β-Interferon cDNA Under the Control of a Thymidine Kinase Promoter From Herpes Simplex Virus," *Nature* 297:598-601, (1982).
Riechmann et al. "Reshaping Human Antibodies for Therapy," *Nature* 332:323-329, (1988).
Ripka, J. et al. "Two Chinese Hamster Ovary Glycosylation Mutants Affected in the Conversion of GDP-Mannose to GDP-Fucose," *Arch. Biochem. Biophys.* 249(2):533-545, (Sep. 1986).
Rosok et al. "A Combinatorial Library Strategy for the Rapid Humanization of Anticarcinoma BR96 Fab" *J. Biol. Chem.* 271(37):22611-22618, (Sep. 13, 1996).
Ruby et al. "Anti-OX40 Stimulation In Vivo Enhances CD8+ Memory T Cell Survival and Significantly Increases Recall Responses," *Eur. J. Immunol.* 37:157-166, (2007).
Saltz et al. "Bevacizumab in Combination With Oxaliplatin-Based Chemotherapy As First-Line Therapy in Metastatic Colorectal Cancer: A Randomized Phase III Study," *J. Clin. Oncol.* 26(12):2013-2019, (Apr. 20, 2008).
Santa Cruz Biotechnology catalog No. sc-10938, retrieved Aug. 13, 2015 from http://www.scbt.com/datasheet-10938-ox40-g-14-antibody.html, last visited Aug. 13, 2015, 3 pages.
Santa Cruz Biotechnology catalog No. sc-11403, retrieved Aug. 13, 2015 from <http://www.scbt.com/datasheet-11403-ox40-h-133-antibody.html>, last visited Aug. 13, 2015, 3 pages.
Santa Cruz Biotechnology catalog No. sc-20073, retrieved Aug. 13, 2015 from http://www.scbt.com/datasheet-20073-ox40-ber-act35-antibody.html, last visited Aug. 13, 2015, 3 pages.
Santa Cruz Biotechnology catalog No. sc-376014, retrieved Aug. 13, 2015 from http://www.scbt.com/datasheet-376014-ox40-h-10-antibody.html, last visited Aug. 13, 2015, 3 pages.
Sato. "Molecular Diagnosis of Tumor Angiogenesis and Anti-Angiogenic Cancer Therapy," *Int. J. Clin. Oncol.* 8:200-206, (2003).
Schlessinger et al. "Growth Factor Signaling by Receptor Tyrosine Kinases," *Neuron* 9:383-391, (1992).
Shalaby et al. "Development of Humanized Bispecific Antibodies Reactive With Cytotoxic Lymphocytes and Tumor Cells Overexpressing the HER2 Protooncogene," *J. Exp. Med.* 175:217-225, (Jan. 1, 1992).
Shames et al. "High Heregulin Expression Is Associated With Activated HER3 and May Define an Actionable Biomarker in

(56) References Cited

OTHER PUBLICATIONS

Patients With Squamous Cell Carcinomas of the Head and Neck," *PloS One* 8(2):e56765, (Feb. 28, 2013).
Sharpe et al. "The B7-CD28 Superfamily," *Nat. Rev. Immunol.* 2(2):116-126, (Feb. 2002).
Sheriff et al. "Redefining the Minimal Antigen-Binding Fragment," *Nature Struct. Biol.* 3(9):733-736, (Sep. 1996).
Shibuya et al. "Nucleotide Sequence and Expression of a Novel Human Receptor-Type Tyrosine Kinase Gene (flt) Closely Related to the fms Family," *Oncogene* 8:519-527, (1990).
Shields, R.L., et al. "High resolution Mapping of the Binding Site on Human IgG1 for FcγRI, FcγRII, FcγRIII, and FcRn and Design of IgG1 Variants With Improved Binding to the FcγR," *J. Biol. Chem.* 276(9):6591-6604, (Mar. 2, 2001).
Sidhu et al. "Phage-Displayed Antibody Libraries of Synthetic Heavy Chain Complementarity Determining Regions," *J. Mol. Biol.* 338:299-310, (2004).
Sims et al. "A Humanized CD18 Antibody Can Block Function Without Cell Destruction," *J. Immunol.* 151(4):2296-2308, (Aug. 15, 1993).
Soker et al. "Neuropilin-1 Is Expressed by Endothelial and Tumor Cells As an Isoform-Specific Receptor for Vascular Endothelial Growth Factor," *Cell* 92:735-745, (Mar. 20, 1998).
Spiess et al. "Bispecific Antibodies With Natural Architecture Produced by Co-Culture of Bacteria Expressing Two Distinct Half-Antibodies," *Nature Biotech.* 31(8):753-758, (Aug. 2013. E-pub. Jul. 7, 2013).
Staunton et al. "The Arrangement of the Immunoglobulin-Like Domains of ICAM-1 and the Binding Sites for LFA-1 and Rhinovirus," *Cell* 61:243-254, (Apr. 20, 1990).
Steinman et al. "Myeloid Dendritic Cells," *J. Leukoc. Biol.* 66:205-208, (Aug. 1999).
Stinchcomb et al. "Isolation and Characterisation of a Yeast Chromosomal Replicator," *Nature* 282:39-43, (Nov. 1, 1979).
Stragliotto et al. "Multiple infusions of Anti-Epidermal Growth Factor Receptor (EGFR) Monoclonal Antibody (EMD 55 900) in Patients With Recurrent Malignant Gliomas," *Eur. J. Cancer* 32A(4):636-640, (1996).
Streit et al. "Angiogenesis, Lymphangiogenesis, and Melanoma Metastasis," *Oncogene* 22:3172-3179, (2003).
Sugamura et al. "Therapeutic Targeting of the Effector T-Cell Co-Stimulatory Molecule OX40," *Nat. Rev. Immunol.* 4:420-431, (Jun. 2004).
Sun et al. "Preparation of Anti-Human OX40 Functional Monoclonal Antibody and Study of Its Biological Characteristics," *Zhongguo Mianyizue Zazhi* 21(6):403-405, (2005). (English abstract).
Suresh et al. "Bispecific Monoclonal Antibodies From Hybrid Hybridomas," *Meth. In Enzymology* 121:210-228, (1986).
Terman et al. "Identification of a New Endothelial Cell Growth Factor Receptor Tyrosine Kinase," *Oncogene* 6:1677-1683, (1991).
Terman et al. "Identification of the KDR Tyrosine Kinase As a Receptor for Vascular Endothelial Cell Growth Factor," *Biochem. Biophys. Res. Comm.* 187(3):1579-1586, (1992).
Therasse et al. "New Guidelines to Evaluate the Response to Treatment in Solid Tumors," *J. Natl. Cancer Inst.* 92(3):205-216, (Feb. 2, 2000).
Thompson et al. "Tumor B7-H1 Is Associated With Poor Prognosis in Renal Cell Carcinoma Patients With Long-Term Follow-Up," *Cancer Res.* 66(7):3381-3385, (Apr. 1, 2006).
Tonini et al. "Molecular Basis of Angiogenesis and Cancer," *Oncogene* 22:6549-6556, (2003).
Topalian et al. "Targeting the PD-1/B7-H1(PD-L1) Pathway to Activate Anti-Tumor Immunity," *Curr. Opin. Immunol.* 24(2):207-212, (2012, e-pub. Jan. 9, 2012).
Topalian et al. "Safety, Activity, and Immune Correlates of Anti-PD-1 Antibody in Cancer," *N. Engl. J. Med.* 366(26):2443-2454, (Jun. 28, 2012).
Torgov, M.Y., et al., "Generation of an Intensely Potent Anthracycline by a Monoclonal Antibody-Beta-Galactosidase Conjugate," *Bioconjug. Chem.* 16:717-721, (2005, e-pub. Apr. 27, 2005).
Traunecker et al. "Bispecific Single Chain Molecules (Janusins) Target Cytotoxic Lymphocytes on HIV Infected Cells," *Embo J.* 10(12):3655-3659, (1991).
Trotman et al. "Pten Dose Dictates Cancer Progression in the Prostate," *PloS Biol.* 1(3)385-396, (2003).
Tutt et al. "Trispecific F(ab')3 Derivatives That Use Cooperative Signaling Via the TCR/CD3 Complex and CD2 to Activate and Redirect Resting Cytotoxic T Cells," *J. Immunol.* 147(1):60-69, (Jul. 1, 1991).
Ullrich et al. "Signal Transduction by Receptors with Tyrosine Kinase Activity," *Cell* 61:203-212, (Apr. 20, 1990).
UniProtKB Swiss-Prot Accession No. Q9NZQ7.1, located at <http://www.uniprot.org/uniprot/Q9NZQ7>, last visited Aug. 14, 2015, 12 pages.
Urlaub, G. et al. "Isolation of Chinese Hamster Cell Mutants Deficient in Dihydrofolate Reductase Activity," *Proc. Natl. Acad. Sci. U.S.A.* 77:4216-4220, (Jul. 1980).
Van Den Berg "*Kluyveromyces* As a Host for Heterologous Gene Expression: Expression and Secretion of Prochymosin," *Biotech.* 8:135-139, (Feb. 1990).
Van Dijk et al. "Human Antibodies As Next Generation Therapeutics," *Curr. Opin. Pharmacol.* 5:368-374, (2001).
Vaswani et al. "Humanized Antibodies As Potential Therapeutic Drugs," *Ann. Allergy, Asthma & Immunol.* 81:105-115, (Aug. 1998).
Vitetta, E.S. et al., "Redesigning Nature's Poisons to Create Anti-Tumor Reagents," *Science* 238:1098-1104, (1987).
Vollmers et al. "Death by Stress: Natural IgM-Induced Apoptosis," *Methods and Findings in Experimental and Clinical Pharmacology* 27(3):185-191, (2005).
Vollmers et al. "The 'Early Birds': Natural IgM Antibodies and Immune Surveillance," *Histology and Histopathology* 20:927-937, (2005).
Voo et al. "Antibodies Targeting Human OX40 Expand Effector T Cells and Block Inducible and Natural Regulatory T Cell Function," *J. Immunol.* 191:3641-3650, (2013).
Wagner et al. "Transferrin-Polycation Conjugates As Carriers for DNA Uptake Into Cells," *Proc. Natl. Acad. Sci. U.S.A.* 87:3410-3414, (May 1990).
Weinberg. "Antibodies to OX-40 (CD134) Can Identify and Eliminate Autoreactive T Cells: Implications for Human Autoimmune Disease," *Mol. Med. Today* 4:76-83, (1998).
Weinberg et al. "Anti-OX40 (CD134) Administration to Nonhuman Primates: Immunostimulatory Effects and Toxicokinetic Study," *J. of Immunotherapy* 29(6):575-585, (Nov./Dec. 2006).
Weinberg et al. "Science Gone Translational: The OX40 Agonist Story," *Immunol. Rev.* 244:218-231, (2011).
Wherry. "T Cell Exhaustion," *Nature Immunol.* 12(6):492-499, (Jun. 2011, e-pub. May 18, 2011).
Willett et al. "Probing the Interaction Between Feline Immunodeficiency Virus and CD134 by Using the Novel Monoclonal Antibody 7D6 and the CD134 (Ox40) Ligand," *J. Virol.* 81(18):9665-9679, (Sep. 2007).
Winter et al. "Making Antibodies by Phage Display Technology," *Ann. Rev. Immunol.* 12:433-455, (1994).
Wolchok et al. "Guidelines for the Evaluation of Immune Therapy Activity in Solid Tumors: Immune-Related Response Criteria," *Clin. Can. Res.* 15(23):7412-7420, (Dec. 1, 2009).
Wright et al. "Effect of Glycosylation on Antibody Function: Implications for Genetic Engineering," *Trends Biotech.* 15:26-32, (Jan. 1997).
Wu et al. "Receptor-Mediated In Vitro Gene Transformation by a Soluble DNA Carrier System," *J. Biol. Chem.* 262(10):4429-4432, (Apr. 5, 1987).
Xie et al. "Characterization and Application of Two Novel Monoclonal Antibodies Against Human OX40: Costimulation of T Cells and Expression on Tumor As Well As Normal Gland Tissues," *Tissue Antigens* 67:307-317, (2006).
Xu et al. "Diversity in the CDR3 Region of $V_H$ is Sufficient for Most Antibody Specificities," *Immunity* 13:37-45, (Jul. 2000).
Yamada et al. "Next-Generation Peptide Vaccines for Advanced Cancer," *Cancer Sci.* 104(1):15-21, (2013, e-pub. Dec. 4, 2012).
Yamane-Ohnuki et al. "Establishment of FUT8 Knockout Chinese Hamster Ovary Cells: An Ideal Host Cell Line for Producing

(56) References Cited

OTHER PUBLICATIONS

Completely Defucosylated Antibodies With Enhanced Antibody-Dependent Cellular Cytotoxicity," *Biotech. Bioeng.* 87:614-622, (2004, e-pub. Aug. 6, 2004).
Yang et al. "Gene Expression Profile and Angiogenic Marker Correlates With Response to Neoadjuvant Bevacizumab Followed by Bevacizumab Plus Chemotherapy in Breast Cancer," *Clin. Cancer Res.* 14(18):5893-5899, (Sep. 15, 2008), 13 pages.
Yaniv. "Enhancing Elements for Activation of Eukaryotic Promoters," *Nature* 297:17-18, (1982).
Yarden et al. "Growth Factor Receptor Tyrosine Kinases," *Ann. Rev. Biochem.* 57:433-478, (1988).
Zamyatnin. "Protein Volume In Solution," *Prog. Biophys. Mol. Biol.* 24:107-123, (1972).
Zapata et al. "Engineering Linear F(ab')$_2$ Fragments for Efficient Production in *Escherichia coli* and Enhanced Antiproliferative Activity," *Protein Eng.* 8(10):1057-1062, (1995).
Zhang et al. "Intratumoral T Cells, Recurrence, and Survival in Epithelial Ovarian Cancer," *N. Engl. J. Med.* 348:203-213, (Jan. 16, 2003).
Co-pending U.S. Appl. No. 15/176,100, filed Jun. 7, 2016, Inventor Rhee et al., Applicant Genentech, Inc., title "Methods of Treating Cancer Using Anti-Ox40 Antibodies".
Co-pending U.S. Appl. No. 15/176,106, filed Jun. 7, 2016, Inventor Rhee et al., Applicant Genentech, Inc., title "Methods of Treating Cancer Using Anti-0x40 Antibodies and Pd-1 Axis Binding Antagonists ".
Co-pending U.S. Appl. No. 15/184,928, filed Jun. 16, 2016, Inventor Dennis et al, Applicant Genentech, Inc., title "Methods of Treating HER2-Positive Cancers Using PD-1 Axis Binding Antagonists and Anti-HER2 Antibodies".
Co-pending U.S. Appl. No. 15/184,966, filed Jun. 16, 2016, Inventor Dennis et al, Applicant Genentech, Inc., title "Methods of Treating HER2-Positive Cancers Using PD-1 Axis Binding Antagonists and Anti-HER2 Antibodies".
International Search Report dated Apr. 8, 2016, for PCT Patent Application No. PCT/US2015/060941, filed on Nov. 16, 2015, 14 pages.
International Search Report dated Sep. 20, 2016, for PCT Patent Application No. PCT/US2016/036256, filed Jun. 7 2016, 7 pages.
International Search Report dated Jul. 7, 2015, for PCT Patent Application No. PCT/US2015/023434, filed on Mar. 30, 2015, 7 pages.
International Search Report dated Jun. 18, 2015, for PCT Patent Application No. PCT/US2015/023432, filed on Mar. 30, 2015, 8 pages.
International Search Report dated Jun. 25, 2015, for PCT Patent Application No. PCT/US2014/070998, filed on Dec. 17, 2014, 10 pages.
Written Opinion dated Apr. 8, 2016, for PCT Patent Application No. PCT/US2015/060941, filed on Nov. 16, 2015, 14 pages.
Written Opinion of the International Searching Authority dated Jun. 18, 2015, for PCT Patent Application No. PCT/US2015/023432, filed on Mar. 30, 2015, 6 pages.
Written Opinion of the International Searching Authority dated Jun. 25, 2015, for PCT Patent Application No. PCT/US2014/070998, filed on Dec. 17, 2014, 14 pages.
Written Opinion of the International Searching Authority dated Jul. 7, 2015, for PCT Patent Application No. PCT/US2015/023434, filed on Mar. 30, 2015, 6 pages.
Weinberg, A.D. "Engagement of the OX-40 Receptor In Vivo Enhances Antitumor Immunity," *J. Immunol.* 164:2160-2169, (2000).
Forde, P. "What Lies Within: Novel Strategies in Immunotherapy for Non-Small Cell Lung Cancer," *The Oncologist* 18(11):1203-1213, (2013, e-pub. Oct. 8, 2013).
Kowanetz, M. et al. "Circulating and Tumor-Based Biomarkers Predict Clinical Activity in Cancer Patients Treated With the Engineered Anti-PD-L 1 Antibody MPDL3280A," *Journal for Immunotherapy of Cancer* 2(Suppl. 3):136, (Nov. 6, 2014).
Powderly J.D. et al. "Biomarkers and Associations With the Clinical Activity of PD-L 1 Blockade in a MPDL3280A Study." Abstract 3001. Retrieved from the Internet: <URL:http://carolinabiooncology.org/wp-content/uploads/ASCO-2013-Presentation-Anti-PDL-1-Biomarkers.pdf>, last visited Sep. 10, 2018. (May 20, 2013).
Butte, M.J. et al. (2008, e-pub. Jun. 27, 2018). "Interaction of Human PD-L 1 and B7-1," Molecular Immunology 45:3567-3572.
Butte, M.J. et al. (Jul. 2007). "Programmed Death-1 Ligand 1 Interacts Specifically with the B7-1 Costimulatory Molecule to Inhibit T Cell Responses," Immunity 27:111-122.
ClinicalTrials.gov (Jul. 2012). "A Study of Atezolizumab Administered in Combination With Bevacizumab and/or With Chemotherapy in Participants With Locally Advance or Metastatic Solid Tumors," NCT01633970.
ClinicalTrials.gov (Jul. 31, 2014). "A Phase 1b/2 Safety and Tolerability Study of MEDI6469 in Combination With Therapeutic Immune Agents or Monoclonal Antibodies (MEDI6469)," NCT02205333.
Curiel, T.J. et al. (May 2003, e-pub. Apr. 21, 2003). "Blockade of B7-HI Improves Myeloid Dendritic Cell-Mediated Antitumor Immunity," Nature Medicine 9(5):562-567.
Iwai, Y. et al. (2004, e-pub. Dec. 20, 2004). "PD-1 Blockade Inhibits Hematogenous Spread of Poorly Immunogenic Tumor Cells by Enhanced Recruitment of Effector T Cells," International Immunology 17(2):133-144.
Nimmerjahn, F. et al. (May 1, 2012). "Translating Basic Mechanisms of IgG Effector Activity Into Next Generation Cancer Therapies," Cancer Immunity 12:13, 7 pages.
Park, J.-J. et al. (Aug. 2010). "B7-HI/CD80 Interaction is Required for the Induction and Maintenance of Peripheral T-2 cell Tolerance," Blood 116(8):1291-1298.
Paterson, A.M. et al. (2011). "The Programmed Death-1 Ligand 1 :B7-1 Pathway Restrains Diabetogenic Effector T Cells In Vivo," The Journal of Immunology 187(3):1097-1105.
Sharma, A. et al. (Feb. 15, 2019, e-pub. Jul. 27, 2018). "Anti-CTLA-4 Immunotherapy Does Not Deplete FOXP3+ Regulatory T Cells (Tregs) in Human Cancers," Clin. Cancer Res. 25(4):1233-1238.
Stewart, R. et al. (2014). "The Role of Fc Gamma Receptors in the Activity of Immunomodulatory Antibodies for Cancer," Journal for Immunotherapy of Cancer 2:29, 10 pages.
Yang, J. et al. (2011). "The Novel Costimulatory Programmed Death Ligand 1/B7.1 Pathway is Functional in Inhibiting Alloimmune Responses In Vivo," The Journal of Immunology 187(3)1113-1119.

\* cited by examiner

```
1D2      SLQVDDTAIYYCVREEM...DYWGQGTSVTVSS
1D2.gr.1 SVTAADTAVYYCVREEM...DYWGQGTLVTVSS
1D2.gr.2 SVTAADTAVYYCVREEM...DYWGQGTLVTVSS
1D2.gr.3 SVTAADTAVYYCVREEM...DYWGQGTLVTVSS
```

FIG. 11I

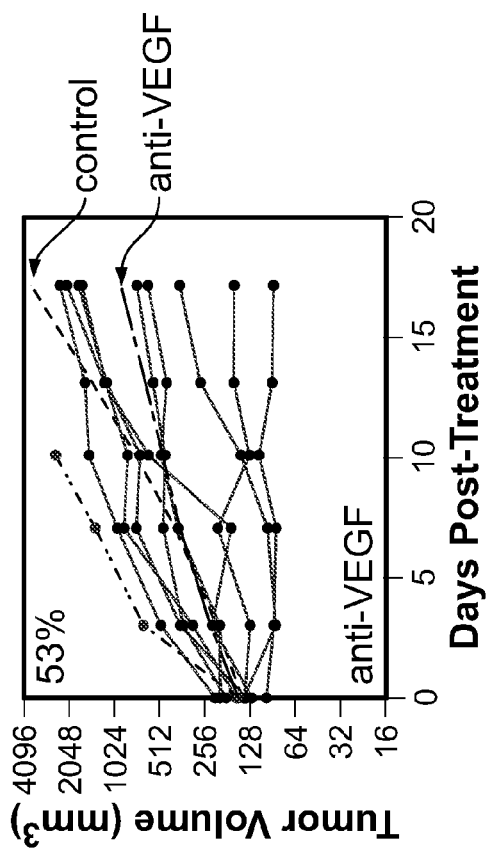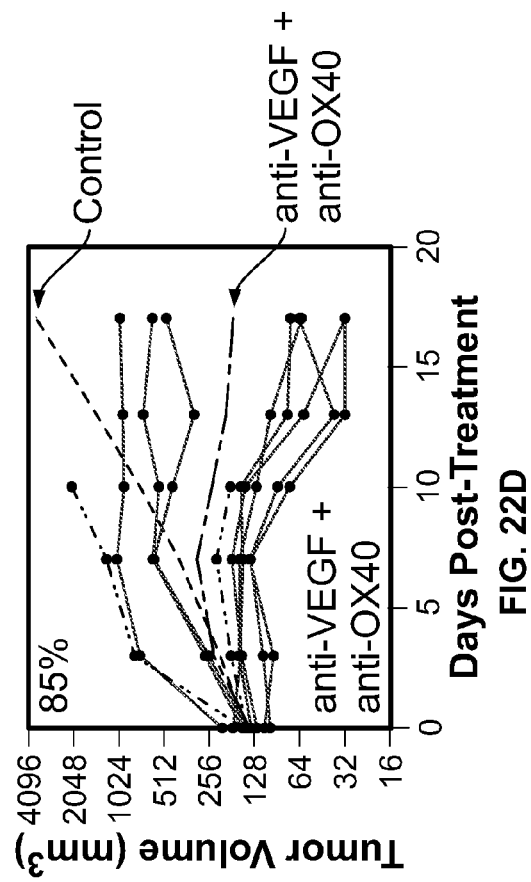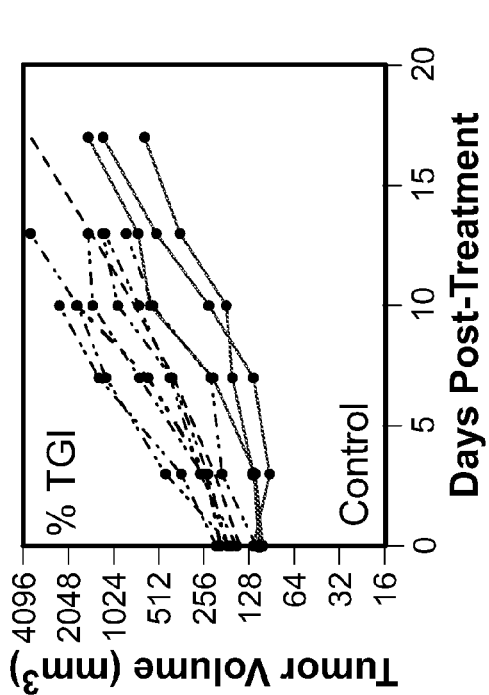
FIG. 22A, FIG. 22B, FIG. 22C, FIG. 22D

SEQUENCE LISTING

```
<160> NUMBER OF SEQ ID NOS: 254

<210> SEQ ID NO 1
<211> LENGTH: 249
<212> TYPE: PRT
<213> ORGANISM: Homo sapiens

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30
```

-continued

```
Asn Thr Val Cys Arg Pro Cys Pro Gly Phe Tyr Asn Asp Val Val
         35                  40                  45

Ser Ser Lys Pro Cys Lys Pro Cys Thr Trp Cys Asn Leu Arg Ser Gly
 50                  55                  60

Ser Glu Arg Lys Gln Leu Cys Thr Ala Thr Gln Asp Thr Val Cys Arg
 65                  70                  75                  80

Cys Arg Ala Gly Thr Gln Pro Leu Asp Ser Tyr Lys Pro Gly Val Asp
                 85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
            195                 200                 205

Leu Tyr Leu Leu Arg Arg Asp Gln Arg Leu Pro Pro Asp Ala His Lys
210                 215                 220

Pro Pro Gly Gly Gly Ser Phe Arg Thr Pro Ile Gln Glu Glu Gln Ala
225                 230                 235                 240

Asp Ala His Ser Thr Leu Ala Lys Ile
                245
```

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

```
Asp Ser Tyr Met Ser
 1               5
```

<210> SEQ ID NO 3
<211> LENGTH: 17
<212> TYPE: PRT
<213> ORGANISM: Artificial Sequence
<220> FEATURE:
<223> OTHER INFORMATION: Synthetic Construct

<400> SEQUENCE: 3

```
Asp Met Tyr Pro Asp Asn Gly Asp Ser Ser Tyr Asn Gln Lys Phe Arg
 1               5                  10                  15

Glu
```

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

```
Ala Pro Arg Trp Tyr Phe Ser Val
1               5

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Arg Ala Ser Gln Asp Ile Ser Asn Tyr Leu Asn
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Tyr Thr Ser Arg Leu Arg Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic Construct

<400> SEQUENCE: 7

Gln Gln Gly His Thr Leu Pro Pro Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic Construct

<400> SEQUENCE: 8

Asp Ala Tyr Met Ser
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Glu Ser Tyr Met Ser
1               5

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10
```

```
Asp Met Tyr Pro Asp Asn Ala Asp Ser Ser Tyr Asn Gln Lys Phe Arg
1               5                   10                  15

Glu

<210> SEQ ID NO 11
<211> LENGTH: 17
<212> TYPE: PRT
<213> ORGANISM: Artificial Sequence
<220> FEATURE:
<223> OTHER INFORMATION: Synthetic Construct

<400> SEQUENCE: 11

Asp Met Tyr Pro Asp Asn Ala Asp Ala Ser Tyr Asn Gln Lys Phe Arg
1               5                   10                  15

Glu

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Asp Met Tyr Pro Asp Asn Gly Asp Ala Ser Tyr Asn Gln Lys Phe Arg
1               5                   10                  15

Glu

<210> SEQ ID NO 13
<211> LENGTH: 17
<212> TYPE: PRT
<213> ORGANISM: Artificial Sequence
<220> FEATURE:
<223> OTHER INFORMATION: Synthetic Construct

<400> SEQUENCE: 13

Asp Met Tyr Pro Asp Ser Gly Asp Ser Ser Tyr Asn Gln Lys Phe Arg
1               5                   10                  15

Glu

<210> SEQ ID NO 14
<211> LENGTH: 17
<212> TYPE: PRT
<213> ORGANISM: Artificial Sequence
<220> FEATURE:
<223> OTHER INFORMATION: Synthetic Construct

<400> SEQUENCE: 14

Asp Met Tyr Pro Asp Asn Gly Ser Ser Ser Tyr Asn Gln Lys Phe Arg
1               5                   10                  15

Glu

<210> SEQ ID NO 15
<211> LENGTH: 8
<212> TYPE: PRT
<213> ORGANISM: Artificial Sequence
<220> FEATURE:
<223> OTHER INFORMATION: Synthetic Construct

<400> SEQUENCE: 15

Ala Pro Arg Trp Tyr Phe Ser Ala
1               5
```

```
<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Ala Pro Arg Trp Tyr Ala Ser Val
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ala Pro Arg Trp Ala Phe Ser Val
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Construct

<400> SEQUENCE: 18

Ala Pro Ala Trp Tyr Phe Ser Val
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Ala Pro Arg Trp Tyr Phe Ala Val
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic Construct

<400> SEQUENCE: 20

Ala Pro Arg Ala Tyr Phe Ser Val
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Construct

<400> SEQUENCE: 21

Ala Ala Arg Trp Tyr Phe Ser Val
1               5

<210> SEQ ID NO 22
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Gly His Thr Leu Pro Ala Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly His Thr Ala Pro Pro Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct

<400> SEQUENCE: 24

Gln Gln Gly Ala Thr Leu Pro Pro Thr
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic Construct

<400> SEQUENCE: 25

Gln Gln Gly His Ala Leu Pro Pro Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Ala His Thr Leu Pro Pro Thr
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Gln Gln Gly His Thr Leu Ala Pro Thr
1               5

<210> SEQ ID NO 28
<211> LENGTH: 9
```

```
<212> TYPE: PRT
<213> ORGANISM: Artificial Sequence
<220> FEATURE:
<223> OTHER INFORMATION: Synthetic Construct

<400> SEQUENCE: 28

Gln Ala Gly His Thr Leu Pro Pro Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Construct

<400> SEQUENCE: 29

Asn Tyr Leu Ile Glu
1               5

<210> SEQ ID NO 30
<211> LENGTH: 17
<212> TYPE: PRT
<213> ORGANISM: Artificial Sequence
<220> FEATURE:
<223> OTHER INFORMATION: Synthetic Construct

<400> SEQUENCE: 30

Val Ile Asn Pro Gly Ser Gly Asp Thr Tyr Tyr Ser Glu Lys Phe Lys
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Val Ile Asn Pro Gly Ser Gly Asp Ala Tyr Tyr Ser Glu Lys Phe Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

Val Ile Asn Pro Gly Ser Gly Asp Gln Tyr Tyr Ser Glu Lys Phe Lys
1               5                   10                  15

Gly

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct

<400> SEQUENCE: 33

Asp Arg Leu Asp Tyr
```

1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Construct

<400> SEQUENCE: 34

Ala Arg Leu Asp Tyr
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asp Ala Leu Asp Tyr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asp Arg Ala Asp Tyr
1               5

<210> SEQ ID NO 37
<211> LENGTH: 11
<212> TYPE: PRT
<213> ORGANISM: Artificial Sequence
<220> FEATURE:
<223> OTHER INFORMATION: Synthetic Construct

<400> SEQUENCE: 37

His Ala Ser Gln Asp Ile Ser Ser Tyr Ile Val
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic Construct

<400> SEQUENCE: 38

His Gly Thr Asn Leu Glu Asp
1               5

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

His Gly Thr Asn Leu Glu Ser
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

His Gly Thr Asn Leu Glu Glu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

His Gly Thr Asn Leu Glu Gln
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic Construct

<400> SEQUENCE: 42

Val His Tyr Ala Gln Phe Pro Tyr Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic Construct

<400> SEQUENCE: 43

Ala His Tyr Ala Gln Phe Pro Tyr Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic Construct

<400> SEQUENCE: 44

Val Ala Tyr Ala Gln Phe Pro Tyr Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Construct

<400> SEQUENCE: 45

Val His Ala Ala Gln Phe Pro Tyr Thr
1               5

```
<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Val His Tyr Ala Ala Phe Pro Tyr Thr
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Val His Tyr Ala Gln Ala Pro Tyr Thr
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Val His Tyr Ala Gln Phe Ala Tyr Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Val His Tyr Ala Gln Phe Pro Ala Thr
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Construct

<400> SEQUENCE: 50

Asp Tyr Gly Val Leu
1               5

<210> SEQ ID NO 51
<211> LENGTH: 16
<212> TYPE: PRT
<213> ORGANISM: Artificial Sequence
<220> FEATURE:
<223> OTHER INFORMATION: Synthetic Construct

<400> SEQUENCE: 51

Met Ile Trp Ser Gly Gly Thr Thr Asp Tyr Asn Ala Ala Phe Ile Ser
1               5                   10                  15
```

```
<210> SEQ ID NO 52
<211> LENGTH: 5
<212> TYPE: PRT
<213> ORGANISM: Artificial Sequence
<220> FEATURE:
<223> OTHER INFORMATION: Synthetic Construct

<400> SEQUENCE: 52

Glu Glu Met Asp Tyr
1               5

<210> SEQ ID NO 53
<211> LENGTH: 11
<212> TYPE: PRT
<213> ORGANISM: Artificial Sequence
<220> FEATURE:
<223> OTHER INFORMATION: Synthetic Construct

<400> SEQUENCE: 53

Arg Ala Ser Gln Asp Ile Ser Asn Phe Leu Asn
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Tyr Thr Ser Arg Leu His Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic Construct

<400> SEQUENCE: 55

Gln Gln Gly Asn Thr Leu Pro Trp Thr
1               5

<210> SEQ ID NO 56
<211> LENGTH: 117
<212> TYPE: PRT
<213> ORGANISM: Artificial Sequence
<220> FEATURE:
<223> OTHER INFORMATION: Synthetic Construct

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95
```

```
Val Leu Ala Pro Arg Trp Tyr Phe Ser Val Trp Gly Gln Gly Thr Leu
                100                 105                 110

Val Thr Val Ser Ser
        115

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 58
<211> LENGTH: 117
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct
```

```
<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 60
<211> LENGTH: 117
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asn Gly Asp Ser Ser Tyr Asn Gln Lys Phe
50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 63
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 64
<211> LENGTH: 117
<212> TYPE: PRT
<213> ORGANISM: Artificial Sequence

```
<220> FEATURE:
<223> OTHER INFORMATION: Synthetic Construct

<400> SEQUENCE: 64

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 66
<211> LENGTH: 117
<212> TYPE: PRT
<213> ORGANISM: Artificial Sequence
<220> FEATURE:
<223> OTHER INFORMATION: Synthetic Construct

<400> SEQUENCE: 66

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45
```

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
                115

<210> SEQ ID NO 67
<211> LENGTH: 107
<212> TYPE: PRT
<213> ORGANISM: Artificial Sequence
<220> FEATURE:
<223> OTHER INFORMATION: Synthetic Construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
                100                 105

<210> SEQ ID NO 68
<211> LENGTH: 117
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
                115

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
            100                 105

<210> SEQ ID NO 70
<211> LENGTH: 117
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ala
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 71
<211> LENGTH: 107
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 72
<211> LENGTH: 117
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 73
<211> LENGTH: 107
<212> TYPE: PRT
<213> ORGANISM: Artificial Sequence
<220> FEATURE:
<223> OTHER INFORMATION: Synthetic Construct

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

```
Thr Phe Gly Gln Gly Thr Lys Val Glu Ile Lys
            100                 105
```

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Ala Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115
```

<210> SEQ ID NO 75
<211> LENGTH: 107
<212> TYPE: PRT
<213> ORGANISM: Artificial Sequence
<220> FEATURE:
<223> OTHER INFORMATION: Synthetic Construct

<400> SEQUENCE: 75

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 76
<211> LENGTH: 117
<212> TYPE: PRT
<213> ORGANISM: Artificial Sequence
<220> FEATURE:
<223> OTHER INFORMATION: Synthetic Construct

<400> SEQUENCE: 76

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ala Ser Tyr Asn Gln Lys Phe
    50                  55                  60

Arg Glu Arg Val Thr Ile Thr Arg Asp Thr Ser Thr Thr Ala Tyr
65                  70                  75                  80

Leu Glu Leu Ser Ser Leu Arg Ser Glu Asp Thr Ala Val Tyr Tyr Cys
            85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
            85                  90                  95

Thr Phe Gly Gln Gly Thr Lys Val Glu Ile Lys
            100                 105

<210> SEQ ID NO 78
<211> LENGTH: 117
<212> TYPE: PRT
<213> ORGANISM: Artificial Sequence
<220> FEATURE:
<223> OTHER INFORMATION: Synthetic Construct

<400> SEQUENCE: 78

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ala Ser Tyr Asn Gln Lys Phe
    50                  55                  60

Arg Glu Arg Val Thr Ile Thr Arg Asp Thr Ser Thr Ser Thr Ala Tyr
65                  70                  75                  80
```

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 79
<211> LENGTH: 107
<212> TYPE: PRT
<213> ORGANISM: Artificial Sequence
<220> FEATURE:
<223> OTHER INFORMATION: Synthetic Construct

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 80
<211> LENGTH: 117
<212> TYPE: PRT
<213> ORGANISM: Artificial Sequence
<220> FEATURE:
<223> OTHER INFORMATION: Synthetic Construct

<400> SEQUENCE: 80

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Ser Gly Asp Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 81
<211> LENGTH: 107
<212> TYPE: PRT

<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 82
<211> LENGTH: 117
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 83
<211> LENGTH: 107
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

```
Tyr Tyr Thr Ser Arg Leu Arg Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
                100                 105
```

<210> SEQ ID NO 84
<211> LENGTH: 117
<212> TYPE: PRT
<213> ORGANISM: Artificial Sequence
<220> FEATURE:
<223> OTHER INFORMATION: Synthetic Construct

<400> SEQUENCE: 84

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ala
                 20                  25                  30

Tyr Met Ser Trp Val Arg Gln Ala Pro Gly Gln Gly Leu Glu Trp Ile
             35                  40                  45

Gly Asp Met Tyr Pro Asn Ala Asp Ala Ser Tyr Asn Gln Lys Phe
         50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
                100                 105                 110

Val Thr Val Ser Ser
            115
```

<210> SEQ ID NO 85
<211> LENGTH: 107
<212> TYPE: PRT
<213> ORGANISM: Artificial Sequence
<220> FEATURE:
<223> OTHER INFORMATION: Synthetic Construct

<400> SEQUENCE: 85

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
             35                  40                  45

Tyr Tyr Thr Ser Arg Leu Arg Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
                100                 105
```

```
<210> SEQ ID NO 86
<211> LENGTH: 117
<212> TYPE: PRT
<213> ORGANISM: Artificial Sequence
<220> FEATURE:
<223> OTHER INFORMATION: Synthetic Construct

<400> SEQUENCE: 86
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

```
<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Ala
                85                  90                  95

Thr Phe Gly Gln Gly Thr Lys Val Glu Ile Lys
            100                 105

```
<210> SEQ ID NO 88
<211> LENGTH: 117
<212> TYPE: PRT
<213> ORGANISM: Artificial Sequence
<220> FEATURE:
<223> OTHER INFORMATION: Synthetic Construct

<400> SEQUENCE: 88
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

```
Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
               100                 105                 110

Val Thr Val Ser Ser
            115

<210> SEQ ID NO 89
<211> LENGTH: 107
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Ala Pro Pro
                85                  90                  95

Thr Phe Gly Gln Gly Thr Lys Val Glu Ile Lys
               100                 105

<210> SEQ ID NO 90
<211> LENGTH: 117
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
```

Val Thr Val Ser Ser
        115

<210> SEQ ID NO 91
<211> LENGTH: 107
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Pro
                85                  90                  95

Thr Phe Gly Gln Gly Thr Lys Val Glu Ile Lys
            100                 105

<210> SEQ ID NO 92
<211> LENGTH: 117
<212> TYPE: PRT
<213> ORGANISM: Artificial Sequence
<220> FEATURE:
<223> OTHER INFORMATION: Synthetic Construct

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 93
<211> LENGTH: 107
<212> TYPE: PRT
<213> ORGANISM: Artificial Sequence
<220> FEATURE:
<223> OTHER INFORMATION: Synthetic Construct

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Gly His Ala Leu Pro Pro
                85                  90                  95

Thr Phe Gly Gln Gly Thr Lys Val Glu Ile Lys
            100                 105

<210> SEQ ID NO 94
<211> LENGTH: 117
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65              70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 95
<211> LENGTH: 107
<212> TYPE: PRT
<213> ORGANISM: Artificial Sequence
<220> FEATURE:
<223> OTHER INFORMATION: Synthetic Construct

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro

Glu Asp Phe Ala Thr Tyr Tyr Cys Gln Gln Ala His Thr Leu Pro Pro
65                  70                  75                  80

Thr Phe Gly Gln Gly Thr Lys Val Glu Ile Lys
                85                  90                  95

100                 105

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct

<400> SEQUENCE: 96

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 97
<211> LENGTH: 107
<212> TYPE: PRT
<213> ORGANISM: Artificial Sequence
<220> FEATURE:
<223> OTHER INFORMATION: Synthetic Construct

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Ala Pro
                85                  90                  95

Thr Phe Gly Gln Gly Thr Lys Val Glu Ile Lys
            100                 105

<210> SEQ ID NO 98
<211> LENGTH: 117
<212> TYPE: PRT
<213> ORGANISM: Artificial Sequence
<220> FEATURE:

<223> OTHER INFORMATION: Synthetic Construct

<400> SEQUENCE: 98

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 99
<211> LENGTH: 107
<212> TYPE: PRT
<213> ORGANISM: Artificial Sequence
<220> FEATURE:
<223> OTHER INFORMATION: Synthetic Construct

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly His Thr Leu Pro Pro
                85                  90                  95

Thr Phe Gly Gln Gly Thr Lys Val Glu Ile Lys
            100                 105

<210> SEQ ID NO 100
<211> LENGTH: 117
<212> TYPE: PRT
<213> ORGANISM: Artificial Sequence
<220> FEATURE:
<223> OTHER INFORMATION: Synthetic Construct

<400> SEQUENCE: 100

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe

```
                    50                  55                  60
Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                    85                  90                  95

Val Leu Ala Pro Arg Trp Tyr Phe Ser Ala Trp Gly Gln Gly Thr Leu
                100                 105                 110

Val Thr Val Ser Ser
            115

<210> SEQ ID NO 101
<211> LENGTH: 107
<212> TYPE: PRT
<213> ORGANISM: Artificial Sequence
<220> FEATURE:
<223> OTHER INFORMATION: Synthetic Construct

<400> SEQUENCE: 101

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 102
<211> LENGTH: 117
<212> TYPE: PRT
<213> ORGANISM: Artificial Sequence
<220> FEATURE:
<223> OTHER INFORMATION: Synthetic Construct

<400> SEQUENCE: 102

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
 50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Ala Ser Val Trp Gly Gln Gly Thr Leu
                100                 105                 110

Val Thr Val Ser Ser
            115
```

<210> SEQ ID NO 103
<211> LENGTH: 107
<212> TYPE: PRT
<213> ORGANISM: Artificial Sequence
<220> FEATURE:
<223> OTHER INFORMATION: Synthetic Construct

<400> SEQUENCE: 103

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

<210> SEQ ID NO 104
<211> LENGTH: 117
<212> TYPE: PRT
<213> ORGANISM: Artificial Sequence
<220> FEATURE:
<223> OTHER INFORMATION: Synthetic Construct

<400> SEQUENCE: 104

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Ala Phe Ser Val Trp Gly Gln Gly Thr Leu
            100                 105                 110

Val Thr Val Ser Ser
            115
```

<210> SEQ ID NO 105
<211> LENGTH: 107
<212> TYPE: PRT
<213> ORGANISM: Artificial Sequence
<220> FEATURE:
<223> OTHER INFORMATION: Synthetic Construct

<400> SEQUENCE: 105

```
Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Ile Ser Asn Tyr
```

```
                20                  25                  30
Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
                100                 105

<210> SEQ ID NO 106
<211> LENGTH: 117
<212> TYPE: PRT
<213> ORGANISM: Artificial Sequence
<220> FEATURE:
<223> OTHER INFORMATION: Synthetic Construct

<400> SEQUENCE: 106

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Ala Trp Tyr Phe Ser Val Trp Gly Gln Gly Thr Leu
                100                 105                 110

Val Thr Val Ser Ser
            115

<210> SEQ ID NO 107
<211> LENGTH: 107
<212> TYPE: PRT
<213> ORGANISM: Artificial Sequence
<220> FEATURE:
<223> OTHER INFORMATION: Synthetic Construct

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95
```

```
Thr Phe Gly Gln Gly Thr Lys Val Glu Ile Lys
        100                 105
```

<210> SEQ ID NO 108
<211> LENGTH: 117
<212> TYPE: PRT
<213> ORGANISM: Artificial Sequence
<220> FEATURE:
<223> OTHER INFORMATION: Synthetic Construct

<400> SEQUENCE: 108

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ala Val Trp Gly Gln Gly Thr Leu
            100                 105                 110

Val Thr Val Ser Ser
        115
```

<210> SEQ ID NO 109
<211> LENGTH: 107
<212> TYPE: PRT
<213> ORGANISM: Artificial Sequence
<220> FEATURE:
<223> OTHER INFORMATION: Synthetic Construct

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
        100                 105
```

<210> SEQ ID NO 110
<211> LENGTH: 117
<212> TYPE: PRT
<213> ORGANISM: Artificial Sequence
<220> FEATURE:
<223> OTHER INFORMATION: Synthetic Construct

<400> SEQUENCE: 110

```
Glu Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Ala Tyr Phe Ser Val Trp Gly Gln Gly Thr Leu
                100                 105                 110

Val Thr Val Ser Ser
            115

<210> SEQ ID NO 111
<211> LENGTH: 107
<212> TYPE: PRT
<213> ORGANISM: Artificial Sequence
<220> FEATURE:
<223> OTHER INFORMATION: Synthetic Construct

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 112
<211> LENGTH: 117
<212> TYPE: PRT
<213> ORGANISM: Artificial Sequence
<220> FEATURE:
<223> OTHER INFORMATION: Synthetic Construct

<400> SEQUENCE: 112

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80
```

-continued

Leu Glu Leu Ser Ser Leu Arg Ser Glu Asp Thr Ala Val Tyr Tyr Cys
                85                  90                  95

Val Leu Ala Ala Arg Trp Tyr Phe Ser Val Trp Gly Gln Gly Thr Leu
            100                 105                 110

Val Thr Val Ser Ser
            115

<210> SEQ ID NO 113
<211> LENGTH: 107
<212> TYPE: PRT
<213> ORGANISM: Artificial Sequence
<220> FEATURE:
<223> OTHER INFORMATION: Synthetic Construct

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 114
<211> LENGTH: 117
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Leu Ala Pro Arg Trp Tyr Phe Ser Val Trp Gly Gln Gly Thr Leu
            100                 105                 110

Val Thr Val Ser Ser
            115

<210> SEQ ID NO 115
<211> LENGTH: 107
<212> TYPE: PRT
<213> ORGANISM: Artificial Sequence

```
<220> FEATURE:
<223> OTHER INFORMATION: Synthetic Construct

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 116
<211> LENGTH: 117
<212> TYPE: PRT
<213> ORGANISM: Artificial Sequence
<220> FEATURE:
<223> OTHER INFORMATION: Synthetic Construct

<400> SEQUENCE: 116

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Ala Ala Pro Arg Trp Tyr Phe Ser Val Trp Gly Gln Gly Thr Leu
            100                 105                 110

Val Thr Val Ser Ser
        115

<210> SEQ ID NO 117
<211> LENGTH: 107
<212> TYPE: PRT
<213> ORGANISM: Artificial Sequence
<220> FEATURE:
<223> OTHER INFORMATION: Synthetic Construct

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45
```

```
Tyr Tyr Thr Ser Arg Leu Arg Ser Gly Val Pro Ser Arg Phe Ser Gly
    50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Gly His Thr Leu Pro Pro
                 85                  90                  95
Thr Phe Gly Gln Gly Thr Lys Val Glu Ile Lys
                100                 105

<210> SEQ ID NO 118
<211> LENGTH: 114
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Gln Ser Gly Ala Glu Val Lys Lys Pro Gly Ala
  1               5                  10                  15
Ser Val Lys Val Ser Cys Lys Ala Ser Gly Tyr Ala Phe Thr Asn Tyr
                 20                  25                  30
Leu Ile Glu Trp Val Arg Gln Ala Pro Gly Gln Gly Leu Glu Trp Ile
             35                  40                  45
Gly Val Ile Asn Pro Gly Ser Gly Asp Thr Tyr Tyr Ser Glu Lys Phe
 50                  55                  60
Lys Gly Arg Val Thr Ile Thr Arg Asp Thr Ser Thr Ser Thr Ala Tyr
 65                  70                  75                  80
Leu Glu Leu Ser Ser Leu Arg Ser Glu Asp Thr Ala Val Tyr Tyr Cys
                 85                  90                  95
Ala Arg Asp Arg Leu Asp Tyr Trp Gly Gln Gly Thr Leu Val Thr Val
                100                 105                 110
Ser Ser

<210> SEQ ID NO 119
<211> LENGTH: 107
<212> TYPE: PRT
<213> ORGANISM: Artificial Sequence
<220> FEATURE:
<223> OTHER INFORMATION: Synthetic Construct

<400> SEQUENCE: 119

Asp Ile Gln Met Thr Gln Ser Pro Ser Ser Leu Ser Ala Ser Val Gly
  1               5                  10                  15
Asp Arg Val Thr Ile Thr Cys His Ala Ser Gln Asp Ile Ser Ser Tyr
                 20                  25                  30
Ile Val Trp Tyr Gln Gln Lys Pro Gly Lys Ala Pro Lys Leu Leu Ile
             35                  40                  45
Tyr His Gly Thr Asn Leu Glu Asp Gly Val Pro Ser Arg Phe Ser Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Val His Tyr Ala Gln Phe Pro Tyr
                 85                  90                  95
Thr Phe Gly Gln Gly Thr Lys Val Glu Ile Lys
                100                 105

<210> SEQ ID NO 120
<211> LENGTH: 114
```

```
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 121
<211> LENGTH: 107
<212> TYPE: PRT
<213> ORGANISM: Artificial Sequence
<220> FEATURE:
<223> OTHER INFORMATION: Synthetic Construct

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 122
<211> LENGTH: 114
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45
```

```
Gly Val Ile Asn Pro Gly Ser Gly Asp Thr Tyr Tyr Ser Glu Lys Phe
            50                  55                  60

Lys Gly Arg Val Thr Leu Thr Ala Asp Thr Ser Ser Thr Ala Tyr
 65              70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 123
<211> LENGTH: 107
<212> TYPE: PRT
<213> ORGANISM: Artificial Sequence
<220> FEATURE:
<223> OTHER INFORMATION: Synthetic Construct

<400> SEQUENCE: 123

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ala Pro Lys Leu Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 124
<211> LENGTH: 114
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Ile Thr Ala Asp Thr Ser Ser Thr Ala Tyr
 65                 70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 125
<211> LENGTH: 107
<212> TYPE: PRT
<213> ORGANISM: Artificial Sequence
<220> FEATURE:
<223> OTHER INFORMATION: Synthetic Construct

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 126
<211> LENGTH: 114
<212> TYPE: PRT
<213> ORGANISM: Artificial Sequence
<220> FEATURE:
<223> OTHER INFORMATION: Synthetic Construct

<400> SEQUENCE: 126

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 127
<211> LENGTH: 107
<212> TYPE: PRT
<213> ORGANISM: Artificial Sequence
<220> FEATURE:
<223> OTHER INFORMATION: Synthetic Construct

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

```
Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 128
<211> LENGTH: 114
<212> TYPE: PRT
<213> ORGANISM: Artificial Sequence
<220> FEATURE:
<223> OTHER INFORMATION: Synthetic Construct

<400> SEQUENCE: 128

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 129
<211> LENGTH: 107
<212> TYPE: PRT
<213> ORGANISM: Artificial Sequence
<220> FEATURE:
<223> OTHER INFORMATION: Synthetic Construct

<400> SEQUENCE: 129

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 130
<211> LENGTH: 114
<212> TYPE: PRT
<213> ORGANISM: Artificial Sequence
<220> FEATURE:
<223> OTHER INFORMATION: Synthetic Construct

<400> SEQUENCE: 130

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser
```

<210> SEQ ID NO 131
<211> LENGTH: 107
<212> TYPE: PRT
<213> ORGANISM: Artificial Sequence
<220> FEATURE:
<223> OTHER INFORMATION: Synthetic Construct

<400> SEQUENCE: 131

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105
```

<210> SEQ ID NO 132
<211> LENGTH: 114
<212> TYPE: PRT
<213> ORGANISM: Artificial Sequence
<220> FEATURE:
<223> OTHER INFORMATION: Synthetic Construct

<400> SEQUENCE: 132

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
```

```
                    20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 133
<211> LENGTH: 107
<212> TYPE: PRT
<213> ORGANISM: Artificial Sequence
<220> FEATURE:
<223> OTHER INFORMATION: Synthetic Construct

<400> SEQUENCE: 133

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Gln Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105
```

<210> SEQ ID NO 134
<211> LENGTH: 114
<212> TYPE: PRT
<213> ORGANISM: Artificial Sequence
<220> FEATURE:
<223> OTHER INFORMATION: Synthetic Construct

<400> SEQUENCE: 134

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Ile Thr Ala Asp Thr Ser Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
```

Ser Ser

<210> SEQ ID NO 135
<211> LENGTH: 107
<212> TYPE: PRT
<213> ORGANISM: Artificial Sequence
<220> FEATURE:
<223> OTHER INFORMATION: Synthetic Construct

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Ala Asp Tyr Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 136
<211> LENGTH: 114
<212> TYPE: PRT
<213> ORGANISM: Artificial Sequence
<220> FEATURE:
<223> OTHER INFORMATION: Synthetic Construct

<400> SEQUENCE: 136

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 137
<211> LENGTH: 107
<212> TYPE: PRT
<213> ORGANISM: Artificial Sequence
<220> FEATURE:
<223> OTHER INFORMATION: Synthetic Construct

<400> SEQUENCE: 137

Asp Ile Gln Met Thr Gln Ser Pro Ser Ser Leu Ser Ala Ser Val Gly

-continued

```
                1               5                  10                 15
Asp Arg Val Thr Ile Thr Cys His Ala Ser Gln Asp Ile Ser Ser Tyr
                20                 25                 30

Ile Val Trp Tyr Gln Gln Lys Pro Gly Lys Ser Phe Lys Gly Leu Ile
        35                 40                 45

Tyr His Gly Thr Asn Leu Glu Asp Gly Val Pro Ser Arg Phe Ser Gly
    50                 55                 60

Ser Gly Ser Gly Ala Asp Tyr Thr Leu Thr Ile Ser Ser Leu Gln Pro
65                 70                 75                 80

Glu Asp Phe Ala Thr Tyr Tyr Cys Val His Tyr Ala Gln Phe Pro Tyr
                85                 90                 95

Thr Phe Gly Gln Gly Thr Lys Val Glu Ile Lys
                100                105
```

<210> SEQ ID NO 138
<211> LENGTH: 114
<212> TYPE: PRT
<213> ORGANISM: Artificial Sequence
<220> FEATURE:
<223> OTHER INFORMATION: Synthetic Construct

<400> SEQUENCE: 138

```
Glu Val Gln Leu Val Gln Ser Gly Ala Glu Val Lys Lys Pro Gly Ala
1               5                  10                 15

Ser Val Lys Val Ser Cys Lys Ala Ser Gly Tyr Ala Phe Thr Asn Tyr
                20                 25                 30

Leu Ile Glu Trp Val Arg Gln Ala Pro Gly Gln Gly Leu Glu Trp Ile
        35                 40                 45

Gly Val Ile Asn Pro Gly Ser Gly Asp Thr Tyr Tyr Ser Glu Lys Phe
    50                 55                 60

Lys Gly Arg Val Thr Leu Thr Arg Asp Thr Ser Thr Ser Thr Ala Tyr
65                 70                 75                 80

Leu Glu Leu Ser Ser Leu Arg Ser Glu Asp Thr Ala Val Tyr Tyr Cys
                85                 90                 95

Ala Arg Asp Arg Leu Asp Tyr Trp Gly Gln Gly Thr Leu Val Thr Val
                100                105                110

Ser Ser
```

<210> SEQ ID NO 139
<211> LENGTH: 107
<212> TYPE: PRT
<213> ORGANISM: Artificial Sequence
<220> FEATURE:
<223> OTHER INFORMATION: Synthetic Construct

<400> SEQUENCE: 139

```
Asp Ile Gln Met Thr Gln Ser Pro Ser Ser Leu Ser Ala Ser Val Gly
1               5                  10                 15

Asp Arg Val Thr Ile Thr Cys His Ala Ser Gln Asp Ile Ser Ser Tyr
                20                 25                 30

Ile Val Trp Tyr Gln Gln Lys Pro Gly Lys Ser Phe Lys Gly Leu Ile
        35                 40                 45

Tyr His Gly Thr Asn Leu Glu Asp Gly Val Pro Ser Arg Phe Ser Gly
    50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Val His Tyr Ala Gln Phe Pro Tyr
```

```
                    85                  90                  95

Thr Phe Gly Gln Gly Thr Lys Val Glu Ile Lys
                100                 105

<210> SEQ ID NO 140
<211> LENGTH: 114
<212> TYPE: PRT
<213> ORGANISM: Artificial Sequence
<220> FEATURE:
<223> OTHER INFORMATION: Synthetic Construct

<400> SEQUENCE: 140

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser

<210> SEQ ID NO 141
<211> LENGTH: 107
<212> TYPE: PRT
<213> ORGANISM: Artificial Sequence
<220> FEATURE:
<223> OTHER INFORMATION: Synthetic Construct

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Pro Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
                100                 105

<210> SEQ ID NO 142
<211> LENGTH: 114
<212> TYPE: PRT
<213> ORGANISM: Artificial Sequence
<220> FEATURE:
<223> OTHER INFORMATION: Synthetic Construct

<400> SEQUENCE: 142
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
50                  55                  60

Lys Gly Arg Val Thr Leu Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser
```

<210> SEQ ID NO 143
<211> LENGTH: 107
<212> TYPE: PRT
<213> ORGANISM: Artificial Sequence
<220> FEATURE:
<223> OTHER INFORMATION: Synthetic Construct

<400> SEQUENCE: 143

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Phe Lys Leu Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105
```

<210> SEQ ID NO 144
<211> LENGTH: 114
<212> TYPE: PRT
<213> ORGANISM: Artificial Sequence
<220> FEATURE:
<223> OTHER INFORMATION: Synthetic Construct

<400> SEQUENCE: 144

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Arg Asp Thr Ser Thr Ser Thr Ala Tyr
65                  70                  75                  80
```

```
Leu Glu Leu Ser Ser Leu Arg Ser Glu Asp Thr Ala Val Tyr Tyr Cys
            85                  90                  95

Ala Arg Asp Arg Leu Asp Tyr Trp Gly Gln Gly Thr Leu Val Thr Val
            100                 105                 110

Ser Ser

<210> SEQ ID NO 145
<211> LENGTH: 107
<212> TYPE: PRT
<213> ORGANISM: Artificial Sequence
<220> FEATURE:
<223> OTHER INFORMATION: Synthetic Construct

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ala Pro Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 146
<211> LENGTH: 114
<212> TYPE: PRT
<213> ORGANISM: Artificial Sequence
<220> FEATURE:
<223> OTHER INFORMATION: Synthetic Construct

<400> SEQUENCE: 146

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 147
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala His Tyr Ala Gln Phe Pro Tyr
                85                  90                  95

Thr Phe Gly Gln Gly Thr Lys Val Glu Ile Lys
            100                 105

<210> SEQ ID NO 148
<211> LENGTH: 114
<212> TYPE: PRT
<213> ORGANISM: Artificial Sequence
<220> FEATURE:
<223> OTHER INFORMATION: Synthetic Construct

<400> SEQUENCE: 148

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 149
<211> LENGTH: 107
<212> TYPE: PRT
<213> ORGANISM: Artificial Sequence
<220> FEATURE:
<223> OTHER INFORMATION: Synthetic Construct

<400> SEQUENCE: 149

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val Ala Tyr Ala Gln Phe Pro Tyr
                85                  90                  95

Thr Phe Gly Gln Gly Thr Lys Val Glu Ile Lys
            100                 105

<210> SEQ ID NO 150
<211> LENGTH: 114
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
        50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Ala Ala Gln Phe Pro Tyr
                85                  90                  95

Thr Phe Gly Gln Gly Thr Lys Val Glu Ile Lys
            100                 105

<210> SEQ ID NO 152
<211> LENGTH: 114
<212> TYPE: PRT
<213> ORGANISM: Artificial Sequence
<220> FEATURE:

<223> OTHER INFORMATION: Synthetic Construct

<400> SEQUENCE: 152

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
                100                 105                 110

Ser Ser
```

<210> SEQ ID NO 153
<211> LENGTH: 107
<212> TYPE: PRT
<213> ORGANISM: Artificial Sequence
<220> FEATURE:
<223> OTHER INFORMATION: Synthetic Construct

<400> SEQUENCE: 153

```
Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Ala Phe Pro Tyr
                85                  90                  95

Thr Phe Gly Gln Gly Thr Lys Val Glu Ile Lys
                100                 105
```

<210> SEQ ID NO 154
<211> LENGTH: 114
<212> TYPE: PRT
<213> ORGANISM: Artificial Sequence
<220> FEATURE:
<223> OTHER INFORMATION: Synthetic Construct

<400> SEQUENCE: 154

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60
```

```
Lys Gly Arg Val Thr Leu Thr Ala Asp Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser

<210> SEQ ID NO 155
<211> LENGTH: 107
<212> TYPE: PRT
<213> ORGANISM: Artificial Sequence
<220> FEATURE:
<223> OTHER INFORMATION: Synthetic Construct

<400> SEQUENCE: 155

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
             20                  25                  30

Ile Val Trp Tyr Gln Gln Lys Pro Gly Lys Ser Phe Lys Gly Leu Ile
         35                  40                  45

Tyr His Gly Thr Asn Leu Glu Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Ala Pro Tyr
                 85                  90                  95

Thr Phe Gly Gln Gly Thr Lys Val Glu Ile Lys
            100                 105

<210> SEQ ID NO 156
<211> LENGTH: 114
<212> TYPE: PRT
<213> ORGANISM: Artificial Sequence
<220> FEATURE:
<223> OTHER INFORMATION: Synthetic Construct

<400> SEQUENCE: 156

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Ile
         35                  40                  45

Gly Val Ile Asn Pro Gly Ser Gly Asp Thr Tyr Tyr Ser Glu Lys Phe
 50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Leu Asp Tyr Trp Gly Gln Gly Thr Leu Val Thr Val
            100                 105                 110

Ser Ser

<210> SEQ ID NO 157
<211> LENGTH: 107
```

```
<212> TYPE: PRT
<213> ORGANISM: Artificial Sequence
<220> FEATURE:
<223> OTHER INFORMATION: Synthetic Construct

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Ala Tyr
                85                  90                  95

Thr Phe Gly Gln Gly Thr Lys Val Glu Ile Lys
            100                 105

<210> SEQ ID NO 158
<211> LENGTH: 114
<212> TYPE: PRT
<213> ORGANISM: Artificial Sequence
<220> FEATURE:
<223> OTHER INFORMATION: Synthetic Construct

<400> SEQUENCE: 158

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 159
<211> LENGTH: 107
<212> TYPE: PRT
<213> ORGANISM: Artificial Sequence
<220> FEATURE:
<223> OTHER INFORMATION: Synthetic Construct

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45
```

Tyr His Gly Thr Asn Leu Glu Asp Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Ala
                 85                  90                  95

Thr Phe Gly Gln Gly Thr Lys Val Glu Ile Lys
                100                 105

<210> SEQ ID NO 160
<211> LENGTH: 114
<212> TYPE: PRT
<213> ORGANISM: Artificial Sequence
<220> FEATURE:
<223> OTHER INFORMATION: Synthetic Construct

<400> SEQUENCE: 160

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
                20                  25                  30

Leu Ile Glu Trp Val Arg Gln Ala Pro Gly Gln Gly Leu Glu Trp Ile
            35                  40                  45

Gly Val Ile Asn Pro Gly Ser Gly Asp Thr Tyr Tyr Ser Glu Lys Phe
     50                  55                  60

Lys Gly Arg Val Thr Leu Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Ala Arg Leu Asp Tyr Trp Gly Gln Gly Thr Leu Val Thr Val
                100                 105                 110

Ser Ser

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
            35                  40                  45

Tyr His Gly Thr Asn Leu Glu Asp Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
                100                 105

<210> SEQ ID NO 162

```
<211> LENGTH: 114
<212> TYPE: PRT
<213> ORGANISM: Artificial Sequence
<220> FEATURE:
<223> OTHER INFORMATION: Synthetic Construct

<400> SEQUENCE: 162
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Thr Tyr Tyr Ser Glu Lys Phe
    50                  55                  60

Lys Gly Arg Val Thr Leu Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Ala Leu Asp Tyr Trp Gly Gln Gly Thr Leu Val Thr Val
            100                 105                 110

Ser Ser

```
<210> SEQ ID NO 163
<211> LENGTH: 107
<212> TYPE: PRT
<213> ORGANISM: Artificial Sequence
<220> FEATURE:
<223> OTHER INFORMATION: Synthetic Construct

<400> SEQUENCE: 163
```

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

```
<210> SEQ ID NO 164
<211> LENGTH: 114
<212> TYPE: PRT
<213> ORGANISM: Artificial Sequence
<220> FEATURE:
<223> OTHER INFORMATION: Synthetic Construct

<400> SEQUENCE: 164
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile

```
            35                  40                  45
Gly Val Ile Asn Pro Gly Ser Gly Asp Thr Tyr Tyr Ser Glu Lys Phe
 50                  55                  60

Lys Gly Arg Val Thr Leu Thr Ala Asp Thr Ser Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Asp Arg Ala Asp Tyr Trp Gly Gln Gly Thr Leu Val Thr Val
                100                 105                 110

Ser Ser

<210> SEQ ID NO 165
<211> LENGTH: 107
<212> TYPE: PRT
<213> ORGANISM: Artificial Sequence
<220> FEATURE:
<223> OTHER INFORMATION: Synthetic Construct

<400> SEQUENCE: 165

Asp Ile Gln Met Thr Gln Ser Pro Ser Ser Leu Ser Ala Ser Val Gly
 1               5                  10                  15

Asp Arg Val Thr Ile Thr Cys His Ala Ser Gln Asp Ile Ser Ser Tyr
                20                  25                  30

Ile Val Trp Tyr Gln Gln Lys Pro Gly Lys Ser Phe Lys Gly Leu Ile
             35                  40                  45

Tyr His Gly Thr Asn Leu Glu Asp Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
                 85                  90                  95

Thr Phe Gly Gln Gly Thr Lys Val Glu Ile Lys
                100                 105

<210> SEQ ID NO 166
<211> LENGTH: 113
<212> TYPE: PRT
<213> ORGANISM: Artificial Sequence
<220> FEATURE:
<223> OTHER INFORMATION: Synthetic Construct

<400> SEQUENCE: 166

Glu Val Gln Leu Val Glu Ser Gly Pro Gly Leu Val Lys Pro Ser Glu
 1               5                  10                  15

Thr Leu Ser Leu Thr Cys Thr Val Ser Gly Phe Ser Leu Thr Asp Tyr
                20                  25                  30

Gly Val Leu Trp Ile Arg Gln Pro Pro Gly Lys Gly Leu Glu Trp Ile
             35                  40                  45

Gly Met Ile Trp Ser Gly Gly Thr Thr Asp Tyr Asn Ala Ala Phe Ile
         50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Val
                 85                  90                  95

Arg Glu Glu Met Asp Tyr Trp Gly Gln Gly Thr Leu Val Thr Val Ser
                100                 105                 110

Ser
```

<210> SEQ ID NO 167
<211> LENGTH: 107
<212> TYPE: PRT
<213> ORGANISM: Artificial Sequence
<220> FEATURE:
<223> OTHER INFORMATION: Synthetic Construct

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 168
<211> LENGTH: 113
<212> TYPE: PRT
<213> ORGANISM: Artificial Sequence
<220> FEATURE:
<223> OTHER INFORMATION: Synthetic Construct

<400> SEQUENCE: 168

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Ile Arg Gln Pro Pro Gly Lys Gly Leu Glu Trp Ile
        35                  40                  45

Gly Met Ile Trp Ser Gly Gly Thr Thr Asp Tyr Asn Ala Ala Phe Ile
50                  55                  60

Ser Arg Val Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Glu Glu Met Asp Tyr Trp Gly Gln Gly Thr Leu Val Thr Val Ser
            100                 105                 110

Ser

<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe

```
                    20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
            100                 105

<210> SEQ ID NO 170
<211> LENGTH: 113
<212> TYPE: PRT
<213> ORGANISM: Artificial Sequence
<220> FEATURE:
<223> OTHER INFORMATION: Synthetic Construct

<400> SEQUENCE: 170

Glu Val Gln Leu Val Glu Ser Gly Pro Gly Leu Val Lys Pro Ser Glu
1               5                   10                  15

Thr Leu Ser Leu Thr Cys Thr Val Ser Gly Phe Ser Leu Thr Asp Tyr
            20                  25                  30

Gly Val Leu Trp Val Arg Gln Pro Pro Gly Lys Gly Leu Glu Trp Leu
        35                  40                  45

Gly Met Ile Trp Ser Gly Gly Thr Thr Asp Tyr Asn Ala Ala Phe Ile
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Val
                85                  90                  95

Arg Glu Glu Met Asp Tyr Trp Gly Gln Gly Thr Leu Val Thr Val Ser
            100                 105                 110

Ser

<210> SEQ ID NO 171
<211> LENGTH: 107
<212> TYPE: PRT
<213> ORGANISM: Artificial Sequence
<220> FEATURE:
<223> OTHER INFORMATION: Synthetic Construct

<400> SEQUENCE: 171

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Phe
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys
```

<210> SEQ ID NO 172
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2
<223> OTHER INFORMATION: Xaa = Ser or Ala

<400> SEQUENCE: 172

Xaa Xaa Tyr Met Ser
1               5

<210> SEQ ID NO 173
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asn or Ser
<220> FEATURE:
<221> NAME/KEY: VARIANT
<222> LOCATION: 7
<223> OTHER INFORMATION: Xaa = Ala or Gly
<220> FEATURE:
<221> NAME/KEY: VARIANT
<222> LOCATION: 8
<223> OTHER INFORMATION: Xaa = Asp or Ser
<220> FEATURE:
<221> NAME/KEY: VARIANT
<222> LOCATION: 9
<223> OTHER INFORMATION: Xaa = Ala or Ser

<400> SEQUENCE: 173

Asp Met Tyr Pro Asp Xaa Xaa Xaa Xaa Ser Tyr Asn Gln Lys Phe Arg
1               5                   10                  15

Glu

<210> SEQ ID NO 174
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Tyr or Ala
<220> FEATURE:
<221> NAME/KEY: VARIANT
<222> LOCATION: 6
<223> OTHER INFORMATION: Xaa = Ala or Phe
<220> FEATURE:
<221> NAME/KEY: VARIANT
<222> LOCATION: 7
<223> OTHER INFORMATION: Xaa = Ser or Ala
<220> FEATURE:
<221> NAME/KEY: VARIANT
<222> LOCATION: 8
<223> OTHER INFORMATION: Xaa = Ala or Val

<400> SEQUENCE: 174

```
Ala Pro Arg Trp Xaa Xaa Xaa Xaa
1               5
```

<210> SEQ ID NO 175
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala or Gln
<220> FEATURE:
<221> NAME/KEY: VARIANT
<222> LOCATION: 3
<223> OTHER INFORMATION: Xaa = Ala or Gly
<220> FEATURE:
<221> NAME/KEY: VARIANT
<222> LOCATION: 4
<223> OTHER INFORMATION: Xaa = Ala or His
<220> FEATURE:
<221> NAME/KEY: VARIANT
<222> LOCATION: 5
<223> OTHER INFORMATION: Xaa = Ala or Thr
<220> FEATURE:
<221> NAME/KEY: VARIANT
<222> LOCATION: 6
<223> OTHER INFORMATION: Xaa = Ala or Leu
<220> FEATURE:
<221> NAME/KEY: VARIANT
<222> LOCATION: 7
<223> OTHER INFORMATION: Xaa = Ala or Pro
<220> FEATURE:
<221> NAME/KEY: VARIANT
<222> LOCATION: 8
<223> OTHER INFORMATION: Xaa = Ala or Pro

<400> SEQUENCE: 175

```
Gln Xaa Xaa Xaa Xaa Xaa Xaa Xaa Thr
1               5
```

<210> SEQ ID NO 176
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Thr, Ala or Gln

<400> SEQUENCE: 176

```
Val Ile Asn Pro Gly Ser Gly Asp Xaa Tyr Tyr Ser Glu Lys Phe Lys
1               5                   10                  15
Gly
```

<210> SEQ ID NO 177
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Ser, Glu, or Gln

<400> SEQUENCE: 177

```
His Gly Thr Asn Leu Glu Xaa
```

```
<210> SEQ ID NO 178
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Val or Ala
<220> FEATURE:
<221> NAME/KEY: VARIANT
<222> LOCATION: 2
<223> OTHER INFORMATION: Xaa = His or Ala
<220> FEATURE:
<221> NAME/KEY: VARIANT
<222> LOCATION: 9
<223> OTHER INFORMATION: Xaa = Tyr or Ala

<400> SEQUENCE: 178

Xaa Xaa Tyr Ala Gln Phe Pro Tyr Xaa
1               5

<210> SEQ ID NO 179
<211> LENGTH: 107
<212> TYPE: PRT
<213> ORGANISM: Artificial Sequence
<220> FEATURE:
<223> OTHER INFORMATION: Synthetic Construct

<400> SEQUENCE: 179

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Phe Leu Thr Ile Ser Asn Leu Glu Gln
65                  70                  75                  80

Glu Asp Val Ala Ala Tyr Phe Cys Gln Gln Gly His Thr Leu Pro Pro
                85                  90                  95

Thr Phe Gly Gly Gly Thr Lys Leu Glu Ile Lys
            100                 105

<210> SEQ ID NO 180
<211> LENGTH: 117
<212> TYPE: PRT
<213> ORGANISM: Artificial Sequence
<220> FEATURE:
<223> OTHER INFORMATION: Synthetic Construct

<400> SEQUENCE: 180

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Ser
            20                  25                  30

Tyr Met Ser Trp Val Lys Gln Ser His Gly Lys Thr Leu Glu Trp Ile
        35                  40                  45

Gly Asp Met Tyr Pro Asp Asn Gly Asp Ser Ser Tyr Asn Gln Lys Phe
    50                  55                  60
```

```
Arg Glu Lys Val Thr Leu Thr Val Asp Lys Ser Ser Thr Thr Ala Tyr
 65                  70                  75                  80

Met Glu Phe Arg Ser Leu Thr Ser Glu Asp Ser Ala Val Tyr Tyr Cys
                 85                  90                  95

Val Leu Ala Pro Arg Trp Tyr Phe Ser Val Trp Gly Thr Gly Thr Thr
                100                 105                 110

Val Thr Val Ser Ser
            115

<210> SEQ ID NO 181
<211> LENGTH: 107
<212> TYPE: PRT
<213> ORGANISM: Artificial Sequence
<220> FEATURE:
<223> OTHER INFORMATION: Synthetic Construct

<400> SEQUENCE: 181

Asp Ile Leu Met Thr Gln Ser Pro Ser Ser Met Ser Val Ser Leu Gly
 1               5                  10                  15

Asp Thr Val Ser Ile Thr Cys His Ala Ser Gln Asp Ile Ser Ser Tyr
                20                  25                  30

Ile Val Trp Leu Gln Gln Lys Pro Gly Lys Ser Phe Arg Gly Leu Ile
            35                  40                  45

Tyr His Gly Thr Asn Leu Glu Asp Gly Ile Pro Ser Arg Phe Ser Gly
     50                  55                  60

Ser Gly Ser Gly Ala Asp Tyr Ser Leu Thr Ile Ser Ser Leu Glu Ser
 65                  70                  75                  80

Glu Asp Phe Ala Asp Tyr Tyr Cys Val His Tyr Ala Gln Phe Pro Tyr
                 85                  90                  95

Thr Phe Gly Gly Gly Thr Lys Leu Glu Ile Lys
            100                 105

<210> SEQ ID NO 182
<211> LENGTH: 114
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Gln Gln Ser Gly Ala Glu Leu Val Arg Pro Gly Thr
 1               5                  10                  15

Ser Val Lys Val Ser Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
            35                  40                  45

Gly Val Ile Asn Pro Gly Ser Gly Asp Thr Tyr Tyr Ser Glu Lys Phe
     50                  55                  60

Lys Gly Lys Val Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Asp Arg Leu Asp Tyr Trp Gly Gln Gly Thr Thr Leu Thr Val
                100                 105                 110

Ser Ser

<210> SEQ ID NO 183
```

<211> LENGTH: 451
<212> TYPE: PRT
<213> ORGANISM: Artificial Sequence
<220> FEATURE:
<223> OTHER INFORMATION: Synthetic Construct

<400> SEQUENCE: 183

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Tyr Ser Gln Val His Tyr Ala Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 184
<211> LENGTH: 219
<212> TYPE: PRT
<213> ORGANISM: Artificial Sequence
<220> FEATURE:
<223> OTHER INFORMATION: Synthetic Construct

<400> SEQUENCE: 184

Asp Ile Val Met Thr Gln Ser Pro Asp Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ala Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Tyr Asn His Pro Thr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 185
<211> LENGTH: 219
<212> TYPE: PRT
<213> ORGANISM: Artificial Sequence
<220> FEATURE:
<223> OTHER INFORMATION: Synthetic Construct

<400> SEQUENCE: 185

Asp Ile Gln Met Thr Gln Ser Pro Asp Ser Leu Pro Val Thr Pro Gly

```
  1               5                  10                 15
Glu Pro Ala Ser Ile Ser Cys Arg Ser Ser Gln Ser Leu Leu His Ser
                 20                  25                 30

Asn Gly Tyr Asn Tyr Leu Asp Trp Tyr Leu Gln Lys Ala Gly Gln Ser
             35                  40                 45

Pro Gln Leu Leu Ile Tyr Leu Gly Ser Asn Arg Ala Ser Gly Val Pro
         50                  55                 60

Asp Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Gln Gln Tyr
                 85                  90                 95

Tyr Asn His Pro Thr Thr Phe Gly Gln Gly Thr Lys Leu Glu Ile Lys
             100                 105                110

Arg Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
     130                 135                 140

Tyr Pro Arg Glu Ala Lys Val Gln Trp Lys Val Asp Asn Ala Leu Gln
145                 150                 155                160

Ser Gly Asn Ser Gln Glu Ser Val Thr Glu Gln Asp Ser Lys Asp Ser
                 165                 170                175

Thr Tyr Ser Leu Ser Ser Thr Leu Thr Leu Ser Lys Ala Asp Tyr Glu
             180                 185                 190

Lys His Lys Val Tyr Ala Cys Glu Val Thr His Gln Gly Leu Ser Ser
         195                 200                 205

Pro Val Thr Lys Ser Phe Asn Arg Gly Glu Cys
     210                 215

<210> SEQ ID NO 186
<211> LENGTH: 450
<212> TYPE: PRT
<213> ORGANISM: Artificial Sequence
<220> FEATURE:
<223> OTHER INFORMATION: Synthetic Construct

<400> SEQUENCE: 186

Glu Val Gln Leu Val Glu Ser Gly Gly Gly Leu Val His Pro Gly Gly
1               5                  10                 15

Ser Leu Arg Leu Ser Cys Ala Gly Ser Gly Phe Thr Phe Ser Ser Tyr
                 20                  25                 30

Ala Met His Trp Val Arg Gln Ala Pro Gly Lys Gly Leu Glu Trp Val
             35                  40                 45

Ser Ala Ile Gly Thr Gly Gly Thr Tyr Tyr Ala Asp Ser Val Met
         50                  55                 60

Gly Arg Phe Thr Ile Ser Arg Asp Asn Ser Lys Asn Thr Leu Tyr Leu
65                  70                  75                 80

Gln Met Asn Ser Leu Arg Ala Glu Asp Thr Ala Val Tyr Tyr Cys Ala
                 85                  90                 95

Arg Tyr Asp Asn Val Met Gly Leu Tyr Trp Phe Asp Tyr Trp Gly Gln
             100                 105                110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
```

```
               145                 150                 155                 160
        Trp Asn Ser Gly Ala Leu Thr Ser Gly Val His Thr Phe Pro Ala Val
                        165                 170                 175
        Leu Gln Ser Ser Gly Leu Tyr Ser Leu Ser Ser Val Val Thr Val Pro
                        180                 185                 190
        Ser Ser Ser Leu Gly Thr Gln Thr Tyr Ile Cys Asn Val Asn His Lys
                        195                 200                 205
        Pro Ser Asn Thr Lys Val Asp Lys Arg Val Glu Pro Lys Ser Cys Asp
                210                 215                 220
        Lys Thr His Thr Cys Pro Pro Cys Pro Ala Pro Glu Leu Leu Gly Gly
        225                 230                 235                 240
        Pro Ser Val Phe Leu Phe Pro Pro Lys Pro Lys Asp Thr Leu Met Ile
                        245                 250                 255
        Ser Arg Thr Pro Glu Val Thr Cys Val Val Val Asp Val Ser His Glu
                        260                 265                 270
        Asp Pro Glu Val Lys Phe Asn Trp Tyr Val Asp Gly Val Glu Val His
                        275                 280                 285
        Asn Ala Lys Thr Lys Pro Arg Glu Glu Gln Tyr Asn Ser Thr Tyr Arg
                290                 295                 300
        Val Val Ser Val Leu Thr Val Leu His Gln Asp Trp Leu Asn Gly Lys
        305                 310                 315                 320
        Glu Tyr Lys Cys Lys Val Ser Asn Lys Ala Leu Pro Ala Pro Ile Glu
                        325                 330                 335
        Lys Thr Ile Ser Lys Ala Lys Gly Gln Pro Arg Glu Pro Gln Val Tyr
                        340                 345                 350
        Thr Leu Pro Pro Ser Arg Glu Glu Met Thr Lys Asn Gln Val Ser Leu
                        355                 360                 365
        Thr Cys Leu Val Lys Gly Phe Tyr Pro Ser Asp Ile Ala Val Glu Trp
                        370                 375                 380
        Glu Ser Asn Gly Gln Pro Glu Asn Asn Tyr Lys Thr Thr Pro Pro Val
        385                 390                 395                 400
        Leu Asp Ser Asp Gly Ser Phe Phe Leu Tyr Ser Lys Leu Thr Val Asp
                        405                 410                 415
        Lys Ser Arg Trp Gln Gln Gly Asn Val Phe Ser Cys Ser Val Met His
                        420                 425                 430
        Glu Ala Leu His Asn His Tyr Thr Gln Lys Ser Leu Ser Leu Ser Pro
                        435                 440                 445
        Gly Lys
            450

<210> SEQ ID NO 187
<211> LENGTH: 214
<212> TYPE: PRT
<213> ORGANISM: Artificial Sequence
<220> FEATURE:
<223> OTHER INFORMATION: Synthetic Construct

<400> SEQUENCE: 187

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Ser Ser Tyr
                20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
```

```
                  50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Ala Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 188
<211> LENGTH: 118
<212> TYPE: PRT
<213> ORGANISM: Artificial Sequence
<220> FEATURE:
<223> OTHER INFORMATION: Synthetic Construct

<400> SEQUENCE: 188

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Tyr Ile Ser Ser Ser Ser Thr Ile Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Glu Ser Gly Trp Tyr Leu Phe Asp Tyr Trp Gly Gln Gly Thr
                100                 105                 110

Leu Val Thr Val Ser Ser
        115

<210> SEQ ID NO 189
<211> LENGTH: 107
<212> TYPE: PRT
<213> ORGANISM: Artificial Sequence
<220> FEATURE:
<223> OTHER INFORMATION: Synthetic Construct

<400> SEQUENCE: 189

Asp Ile Gln Met Thr Gln Ser Pro Ser Ser Leu Ser Ala Ser Val Gly
  1               5                  10                  15
```

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105

<210> SEQ ID NO 190
<211> LENGTH: 124
<212> TYPE: PRT
<213> ORGANISM: Artificial Sequence
<220> FEATURE:
<223> OTHER INFORMATION: Synthetic Construct

<400> SEQUENCE: 190

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Gln Ser Thr Ala Asp Tyr Tyr Phe Tyr Tyr Gly Met Asp
            100                 105                 110

Val Trp Gly Gln Gly Thr Thr Val Thr Val Ser Ser
        115                 120

<210> SEQ ID NO 191
<211> LENGTH: 106
<212> TYPE: PRT
<213> ORGANISM: Artificial Sequence
<220> FEATURE:
<223> OTHER INFORMATION: Synthetic Construct

<400> SEQUENCE: 191

Glu Ile Val Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Thr
                85                  90                  95

Phe Gly Gln Gly Thr Lys Val Glu Ile Lys
            100                 105

<210> SEQ ID NO 192
<211> LENGTH: 122
<212> TYPE: PRT
<213> ORGANISM: Artificial Sequence
<220> FEATURE:
<223> OTHER INFORMATION: Synthetic Construct

<400> SEQUENCE: 192

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
                20                  25                  30

Ser Met His Trp Val Arg Gln Ala Pro Gly Gln Gly Leu Lys Trp Met
            35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120

<210> SEQ ID NO 193
<211> LENGTH: 107
<212> TYPE: PRT
<213> ORGANISM: Artificial Sequence
<220> FEATURE:
<223> OTHER INFORMATION: Synthetic Construct

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 194
<211> LENGTH: 120
<212> TYPE: PRT
<213> ORGANISM: Artificial Sequence
<220> FEATURE:
<223> OTHER INFORMATION: Synthetic Construct

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110

Gly Thr Met Val Thr Val Ser Ser
            115                 120

<210> SEQ ID NO 195
<211> LENGTH: 111
<212> TYPE: PRT
<213> ORGANISM: Artificial Sequence
<220> FEATURE:
<223> OTHER INFORMATION: Synthetic Construct

<400> SEQUENCE: 195

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Val Ser Thr Ser
            20                  25                  30

Gly Tyr Ser Tyr Met His Trp Tyr Gln Gln Lys Pro Gly Gln Ala Pro
        35                  40                  45

Arg Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Glu Leu Pro Leu Thr Phe Gly Gly Gly Thr Lys Val Glu Ile Lys
            100                 105                 110

<210> SEQ ID NO 196
<211> LENGTH: 469
<212> TYPE: PRT
<213> ORGANISM: Artificial Sequence
<220> FEATURE:
<223> OTHER INFORMATION: Synthetic Construct

<400> SEQUENCE: 196

Met Tyr Leu Gly Leu Asn Tyr Val Phe Ile Val Phe Leu Leu Asn Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Ala Ala Ser Gly Phe Thr Phe
        35                  40                  45

Ser Asp Ala Trp Met Asp Trp Val Arg Gln Ser Pro Glu Lys Gly Leu
50                  55                  60

Glu Trp Val Ala Glu Ile Arg Ser Lys Ala Asn Asn His Ala Thr Tyr
65                  70                  75                  80

Tyr Ala Glu Ser Val Asn Gly Arg Phe Thr Ile Ser Arg Asp Asp Ser
                85                  90                  95

Lys Ser Ser Val Tyr Leu Gln Met Asn Ser Leu Arg Ala Glu Asp Thr
            100                 105                 110

Gly Ile Tyr Tyr Cys Thr Trp Gly Glu Val Tyr Phe Asp Tyr Trp
        115                 120                 125

Gly Gln Gly Thr Thr Leu Thr Val Ser Ser Ala Ser Thr Lys Gly Pro
130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
                195                 200                 205

Val Pro Ser Ser Ser Leu Gly Thr Gln Thr Tyr Ile Thr Cys Asn Val
            210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
            275                 280                 285

Ser His Glu Asp Pro Glu Val Lys Phe Asn Trp Tyr Val Asp Gly Val
290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
            355                 360                 365

Gln Val Tyr Thr Leu Pro Pro Ser Arg Asp Glu Leu Thr Lys Asn Gln
370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys
465

<210> SEQ ID NO 197
<211> LENGTH: 233

```
<212> TYPE: PRT
<213> ORGANISM: Artificial Sequence
<220> FEATURE:
<223> OTHER INFORMATION: Synthetic Construct

<400> SEQUENCE: 197
```

| | | | | | | | | | | | | | | | |
|---|---|---|---|---|---|---|---|---|---|---|---|---|---|---|---|
| Met | Arg | Pro | Ser | Ile | Gln | Phe | Leu | Gly | Leu | Leu | Leu | Phe | Trp | Leu | His |
| 1 | | | | 5 | | | | | 10 | | | | | 15 | |
| Gly | Ala | Gln | Cys | Asp | Ile | Gln | Met | Thr | Gln | Ser | Pro | Ser | Ser | Leu | Ser |
| | | | 20 | | | | | 25 | | | | | 30 | | |
| Ala | Ser | Leu | Gly | Gly | Lys | Val | Thr | Ile | Thr | Cys | Lys | Ser | Ser | Gln | Asp |
| | | | 35 | | | | 40 | | | | | 45 | | | |
| Ile | Asn | Lys | Tyr | Ile | Ala | Trp | Tyr | Gln | His | Lys | Pro | Gly | Lys | Gly | Pro |
| | 50 | | | | | 55 | | | | | 60 | | | | |
| Arg | Leu | Leu | Ile | His | Tyr | Thr | Ser | Thr | Leu | Gln | Pro | Gly | Ile | Pro | Ser |
| 65 | | | | | 70 | | | | | 75 | | | | | 80 |
| Arg | Phe | Ser | Gly | Ser | Gly | Ser | Gly | Arg | Asp | Tyr | Ser | Phe | Ser | Ile | Ser |
| | | | | 85 | | | | | 90 | | | | | 95 | |
| Asn | Leu | Glu | Pro | Glu | Asp | Ile | Ala | Thr | Tyr | Tyr | Cys | Leu | Gln | Tyr | Asp |
| | | | 100 | | | | | 105 | | | | | 110 | | |
| Asn | Leu | Leu | Thr | Phe | Gly | Ala | Gly | Thr | Lys | Leu | Glu | Leu | Lys | Arg | Thr |
| | | | 115 | | | | | 120 | | | | | 125 | | |
| Val | Ala | Ala | Pro | Ser | Val | Phe | Ile | Phe | Pro | Pro | Ser | Asp | Glu | Gln | Leu |
| | 130 | | | | | 135 | | | | | 140 | | | | |
| Lys | Ser | Gly | Thr | Ala | Ser | Val | Val | Cys | Leu | Leu | Asn | Asn | Phe | Tyr | Pro |
| 145 | | | | | 150 | | | | | 155 | | | | | 160 |
| Arg | Glu | Ala | Lys | Val | Gln | Trp | Lys | Val | Asp | Asn | Ala | Leu | Gln | Ser | Gly |
| | | | | 165 | | | | | 170 | | | | | 175 | |
| Asn | Ser | Gln | Glu | Ser | Val | Thr | Glu | Gln | Asp | Ser | Lys | Asp | Ser | Thr | Tyr |
| | | | 180 | | | | | 185 | | | | | 190 | | |
| Ser | Leu | Ser | Ser | Thr | Leu | Thr | Leu | Ser | Lys | Ala | Asp | Tyr | Glu | Lys | His |
| | | | 195 | | | | | 200 | | | | | 205 | | |
| Lys | Val | Tyr | Ala | Cys | Glu | Val | Thr | His | Gln | Gly | Leu | Ser | Ser | Pro | Val |
| | 210 | | | | | 215 | | | | | 220 | | | | |
| Thr | Lys | Ser | Phe | Asn | Arg | Gly | Glu | Cys | | | | | | | |
| 225 | | | | | 230 | | | | | | | | | | |

```
<210> SEQ ID NO 198
<211> LENGTH: 138
<212> TYPE: PRT
<213> ORGANISM: Artificial Sequence
<220> FEATURE:
<223> OTHER INFORMATION: Synthetic Construct

<400> SEQUENCE: 198
```

| | | | | | | | | | | | | | | | |
|---|---|---|---|---|---|---|---|---|---|---|---|---|---|---|---|
| Met | Tyr | Leu | Gly | Leu | Asn | Tyr | Val | Phe | Ile | Val | Phe | Leu | Leu | Asn | Gly |
| 1 | | | | 5 | | | | | 10 | | | | | 15 | |
| Val | Gln | Ser | Glu | Val | Lys | Leu | Glu | Glu | Ser | Gly | Gly | Gly | Leu | Val | Gln |
| | | | 20 | | | | | 25 | | | | | 30 | | |
| Pro | Gly | Gly | Ser | Met | Lys | Leu | Ser | Cys | Ala | Ala | Ser | Gly | Phe | Thr | Phe |
| | | | 35 | | | | | 40 | | | | | 45 | | |
| Ser | Asp | Ala | Trp | Met | Asp | Trp | Val | Arg | Gln | Ser | Pro | Lys | Gly | Leu |
| | 50 | | | | | 55 | | | | | 60 | | | | |
| Glu | Trp | Val | Ala | Glu | Ile | Arg | Ser | Lys | Ala | Asn | Asn | His | Ala | Thr | Tyr |
| 65 | | | | | 70 | | | | | 75 | | | | | 80 |
| Tyr | Ala | Glu | Ser | Val | Asn | Gly | Arg | Phe | Thr | Ile | Ser | Arg | Asp | Asp | Ser |
| | | | | 85 | | | | | 90 | | | | | 95 | |

```
Lys Ser Ser Val Tyr Leu Gln Met Asn Ser Leu Arg Ala Glu Asp Thr
            100                 105                 110

Gly Ile Tyr Tyr Cys Thr Trp Gly Val Phe Tyr Phe Asp Tyr Trp
            115                 120                 125

Gly Gln Gly Thr Thr Leu Thr Val Ser Ser
            130                 135

<210> SEQ ID NO 199
<211> LENGTH: 126
<212> TYPE: PRT
<213> ORGANISM: Artificial Sequence
<220> FEATURE:
<223> OTHER INFORMATION: Synthetic Construct

<400> SEQUENCE: 199

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ser Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Leu Thr Phe Gly Ala Gly Thr Lys Leu Glu Leu Lys
            115                 120                 125

<210> SEQ ID NO 200
<211> LENGTH: 119
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Ser Val Thr Val Ser Ser
            115
```

<210> SEQ ID NO 201
<211> LENGTH: 108
<212> TYPE: PRT
<213> ORGANISM: Artificial Sequence
<220> FEATURE:
<223> OTHER INFORMATION: Synthetic Construct

<400> SEQUENCE: 201

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg
            100                 105

<210> SEQ ID NO 202
<211> LENGTH: 121
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Lys Asp Tyr
            20                  25                  30

Thr Met His Trp Val Lys Gln Ser His Gly Lys Ser Leu Glu Trp Ile
        35                  40                  45

Gly Gly Ile Tyr Pro Asn Asn Gly Gly Ser Thr Tyr Asn Gln Asn Phe
    50                  55                  60

Lys Asp Lys Ala Thr Leu Thr Val Asp Lys Ser Ser Ser Thr Ala Tyr
65                  70                  75                  80

Met Glu Phe Arg Ser Leu Thr Ser Glu Asp Ser Ala Val Tyr Tyr Cys
                85                  90                  95

Ala Arg Met Gly Tyr His Gly Pro His Leu Asp Phe Asp Val Trp Gly
            100                 105                 110

Ala Gly Thr Thr Val Thr Val Ser Pro
        115                 120

<210> SEQ ID NO 203
<211> LENGTH: 108
<212> TYPE: PRT
<213> ORGANISM: Artificial Sequence
<220> FEATURE:
<223> OTHER INFORMATION: Synthetic Construct

<400> SEQUENCE: 203

Asp Ile Val Met Thr Gln Ser His Lys Phe Met Ser Thr Ser Leu Gly
1               5                   10                  15

Asp Arg Val Ser Ile Thr Cys Lys Ala Ser Gln Asp Val Gly Ala Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
        50                  55                  60

Gly Gly Ser Gly Thr Asp Phe Thr Leu Thr Ile Ser Asn Val Gln Ser
65                  70                  75                  80

Glu Asp Leu Thr Asp Tyr Phe Cys Gln Gln Tyr Ile Asn Tyr Pro Leu
                85                  90                  95

Thr Phe Gly Gly Gly Thr Lys Leu Glu Ile Lys Arg
                100                 105

<210> SEQ ID NO 204
<211> LENGTH: 119
<212> TYPE: PRT
<213> ORGANISM: Artificial Sequence
<220> FEATURE:
<223> OTHER INFORMATION: Synthetic Construct

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Val Met His Trp Val Arg Gln Ala Pro Gly Gln Arg Leu Glu Trp Met
            35                  40                  45

Gly Tyr Ile Asn Pro Tyr Asn Asp Gly Thr Lys Tyr Asn Glu Lys Phe
        50                  55                  60

Lys Gly Arg Val Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
                100                 105                 110

Thr Leu Val Thr Val Ser Ser
        115

<210> SEQ ID NO 205
<211> LENGTH: 108
<212> TYPE: PRT
<213> ORGANISM: Artificial Sequence
<220> FEATURE:
<223> OTHER INFORMATION: Synthetic Construct

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Val Glu Ile Lys Arg
                100                 105

```
                100                 105

<210> SEQ ID NO 206
<211> LENGTH: 108
<212> TYPE: PRT
<213> ORGANISM: Artificial Sequence
<220> FEATURE:
<223> OTHER INFORMATION: Synthetic Construct

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asn Thr Leu Pro Trp
                85                  90                  95

Thr Phe Gly Gln Gly Thr Lys Val Glu Ile Lys Arg
            100                 105

<210> SEQ ID NO 207
<211> LENGTH: 119
<212> TYPE: PRT
<213> ORGANISM: Artificial Sequence
<220> FEATURE:
<223> OTHER INFORMATION: Synthetic Construct

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Ile Thr Ser Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 208
<211> LENGTH: 119
<212> TYPE: PRT
<213> ORGANISM: Artificial Sequence
<220> FEATURE:
<223> OTHER INFORMATION: Synthetic Construct

<400> SEQUENCE: 208

Gln Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Ser Tyr
            20                  25                  30

Val Met His Trp Val Arg Gln Ala Pro Gly Gln Arg Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Arg Ala Thr Leu Thr Ser Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Tyr Tyr Gly Ser Ser Leu Ser Met Asp Tyr Trp Gly Gln Gly
            100                 105                 110

Thr Leu Val Thr Val Ser Ser
        115

<210> SEQ ID NO 209
<211> LENGTH: 121
<212> TYPE: PRT
<213> ORGANISM: Artificial Sequence
<220> FEATURE:
<223> OTHER INFORMATION: Synthetic Construct

<400> SEQUENCE: 209

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Met
        35                  40                  45

Gly Gly Ile Tyr Pro Asn Asn Gly Gly Ser Thr Tyr Asn Gln Asn Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 210
<211> LENGTH: 108
<212> TYPE: PRT
<213> ORGANISM: Artificial Sequence
<220> FEATURE:
<223> OTHER INFORMATION: Synthetic Construct

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
            20                  25                  30

Val Ala Trp Tyr Gln Gln Lys Pro Gly Lys Ala Pro Lys Leu Leu Ile
        35                  40                  45

Tyr Trp Ala Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Tyr Ile Asn Tyr Pro Leu
                    85                  90                  95

Thr Phe Gly Gly Gly Thr Lys Val Glu Ile Lys Arg
                100                 105

<210> SEQ ID NO 211
<211> LENGTH: 108
<212> TYPE: PRT
<213> ORGANISM: Artificial Sequence
<220> FEATURE:
<223> OTHER INFORMATION: Synthetic Construct

<400> SEQUENCE: 211

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ala Ala
                20                  25                  30

Val Ala Trp Tyr Gln Gln Lys Pro Gly Lys Ala Pro Lys Leu Leu Ile
            35                  40                  45

Tyr Trp Ala Ser Thr Arg His Thr Gly Val Pro Asp Arg Phe Ser Gly
50                  55                  60

Gly Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Asn Tyr Pro Leu
                85                  90                  95

Thr Phe Gly Gly Gly Thr Lys Val Glu Ile Lys Arg
                100                 105

<210> SEQ ID NO 212
<211> LENGTH: 121
<212> TYPE: PRT
<213> ORGANISM: Artificial Sequence
<220> FEATURE:
<223> OTHER INFORMATION: Synthetic Construct

<400> SEQUENCE: 212

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
                20                  25                  30

Thr Met His Trp Val Arg Gln Ala Pro Gly Gln Gly Leu Glu Trp Ile
            35                  40                  45

Gly Gly Ile Tyr Pro Asn Asn Gly Gly Ser Thr Tyr Asn Gln Asn Phe
50                  55                  60

Lys Asp Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
                100                 105                 110

Gln Gly Thr Thr Val Thr Val Ser Ser
        115                 120

<210> SEQ ID NO 213
<211> LENGTH: 121
<212> TYPE: PRT
<213> ORGANISM: Artificial Sequence
<220> FEATURE:
```

<223> OTHER INFORMATION: Synthetic Construct

<400> SEQUENCE: 213

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Lys Asp Tyr
            20                  25                  30

Thr Met His Trp Val Arg Gln Ala Pro Gly Gln Gly Leu Glu Trp Ile
        35                  40                  45

Gly Gly Ile Tyr Pro Asn Asn Gly Gly Ser Thr Tyr Asn Gln Asn Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Met Gly Tyr His Gly Pro His Leu Asp Phe Asp Val Trp Gly
            100                 105                 110

Gln Gly Thr Thr Val Thr Val Ser Ser
        115                 120

<210> SEQ ID NO 214
<211> LENGTH: 108
<212> TYPE: PRT
<213> ORGANISM: Artificial Sequence
<220> FEATURE:
<223> OTHER INFORMATION: Synthetic Construct

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg
            100                 105

<210> SEQ ID NO 215
<211> LENGTH: 123
<212> TYPE: PRT
<213> ORGANISM: Artificial Sequence
<220> FEATURE:
<223> OTHER INFORMATION: Synthetic Construct

<400> SEQUENCE: 215

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe

```
                    50                  55                  60
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120
```

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

```
Gly Tyr Thr Phe Thr Asn Tyr Gly Met Asn
 1               5                  10
```

<210> SEQ ID NO 217
<211> LENGTH: 17
<212> TYPE: PRT
<213> ORGANISM: Artificial Sequence
<220> FEATURE:
<223> OTHER INFORMATION: Synthetic Construct

<400> SEQUENCE: 217

```
Trp Ile Asn Thr Tyr Thr Gly Glu Pro Thr Tyr Ala Ala Asp Phe Lys
 1               5                  10                  15

Arg
```

<210> SEQ ID NO 218
<211> LENGTH: 14
<212> TYPE: PRT
<213> ORGANISM: Artificial Sequence
<220> FEATURE:
<223> OTHER INFORMATION: Synthetic Construct

<400> SEQUENCE: 218

```
Tyr Pro His Tyr Tyr Gly Ser Ser His Trp Tyr Phe Asp Val
 1               5                  10
```

<210> SEQ ID NO 219
<211> LENGTH: 11
<212> TYPE: PRT
<213> ORGANISM: Artificial Sequence
<220> FEATURE:
<223> OTHER INFORMATION: Synthetic Construct

<400> SEQUENCE: 219

```
Ser Ala Ser Gln Asp Ile Ser Asn Tyr Leu Asn
 1               5                  10
```

<210> SEQ ID NO 220
<211> LENGTH: 7
<212> TYPE: PRT
<213> ORGANISM: Artificial Sequence
<220> FEATURE:
<223> OTHER INFORMATION: Synthetic Construct

<400> SEQUENCE: 220

```
Phe Thr Ser Ser Leu His Ser
```

```
1               5

<210> SEQ ID NO 221
<211> LENGTH: 9
<212> TYPE: PRT
<213> ORGANISM: Artificial Sequence
<220> FEATURE:
<223> OTHER INFORMATION: Synthetic Construct

<400> SEQUENCE: 221

Gln Gln Tyr Ser Thr Val Pro Trp Thr
1               5

<210> SEQ ID NO 222
<211> LENGTH: 25
<212> TYPE: PRT
<213> ORGANISM: Artificial Sequence
<220> FEATURE:
<223> OTHER INFORMATION: Synthetic Construct

<400> SEQUENCE: 222

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 223
<211> LENGTH: 13
<212> TYPE: PRT
<213> ORGANISM: Artificial Sequence
<220> FEATURE:
<223> OTHER INFORMATION: Synthetic Construct

<400> SEQUENCE: 223

Trp Val Arg Gln Ala Pro Gly Lys Gly Leu Glu Trp Val
1               5                   10

<210> SEQ ID NO 224
<211> LENGTH: 30
<212> TYPE: PRT
<213> ORGANISM: Artificial Sequence
<220> FEATURE:
<223> OTHER INFORMATION: Synthetic Construct

<400> SEQUENCE: 224

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 225
<211> LENGTH: 11
<212> TYPE: PRT
<213> ORGANISM: Artificial Sequence
<220> FEATURE:
<223> OTHER INFORMATION: Synthetic Construct

<400> SEQUENCE: 225

Trp Gly Gln Gly Thr Leu Val Thr Val Ser Ser
1               5                   10

<210> SEQ ID NO 226
<211> LENGTH: 23
<212> TYPE: PRT
<213> ORGANISM: Artificial Sequence
<220> FEATURE:
```

<223> OTHER INFORMATION: Synthetic Construct

<400> SEQUENCE: 226

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 227
<211> LENGTH: 15
<212> TYPE: PRT
<213> ORGANISM: Artificial Sequence
<220> FEATURE:
<223> OTHER INFORMATION: Synthetic Construct

<400> SEQUENCE: 227

Trp Tyr Gln Gln Lys Pro Gly Lys Ala Pro Lys Leu Leu Ile Tyr
1               5                   10                  15

<210> SEQ ID NO 228
<211> LENGTH: 32
<212> TYPE: PRT
<213> ORGANISM: Artificial Sequence
<220> FEATURE:
<223> OTHER INFORMATION: Synthetic Construct

<400> SEQUENCE: 228

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 229
<211> LENGTH: 10
<212> TYPE: PRT
<213> ORGANISM: Artificial Sequence
<220> FEATURE:
<223> OTHER INFORMATION: Synthetic Construct

<400> SEQUENCE: 229

Phe Gly Gln Gly Thr Lys Val Glu Ile Lys
1               5                   10

<210> SEQ ID NO 230
<211> LENGTH: 17
<212> TYPE: PRT
<213> ORGANISM: Artificial Sequence
<220> FEATURE:
<223> OTHER INFORMATION: Synthetic Construct

<400> SEQUENCE: 230

Asp Met Tyr Pro Asp Ala Ala Ala Ala Ser Tyr Asn Gln Lys Phe Arg
1               5                   10                  15

Glu

<210> SEQ ID NO 231
<211> LENGTH: 8
<212> TYPE: PRT
<213> ORGANISM: Artificial Sequence
<220> FEATURE:
<223> OTHER INFORMATION: Synthetic Construct

<400> SEQUENCE: 231

Ala Pro Arg Trp Ala Ala Ala Ala
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic Construct

<400> SEQUENCE: 232

Gln Ala Ala Ala Ala Ala Ala Ala Thr
1               5

<210> SEQ ID NO 233
<211> LENGTH: 117
<212> TYPE: PRT
<213> ORGANISM: Artificial Sequence
<220> FEATURE:
<223> OTHER INFORMATION: Synthetic Construct

<400> SEQUENCE: 233

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 234
<211> LENGTH: 117
<212> TYPE: PRT
<213> ORGANISM: Artificial Sequence
<220> FEATURE:
<223> OTHER INFORMATION: Synthetic Construct

<400> SEQUENCE: 234

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 235
<211> LENGTH: 10
<212> TYPE: PRT
<213> ORGANISM: Artificial Sequence
<220> FEATURE:
<223> OTHER INFORMATION: Synthetic Construct

<400> SEQUENCE: 235

Ala Leu Ala Pro Arg Trp Tyr Phe Ser Val
1               5                   10

<210> SEQ ID NO 236
<211> LENGTH: 7
<212> TYPE: PRT
<213> ORGANISM: Artificial Sequence
<220> FEATURE:
<223> OTHER INFORMATION: Synthetic Construct

<400> SEQUENCE: 236

Ala Arg Ala Arg Leu Asp Tyr
1               5

<210> SEQ ID NO 237
<211> LENGTH: 7
<212> TYPE: PRT
<213> ORGANISM: Artificial Sequence
<220> FEATURE:
<223> OTHER INFORMATION: Synthetic Construct

<400> SEQUENCE: 237

Ala Arg Asp Ala Leu Asp Tyr
1               5

<210> SEQ ID NO 238
<211> LENGTH: 7
<212> TYPE: PRT
<213> ORGANISM: Artificial Sequence
<220> FEATURE:
<223> OTHER INFORMATION: Synthetic Construct

<400> SEQUENCE: 238

Ala Arg Asp Arg Ala Asp Tyr
1               5

<210> SEQ ID NO 239
<211> LENGTH: 7
<212> TYPE: PRT
<213> ORGANISM: Artificial Sequence
<220> FEATURE:
<223> OTHER INFORMATION: Synthetic Construct

<400> SEQUENCE: 239

Ala Arg Asp Arg Leu Asp Tyr
1               5

<210> SEQ ID NO 240
<211> LENGTH: 10
<212> TYPE: PRT
<213> ORGANISM: Artificial Sequence
<220> FEATURE:
<223> OTHER INFORMATION: Synthetic Construct

<400> SEQUENCE: 240

Val Ala Ala Pro Arg Trp Tyr Phe Ser Val

```
<210> SEQ ID NO 241
<211> LENGTH: 10
<212> TYPE: PRT
<213> ORGANISM: Artificial Sequence
<220> FEATURE:
<223> OTHER INFORMATION: Synthetic Construct

<400> SEQUENCE: 241

Val Leu Ala Ala Arg Trp Tyr Phe Ser Val
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Synthetic Construct

<400> SEQUENCE: 242

Val Leu Ala Pro Ala Trp Tyr Phe Ser Val
1               5                   10

<210> SEQ ID NO 243
<211> LENGTH: 10
<212> TYPE: PRT
<213> ORGANISM: Artificial Sequence
<220> FEATURE:
<223> OTHER INFORMATION: Synthetic Construct

<400> SEQUENCE: 243

Val Leu Ala Pro Arg Ala Tyr Phe Ser Val
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Synthetic Construct

<400> SEQUENCE: 244

Val Leu Ala Pro Arg Trp Ala Phe Ser Val
1               5                   10

<210> SEQ ID NO 245
<211> LENGTH: 10
<212> TYPE: PRT
<213> ORGANISM: Artificial Sequence
<220> FEATURE:
<223> OTHER INFORMATION: Synthetic Construct

<400> SEQUENCE: 245

Val Leu Ala Pro Arg Trp Tyr Ala Ser Val
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Synthetic Construct

<400> SEQUENCE: 246

Val Leu Ala Pro Arg Trp Tyr Phe Ala Val
1               5                   10
```

<210> SEQ ID NO 247
<211> LENGTH: 10
<212> TYPE: PRT
<213> ORGANISM: Artificial Sequence
<220> FEATURE:
<223> OTHER INFORMATION: Synthetic Construct

<400> SEQUENCE: 247

Val Leu Ala Pro Arg Trp Tyr Phe Ser Ala
1               5                   10

<210> SEQ ID NO 248
<211> LENGTH: 10
<212> TYPE: PRT
<213> ORGANISM: Artificial Sequence
<220> FEATURE:
<223> OTHER INFORMATION: Synthetic Construct

<400> SEQUENCE: 248

Val Leu Ala Pro Arg Trp Tyr Phe Ser Val
1               5                   10

<210> SEQ ID NO 249
<211> LENGTH: 107
<212> TYPE: PRT
<213> ORGANISM: Artificial Sequence
<220> FEATURE:
<223> OTHER INFORMATION: Synthetic Construct

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Val His Tyr Ala Gln Phe Pro Tyr
                85                  90                  95

Thr Phe Gly Gln Gly Thr Lys Val Glu Ile Lys
            100                 105

<210> SEQ ID NO 250
<211> LENGTH: 107
<212> TYPE: PRT
<213> ORGANISM: Artificial Sequence
<220> FEATURE:
<223> OTHER INFORMATION: Synthetic Construct

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asp Ile Ser Ser Tyr
            20                  25                  30

Ile Val Trp Tyr Gln Gln Lys Pro Gly Lys Ser Phe Lys Gly Leu Ile
        35                  40                  45

Tyr His Gly Thr Asn Leu Glu Asp Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Val His Tyr Ala Gln Phe Pro Tyr
             85                  90                  95

Thr Phe Gly Gln Gly Thr Lys Val Glu Ile Lys
            100                 105
```

<210> SEQ ID NO 251
<211> LENGTH: 107
<212> TYPE: PRT
<213> ORGANISM: Artificial Sequence
<220> FEATURE:
<223> OTHER INFORMATION: Synthetic Construct

<400> SEQUENCE: 251

```
Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Phe
             20                  25                  30

Leu Asn Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Thr Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
             85                  90                  95

Thr Phe Gly Gly Gly Thr Lys Leu Glu Ile Lys
            100                 105
```

<210> SEQ ID NO 252
<211> LENGTH: 114
<212> TYPE: PRT
<213> ORGANISM: Artificial Sequence
<220> FEATURE:
<223> OTHER INFORMATION: Synthetic Construct

<400> SEQUENCE: 252

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Asn Tyr
             20                  25                  30

Leu Ile Glu Trp Val Arg Gln Ala Pro Gly Gln Gly Leu Glu Trp Ile
         35                  40                  45

Gly Val Ile Asn Pro Gly Ser Gly Asp Ala Tyr Tyr Ser Glu Lys Phe
 50                  55                  60

Lys Gly Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
             85                  90                  95

Ala Arg Asp Arg Leu Asp Tyr Trp Gly Gln Gly Thr Leu Val Thr Val
            100                 105                 110

Ser Ser
```

<210> SEQ ID NO 253
<211> LENGTH: 114
<212> TYPE: PRT
<213> ORGANISM: Artificial Sequence

```
<220> FEATURE:
<223> OTHER INFORMATION: Synthetic Construct

<400> SEQUENCE: 253

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Tyr
            20                  25                  30

Leu Ile Glu Trp Val Arg Gln Ala Pro Gly Gln Gly Leu Glu Trp Ile
        35                  40                  45

Gly Val Ile Asn Pro Gly Ser Gly Asp Gln Tyr Tyr Ser Glu Lys Phe
    50                  55                  60

Lys Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Asp Arg Leu Asp Tyr Trp Gly Gln Gly Thr Leu Val Thr Val
            100                 105                 110

Ser Ser

<210> SEQ ID NO 254
<211> LENGTH: 113
<212> TYPE: PRT
<213> ORGANISM: Artificial Sequence
<220> FEATURE:
<223> OTHER INFORMATION: Synthetic Construct

<400> SEQUENCE: 254

Gln Val Gln Leu Lys Gln Ser Gly Pro Gly Leu Val Gln Pro Ser Leu
1               5                   10                  15

Ser Leu Ser Ile Thr Cys Thr Val Ser Gly Phe Ser Leu Thr Asp Tyr
            20                  25                  30

Gly Val Leu Trp Val Arg Gln Ser Pro Gly Lys Gly Leu Glu Trp Leu
        35                  40                  45

Gly Met Ile Trp Ser Gly Gly Thr Thr Asp Tyr Asn Ala Ala Phe Ile
    50                  55                  60

Ser Arg Leu Ser Ile Asn Lys Asp Asn Ser Lys Ser Gln Val Phe Phe
65                  70                  75                  80

Lys Met Asn Ser Leu Gln Val Asp Asp Thr Ala Ile Tyr Tyr Cys Val
                85                  90                  95

Arg Glu Glu Met Asp Tyr Trp Gly Gln Gly Thr Ser Val Thr Val Ser
            100                 105                 110

Ser
```

ANTI-OX40 ANTIBODIES AND METHODS OF USE

CROSS REFERENCE TO RELATED APPLICATIONS

This application is a Divisional of U.S. patent application Ser. No. 14/673,792, filed Mar. 30, 2015, which claims priority to and the priority benefit of U.S. Provisional Application Ser. No. 61/973,193, filed Mar. 31, 2014; 61/989,448, filed May 6, 2014; 62/073,873, filed Oct. 31, 2014; 62/080,171, filed Nov. 14, 2014; and 62/113,345, filed Feb. 6, 2015; each of which is incorporated herein by reference in its entirety.

SEQUENCE LISTING

The content of the following submission on ASCII text file is incorporated herein by reference in its entirety: a computer readable form (CRF) of the Sequence Listing (file name: 146392029110SEQLIST.TXT, date recorded: Feb. 22, 2018, size: 197 KB).

FIELD OF THE INVENTION

The present invention relates to anti-OX40 antibodies and methods of using the same.

BACKGROUND

OX40 (also known as CD34, TNFRSF4 and ACT35) is a member of the tumor necrosis factor receptor superfamily. OX40 is not constitutively expressed on naïve T cells, but is induced after engagement of the T cell receptor (TCR). The ligand for OX40, OX40L, is predominantly expressed on antigen presenting cells. OX40 is highly expressed by activated CD4+ T cells, activated CD8+ T cells, memory T cells, and regulatory T cells. OX40 signaling can provide costimulatory signals to CD4 and CD8 T cells, leading to enhanced cell proliferation, survival, effector function and migration. OX40 signaling also enhances memory T cell development and function.

Regulatory T cells (Treg) cells are highly enriched in tumors and tumor draining lymph nodes derived from multiple cancer indications, including melanoma, NSCLC, renal, ovarian, colon, pancreatic, hepatocellular, and breast cancer. In a subset of these indications, increased intratumoral T reg cell densities are associated with poor patient prognosis, suggesting that these cells play an important role in suppressing antitumor immunity. OX40 positive tumor infiltrating lymphocytes have been described.

It is clear that there continues to be a need for agents that have clinical attributes that are optimal for development as therapeutic agents. The invention described herein meets this need and provides other benefits.

Bevacizumab (Avastin®) is a recombinant humanized monoclonal IgG1 antibody that specifically binds to and blocks the biological effects of VEGF. Bevacizumab has been approved in Europe for the treatment of the advanced stages of six common types of cancer: colorectal cancer, breast cancer, non-small cell lung cancer (NSCLC), ovarian cancer, cervical cancer, and kidney cancer, which collectively cause over 2.5 million deaths each year. In the United States, bevacizumab was the first anti-angiogenesis therapy approved by the FDA, and it is now approved for the treatment of six tumor types: colorectal cancer, NSCLC, brain cancer (glioblastoma), kidney cancer (renal cell carcinoma), ovarian cancer, and cervical cancer. Over half a million patients have been treated with bevacizumab so far, and a comprehensive clinical program is investigating the further use of bevacizumab in the treatment of multiple cancer types.

Bevacizumab has shown promise as a co-therapeutic, demonstrating efficacy when combined with a broad range of chemotherapies and other anti-cancer treatments. For example, phase-III studies have demonstrated the beneficial effects of combining bevacizumab with standard chemotherapeutic regimens (see, e.g., Saltz et al., 2008, J. Clin. Oncol., 26:2013-2019; Yang et al., 2008, Clin. Cancer Res., 14:5893-5899; Hurwitz et al., 2004, N. Engl. J. Med., 350:2335-2342). However, as in previous studies of angiogenesis inhibitors, some of these phase-III studies have shown that a portion of patients experience incomplete response to the addition of bevacizumab to their chemotherapeutic regimens. Accordingly, there is a need for methods of identifying those patients that are likely to respond or have an improved response to not only angiogenesis inhibitors (e.g., bevacizumab) alone, but also combination therapies comprising angiogenesis inhibitors (e.g., bevacizumab).

Accordingly, there is a need for combination therapies that may increase the efficacy of anti-angiogenic cancer therapy. Combination therapies may increase responsiveness in patients that show incomplete response and/or further increase responsiveness in patients that do respond to anti-angiogenic cancer therapy.

All references cited herein, including patent applications and publications, are incorporated by reference in their entirety.

SUMMARY

In one aspect, provided are isolated antibodies that bind to human OX40.

In another aspect, provided are anti-human OX40 agonist antibodies wherein the antibody is a depleting antibody. In another aspect, provided are anti-human OX40 agonist antibodies wherein the antibody depletes cells that express human OX40 in vitro and binds human OX40 with an affinity of less than or equal to about 1 nM. In some embodiments, the antibodies deplete CD4+ effector T cells. In some embodiments the antibodies deplete regulatory T cells (Treg). In some embodiments, the depleting is by ADCC and/or phagocytosis. In some embodiments, the depleting is by ADCC.

In another aspect, provided are anti-human OX40 agonist antibodies that bind human OX40 with an affinity of less than or equal to about 0.45 nM. In some embodiments, the antibody binds human OX40 with an affinity of less than or equal to about 0.4 nM. In some embodiments, antibody binding affinity is determined using radioimmunoassay. In some embodiments, the antibody binds human OX40 and cynomolgus OX40. In some embodiments, binding to human and cynomolgus OX40 is determined using a FACS assay. In some embodiments, binding to human OX40 has an EC50 of less than or equal to 0.2 ug/ml. In some embodiments, binding to human OX40 has an EC50 of less than or equal to 0.3 ug/ml or lower. In some embodiments, binding to cynomolgus OX40 has an EC50 of less than or equal to 1.5 ug/ml. In some embodiments, binding to cynomolgus OX40 has an EC50 of less than or equal to 1.4 ug/ml.

In another aspect, the invention provides anti-human OX40 agonist antibodies that increase (are capable of increasing) CD4+ effector T cell proliferation and/or increasing cytokine production by the CD4+ effector T cell as compared to proliferation and/or cytokine production prior to treatment with anti-human OX40 agonist antibody. In some embodiments, the cytokine is gamma interferon.

In another aspect, the invention provides anti-human OX40 agonist antibodies that increase (are capable of increasing) memory T cell proliferation and/or increasing cytokine production by the memory cell. In some embodiments, the cytokine is gamma interferon.

In another aspect, the invention provides anti-human OX40 agonist that inhibit (are capable of inhibiting) Treg function. In some embodiments, the antibodies inhibit Treg suppression of effector T cell function. In some embodiments, effector T cell function is effector T cell proliferation and/or cytokine production. In some embodiments, the effector T cell is a CD4+ effector T cell.

In another aspect, the invention provides anti-human OX40 agonist antibodies that increase (are capable of increasing) OX40 signal transduction in a target cell that expresses OX40. In some embodiments, OX40 signal transduction is detected by monitoring NFkB downstream signaling (e.g., in the OX40 expressing cell, e.g., CD4+ effector T cell, CD8+ effector T cell, CD4+ memory T cell).

In another aspect, provided are anti-human OX40 agonist antibodies that are stable after treatment at 40° C. for two weeks.

In another aspect, provided are anti-human OX40 agonist antibodies, wherein the antibodies comprise a variant IgG1 Fc polypeptide comprising a mutation that eliminates binding to human effector cells, wherein the antibodies have diminished activity relative to anti-human OX40 agonist antibodies comprising native sequence IgG1 Fc portion. In some embodiments, the antibodies comprise a variant Fc portion comprising a mutation that eliminates binding to FcR (e.g., a DANA or N297G mutation). In some embodiments, the activity is one or more of: increasing CD4+ effector T cell proliferation and/or cytokine production, increasing CD4+ memory T cell proliferation and/or cytokine production, and/or depleting cells by ADCC and/or phagocytosis.

In another aspect, provided are anti-human OX40 agonist antibodies, wherein antibody cross-linking is required for anti-human OX40 agonist antibody function. In some embodiments, anti-human OX40 agonist antibody function is one or more of: increasing CD4+ effector T cell proliferation and/or cytokine production, increasing CD4+ memory T cell proliferation and/or cytokine production, and/or depleting cells by ADCC and/or phagocytosis.

In another aspect, provided are anti-human OX40 agonist antibodies, wherein the antibody comprises (a) a VH domain comprising (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (iv) HVR-L1 comprising the amino acid sequence of SEQ ID NO:5, (v) HVR-L2 comprising the amino acid sequence of SEQ ID NO:6, and (vi) HVR-L3 comprising the amino acid sequence of SEQ ID NO: 7, 22, 23, 24, 25, 26, 27, or 28.

In another aspect, provided are anti-human OX40 agonist antibodies, wherein the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In another aspect, provided are anti-human OX40 agonist antibodies, wherein the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26.

In another aspect, provided are anti-human OX40 agonist antibodies, wherein the antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27.

In another aspect, provided are anti-human OX40 agonist antibodies, wherein the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114, 116, 233, or 234.

In another aspect, provided are anti-human OX40 agonist antibodies, wherein the antibody comprises, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117.

In another aspect, provided are anti-human OX40 agonist antibodies, wherein the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In some embodiments, the VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to human OX40. In some embodiments, total of 1 to 10 amino acids have been substituted, inserted and/or deleted in SEQ ID NO:56. In some embodiments, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, provided are anti-human OX40 agonist antibodies, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57. In some embodiments, the VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to human OX40. In some embodiments, a total of 1 to 10 amino acids have been substituted, inserted and/or deleted in SEQ ID NO: 57. In some embodiments, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, provided are anti-human OX40 agonist antibodies comprising a VH sequence of SEQ ID NO: 56.

In another aspect, provided are anti-human OX40 agonist antibodies comprising a VL sequence of SEQ ID NO: 57.

In another aspect, provided are anti-human OX40 agonist antibodies comprising a VH sequence of SEQ ID NO:56 and a VL sequence of SEQ ID NO: 57.

In another aspect, provided are anti-human OX40 agonist antibodies comprising a VH sequence of SEQ ID NO: 94.

In another aspect, provided are anti-human OX40 agonist antibodies comprising a VL sequence of SEQ ID NO: 95.

In another aspect, provided are anti-human OX40 agonist antibodies comprising a VH sequence of SEQ ID NO:94 and a VL sequence of SEQ ID NO: 95.

In another aspect, provided are anti-human OX40 agonist antibodies comprising a VH sequence of SEQ ID NO: 96.

In another aspect, provided are anti-human OX40 agonist antibodies comprising a VL sequence of SEQ ID NO: 97.

In another aspect, provided are anti-human OX40 agonist antibodies comprising a VH sequence of SEQ ID NO:96 and a VL sequence of SEQ ID NO: 97.

In another aspect, provided are anti-human OX40 agonist antibodies comprising a VH sequence of SEQ ID NO: 180.

In another aspect, provided are anti-human OX40 agonist antibodies comprising a VL sequence of SEQ ID NO: 179.

In another aspect, provided are anti-human OX40 agonist antibodies comprising a VH sequence of SEQ ID NO: 180 and a VL sequence of SEQ ID NO: 179.

In another aspect, provided are anti-human OX40 agonist antibodies comprising a VH sequence of SEQ ID NO: 182.

In another aspect, provided are anti-human OX40 agonist antibodies comprising a VL sequence of SEQ ID NO: 181.

In another aspect, provided are anti-human OX40 agonist antibodies comprising a VH sequence of SEQ ID NO:182 and a VL sequence of SEQ ID NO: 181.

In some embodiments of any of the antibodies of the invention, the antibody is a full length human IgG1 antibody.

In some embodiments of any of the antibodies of the invention, the antibody is a human antibody. In some embodiments of any of the antibodies of the invention, the antibody is a humanized antibody. In some embodiments of any of the antibodies of the invention, the antibody is a chimeric antibody.

In some embodiments of any of the antibodies of the invention, the antibody is a naked antibody.

In another aspect, provided are isolated nucleic acids encoding any of the anti-human OX40 antibodies (e.g., agonist antibodies) provided herein.

In another aspect, provided are host cells comprising the nucleic acid encoding any of the anti-human OX40 antibodies (e.g., agonist antibodies) provided herein.

In another aspect, provided are methods of producing an antibody comprising culturing the host cell so that the antibody is produced. In some embodiments, the methods further comprise recovering the antibody from the host cell.

In another aspect, provided are immunoconjugates comprising any of the anti-human OX40 antibodies (e.g., agonist antibodies) provided herein and a cytotoxic agent.

In another aspect, provided are pharmaceutical formulations comprising any of the anti-human OX40 antibodies (e.g., agonist antibodies) provided herein and a pharmaceutically acceptable carrier. In some embodiments, the pharmaceutical formulation comprises (a) any of the anti-human OX40 agonist antibodies described herein at a concentration between about 10 mg/mL and about 100 mg/mL, (b) a polysorbate, wherein the polysorbate concentration is about 0.02% to about 0.06%; (c) a histidine buffer at about pH 5.0 to about pH 6.0; and (d) a saccharide, wherein the saccharide concentration is about 120 mM to about 320 mM. In some embodiments, the histidine buffer is at pH 5.0 to 6.0. In some embodiments, the saccharide is sucrose. In some embodiments, the pharmaceutical formulation comprises (a) any of the anti-human OX40 agonist antibodies described herein, (b) polysorbate 20, wherein the polysorbate concentration is about 0.02%; (c) a histidine acetate buffer at pH 6.0; and (d) sucrose, wherein the sucrose concentration is about 320 mM. In some embodiments, the pharmaceutical formulation comprises (a) any of the anti-human OX40 agonist antibodies described herein, (b) polysorbate 20, wherein the polysorbate concentration is about 0.02%; (c) a histidine acetate buffer at pH 5.5; and (d) sucrose, wherein the sucrose concentration is about 240 mM. In some embodiments, the pharmaceutical formulation comprises (a) any of the anti-human OX40 agonist antibodies described herein, (b) polysorbate 20, wherein the polysorbate concentration is about 0.04%; (c) a histidine acetate buffer at pH 6.0; and (d) sucrose, wherein the sucrose concentration is about 120 mM. In some embodiments, the pharmaceutical formulation comprises (a) any of the anti-human OX40 agonist antibodies described herein, (b) polysorbate 40, wherein the polysorbate concentration is about 0.04%; (c) a histidine acetate buffer at pH 5.0; and (d) sucrose, wherein the sucrose concentration is about 240 mM. In some embodiments, the pharmaceutical formulation comprises (a) any of the anti-human OX40 agonist antibodies described herein, (b) polysorbate 40, wherein the polysorbate concentration is about 0.04%; (c) a histidine acetate buffer at pH 6.0; and (d) sucrose, wherein the sucrose concentration is about 120 mM. In some embodiments, the antibody of the formulation comprises (a) a VH domain comprising (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (iv) HVR-L1 comprising the amino acid sequence of SEQ ID NO:5, (v) HVR-L2 comprising the amino acid sequence of SEQ ID NO:6, and (vi) HVR-L3 comprising the amino acid sequence of SEQ ID NO: 7, 22, 23, 24, 25, 26, 27, or 28. In some embodiments, the antibody of the formulation comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7. In some embodiments, the antibody of the formulation comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26. In some embodiments, the antibody of the formulation comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27. In some embodiments, the antibody of the formulation comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114, 116, 233, or 234. In some embodiments, the antibody of the formulation comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117. In some embodiments, the antibody of the formulation comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In some embodiments, the VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to human OX40. In some embodiments, total of 1 to 10 amino acids have been substituted, inserted and/or deleted in SEQ ID NO:56. In some embodiments, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4. In some embodiments, the antibody of the formulation comprises a light chain variable domain (VL) having at least 90%, 91%, 92%, 93%, 94%, 95%, 96%, 97%, 98%, 99%, or 100% sequence identity to the amino acid sequence of SEQ ID NO:57. In some embodiments, the VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to human OX40. In some embodiments, a total of 1 to 10 amino acids have been substituted, inserted and/or deleted in SEQ ID NO: 57. In some embodiments, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In some embodiments, the antibody of the formulation comprises a VH sequence of SEQ ID NO: 56. In some embodiments, the antibody of the formulation comprises a VL sequence of SEQ ID NO: 57. In some embodiments, the antibody of the formulation comprises a VH sequence of SEQ ID NO:56 and a VL sequence of SEQ ID NO: 57. In some embodiments, the antibody of the formulation comprises a VH sequence of SEQ ID NO: 94. In some embodiments, the antibody of the formulation comprises a VL sequence of SEQ ID NO: 95. In some embodiments, the antibody of the formulation comprises a VH sequence of SEQ ID NO:94 and a VL sequence of SEQ ID NO: 95. In some embodiments, the antibody of the formulation comprises a VH sequence of SEQ ID NO: 96. In some embodiments, the antibody of the formulation comprises a VL sequence of SEQ ID NO: 97. In some embodiments, the antibody of the formulation comprises a VH sequence of SEQ ID NO:96 and a VL sequence of SEQ ID NO: 97. In some embodiments, the antibody of the formulation comprises a VH sequence of SEQ ID NO: 180. In some embodiments, the antibody of the formulation comprises a VL sequence of SEQ ID NO: 179. In some embodiments, the antibody of the formulation comprises a VH sequence of SEQ ID NO: 180 and a VL sequence of SEQ ID NO: 179. In some embodiments, the antibody of the formulation comprises a VH sequence of SEQ ID NO: 182. In some embodiments, the antibody of the formulation comprises a VL sequence of SEQ ID NO: 181. In some embodiments, the antibody of the formulation comprises a VH sequence of SEQ ID NO: 182 and a VL sequence of SEQ ID NO: 181.

In another aspect, an anti-human OXO agonist antibodies provided herein is for use as a medicament.

In another aspect, an anti-human OXO agonist antibody provided herein is for use in treating cancer.

In another aspect, an anti-human OXO agonist antibody provided herein is for use in one or more of: inhibiting Treg function (e.g., inhibiting the suppressive function of Tregs), killing OX40 expressing cells (e.g., cells that express high levels of OX40), increasing effector T cell function and/or increasing memory T cell function, decrease tumor immunity, enhance T cell function and/or depleting OX-40 expressing cells.

In another aspect, provided is use of an anti-human OXO agonist antibody provided herein in the manufacture of a medicament for treatment of cancer.

In another aspect, provided is use of an anti-human OXO agonist antibody provided herein in the manufacture of a medicament for one or more of: inhibiting Treg function (e.g., inhibiting the suppressive function of Tregs), killing OX40 expressing cells (e.g., cells that express high levels of OX40), increasing effector T cell function and/or increasing memory T cell function, decrease tumor immunity, enhance T cell function and/or depleting OX-40 expressing cells.

In another aspect, provided are methods of treating an individual having cancer comprising administering to the individual an effective amount of any of the anti-human OX40 agonist antibodies provided herein. In some embodiments, the methods further comprise administering an additional therapeutic agent. In some embodiments, the additional therapeutic agent comprises a chemotherapeutic agent. In some embodiments, the additional therapeutic agent comprises a PD-1 axis binding antagonist.

In another aspect, provided are methods of diagnosis or detection using any of the anti-human OX40 antibodies disclosed herein.

In another aspect, provided are kits or articles of manufacture comprising any of the anti-human OX40 antibodies disclosed herein.

In one aspect, provided herein is a method for treating or delaying progression of cancer in an individual comprising administering to the individual an effective amount of an anti-angiogenesis agent and an OX40 binding agonist.

In another aspect, provided herein is a use of an anti-angiogenesis agent in the manufacture of a medicament for treating or delaying progression of cancer in an individual, wherein the medicament comprises the anti-angiogenesis agent and an optional pharmaceutically acceptable carrier, and wherein the treatment comprises administration of the medicament in combination with a composition comprising an OX40 binding agonist and an optional pharmaceutically acceptable carrier. Further provided herein is a use of an OX40 binding agonist in the manufacture of a medicament for treating or delaying progression of cancer in an individual, wherein the medicament comprises the OX40 binding agonist and an optional pharmaceutically acceptable carrier, and wherein the treatment comprises administration of the medicament in combination with a composition comprising an anti-angiogenesis agent and an optional pharmaceutically acceptable carrier.

In still another aspect, provided herein is a composition comprising an anti-angiogenesis agent and an optional pharmaceutically acceptable carrier for use in treating or delaying progression of cancer in an individual, wherein the treatment comprises administration of said composition in combination with a second composition, wherein the second composition comprises OX40 binding agonist and an optional pharmaceutically acceptable carrier. Further provided herein is a composition comprising an OX40 binding agonist and an optional pharmaceutically acceptable carrier for use in treating or delaying progression of cancer in an individual, wherein the treatment comprises administration of said composition in combination with a second composition, wherein the second composition comprises an anti-angiogenesis agent and an optional pharmaceutically acceptable carrier.

In yet another aspect, provided herein is a kit comprising a medicament comprising an anti-angiogenesis agent and an optional pharmaceutically acceptable carrier, and a package insert comprising instructions for administration of the medicament in combination with a composition comprising an OX40 binding agonist and an optional pharmaceutically acceptable carrier for treating or delaying progression of cancer in an individual. Further provided here is a kit comprising a first medicament comprising an anti-angiogenesis agent and an optional pharmaceutically acceptable carrier, and a second medicament comprising an OX40 binding agonist and an optional pharmaceutically acceptable carrier. In some embodiments, the kit further comprises a package insert comprising instructions for administration of the first medicament and the second medicament for treating or delaying progression of cancer in an individual. Still further provided herein is a kit comprising a medicament comprising an OX40 binding agonist and an optional pharmaceutically acceptable carrier, and a package insert comprising instructions for administration of the medicament in combination with a composition comprising an anti-angiogenesis agent and an optional pharmaceutically acceptable carrier for treating or delaying progression of cancer in an individual.

In some embodiments, the anti-angiogenesis agent is selected from the group consisting of an anti-VEGFR2 antibody; an anti-VEGFR1 antibody; a VEGF-trap; a bispecific VEGF antibody; a bispecific antibody comprising a combination of two arms selected from the group consisting of an anti-VEGF arm, an anti-VEGFR1 arm, and an anti-VEGFR2 arm; an anti-VEGF-A antibody; an anti-VEGFB antibody; an anti-VEGFC antibody; an anti-VEGFD antibody; a nonpeptide small molecule VEGF antagonist; an anti-PDGFR inhibitor; and a native angiogenesis inhibitor. In some embodiments, the anti-angiogenesis agent is selected from the group consisting of ramucirumab, tanibirumab, aflibercept, icrucumab, ziv-aflibercept, MP-0250, vanucizumab, sevacizumab, VGX-100, pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, imatinib, and tivozanib.

In some embodiments, the anti-angiogenesis agent is an anti-angiogenesis antibody. In some embodiments, the anti-angiogenesis antibody is a monoclonal antibody. In some embodiments, the anti-angiogenesis antibody is a human or humanized antibody. In some embodiments, the anti-angiogenesis agent is a VEGF antagonist. In some embodiments, the VEGF antagonist reduces the expression level or biological activity of VEGF by at least 10%, 20%, 30%, 40%, 50%, 60%, 70%, 80%, or 90%. In some embodiments, the VEGF is VEGF (8-109), VEGF (1-109), or $VEGF_{165}$. In some embodiments, the VEGF antagonist increases MHC class II expression on dendritic cells as compared to MHC class II expression on dendritic cells prior to treatment with the VEGF antagonist. In some embodiments, the VEGF antagonist increases OX40L expression on dendritic cells as compared to OX40L expression on dendritic cells prior to treatment with the VEGF antagonist. In some embodiments, the dendritic cells are myeloid dendritic cells. In some embodiments, the dendritic cells are non-myeloid dendritic cells. In some embodiments, the VEGF antagonist comprises a soluble VEGF receptor or a soluble VEGF receptor fragment that specifically binds to VEGF. In some embodiments, the VEGF antagonist is a chimeric VEGF receptor protein. In some embodiments, the VEGF antagonist is administered by gene therapy.

In some embodiments, the VEGF antagonist is an anti-VEGF antibody. In some embodiments, the anti-VEGF antibody is a human or humanized antibody. In some embodiments, the anti-VEGF antibody binds to the A4.6.1 epitope. In some embodiments, the anti-VEGF antibody binds to a functional epitope comprising residues F17, M18, D19, Y21, Y25, Q89, 191, K101, E103, and C104 of human VEGF. In some embodiments, the anti-VEGF antibody binds to a functional epitope comprising residues F17, Y21, Q22, Y25, D63, 183, and Q89 of human VEGF. In some embodiments, the anti-VEGF antibody is a G6 series antibody. In some embodiments, the anti-VEGF antibody is a B20 series antibody. In some embodiments, the anti-VEGF antibody is a monoclonal anti-VEGF antibody. In some embodiments, the monoclonal anti-VEGF antibody is bevacizumab. In some embodiments, the anti-VEGF antibody comprises a light chain variable region comprising the amino acid sequence of DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKR. (SEQ ID NO:214). In some embodiments, the anti-VEGF antibody comprises a heavy chain variable region comprising the amino acid sequence of EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSS (SEQ ID NO:215). In some embodiments, the anti-VEGF antibody comprises a light chain variable region comprising the amino acid sequence of DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKR. (SEQ ID NO:214) and a heavy chain variable region comprising the amino acid sequence of EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSS (SEQ ID NO:215). In some embodiments, the anti-VEGF antibody comprises one, two, three, four, five, or six hypervariable region (HVR) sequences of bevacizumab. In some embodiments, the anti-VEGF antibody comprises one, two, three, four, five, or six hypervariable region (HVR) sequences of selected from (a) HVR-H1 comprising the amino acid sequence of GYTFTNYGMN (SEQ ID NO:216); (b) HVR-H2 comprising the amino acid sequence of WINTYTGEPTYAADFKR (SEQ ID NO:217); (c) HVR-H3 comprising the amino acid sequence of YPHYYGSSH-WYFDV (SEQ ID NO:218); (d) HVR-L1 comprising the amino acid sequence of SASQDISNYLN (SEQ ID NO:219); (e) HVR-L2 comprising the amino acid sequence of FTSSLHS (SEQ ID NO:220); and (f) HVR-L3 comprising the amino acid sequence of QQYSTVPWT (SEQ ID NO:221). In some embodiments, the anti-VEGF antibody comprises one, two, three, four, five, or six hypervariable region (HVR) sequences of an antibody described in U.S. Pat. No. 6,884,879. In some embodiments, the anti-VEGF antibody comprises one, two, or three hypervariable region (HVR) sequences of a light chain variable region comprising the following amino acid sequence: DIQMTQSPSS LSAS-VGDRVT ITCSASQDIS NYLNWYQQKP GKAPKVLIYF TSSLHSGVPS RFSGSGSGTD FTLTISSLQP EDFATYY-CQQ YSTVPWTFGQ GTKVEIKR. (SEQ ID NO:214) and/or one, two, or three hypervariable region (HVR) sequences of a heavy chain variable region comprising the following amino acid sequence: EVQLVESGGG LVQPGGSLRL SCAASGYTFT NYGMNWVRQA PGKGLEWVGW INTYTGEPTY AADFKRRFTF SLDTSKSTAY LQMNSL-RAED TAVYYCAKYP HYYGSSHWYF DVWGQGTLVT VSS (SEQ ID NO:215). In some embodiments, the anti-VEGF antibody comprises one, two, three, four, five, or six hypervariable region (HVR) sequences of bevacizumab.

In some embodiments, the OX40 binding agonist for use in conjunction with an anti-angiogenesis agent is selected from the group consisting of an OX40 agonist antibody, an OX40L agonist fragment, an OX40 oligomeric receptor, and an OX40 immunoadhesin. In some embodiments, the OX40 binding agonist is a trimeric OX40L-Fc protein. In some embodiments, the OX40 binding agonist is an OX40L agonist fragment comprising one or more extracellular domains of OX40L. In some embodiments, the OX40 binding agonist is an OX40 agonist antibody that binds OX40. In some embodiments, the OX40 agonist antibody depletes cells that express human OX40. In some embodiments, the OX40 agonist antibody depletes cells that express human OX40 in vitro. In some embodiments, the cells are CD4+ effector T cells. In some embodiments, the cells are Treg cells. In some embodiments, the depleting is by ADCC and/or phagocytosis. In some embodiments, the depleting is by ADCC. In some embodiments, the OX40 agonist antibody binds human OX40 with an affinity of less than or equal to about 1 nM. In some embodiments, the OX40 agonist antibody depletes cells that express human OX40 in vitro and binds human OX40 with an affinity of less than or equal to about 1 nM. In some embodiments, the OX40 agonist antibody binds human OX40 with an affinity of less than or equal to about 0.45 nM. In some embodiments, the OX40 agonist antibody binds human OX40 with an affinity of less than or equal to about 0.4 nM. In some embodiments, OX40 agonist antibody binding affinity is determined using radioimmunoassay. In some embodiments, binding to human OX40 has an EC50 of less than or equal to 0.2 ug/ml. In some embodiments, binding to human OX40 has an EC50 of less than or equal to 0.3 ug/ml. In some embodiments, the OX40 agonist antibody increases CD4+ effector T cell proliferation and/or increasing cytokine production by the CD4+ effector T cell as compared to proliferation and/or cytokine production prior to treatment with anti-human OX40 agonist antibody. In some embodiments, the cytokine is gamma interferon. In some embodiments, the OX40 agonist antibody increases memory T cell proliferation and/or increasing cytokine production by the memory cell. In some embodiments, the cytokine is gamma interferon. In some embodiments, the OX40 agonist antibody inhibits Treg function. In some embodiments, the OX40 agonist antibody inhibits Treg suppression of effector T cell function. In some embodiments, effector T cell function is effector T cell proliferation and/or cytokine production. In some embodiments, the effector T cell is a CD4+ effector T cell. In some embodiments, the OX40 agonist antibody increases OX40 signal transduction in a target cell that expresses OX40. In some embodiments, OX40 signal transduction is detected by monitoring NFkB downstream signaling. In some embodiments, the OX40 agonist antibody is stable after treatment at 40° C. for two weeks. In some embodiments, the OX40 agonist antibody comprises a variant IgG1 Fc polypeptide comprising a mutation that eliminates binding to human effector cells, and wherein the antibody has diminished activity relative to an anti-human OX40 agonist antibody comprising a native sequence IgG1 Fc portion. In some embodiments, the OX40 agonist antibody comprises a variant Fc portion comprising a DANA mutation. In some embodiments, OX40 agonist antibody cross-linking is required for anti-human OX40 agonist antibody function. In some embodiments, the OX40 agonist antibody comprises (a) a VH domain comprising (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (iv) HVR-L1 comprising the amino acid sequence of SEQ ID NO:5, (v) HVR-L2 comprising the amino acid sequence of SEQ ID NO:6, and (vi) HVR-L3 comprising the amino acid sequence of SEQ ID NO: 7, 22, 23, 24, 25, 26, 27, or 28. In some embodiments, the OX40 agonist antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence of SEQ ID NO:7. In some embodiments, the OX40 agonist antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence of SEQ ID NO:26. In some embodiments, the OX40 agonist antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence of SEQ ID NO:27. In some embodiments, the OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114, 116, 233, or 234. In some embodiments, the OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117. In some embodiments, the OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In some embodiments, the OX40 agonist VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to human OX40. In some embodiments, a total of 1 to 10 amino acids have been substituted, inserted and/or deleted in SEQ ID NO:56. In some embodiments, the OX40 agonist VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4. In some embodiments, the OX40 agonist antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57. In some embodiments, the OX40 agonist VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to human OX40. In some embodiments, a total of 1 to 10 amino acids have been substituted, inserted and/or deleted in SEQ ID NO: 57. In some embodiments, the OX40 agonist VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In some embodiments, the OX40 agonist antibody comprises a VH sequence of SEQ ID NO: 56. In some embodiments, the OX40 agonist antibody comprises a VL sequence of SEQ ID NO: 57. In some embodiments, the OX40 agonist antibody comprises a VH sequence of SEQ ID NO:56 and a VL sequence of SEQ ID NO: 57. In some embodiments, the OX40 agonist antibody comprises a VH sequence of SEQ ID NO: 94. In some embodiments, the OX40 agonist antibody comprises a VL sequence of SEQ ID NO: 95. In some embodiments, the OX40 agonist antibody comprises a VH sequence of SEQ ID NO:94 and a VL sequence of SEQ ID NO: 95. In some embodiments, the OX40 agonist antibody comprises a VH sequence of SEQ ID NO: 96. In some embodiments, the OX40 agonist antibody comprises a VL sequence of SEQ ID NO: 97. In some embodiments, the OX40 agonist antibody comprises a VH sequence of SEQ ID NO:96 and a VL sequence of SEQ ID NO: 97. In some embodiments, the OX40 agonist antibody is MEDI6469, MEDI0562, or MEDI6383.

In some embodiments, the cancer is lung cancer, glioblastoma, cervical cancer, ovarian cancer, breast cancer, colon cancer, colorectal cancer, fallopian tube cancer, peritoneal cancer, kidney cancer, renal cancer, non-Hodgkins lymphoma, prostate cancer, pancreatic cancer, soft-tissue sarcoma, kaposi's sarcoma, carcinoid carcinoma, head and neck cancer, mesothelioma, multiple myeloma, non-small cell lung cancer, neuroblastoma, melanoma, gastric cancer, or liver cancer. In some embodiments, the cancer is a gynecologic cancer. In some embodiments, the cancer is advanced, refractory, recurrent, chemotherapy-resistant, and/or platinum-resistant. In some embodiments, the individual has cancer or has been diagnosed with cancer. In some embodiments, the treatment results in a sustained response in the individual after cessation of the treatment. In some embodiments, the OX40 binding agonist is administered before the anti-angiogenesis agent, simultaneous with the anti-angiogenesis agent, or after the anti-angiogenesis agent. In some embodiments, the individual is a human. In some embodiments, the anti-angiogenesis agent and/or the OX40 binding agonist are administered intravenously, intramuscularly, subcutaneously, intracerobrospinally, topically, orally, transdermally, intraperitoneally, intraorbitally, by implantation, by inhalation, intrathecally, intraventricularly, intra-articularly, intrasynovially or intranasally. In some embodiments, the method further comprises administering a chemotherapeutic agent for treating or delaying progression of cancer.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE FIGURES

(FIG. 3A) Mab 1A7.gr.1 had no effect on T cell proliferation in the absence of crosslinking. Increasing concentration of mab 1A7.gr.1 costimulated CD4+ memory T cell proliferation in response to anti-CD3 crosslinking. The calculated EC50 for the costimulatory effect of mab 1A7.gr. 1 was 9.96 ng/mL (n=2). (FIG. 3B) Increasing concentrations of mab 1A7.gr.1 costimulated CD4+ memory T cell production of interferon gamma in response to anti-CD3 crosslinking.

(FIG. 7A) Treatment with mab 1A7.gr.1 induced ADCC of OX40-expressing T cells. (FIG. 7B) Treatment with mab A7.gr1 (IgG1) induced greater ADCC of OX40-expressing CD4+ T cells compared to level of ADCC induced by mab 1A7.gr1 (IgG4).

FIG. 8A, low OX40 expressing BT474 cells. FIG. 8B, high OX40 expressing BT474 cells.

Figure 11A:
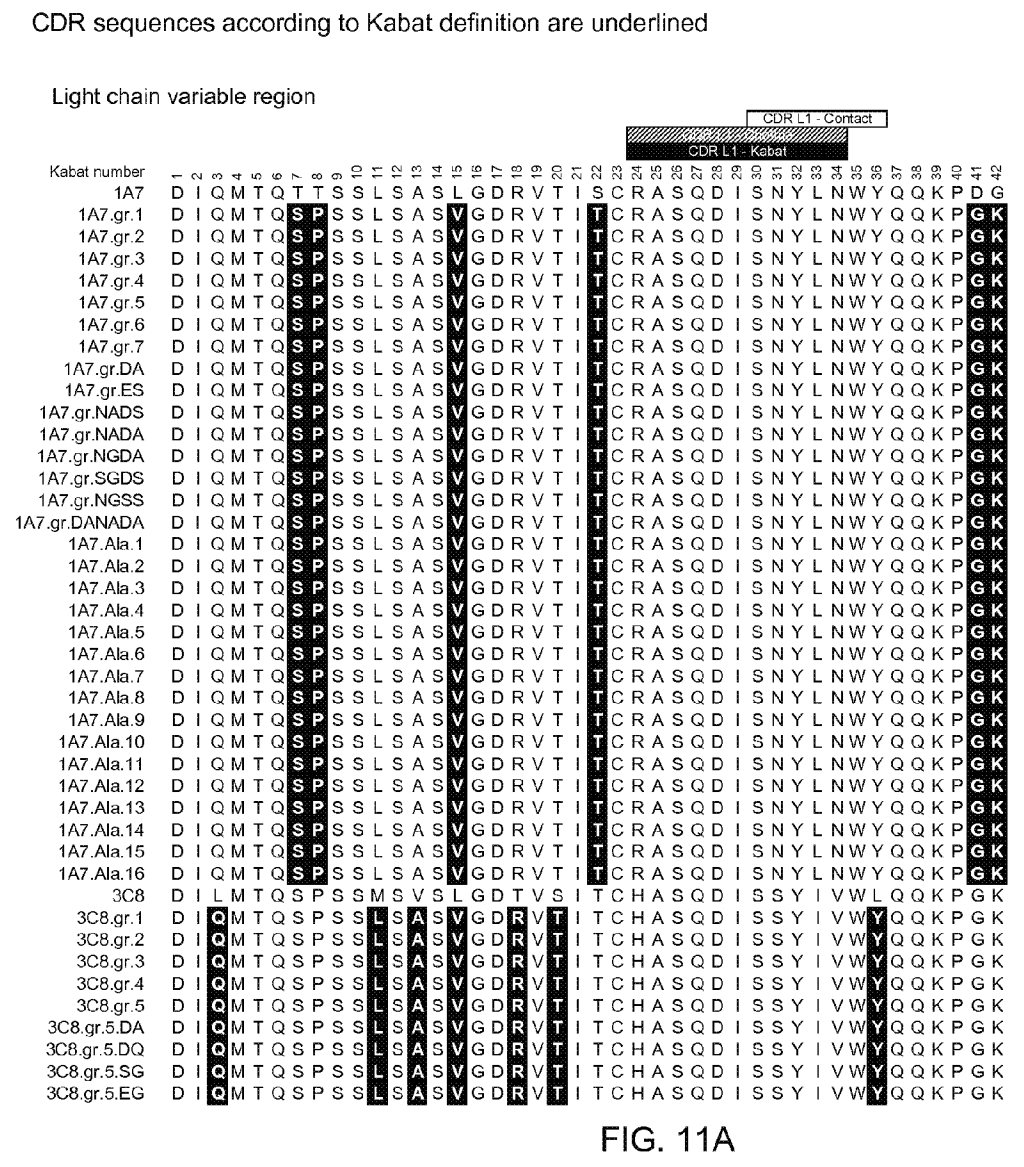
Figure 11B:
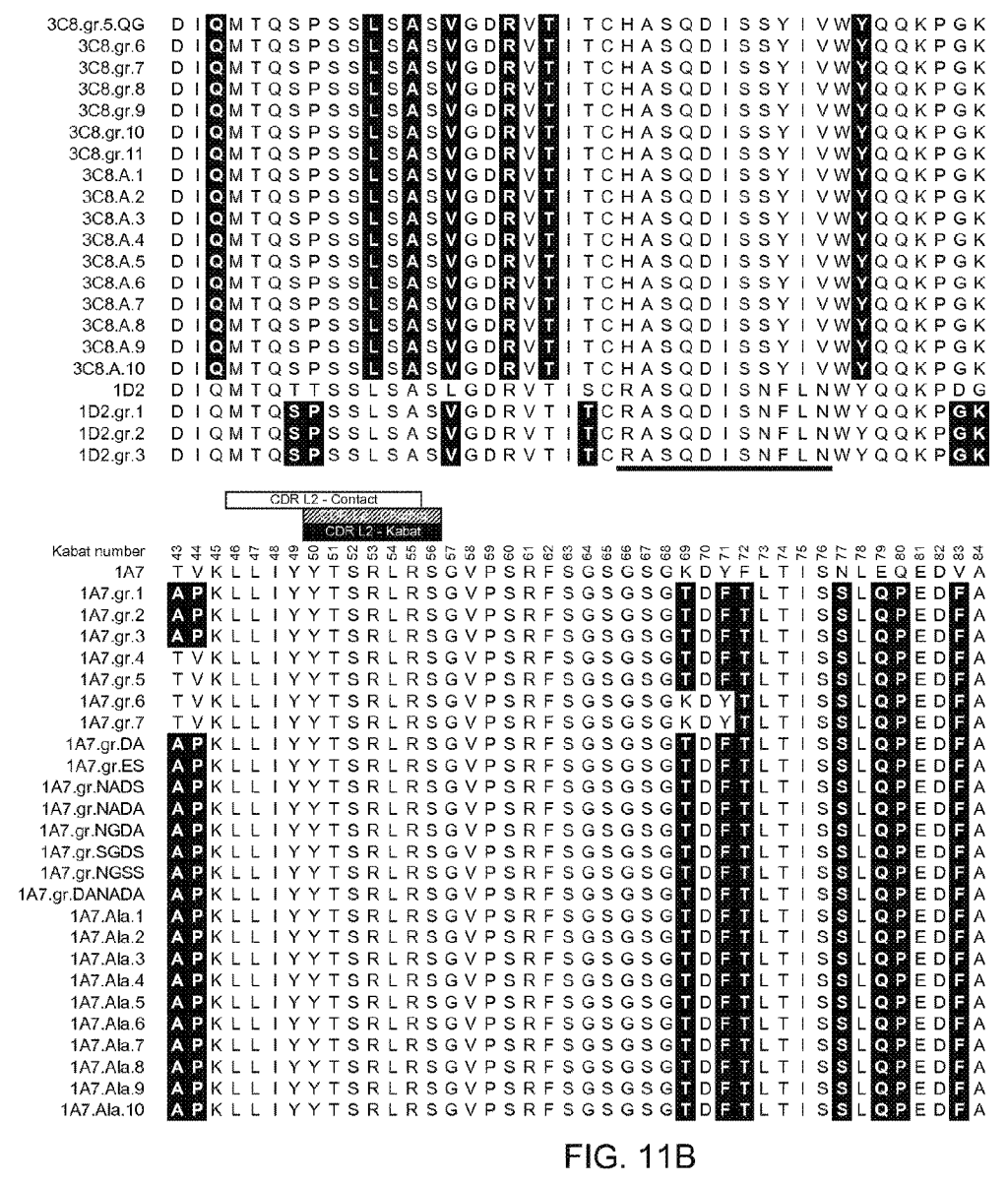
Figure 11E:
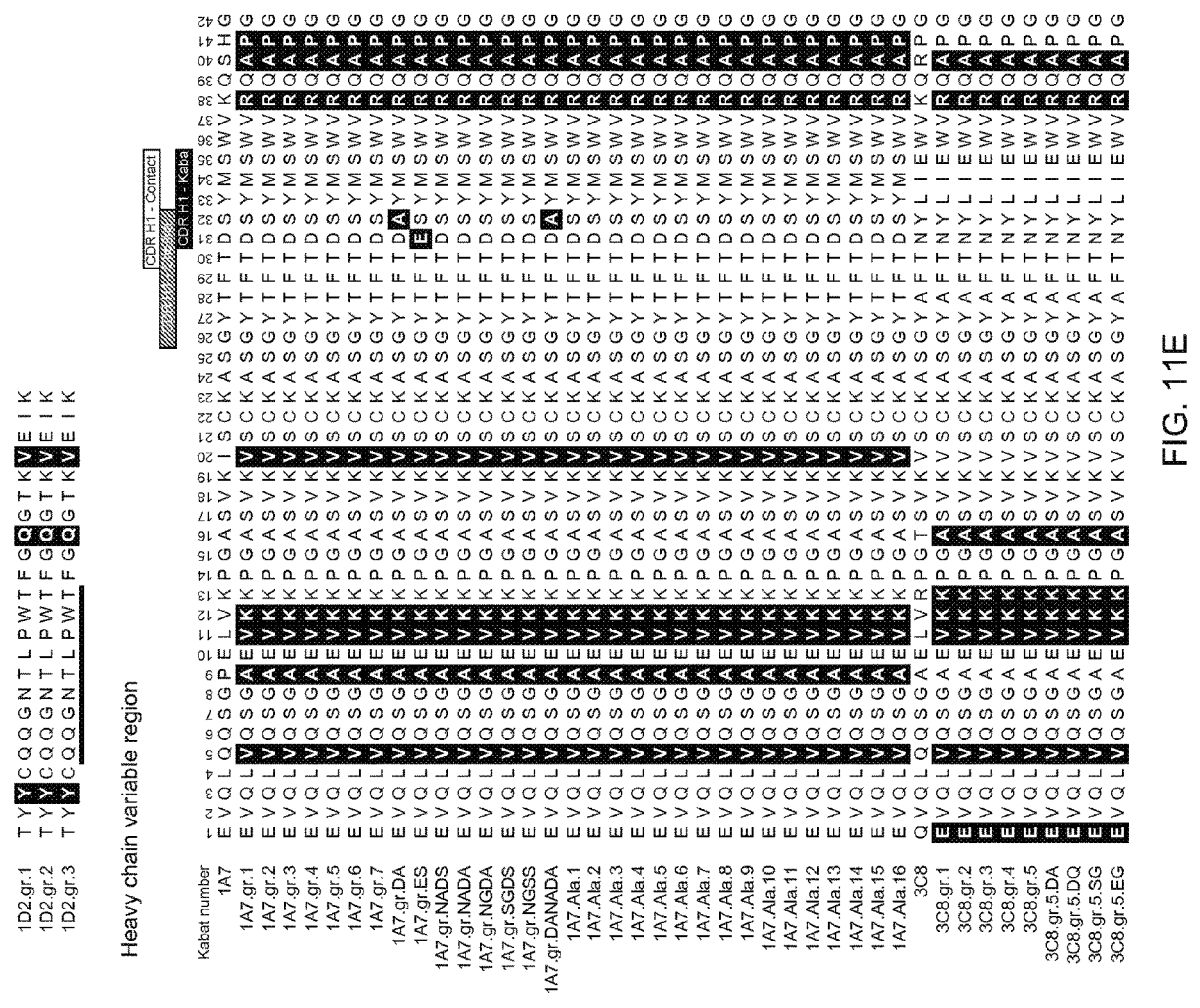
Figure 11F:
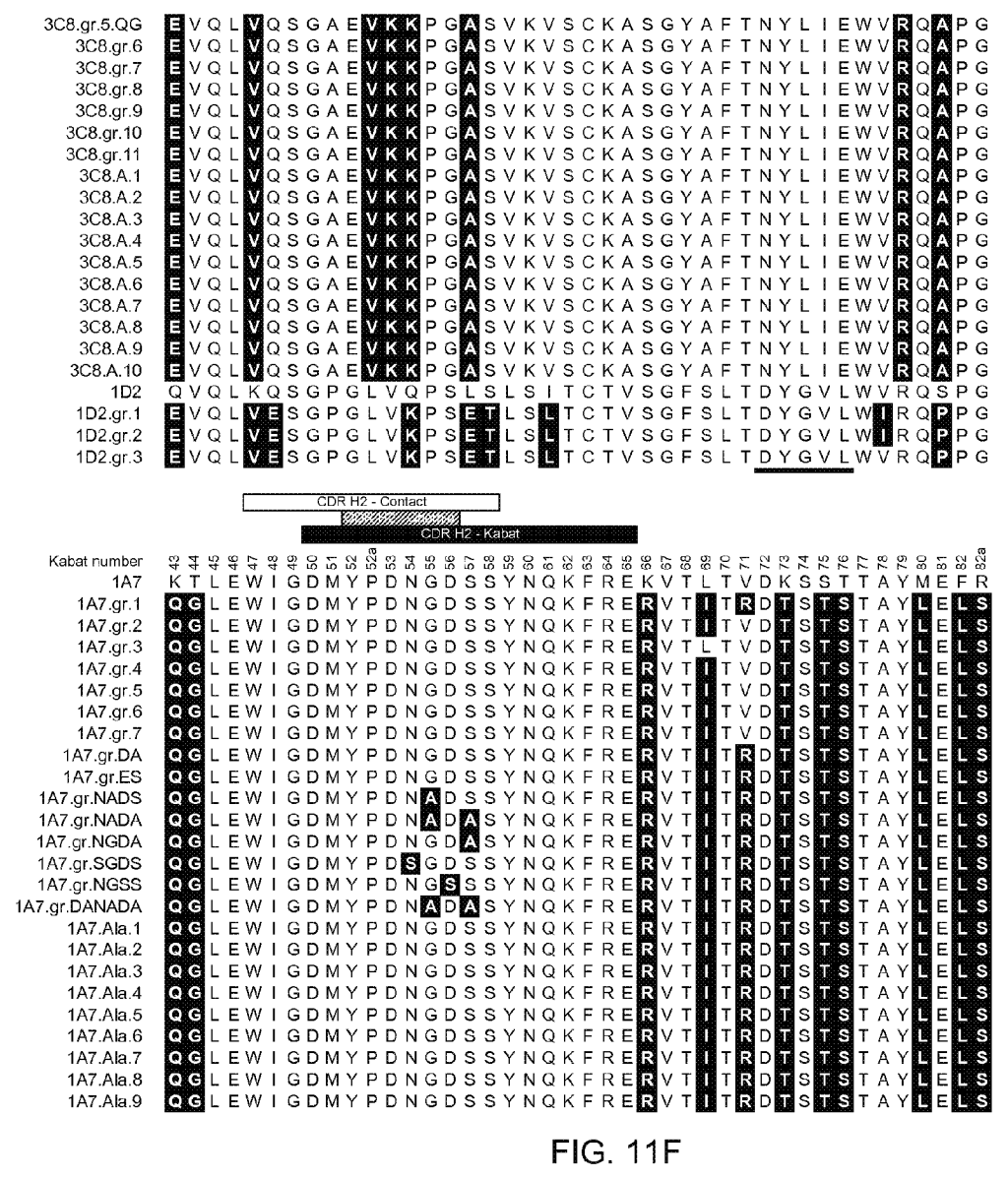
Figure 11H:
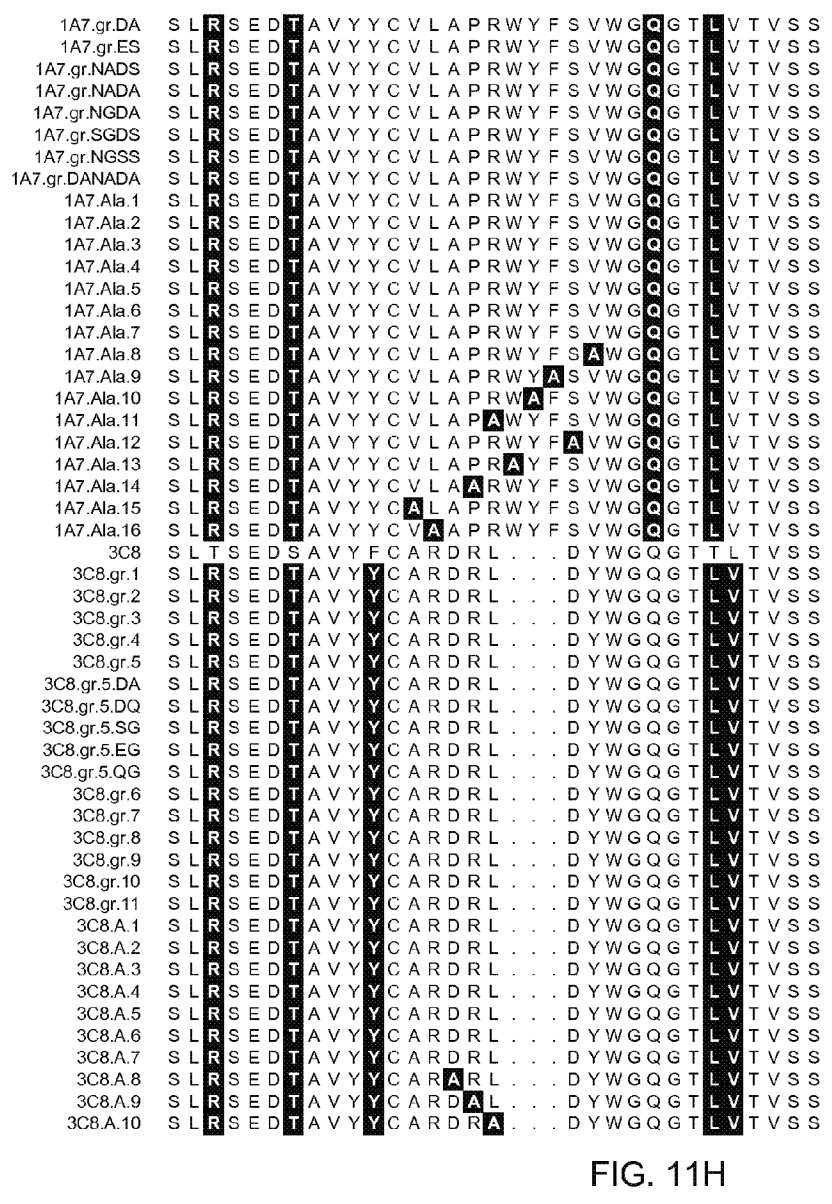

FIGS. 11A-11I: Amino acid sequences of variable regions of anti-OX40 antibodies. Heavy chain HVR-H1, -H2, and -H3, and light chain HVR-L1, -L2, and -L3 sequences are marked. Amino acid positions are numbered according to the Kabat numbering system as described herein. Light chain variable region sequences shown in FIGS. 11A-11E correspond (from top to bottom) with SEQ ID NOs: 179, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 181, 119, 121, 123, 125, 127, 249, 250, 129, 131, 133, 135, 137, 139, 141, 143, 145, 147, 149, 151, 153, 155, 157, 159, 161, 163, 165, 251, 167, 169, and 171, respectively. Heavy chain variable region sequences shown in FIGS. 11E-11I correspond (from top to bottom) with SEQ ID NOs: 180, 56, 58, 60, 62, 64, 66, 68, 70, 74, 76, 78, 80, 82, 84, 86, 88, 90, 92, 94, 96, 98, 100, 102, 104, 106, 108, 110, 112, 114, 116, 182, 118, 120, 122, 124, 126, 252, 253, 128, 130, 132, 134, 136, 138, 140, 142, 144, 146, 148, 150, 152, 154, 156, 158, 160, 162, 164, 254, 166, 168, and 170, respectively.

(FIG. 14A) CRP levels over time observed in monkeys given 0 mg/kg or 0.01 mg/kg doses. (FIG. 14B) CRP levels over time observed in monkeys given 0.3 mg/kg or 10 mg/kg doses.

(FIG. 15A) Levels of pro-inflammatory cytokines IL6 and MCP1 over time. (FIG. 15B) Levels of anti-inflammatory cytokines IL10 and IL1ra over time. In FIGS. 15A and 15B, individual monkeys in the 10 mg/kg dose group that demonstrated transient increases in cytokine levels are labeled with arrows.

(FIG. 16A) Serum PK of monkeys administered 0.01, 0.3, or 10 mg/kg of 1A7.gr1. (FIG. 16B) OX40 receptor occupancy on peripheral CD4+ T cells over time in monkeys administered 0.01, 0.3, or 10 mg/kg of 1A7.gr1.

FIGS. 22A-22D track tumor volumes from individual mice over time in the following treatment groups: anti-GP120 (control; FIG. 22A), anti-VEGF+anti-GP120 (FIG. 22B), anti-OX40+anti-GP120 (FIG. 22C), and anti-VEGF+anti-OX40 (FIG. 22D). Solid black and dashed and dotted lines represent tumors from individual mice within each experimental group. Solid black lines represent mice that remained alive at the termination of the experiment, and dashed and dotted lines represent mice that were euthanized prior to experiment termination due to tumor ulceration or tumor size exceeding 2000 mm$^3$. Evenly dashed lines depict the average tumor volume over time in mice that received anti-GP120 alone (as labeled by arrows). Unevenly dashed lines are representative of the average tumor volume over time within each experimental group (as labeled by arrows). Percentages in top left corner of each individual graph are % tumor growth inhibition (TGI), as judged against mice that received anti-GP120 alone.

FIG. 23A shows increased activation of myeloid dendritic cells (CD11b+). FIG. 23B shows increased activation of non-myeloid dendritic cells (CD11b−). Asterisks indicate statistical significance determined using a Student's t-test, assuming unequal variance and a significance level of 0.05 (* indicates $p<0.05$).

DETAILED DESCRIPTION OF EMBODIMENTS OF THE INVENTION

Figure 1:
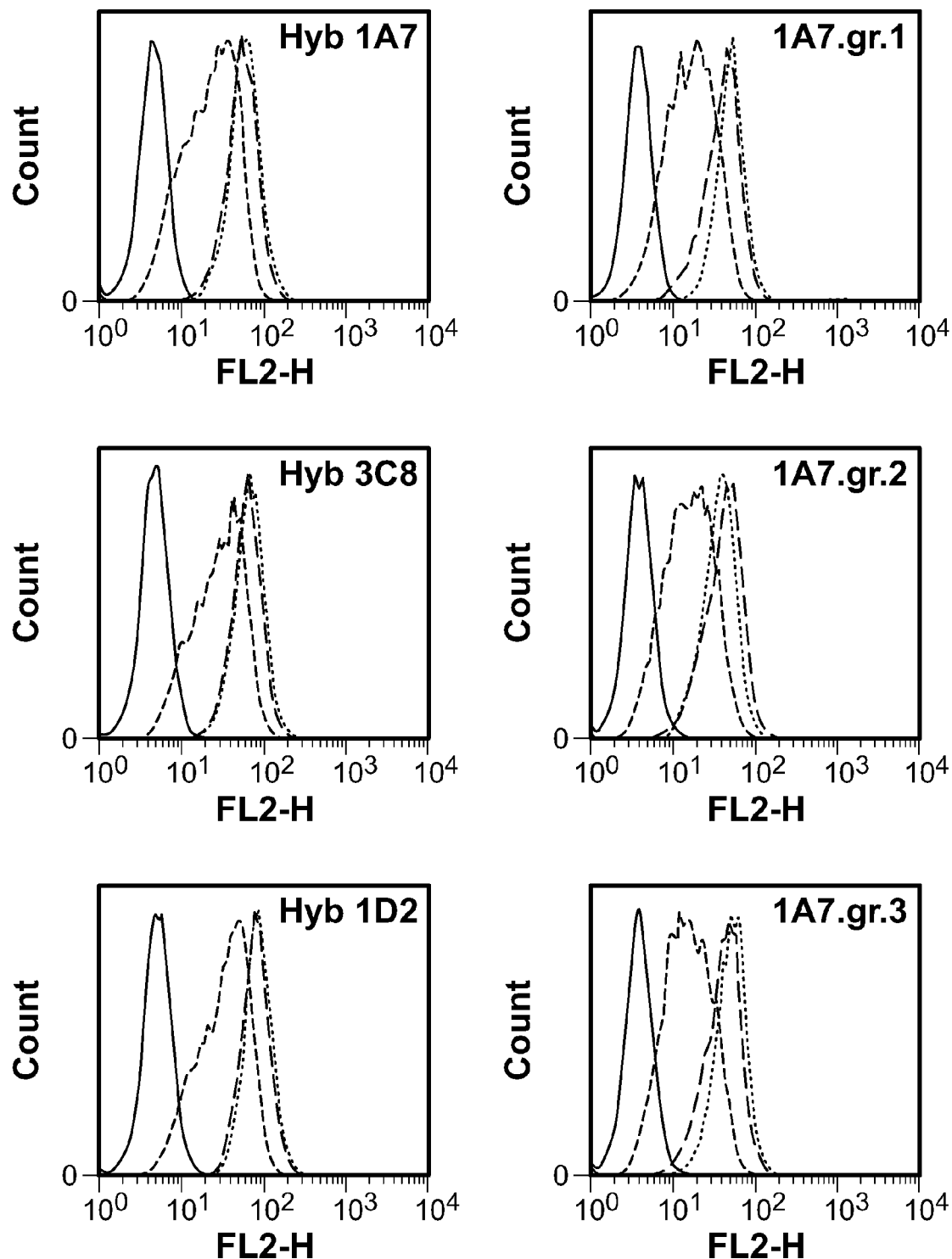
FIG. 1: Humanized OX40 antibody variants were analyzed by FACS to evaluate antibody binding to huOX40 expressed on the surface of Hut78 cells.
Figure 1:
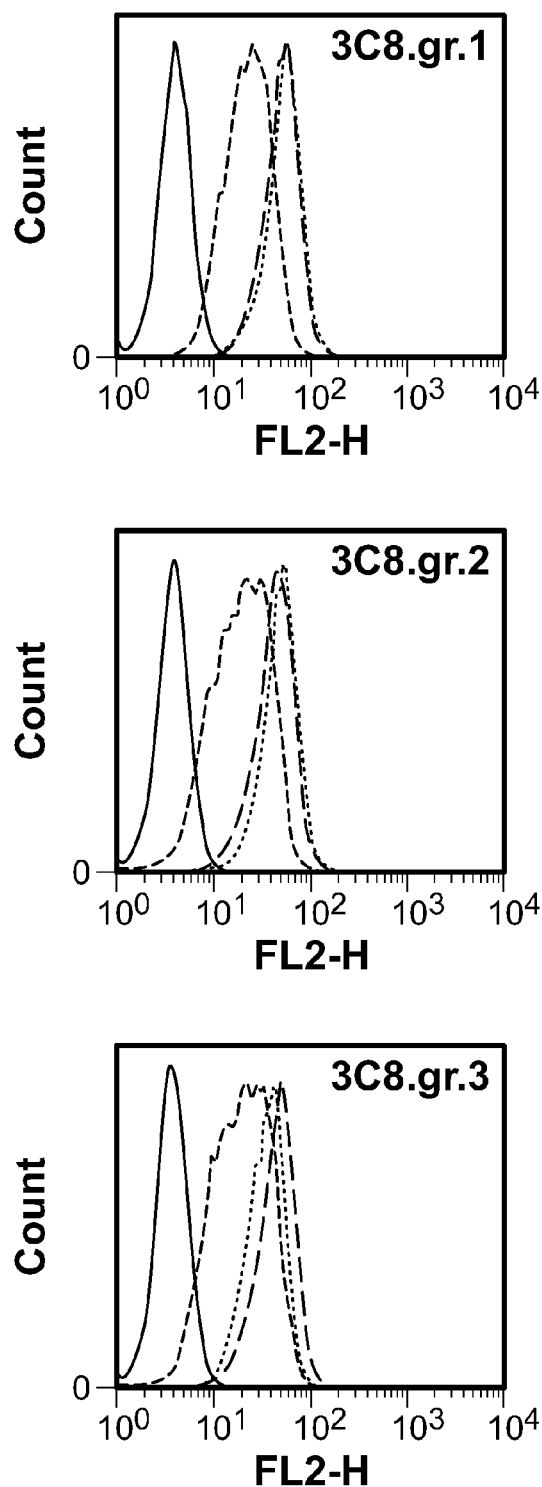

In one aspect, provided herein are isolated antibodies that bind to human OX40 (e.g., anti-human OX40 agonist antibodies wherein the antibody depletes cells that express human OX40 in vitro and binds human OX40 with an affinity of less than or equal to about 1 nM), as well as methods of production, methods of use, formulations and other compositions, and kits or articles of manufacture related thereto.

In another aspect, provided herein are methods, compositions and uses for treating or delaying progression of cancer in an individual comprising administering an effective amount of an anti-angiogenesis agent and an OX40 binding agonist.

I. Definitions

The term "dysfunction" in the context of immune dysfunction, refers to a state of reduced immune responsiveness to antigenic stimulation.

The term "dysfunctional", as used herein, also includes refractory or unresponsive to antigen recognition, specifically, impaired capacity to translate antigen recognition into downstream T-cell effector functions, such as proliferation, cytokine production (e.g., gamma interferon) and/or target cell killing.

"Enhancing T cell function" means to induce, cause or stimulate an effector or memory T cell to have a renewed, sustained or amplified biological function. Examples of enhancing T-cell function include: increased secretion of γ-interferon from CD8+ effector T cells, increased secretion of γ-interferon from CD4+ memory and/or effector T-cells, increased proliferation of CD4+ effector and/or memory T cells, increased proliferation of CD8+ effector T-cells, increased antigen responsiveness (e.g., clearance), relative to such levels before the intervention. In one embodiment, the level of enhancement is at least 50%, alternatively 60%, 70%, 80%, 90%, 100%, 120%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenicity" refers to the ability of a particular substance to provoke an immune response. Tumors are immunogenic and enhancing tumor immunogenicity aids in the clearance of the tumor cells by the immune response.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "agonist antibody," as used herein, is an antibody which activates a biological activity of the antigen it binds.

An "anti-angiogenic agent" refers to a compound which blocks, or interferes with to some degree, the development of blood vessels. An anti-angiogenic agent may, for instance, be a small molecule or antibody that binds to a growth factor or growth factor receptor involved in promoting angiogenesis. In one embodiment, an anti-angiogenic agent is an antibody that binds to vascular endothelial growth factor (VEGF), such as bevacizumab (AVASTIN).

"Antibody-dependent cell-mediated cytotoxicity" or "ADCC" refers to a form of cytotoxicity in which secreted immunoglobulin bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998). An exemplary assay for assessing ADCC activity is provided in the examples herein.

The terms "anti-OX40 antibody" and "an antibody that binds to OX40" refer to an antibody that is capable of binding OX40 with sufficient affinity such that the antibody is useful as a diagnostic and/or therapeutic agent in targeting OX40. In one embodiment, the extent of binding of an anti-OX40 antibody to an unrelated, non-OX40 protein is less than about 10% of the binding of the antibody to OX40 as measured, e.g., by a radioimmunoassay (RIA). In certain embodiments, an antibody that binds to OX40 has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-OX40 antibody binds to an epitope of OX40 that is conserved among OX40 from different species.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "binding domain" refers to the region of a polypeptide that binds to another molecule. In the case of an FcR, the binding domain can comprise a portion of a polypeptide chain thereof (e.g. the alpha chain thereof) which is responsible for binding an Fc region. One useful binding domain is the extracellular domain of an FcR alpha chain.

A polypeptide with a variant IgG Fc with "altered" FcR, ADCC or phagocytosis activity is one which has either enhanced or diminished FcR binding activity (e.g., FcγR) and/or ADCC activity and/or phagocytosis activity compared to a parent polypeptide or to a polypeptide comprising a native sequence Fc region.

The term "OX40," as used herein, refers to any native OX40 from any vertebrate source, including mammals such as primates (e.g. humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary human OX40 is shown in SEQ ID NO: 1.

"OX40 activation" refers to activation, of the OX40 receptor. Generally, OX40 activation results in signal transduction.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B-cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In certain embodiments, cancers that are amenable to treatment by the antibodies of the invention include breast cancer, colorectal cancer, rectal cancer, non-small cell lung cancer, glioblastoma, non-Hodgkins lymphoma (NHL), renal cell cancer, prostate cancer, liver cancer, pancreatic cancer, soft-tissue sarcoma, kaposi's sarcoma, carcinoid carcinoma, head and neck cancer, ovarian cancer, mesothelioma, and multiple myeloma. In some embodiments, the cancer is selected from: non-small cell lung cancer, glioblastoma, neuroblastoma, melanoma, breast carcinoma (e.g. triple-negative breast cancer), gastric cancer, colorectal cancer (CRC), and hepatocellular carcinoma. Yet, in some embodiments, the cancer is selected from: non-small cell lung cancer, colorectal cancer, glioblastoma and breast carcinoma (e.g. triple-negative breast cancer), including metastatic forms of those cancers.

The terms "cell proliferative disorder" and "proliferative disorder" refer to disorders that are associated with some degree of abnormal cell proliferation. In one embodiment, the cell proliferative disorder is cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J Immunol.* 164: 4178-4184 (2000).

The term "cytostatic agent" refers to a compound or composition which arrests growth of a cell either in vitro or in vivo. Thus, a cytostatic agent may be one which significantly reduces the percentage of cells in S phase. Further examples of cytostatic agents include agents that block cell cycle progression by inducing G0/G1 arrest or M-phase arrest. The humanized anti-Her2 antibody trastuzumab (HERCEPTIN®) is an example of a cytostatic agent that induces G0/G1 arrest. Classical M-phase blockers include the vincas (vincristine and vinblastine), taxanes, and topoisomerase II inhibitors such as doxorubicin, epirubicin, daunorubicin, etoposide, and bleomycin. Certain agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., *The Molecular Basis of Can-* cer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anti-cancer agents disclosed below.

A "depleting anti-OX40 antibody," is an anti-OX40 antibody that kills or depletes OX40-expressing cells. Depletion of OX40 expressing cells can be achieved by various mechanisms, such as antibody-dependent cell-mediated cytotoxicity and/or phagocytosis. Depletion of OX40-expressing cells may be assayed in vitro, and exemplary methods for in vitro ADCC and phagocytosis assays are provided herein. In some embodiments, the OX40-expressing cell is a human CD4+ effector T cell. In some embodiments, the OX40-expressing cell is a transgenic BT474 cell that expresses human OX40.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daeron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8): 6213-6216 (2004); WO 2004/92219 (Hinton et al.). Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

"Human effector cells" refer to leukocytes that express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:
(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));
(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest,* 5th Ed. Public Health Service, National Institutes of Health, Bethesda, Md. (1991));
(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and
(d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3). Unless otherwise indicated, HVR residues and other residues in the variable domain (e.g., FR residues) are numbered herein according to Kabat et al., supra.

In one embodiment, HVR residues comprise those identified in FIGS. 11A-I or elsewhere in the specification.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

"Promoting cell growth or proliferation" means increasing a cell's growth or proliferation by at least 10%, 20%, 30%, 40%, 50%, 60%, 70%, 80%, 90%, 95%, or 100%.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-OX40 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain. A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVES-GGGLVQPGGSLRLSCAAS (SEQ ID NO:222)-H1-WVRQAPGKGLEWV (SEQ ID NO:223)-H2-RFTISRDN-SKNTLYLQMNSLRAEDTAVYYC (SEQ ID NO:224)-H3-WGQGTLVTVSS (SEQ ID NO:225).

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

```
                                    (SEQ ID NO: 226)
DIQMTQSPSSLSASVGDRVTITC (SEQ ID NO: 227)
L1-WYQQKPGKAPKLLIY (SEQ ID NO: 228)
L2-GVPSRFSGSGSGTDFTLTISSLQPEDFATYYC (SEQ ID NO: 229)
L3-FGQGTKVEIK.
```

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signalling inhibitors; HDAC inhibitors, proteasome inhibitors; and inhibitors of cancer metabolism.

In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signalling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine (e.g., erlotinib). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) antiandrogens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6 [5 [[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-MI prime; Secreted homotrimeric LTa3 and membrane bound heterotrimer LTal/ 32 blockers such as Anti-lymphotoxin alpha (LTa); radioactive isotopes (e.g., At211, 1131, 1125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASARTM); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

The term "cytokine" is a generic term for proteins released by one cell population that act on another cell as intercellular mediators. Examples of such cytokines are lymphokines, monokines; interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL) and gamma interferon. As used herein, the term cytokine includes proteins from natural sources or from recombinant cell culture and biologically active equivalents of the native-sequence cytokines, including synthetically produced small-molecule entities and pharmaceutically acceptable derivatives and salts thereof.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1 106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1 105 described herein. In still another specific aspect, an anti-PD-L1 antibody is MPDL3280A described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "phagocytosis" means the internalization of cells or particulate matter by cells. In some embodiments, the phagocytic cells or phagocytes are macrophages or neutrophils. In some embodiments, the cells are cells that express human OX40. Methods for assaying phagocytosis are known in the art and include use of microscopy to detect the presence of cells internalized within another cells. In other embodiments, phagocytosis is detected using FACS, e.g., by detecting presence of a detectably labeled cell within another cell (which may be detectably labeled, e.g., with a different label than the first cell).

The phrase "does not possess substantial activity" or "substantially no activity" with respect to an antibody, as used herein, means the antibody does not exhibit an activity that is above background level (in some embodiments, that is above background level that is statistically significant). The phrase "little to no activity" with respect to an antibody, as used herein, means the antibody does not display a biologically meaningful amount of a function. The function can be measured or detected according to any assay or technique known in the art, including, e.g., those described herein. In some embodiments, antibody function is stimulation of effector T cell proliferation and/or cytokine secretion.

The term "biomarker" or "marker" as used herein refers generally to a molecule, including a gene, mRNA, protein, carbohydrate structure, or glycolipid, the expression of which in or on a tissue or cell or secreted can be detected by known methods (or methods disclosed herein) and is predictive or can be used to predict (or aid prediction) for a cell, tissue, or patient's responsiveness to treatment regimes.

By "patient sample" is meant a collection of cells or fluids obtained from a cancer patient. The source of the tissue or cell sample may be solid tissue as from a fresh, frozen and/or preserved organ or tissue sample or biopsy or aspirate; blood or any blood constituents; bodily fluids such as cerebrospinal fluid, amniotic fluid, peritoneal fluid, or interstitial fluid; cells from any time in gestation or development of the subject. The tissue sample may contain compounds which are not naturally intermixed with the tissue in nature such as preservatives, anticoagulants, buffers, fixatives, nutrients, antibiotics, or the like. Examples of tumor samples herein include, but are not limited to, tumor biopsy, fine needle aspirate, bronchiolar lavage, pleural fluid, sputum, urine, a surgical specimen, circulating tumor cells, serum, plasma, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

The phrase "based on expression of" when used herein means that information about expression level or presence or absence of expression (e.g., presence or absence or prevalence of (e.g., percentage of cells displaying) of the one or more biomarkers herein (e.g., presence or absence of or amount or prevalence of FcR-expressing cells, or e.g., presence or absence or amount or prevalence of human effector cells) is used to inform a treatment decision, information provided on a package insert, or marketing/promotional guidance etc.

A cancer or biological sample which "has human effector cells" is one which, in a diagnostic test, has human effector cells present in the sample (e.g., infiltrating human effector cells).

A cancer or biological sample which "has FcR-expressing cells" is one which, in a diagnostic test, has FcR-expressing present in the sample (e.g., infiltrating FcR-expressing cells). In some embodiments, FcR is FcγR. In some embodiments, FcR is an activating FcγR.

The phrase "recommending a treatment" as used herein refers to using the information or data generated relating to the level or presence of c-met in a sample of a patient to identify the patient as suitably treated or not suitably treated with a therapy. In some embodiments the therapy may comprise c-met antibody (e.g., onartuzumab). In some embodiments, the therapy may comprise VEGF antagonist (e.g., bevacizumab). In some embodiments, the therapy may comprise anti-human OX40 agonist antibody. The information or data may be in any form, written, oral or electronic. In some embodiments, using the information or data generated includes communicating, presenting, reporting, storing, sending, transferring, supplying, transmitting, delivering, dispensing, or combinations thereof. In some embodiments, communicating, presenting, reporting, storing, sending, transferring, supplying, transmitting, delivering, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by an individual (e.g., a laboratory or medical professional). In some embodiments, the information or data includes a comparison of the amount or prevalence of FcR expressing cells to a reference level. In some embodiments, the information or data includes a comparison of the amount or prevalence of human effector cells to a reference level. In some embodiments, the information or data includes an indication that human effector cells or FcR-expressing cells are present or absent in the sample. In some embodiments, the information or data includes an indication that FcR-expressing cells and/or human effector cells are present in a particular percentage of cells (e.g., high prevalence). In some embodiments, the information or data includes an indication that the patient is suitably treated or not suitably treated with a therapy comprising anti-human OX40 agonist antibody.

II. Compositions and Methods

In one aspect, the invention is based, in part, on identification of a variety of OX40 binding agents. In certain embodiments, antibodies (e.g., agonist antibodies) that bind to human OX40 are provided. Antibodies of the invention are useful, e.g., for the diagnosis or treatment of cancer and other disorders associated with OX40 expression and/or activity.

A. Exemplary Anti-OX40 Antibodies

In one aspect, the invention provides isolated antibodies that bind to human OX40.

In some embodiments, the anti-human OX40 agonist antibody binds human OX40 with an affinity of less than or equal to about 0.45 nM. In some embodiments, the OX40 agonist antibody binds human OX40 with an affinity of less than or equal to about 1 nM. In some embodiments, the anti-human OX40 antibody binds human OX40 with an affinity of less than or equal to about 0.4 nM. In some embodiments, the anti-human OX40 antibody binds human OX40 with an affinity of less than or equal to about 0.5 nM. In some embodiments, the binding affinity is determined using radioimmunoassay.

In some embodiments, the anti-human OX40 agonist antibody binds human OX40 and cynomolgus OX40. In some embodiments, binding is determined using a FACS assay. In some embodiments, binding to human OX40 has an EC50 of about 0.2 ug/ml. In some embodiments, binding to human OX40 has an EC50 of about 0.3 ug/ml or lower.

In some embodiments, binding to cynomolgus OX40 has an EC50 of about 1.5 ug/ml. In some embodiments, binding to cynomolgus OX40 has an EC50 of about 1.4 ug/ml.

In some embodiments, the anti-human OX40 agonist antibody does not bind to rat OX40 or mouse OX40.

In some embodiments, the anti-human OX40 agonist antibody is a depleting anti-human OX40 antibody (e.g., depletes cells that express human OX40). In some embodiments, the OX40 agonist antibody depletes cells that express human OX40 in vitro. In some embodiments, the human OX40 expressing cells are CD4+ effector T cells. In some embodiments, the human OX40 expressing cells are Treg cells. In some embodiments, depleting is by ADCC and/or phagocytosis. In some embodiments, the antibody mediates ADCC by binding FcγR expressed by a human effector cell and activating the human effector cell function. In some embodiments, the antibody mediates phagocytosis by binding FcγR expressed by a human effector cell and activating the human effector cell function. Exemplary human effector cells include, e.g., macrophage, natural killer (NK) cells, monocytes, neutrophils. In some embodiments, the human effector cell is macrophage. In some embodiments, the human effector cell is NK cells. In some embodiments, depletion is not by apoptosis.

In some embodiments, the anti-human OX40 agonist antibody has a functional Fc region. In some embodiments, effector function of a functional Fc region is ADCC. In some embodiments, effector function of a functional Fc region is phagocytosis. In some embodiments, effector function of a functional Fc region is ADCC and phagocytosis. In some embodiments, the Fc region is human IgG1. In some embodiments, the Fc region is human IgG4.

In some embodiments, the anti-human OX40 agonist antibody does not induce apoptosis in OX40-expressing cells (e.g., Treg). In some embodiments, apoptosis is assayed using an antibody concentration of 30 ug/ml, e.g., by determining whether apoptosis has occurred using annexin V and proprodium iodide stained Treg.

In some embodiments, the anti-human OX40 agonist antibody enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody). In some embodiments, the cytokine is gamma interferon. In some embodiments, the anti-human OX40 agonist antibody increases number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with anti-human OX40 agonist antibody. In some embodiments, the anti-human OX40 agonist antibody increases number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment with anti-human OX40 agonist antibody.

In some embodiments, the anti-human OX40 agonist antibody increases number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+T effector cells prior to treatment with anti-human OX40 agonist antibody. In some embodiments, the anti-human OX40 agonist antibody increases number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human OX40 agonist antibody.

In some embodiments, the anti-human OX40 agonist antibody enhances memory T cell function, for example by increasing memory T cell proliferation and/or increasing cytokine production by the memory cell. In some embodiments, the cytokine is gamma interferon.

In some embodiments, the anti-human OX40 agonist antibody inhibits Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the anti-human OX40 agonist antibody reduces the number of intratumoral (infiltrating) Treg (e.g., total number of Treg or e.g., percentage of Fox3p+ cells in CD4+ cells).

In some embodiments, the anti-human OX40 agonist antibody is engineered to increase effector function (e.g., compared to effector function in a wild-type IgG1). In some embodiments, the antibody has increased binding to a Fcγ receptor. In some embodiments, the antibody lacks fucose attached (directly or indirectly) to the Fc region. For example, the amount of fucose in such antibody may be from 1% to 80%, from 1% to 65%, from 5% to 65% or from 20% to 40%. In some embodiments, the Fc region comprises bisected oligosaccharides, e.g., in which a biantennary oligosaccharide attached to the Fc region of the antibody is bisected by GlcNAc. In some embodiments, the antibody comprises an Fc region with one or more amino acid substitutions which improve ADCC, e.g., substitutions at positions 298, 333, and/or 334 of the Fc region (EU numbering of residues).

In some embodiments, the anti-human OX40 agonist antibody increases OX40 signal transduction in a target cell that expresses OX40. In some embodiments, OX40 signal transduction is detected by monitoring NFkB downstream signaling.

In some embodiments, the anti-human OX40 agonist antibody is stable after treatment at 40° C. for two weeks.

In some embodiments, the anti-human OX40 agonist antibody binds human effector cells, e.g., binds FcγR (e.g., an activating FcγR) expressed by human effector cells. In some embodiments, the human effector cell performs (is capable of performing) ADCC effector function. In some embodiments, the human effector cell performs (is capable of performing) phagocytosis effector function.

In some embodiments, the anti-human OX40 agonist antibody comprising a variant IgG1 Fc polypeptide comprising a mutation that eliminates binding to human effector cells (e.g., a DANA mutation) has diminished activity (e.g., CD4+ effector T cell function, e.g., proliferation), relative to anti-human OX40 agonist antibody comprising native sequence IgG1 Fc portion. In some embodiment, the anti-human OX40 agonist antibody comprising a variant IgG1 Fc polypeptide comprising a mutation that eliminates binding to human effector cells (e.g., a DANA mutation) does not possess substantial activity (e.g., CD4+ effector T cell function, e.g., proliferation).

In some embodiments, antibody cross-linking is required for anti-human OX40 agonist antibody function. In some embodiments, function is stimulation of CD4+ effector T cell proliferation. In some embodiments, antibody crosslinking is determined by providing anti-human OX40 agonist antibody adhered on a solid surface (e.g., a cell culture plate). In some embodiments, antibody cross-linking is determined by introducing a mutation in the antibody's IgG1 Fc portion (e.g., a DANA mutation) and testing function of the mutant antibody.

In some embodiments, the anti-human OX40 agonist antibody competes for binding to human OX40 with OX40L. In some embodiments, addition of OX40L does not enhance anti-human OX40 antibody function in an in vitro assay.

According to another embodiment, the anti-human OX40 agonist antibodies include any one, any combination, or all of the following properties: (1) binds human OX40 with an affinity of less than or equal to about 0.45 nM, in some embodiments, binds human OX40 with an affinity of less than or equal to about 0.4 nM, in some embodiments, binds human OX40 with an affinity of less than or equal to about 0.5 nM, in some embodiments, the binding affinity is determined using radioimmunoassay; (2) binds human OX40 and cynomolgus OX40, in some embodiments, binding is determined using a FACS assay, (3) binds human OX40 with an EC50 of about 0.2 ug/ml, in some embodiments, binds to human OX40 has an EC50 of about 0.3 ug/ml or lower, in some embodiments, binds to cynomolgus OX40 with an EC50 of about 1.5 ug/ml, in some embodiments, binds to cynomolgus OX40 has an EC50 of about 1.4 ug/ml, (4) does not substantially bind to rat OX40 or mouse OX40, (6) is a depleting anti-human OX40 antibody (e.g., depletes cells that express human OX40), in some embodiments, the cells are CD4+ effector T cells and/or Treg cells, (7) enhances CD4+ effector T cell function, for example, by increasing CD4+ effector T cell proliferation and/or increasing gamma interferon production by the CD4+ effector T cell (for example, as compared to proliferation and/or cytokine production prior to treatment with anti-human OX40 agonist antibody), (8) enhances memory T cell function, for example by increasing memory T cell proliferation and/or increasing cytokine production by the memory cell, (9) inhibits Treg function, for example, by decreasing Treg suppression of effector T cell function (e.g., effector T cell proliferation and/or effector T cell cytokine secretion). In some embodiments, the effector T cell is a CD4+ effector T cell, (10) increases OX40 signal transduction in a target cell that expresses OX40 (in some embodiments, OX40 signal transduction is detected by monitoring NFkB downstream signaling), (11) is stable after treatment at 40° C. for two weeks, (12) binds human effector cells, e.g., binds FcγR expressed by human effector cells, (13) anti-human OX40 agonist antibody comprising a variant IgG1 Fc polypeptide comprising a mutation that eliminates binding to human effector cells (e.g., N297G) has diminished activity (e.g., CD4+ effector T cell function, e.g., proliferation), relative to anti-human OX40 agonist antibody comprising native sequence IgG1 Fc portion, in some embodiment, the anti-human OX40 agonist antibody comprising a variant IgG1 Fc polypeptide comprising a mutation that eliminates binding to human effector cells (e.g., N297G) does not possess substantial activity (e.g., CD4+ effector T cell function, e.g., proliferation), (14) antibody cross-linking (e.g., by Fc receptor binding) is required for anti-human OX40 agonist antibody function.

In one aspect, the invention provides an anti-human OX40 agonist antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7.

In one aspect, the invention provides an anti-human OX40 agonist antibody comprising at least one, at least two, or all three VH HVR sequences selected from (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4. In one embodiment, the antibody comprises HVR-H3 comprising the amino acid sequence of SEQ ID NO:4. In another embodiment, the antibody comprises HVR-H3 comprising the amino acid sequence of SEQ ID NO:4 and HVR-L3 comprising the amino acid sequence of SEQ ID NO:7. In a further embodiment, the antibody comprises HVR-H3 comprising the amino acid sequence of SEQ ID NO:4, HVR-L3 comprising the amino acid sequence of SEQ ID NO:7, and HVR-H2 comprising the amino acid sequence of SEQ ID NO:3. In a further embodiment, the antibody comprises (a) HVR-H1 comprising the amino acid sequence of SEQ ID NO:2; (b) HVR-H2 comprising the amino acid sequence of SEQ ID NO:3; and (c) HVR-H3 comprising the amino acid sequence of SEQ ID NO:4.

In another aspect, the invention provides an anti-human OX40 agonist antibody comprising at least one, at least two, or all three VL HVR sequences selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody of the invention comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7.

In another aspect, the invention provides an anti-human OX40 agonist antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7.

In one aspect, the invention provides an anti-human OX40 agonist antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:26.

In another embodiment, the antibody comprises HVR-H3 comprising the amino acid sequence of SEQ ID NO:4 and HVR-L3 comprising the amino acid sequence of SEQ ID NO:26. In a further embodiment, the antibody comprises HVR-H3 comprising the amino acid sequence of SEQ ID NO:4, HVR-L3 comprising the amino acid sequence of SEQ ID NO:26, and HVR-H2 comprising the amino acid sequence of SEQ ID NO:3.

In another aspect, an antibody of the invention comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:26.

In another aspect, the invention provides an antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:26.

In one aspect, the invention provides an anti-human OX40 agonist antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:27.

In another embodiment, the antibody comprises HVR-H3 comprising the amino acid sequence of SEQ ID NO:4 and HVR-L3 comprising the amino acid sequence of SEQ ID NO:27. In a further embodiment, the antibody comprises HVR-H3 comprising the amino acid sequence of SEQ ID NO:4, HVR-L3 comprising the amino acid sequence of SEQ ID NO:27, and HVR-H2 comprising the amino acid sequence of SEQ ID NO:3.

In another aspect, an antibody of the invention comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:27.

In another aspect, the invention provides an antibody comprising (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:27.

In one aspect, the invention provides an anti-human OX40 agonist antibody comprising at least one, two, three, four, five, or six HVRs selected from (a) HVR-H1 comprising the amino acid sequence of SEQ ID NO:2, 8 or 9; (b) HVR-H2 comprising the amino acid sequence of SEQ ID NO:3, 10, 11, 12, 13 or 14; (c) HVR-H3 comprising the amino acid sequence of SEQ ID NO:4, 15, or 19; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7, 22, 23, 24, 25, 26, 27, or 28.

In one aspect, the invention provides an antibody comprising at least one, at least two, or all three VH HVR sequences selected from (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19. In one embodiment, the antibody comprises HVR-H3 comprising the amino acid sequence of SEQ ID NO: 4, 15, or 19. In another embodiment, the antibody comprises HVR-H3 comprising the amino acid sequence of SEQ ID NO:4, 15, or 19 and HVR-L3 comprising the amino acid sequence of SEQ ID NO: 7, 22, 23, 24, 25, 26, 27, or 28. In a further embodiment, the antibody comprises HVR-H3 comprising the amino acid sequence of SEQ ID NO: 4, 15, or 19, HVR-L3 comprising the amino acid sequence of SEQ ID NO: 7, 22, 23, 24, 25, 26, 27, or 28, and HVR-H2 comprising the amino acid sequence of SEQ ID NO: 3, 10, 11, 12, 13 or 14. In a further embodiment, the antibody comprises (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; and (c) HVR-H3 comprising the amino acid sequence of SEQ ID NO: 4, 15, or 19.

In another aspect, the invention provides an antibody comprising at least one, at least two, or all three VL HVR sequences selected from (a) HVR-L1 comprising the amino acid sequence of SEQ ID NO: 5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28. In one embodiment, the antibody comprises (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO: 7, 22, 23, 24, 25, 26, 27, or 28.

In another aspect, an antibody of the invention comprises (a) a VH domain comprising at least one, at least two, or all three VH HVR sequences selected from (i) HVR-H1 comprising the amino acid sequence of SEQ ID NO: 2, 8 or 9, (ii) HVR-H2 comprising the amino acid sequence of SEQ ID NO: 3, 10, 11, 12, 13 or 14, and (iii) HVR-H3 comprising an amino acid sequence selected from SEQ ID NO: 4, 15, or 19; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO: 7, 22, 23, 24, 25, 26, 27, or 28.

In another aspect, the invention provides an antibody comprising (a) HVR-H1 comprising the amino acid sequence of SEQ ID NO: 2, 8 or 9; (b) HVR-H2 comprising the amino acid sequence of SEQ ID NO: 3, 10, 11, 12, 13 or 14; (c) HVR-H3 comprising the amino acid sequence of SEQ ID NO: 4, 15, or 19; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO: 7, 22, 23, 24, 25, 26, 27, or 28.

In one aspect, the invention provides an anti-human OX40 agonist antibody comprising at least one, two, three, four, five, or six HVRs selected from (a) HVR-H1 comprising the amino acid sequence of SEQ ID NO: 172; (b) HVR-H2 comprising the amino acid sequence of SEQ ID NO: 173; (c) HVR-H3 comprising the amino acid sequence of SEQ ID NO: 174; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO: 175. In some embodiment, HVR-H2 is not DMYPDAAAASYNQKFRE (SEQ ID NO:230). In some embodiments, HVR-H3 is not APRWAAAA (SEQ ID NO:231). In some embodiments, HVR-L3 is not QAAAAAAAT (SEQ ID NO:232).

In one aspect, the invention provides an antibody comprising at least one, at least two, or all three VH HVR sequences selected from (a) HVR-H1 comprising the amino acid sequence of SEQ ID NO: 172; (b) HVR-H2 comprising the amino acid sequence of SEQ ID NO: 173; and (c) HVR-H3 comprising the amino acid sequence of SEQ ID NO: 174. In one embodiment, the antibody comprises HVR-H3 comprising the amino acid sequence of SEQ ID NO: 174. In another embodiment, the antibody comprises HVR-H3 comprising the amino acid sequence of SEQ ID NO: 174 and HVR-L3 comprising the amino acid sequence of SEQ ID NO: 175. In a further embodiment, the antibody comprises HVR-H3 comprising the amino acid sequence of SEQ ID NO: 174, HVR-L3 comprising the amino acid sequence of SEQ ID NO: 175, and HVR-H2 comprising the amino acid sequence of SEQ ID NO: 173. In a further embodiment, the antibody comprises (a) HVR-H1 comprising the amino acid sequence of SEQ ID NO: 172; (b) HVR-H2 comprising the amino acid sequence of SEQ ID NO: 173; and (c) HVR-H3 comprising the amino acid sequence of SEQ ID NO: 174. In some embodiment, HVR-H2 is not DMYPDAAAASYNQKFRE (SEQ ID NO:230). In some embodiments, HVR-H3 is not APRWAAAA (SEQ ID NO:231). In some embodiments, HVR-L3 is not QAAAAAAAT (SEQ ID NO:232).

In another aspect, the invention provides an antibody comprising (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO: 175. In some embodiments, HVR-L3 is not QAAAAAAAT (SEQ ID NO:232).

In another aspect, an antibody of the invention comprises (a) a VH domain comprising at least one, at least two, or all three VH HVR sequences selected from (i) HVR-H1 comprising the amino acid sequence of SEQ ID NO: 172, (ii) HVR-H2 comprising the amino acid sequence of SEQ ID NO: 173, and (iii) HVR-H3 comprising an amino acid sequence selected from SEQ ID NO: 174; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO: 175.

In another aspect, the invention provides an antibody comprising (a) HVR-H1 comprising the amino acid sequence of SEQ ID NO: 172; (b) HVR-H2 comprising the amino acid sequence of SEQ ID NO: 173; (c) HVR-H3 comprising the amino acid sequence of SEQ ID NO: 174; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO: 175. In some embodiment, HVR-H2 is not DMYPDAAAASYNQKFRE (SEQ ID NO:230). In some embodiments, HVR-H3 is not APRWAAAA (SEQ ID NO:231). In some embodiments, HVR-L3 is not QAAAAAAAT (SEQ ID NO:232).

All possible combinations of the above substitutions are encompassed by the consensus sequences of SEQ ID NO: 172, 173, 174 and 175.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising the amino acid sequence of SEQ ID NO:42.

In one aspect, the invention provides an antibody comprising at least one, at least two, or all three VH HVR sequences selected from (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33. In one embodiment, the antibody comprises HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO:42. In a further embodiment, the antibody comprises HVR-H3 comprising the amino acid sequence of SEQ ID NO:33, HVR-L3 comprising the amino acid sequence of SEQ ID NO:42, and HVR-H2 comprising the amino acid sequence of SEQ ID NO:30. In a further embodiment, the antibody comprises (a) HVR-H1 comprising the amino acid sequence of SEQ ID NO:29; (b) HVR-H2 comprising the amino acid sequence of SEQ ID NO:30; and (c) HVR-H3 comprising the amino acid sequence of SEQ ID NO:33.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:39, and (c) HVR-L3 comprising the amino acid sequence of SEQ ID NO:42.

In another aspect, the invention provides an antibody comprising (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39; and (f) HVR-L3 comprising an amino acid sequence selected from SEQ ID NO:42.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising the amino acid sequence of SEQ ID NO:42.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42. In one embodiment, the antibody comprises (a) HVR-L1 comprising the amino acid sequence of SEQ ID NO:37; (b) HVR-L2 comprising the amino acid sequence of SEQ ID NO:40; and (c) HVR-L3 comprising the amino acid sequence of SEQ ID NO:42.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:40, and (c) HVR-L3 comprising the amino acid sequence of SEQ ID NO:42.

In another aspect, the invention provides an antibody comprising (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:40; and (f) HVR-L3 comprising an amino acid sequence selected from SEQ ID NO:42.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO:39, 40 or 41; and (f) HVR-L3 comprising the amino acid sequence of SEQ ID NO:42, 43, or 44.

In one aspect, the invention provides an antibody comprising at least one, at least two, or all three VH HVR sequences selected from (a) HVR-H1 comprising the amino acid sequence of SEQ ID NO:29; (b) HVR-H2 comprising the amino acid sequence of SEQ ID NO: 30, 31, or 32; and (c) HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO: 42, 43, or 44. In a further embodiment, the antibody comprises HVR-H3 comprising the amino acid sequence of SEQ ID NO:33, HVR-L3 comprising the amino acid sequence of SEQ ID NO: 42, 43, or 44, and HVR-H2 comprising the amino acid sequence of SEQ ID NO: 39, 40 or 41. In a further embodiment, the antibody comprises (a) HVR-H1 comprising the amino acid sequence of SEQ ID NO:29; (b) HVR-H2 comprising the amino acid sequence of SEQ ID NO:30, 31, or 32; and (c) HVR-H3 comprising the amino acid sequence of SEQ ID NO:33.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44. In one embodiment, the antibody comprises (a) HVR-L1 comprising the amino acid sequence of SEQ ID NO:37; (b) HVR-L2 comprising the amino acid sequence of SEQ ID NO: 39, 40 or 41; and (c) HVR-L3 comprising the amino acid sequence of SEQ ID NO: 42, 43, or 44.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO: 30, 31, or 32, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO: 39, 40 or 41, and (c) HVR-L3 comprising the amino acid sequence of SEQ ID NO: 42, 43, or 44.

In another aspect, the invention provides an antibody comprising (a) HVR-H1 comprising the amino acid sequence of SEQ ID NO:29; (b) HVR-H2 comprising the amino acid sequence of SEQ ID NO: 30, 31, or 32; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO: 39, 40 or 41; and (f) HVR-L3 comprising an amino acid sequence selected from SEQ ID NO: 42, 43, or 44.

In one aspect, the invention provides an anti-human OX40 agonist antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO: 175; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO: 177; and (f) HVR-L3 comprising the amino acid sequence of SEQ ID NO: 178.

In one aspect, the invention provides an antibody comprising at least one, at least two, or all three VH HVR sequences selected from (a) HVR-H1 comprising the amino acid sequence of SEQ ID NO:29; (b) HVR-H2 comprising the amino acid sequence of SEQ ID NO: 175; and (c) HVR-H3 comprising the amino acid sequence of SEQ ID NO:33. In another embodiment, the antibody comprises HVR-H3 comprising the amino acid sequence of SEQ ID NO:33 and HVR-L3 comprising the amino acid sequence of SEQ ID NO: 177. In a further embodiment, the antibody comprises HVR-H3 comprising the amino acid sequence of SEQ ID NO:33, HVR-L3 comprising the amino acid sequence of SEQ ID NO: 178, and HVR-H2 comprising the amino acid sequence of SEQ ID NO: 176. In a further embodiment, the antibody comprises (a) HVR-H1 comprising the amino acid sequence of SEQ ID NO:29; (b) HVR-H2 comprising the amino acid sequence of SEQ ID NO: 176; and (c) HVR-H3 comprising the amino acid sequence of SEQ ID NO:33.

In another aspect, the invention provides an antibody comprising at least one, at least two, or all three VL HVR sequences selected from (a) HVR-L1 comprising the amino acid sequence of SEQ ID NO:37; (b) HVR-L2 comprising the amino acid sequence of SEQ ID NO: 177; and (c) HVR-L3 comprising the amino acid sequence of SEQ ID NO: 177. In one embodiment, the antibody comprises (a) HVR-L1 comprising the amino acid sequence of SEQ ID NO:37; (b) HVR-L2 comprising the amino acid sequence of SEQ ID NO: 177; and (c) HVR-L3 comprising the amino acid sequence of SEQ ID NO: 178.

In another aspect, an antibody of the invention comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO: 176, and (iii) HVR-H3 comprising an amino acid sequence selected from SEQ ID NO:33; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO: 177, and (c) HVR-L3 comprising the amino acid sequence of SEQ ID NO: 178.

In another aspect, the invention provides an antibody comprising (a) HVR-H1 comprising the amino acid sequence of SEQ ID NO:29; (b) HVR-H2 comprising the amino acid sequence of SEQ ID NO: 176; (c) HVR-H3 comprising the amino acid sequence of SEQ ID NO:33; (d) HVR-L1 comprising the amino acid sequence of SEQ ID NO:37; (e) HVR-L2 comprising the amino acid sequence of SEQ ID NO: 177; and (f) HVR-L3 comprising an amino acid sequence selected from SEQ ID NO: 178.

In any of the above embodiments, an anti-OX40 agonist antibody is humanized. In one embodiment, an anti-OX40 antibody comprises HVRs as in any of the above embodiments or for any of the embodiments in FIGS. 11A-I, and further comprises an acceptor human framework, e.g. a human immunoglobulin framework or a human consensus framework. In another embodiment, an anti-OX40 antibody comprises HVRs as in any of the above embodiments, and further comprises a VH and/or VL comprising an FR sequence shown in FIGS. 11A-I.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56, 58, 60, 62, 64, 66, 68, 70, 72, 74, 76, 78, 80, 82, 84, 86, 88, 90, 92, 94, 96, 98, 100, 108, 114, 116, 233, or 234. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:56, 58, 60, 62, 64, 66, 68, 70, 72, 74, 76, 78, 80, 82, 84, 86, 88, 90, 92, 94, 96, 98, 100, 108, 114, 116, 233, or 234. In certain embodiments, substitutions, insertions, or deletions occur in regions outside the HVRs (i.e., in the FRs). Optionally, the anti-human OX40 agonist antibody comprises the VH sequence in SEQ ID NO: SEQ ID NO:56, 58, 60, 62, 64, 66, 68, 70, 72, 74, 76, 78, 80, 82, 84, 86, 88, 90, 92, 94, 96, 98, 100, 108, 114, 116, 233, or 234, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57, 59, 61, 63, 65, 67, 69, 71, 73, 75, 77, 79, 81, 83, 85, 87, 89, 91, 93, 95, 97, 99, 101, 109, 115 or 117. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 57, 59, 61, 63, 65, 67, 69, 71, 73, 75, 77, 79, 81, 83, 85, 87, 89, 91, 93, 95, 97, 99, 101, 109, 115 or 117. In certain embodiments, the substitutions, insertions, or deletions occur in regions outside the HVRs (i.e., in the FRs). Optionally, the anti-human OX40 agonist antibody comprises the VL sequence in SEQ ID NO: 57, 59, 61, 63, 65, 67, 69, 71, 73, 75, 77, 79, 81, 83, 85, 87, 89, 91, 93, 95, 97, 99, 101, 109, 115 or 117, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:56. In certain embodiments, substitutions, insertions, or deletions occur in regions outside the HVRs (i.e., in the FRs). Optionally, the anti-human OX40 agonist antibody comprises the VH sequence in SEQ ID NO:56, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:57. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 57. In certain embodiments, the substitutions, insertions, or deletions occur in regions outside the HVRs (i.e., in the FRs). Optionally, the anti-human OX40 agonist antibody comprises the VL sequence in SEQ ID NO: 57, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 180. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 180. In certain embodiments, substitutions, insertions, or deletions occur in regions outside the HVRs (i.e., in the FRs). Optionally, the anti-human OX40 agonist antibody comprises the VH sequence in SEQ ID NO: 180, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 179. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 179. In certain embodiments, the substitutions, insertions, or deletions occur in regions outside the HVRs (i.e., in the FRs). Optionally, the anti-human OX40 agonist antibody comprises the VL sequence in SEQ ID NO: 179, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:94. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:94. In certain embodiments, substitutions, insertions, or deletions occur in regions outside the HVRs (i.e., in the FRs). Optionally, the anti-human OX40 agonist antibody comprises the VH sequence in SEQ ID NO:94, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:95. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:95. In certain embodiments, the substitutions, insertions, or deletions occur in regions outside the HVRs (i.e., in the FRs). Optionally, the anti-human OX40 agonist antibody comprises the VL sequence in SEQ ID NO:95, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:26.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:96. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:96. In certain embodiments, substitutions, insertions, or deletions occur in regions outside the HVRs (i.e., in the FRs). Optionally, the anti-human OX40 agonist antibody comprises the VH sequence in SEQ ID NO:96, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:97. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO:97. In certain embodiments, the substitutions, insertions, or deletions occur in regions outside the HVRs (i.e., in the FRs). Optionally, the anti-human OX40 agonist antibody comprises the VL sequence in SEQ ID NO:97, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:27.

In another aspect, an anti-human OX40 agonist antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 118, 120, 122, 124, 126, 128, 130, 132, 134, 136, 138, 140, 142, 144, 146, 148. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 118, 120, 122, 124, 126, 128, 130, 132, 134, 136, 138, 140, 142, 144, 146, 148. In certain embodiments, substitutions, insertions, or deletions occur in regions outside the HVRs (i.e., in the FRs). Optionally, the anti-human OX40 agonist antibody comprises the VH sequence in SEQ ID NO: SEQ ID NO: 118, 120, 122, 124, 126, 128, 130, 132, 134, 136, 138, 140, 142, 144, 146, 148, including post-translational modifications of that sequence. In a particular embodiment, the VH comprises one, two or three HVRs selected from: (a) HVR-H1 comprising the amino acid sequence of SEQ ID NO: 29, (b) HVR-H2 comprising the amino acid sequence of SEQ ID NO:30, and (c) HVR-H3 comprising the amino acid sequence of SEQ ID NO:33.

In another aspect, an anti-human OX40 agonist antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 119, 121, 123, 125, 127, 129, 131, 133, 135, 137, 139, 141, 143, 145, 147, 149. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 119, 121, 123, 125, 127, 129, 131, 133, 135, 137, 139, 141, 143, 145, 147, 149. In certain embodiments, the substitutions, insertions, or deletions occur in regions outside the HVRs (i.e., in the FRs). Optionally, the anti-human OX40 agonist antibody comprises the VL sequence in SEQ ID NO: 119, 121, 123, 125, 127, 129, 131, 133, 135, 137, 139, 141, 143, 145, 147, 149, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In one embodiment, the antibody comprises the VH and VL sequences in SEQ ID NO:56 and SEQ ID NO:57, respectively, including post-translational modifications of those sequences. In one embodiment, the antibody comprises the VH and VL sequences in SEQ ID NO:58 and SEQ ID NO:59, respectively, including post-translational modifications of those sequences. In one embodiment, the antibody comprises the VH and VL sequences in SEQ ID NO:60 and SEQ ID NO:61, respectively, including post-translational modifications of those sequences. In one embodiment, the antibody comprises the VH and VL sequences in SEQ ID NO:62 and SEQ ID NO:63, respectively, including post-translational modifications of those sequences. In one embodiment, the antibody comprises the VH and VL sequences in SEQ ID NO:64 and SEQ ID NO:65, respectively, including post-translational modifications of those sequences. In one embodiment, the antibody comprises the VH and VL sequences in SEQ ID NO:66 and SEQ ID NO:67, respectively, including post-translational modifications of those sequences. In one embodiment, the antibody comprises the VH and VL sequences in SEQ ID NO:68 and SEQ ID NO:69, respectively, including post-translational modifications of those sequences. In one embodiment, the antibody comprises the VH and VL sequences in SEQ ID NO:70 and SEQ ID NO:71, respectively, including post-translational modifications of those sequences. In one embodiment, the antibody comprises the VH and VL sequences in SEQ ID NO:72 and SEQ ID NO:73, respectively, including post-translational modifications of those sequences. In one embodiment, the antibody comprises the VH and VL sequences in SEQ ID NO:74 and SEQ ID NO:75, respectively, including post-translational modifications of those sequences. In one embodiment, the antibody comprises the VH and VL sequences in SEQ ID NO:76 and SEQ ID NO:77, respectively, including post-translational modifications of those sequences. In one embodiment, the antibody comprises the VH and VL sequences in SEQ ID NO:78 and SEQ ID NO:79, respectively, including post-translational modifications of those sequences. In one embodiment, the antibody comprises the VH and VL sequences in SEQ ID NO:80 and SEQ ID NO:81, respectively, including post-translational modifications of those sequences. In one embodiment, the antibody comprises the VH and VL sequences in SEQ ID NO:82 and SEQ ID NO:83, respectively, including post-translational modifications of those sequences. In one embodiment, the antibody comprises the VH and VL sequences in SEQ ID NO:84 and SEQ ID NO:85, respectively, including post-translational modifications of those sequences. In one embodiment, the antibody comprises the VH and VL sequences in SEQ ID NO:86 and SEQ ID NO:87, respectively, including post-translational modifications of those sequences. In one embodiment, the antibody comprises the VH and VL sequences in SEQ ID NO:88 and SEQ ID NO:89, respectively, including post-translational modifications of those sequences. In one embodiment, the antibody comprises the VH and VL sequences in SEQ ID NO:90 and SEQ ID NO:91, respectively, including post-translational modifications of those sequences. In one embodiment, the antibody comprises the VH and VL sequences in SEQ ID NO:92 and SEQ ID NO:93, respectively, including post-translational modifications of those sequences. In one embodiment, the antibody comprises the VH and VL sequences in SEQ ID NO:94 and SEQ ID NO:95, respectively, including post-translational modifications of those sequences. In one embodiment, the antibody comprises the VH and VL sequences in SEQ ID NO:96 and SEQ ID NO:97, respectively, including post-translational modifications of those sequences. In one embodiment, the antibody comprises the VH and VL sequences in SEQ ID NO:98 and SEQ ID NO:99, respectively, including post-translational modifications of those sequences. In one embodiment, the antibody comprises the VH and VL sequences in SEQ ID NO: 100 and SEQ ID NO: 101, respectively, including post-translational modifications of those sequences. In one embodiment, the antibody comprises the VH and VL sequences in SEQ ID NO: 108 and SEQ ID NO: 109, respectively, including post-translational modifications of those sequences. In one embodiment, the antibody comprises the VH and VL sequences in SEQ ID NO: 114 and SEQ ID NO: 115, respectively, including post-translational modifications of those sequences. In one embodiment, the antibody comprises the VH and VL sequences in SEQ ID NO: 116 and SEQ ID NO: 117, respectively, including post-translational modifications of those sequences. In one embodiment, the antibody comprises the VH and VL sequences in SEQ ID NO:233 and SEQ ID NO:65, respectively, including post-translational modifications of those sequences. In one embodiment, the antibody comprises the VH and VL sequences in SEQ ID NO:234 and SEQ ID NO:69, respectively, including post-translational modifications of those sequences.

In one embodiment, the antibody comprises the VH and VL sequences in SEQ ID NO: 118 and SEQ ID NO: 119, respectively, including post-translational modifications of those sequences. In one embodiment, the antibody comprises the VH and VL sequences in SEQ ID NO: 120 and SEQ ID NO: 121, respectively, including post-translational modifications of those sequences. In one embodiment, the antibody comprises the VH and VL sequences in SEQ ID NO: 122 and SEQ ID NO: 123, respectively, including post-translational modifications of those sequences. In one embodiment, the antibody comprises the VH and VL sequences in SEQ ID NO: 124 and SEQ ID NO: 125, respectively, including post-translational modifications of those sequences. In one embodiment, the antibody comprises the VH and VL sequences in SEQ ID NO: 126 and SEQ ID NO: 127, respectively, including post-translational modifications of those sequences. In one embodiment, the antibody comprises the VH and VL sequences in SEQ ID NO: 128 and SEQ ID NO: 129, respectively, including post-translational modifications of those sequences. In one embodiment, the antibody comprises the VH and VL sequences in SEQ ID NO: 130 and SEQ ID NO:131, respectively, including post-translational modifications of those sequences. In one embodiment, the antibody comprises the VH and VL sequences in SEQ ID NO: 132 and SEQ ID NO: 133, respectively, including post-translational modifications of those sequences. In one embodiment, the antibody comprises the VH and VL sequences in SEQ ID NO: 134 and SEQ ID NO: 135, respectively, including post-translational modifications of those sequences. In one embodiment, the antibody comprises the VH and VL sequences in SEQ ID NO: 136 and SEQ ID NO: 137, respectively, including post-translational modifications of those sequences. In one embodiment, the antibody comprises the VH and VL sequences in SEQ ID NO: 138 and SEQ ID NO: 139, respectively, including post-translational modifications of those sequences. In one embodiment, the antibody comprises the VH and VL sequences in SEQ ID NO: 140 and SEQ ID NO:141, respectively, including post-translational modifications of those sequences. In one embodiment, the antibody comprises the VH and VL sequences in SEQ ID NO: 142 and SEQ ID NO: 143, respectively, including post-translational modifications of those sequences. In one embodiment, the antibody comprises the VH and VL sequences in SEQ ID NO: 144 and SEQ ID NO: 145, respectively, including post-translational modifications of those sequences. In one embodiment, the antibody comprises the VH and VL sequences in SEQ ID NO: 146 and SEQ ID NO: 147, respectively, including post-translational modifications of those sequences.

In another aspect, an anti-human OX40 agonist antibody is provided, wherein the antibody comprises a VH as in any of the embodiments provided above or as in any of the antibodies shown in FIGS. 11A-I, and a VL as in any of the embodiments provided above or as in any of the antibodies shown in FIGS. 11A-I.

In a further aspect, the invention provides an antibody that binds to the same epitope as an anti-human OX40 antibody provided herein. In some embodiments, the antibody is an anti-human OX40 agonist antibody.

In a further aspect of the invention, an anti-OX40 antibody according to any of the above embodiments is a monoclonal antibody, including a chimeric, humanized or human antibody. In one embodiment, an anti-OX40 antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein. In some embodiments, the antibody is a full length intact IgG4 antibody.

In a further aspect, an anti-OX40 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^8$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIA-CORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds 106 M−1 s−1 by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall' Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA*, 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J Immunol.,* 133: 3001 (1984); Brodeur et al., *Monoclonal Antibody Production Techniques and Applications*, pp. 51-63 (Marcel Dekker, Inc., New York, 1987); and Boerner et al., *J. Immunol.,* 147: 86 (1991)). Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for OX40 and the other is for any other antigen. In certain embodiments, bispecific antibodies may bind to two different epitopes of OX40. Bispecific antibodies may also be used to localize cytotoxic agents to cells which express OX40. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bispecific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see e.g., Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to OX40 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-OX40 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-OX40 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-OX40 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N. Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-OX40 antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc. OX40 binding may be determined using methods known in the art and exemplary methods are disclosed herein. In one embodiment, binding is measured using radioimmunoassay. An exemplary radioimmunoassay is exemplified in the Examples. OX40 antibody is iodinated, and competition reaction mixtures are prepared containing a fixed concentration of iodinated antibody and decreasing concentrations of serially diluted, unlabeled OZ X40 antibody. Cells expressing OX40 (e.g., BT474 cells stably transfected with human OX40) are added to the reaction mixture. Following an incubation, cells are washed to separate the free iodinated OX40 antibody from the OX40 antibody bound to the cells. Level of bound iodinated OX40 antibody is determined, e.g., by counting radioactivity associated with cells, and binding affinity determined using standard methods. In another embodiment, ability of OX40 antibody to bind to surface-expressed OX40 (e.g., on T cell subsets) is assessed using flow cytometry. Peripheral white blood cells are obtained (e.g., from human, cynomolgus monkey, rat or mouse) and cells are blocked with serum. Labeled OX40 antibody is added in serial dilutions, and T cells are also stained to identify T cell subsets (using methods known in the art). Following incubation of the samples and washing, the cells are sorted using flow cytometer, and data analyzed using methods well known in the art. In another embodiment, OX40 binding may be analyzed using surface plasmon resonance. An exemplary surface plasmon resonance method is exemplified in the Examples.

In another aspect, competition assays may be used to identify an antibody that competes with any of the anti-OX40 antibodies disclosed herein for binding to OX40. In certain embodiments, such a competing antibody binds to the same epitope (e.g., a linear or a conformational epitope) that is bound by any of the anti-OX40 antibodies disclosed herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.). A competition assay is exemplified in the Examples.

In an exemplary competition assay, immobilized OX40 is incubated in a solution comprising a first labeled antibody that binds to OX40 (e.g., mab 1A7.gr.1, mab 3C8.gr5) and a second unlabeled antibody that is being tested for its ability to compete with the first antibody for binding to OX40. The second antibody may be present in a hybridoma supernatant. As a control, immobilized OX40 is incubated in a solution comprising the first labeled antibody but not the second unlabeled antibody. After incubation under conditions permissive for binding of the first antibody to OX40, excess unbound antibody is removed, and the amount of label associated with immobilized OX40 is measured. If the amount of label associated with immobilized OX40 is substantially reduced in the test sample relative to the control sample, then that indicates that the second antibody is competing with the first antibody for binding to OX40. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-OX40 antibodies thereof having biological activity. Biological activity may include, e.g., binding OX40 (e.g., binding human and/or cynomolgus OX40), increasing OX40-mediated signal transduction (e.g., increasing NFkB-mediated transcription), depleting cells that express human OX40 (e.g., T cells), depleting cells that express human OX40 by ADCC and/or phagocytosis, enhancing T effector cell function (e.g., CD4+ effector T cell), e.g., by increasing effector T cell proliferation and/or increasing cytokine production (e.g., gamma interferon) by effector T cells, enhancing memory T cell function (e.g., CD4+ memory T cell), e.g., by increasing memory T cell proliferation and/or increasing cytokine production by memory T cells (e.g., gamma interferon), inhibiting regulatory T cell function (e.g., by decreasing Treg suppression of effector T cell function (e.g., CD4+ effector T cell function), binding human effector cells. Antibodies having such biological activity in vivo and/or in vitro are also provided.

In certain embodiments, an antibody of the invention is tested for such biological activity.

T cell costimulation may be assayed using methods known in the art and exemplary methods are disclosed herein. For example, T cells (e.g., memory or effector T cells) may be obtained from peripheral white blood cells (e.g., isolated from human whole blood using Ficoll gradient centrifugation). Memory T cells (e.g., CD4+ memory T cells) or effector T cells (e.g. CD4+ Teff cells) may be isolated from PBMC using methods known in the art. For example, the Miltenyi CD4+ memory T cell isolation kit or Miltenyi naïve CD4+ T cell isolation kit may be used. Isolated T cells are cultured in the presence of antigen presenting cells (e.g., irradiated L cells that express CD32 and CD80), and activated by addition of anti-CD3 antibody in the presence or absence of OX40 agonist antibody. Effect of agonist OX40 antibody of T cell proliferation may be measured using methods well known in the art. For example, the CellTiter Glo kit (Promega) may be used, and results read on a Multilabel Reader (Perkin Elmer). Effect of agonist OX40 antibody on T cell function may also be determined by analysis of cytokines produced by the T cell. In one embodiment, production of interferon gamma by CD4+ T cells is determined, e.g., by measurement of interferon gamma in cell culture supernatant. Methods for measuring interferon gamma are well-known in the art.

Treg cell function may be assayed using methods known in the art and exemplary methods are disclosed herein. In one example, the ability of Treg to suppress effector T cell proliferation is assayed. T cells are isolated from human whole blood using methods known in the art (e.g., isolating memory T cells or naïve T cells). Purified CD4+ naïve T cells are labeled (e.g., with CFSE) and purified Treg cells are labeled with a different reagent. Irradiated antigen presenting cells (e.g., L cells expressing CD32 and CD80) are co-cultured with the labeled purified naïve CD4+ T cells and purified Tregs. The co-cultures are activated using anti-CD3 antibody and tested in the presence or absence of agonist OX40 antibody. Following a suitable time (e.g., 6 days of coculture), level of CD4+ naïve T cell proliferation is tracked by dye dilution in reduced label staining (e.g., reduced CFSE label staining) using FACS analysis.

OX40 signaling may be assayed using methods well known in the art and exemplary methods are disclosed herein. In one embodiment, transgenic cells are generated that express human OX40 and a reporter gene comprising the NFkB promoter fused to a reporter gene (e.g., beta luciferase). Addition of OX40 agonist antibody to the cells results in increased NFkB transcription, which is detected using an assay for the reporter gene.

Phagocytosis may be assayed, e.g., by using monocyte-derived macrophages, or U937 cells (a human histiocytic lymphoma cells line with the morphology and characteristics of mature macrophages). OX40 expressing cells are added to the monocyte-derived macrophages or U937 cells in the presence or absence of anti-OX40 agonist antibody. Following culturing of the cells for a suitable period of time, the percentage of phagocytosis is determined by examining percentage of cells that double stain for markers of 1) the macrophage or U937 cell and 2) the OX40 expressing cell, and dividing this by the total number of cells that show markers of the OX40 expressing cell (e.g., GFP). Analysis may be done by flow cytometry. In another embodiment, analysis may be done by fluorescent microscopy analysis.

ADCC may be assayed, e.g., using methods well known in the art. Exemplary methods are described in the definition section and an exemplary assay is disclosed in the Examples. In some embodiments, level of OX40 is characterized on an OX40 expressing cell that is used for testing in an ADCC assay. The cell may be stained with a detectably labeled anti-OX40 antibody (e.g., PE labeled), then level of fluorescence determined using flow cytometry, and results presented as median fluorescence intensity (MFI). In another embodiment, ADCC may be analyzed by CellTiter Glo assay kit and cell viability/cytotoxicity may be determined by chemioluminescence.

The binding affinities of various antibodies to FcγRIA, FcγRIIA, FcγRIIB, and two allotypes of FcγRIIIA (F158 and V158) may be measured in ELISA-based ligand-binding assays using the respective recombinant Fcγ receptors. Purified human Fcγ receptors are expressed as fusion proteins containing the extracellular domain of the receptor γ chain linked to a Gly/6×His/glutathione S-transferase (GST) polypeptide tag at the C-terminus. The binding affinities of antibodies to those human Fcγ receptors are assayed as follows. For the low-affinity receptors, i.e. FcγRIIA (CD32A), FcγRIIB (CD32B), and the two allotypes of FcγRIIIA (CD16), F-158 and V-158, antibodies may be tested as multimers by cross-linking with a F(ab')2 fragment of goat anti-human kappa chain (ICN Biomedical; Irvine, Calif.) at an approximate molar ratio of 1:3 antibody:cross-linking F(ab')$_2$. Plates are coated with an anti-GST antibody (Genentech) and blocked with bovine serum albumin (BSA). After washing with phosphate-buffered saline (PBS) containing 0.05% Tween-20 with an ELx405™ plate washer (Biotek Instruments; Winooski, Vt.), Fcγ receptors are added to the plate at 25 ng/well and incubated at room temperature for 1 hour. After the plates are washed, serial dilutions of test antibodies are added as multimeric complexes and the plates were incubated at room temperature for 2 hours. Following plate washing to remove unbound antibodies, the antibodies bound to the Fcγ receptor are detected with horseradish peroxidase (HRP)-conjugated F(ab')$_2$ fragment of goat anti-human F(ab')$_2$ (Jackson ImmunoResearch Laboratories; West Grove, Pa.) followed by the addition of substrate, tetramethylbenzidine (TMB) (Kirkegaard & Perry Laboratories; Gaithersburg, Md.). The plates are incubated at room temperature for 5-20 minutes, depending on the Fcγ receptors tested, to allow color development. The reaction is terminated with 1 M H$_3$PO$_4$ and absorbance at 450 nm was measured with a microplate reader (SpectraMax®190, Molecular Devices; Sunnyvale, Calif.). Dose-response binding curves are generated by plotting the mean absorbance values from the duplicates of antibody dilutions against the concentrations of the antibody. Values for the effective concentration of the antibody at which 50% of the maximum response from binding to the Fcγ receptor is detected (EC$_{50}$) were determined after fitting the binding curve with a four-parameter equation using SoftMax Pro (Molecular Devices).

To select for antibodies which induce cell death, loss of membrane integrity as indicated by, e.g., propidium iodide (PI), trypan blue or 7AAD uptake may be assessed relative to control. A PI uptake assay can be performed in the absence of complement and immune effector cells. OX40 expressing cells are incubated with medium alone or medium containing of the appropriate monoclonal antibody at e.g., about 10 g/ml. The cells are incubated for a time period (e.g., 1 or 3 days). Following each treatment, cells are washed and aliquoted. In some embodiments, cells are aliquoted into 35 mm strainer-capped 12×75 tubes (1 ml per tube, 3 tubes per treatment group) for removal of cell clumps. Tubes then receive PI (10 g/ml). Samples may be analyzed using a FACSCAN™ flow cytometer and FACSCONVERT™ CellQuest software (Becton Dickinson).

Cells for use in any of the above in vitro assays include cells or cell lines that naturally express OX40 or that have been engineered to express OX40. Such cells include activated T cells, Treg cells and activated memory T cells that naturally express OX40. Such cells also include cell lines that express OX40 and cell lines that do not normally express OX40 but have been transfected with nucleic acid encoding OX40. Exemplary cell lines provided herein for use in any of the above in vitro assays include transgenic BT474 cells (a human breast cancer cell line) that express human OX40

It is understood that any of the above assays may be carried out using an immunoconjugate of the invention in place of or in addition to an anti-OX40 antibody.

It is understood that any of the above assays may be carried out using anti-OX40 antibody and an additional therapeutic agent.

D. Immunoconjugates

The invention also provides immunoconjugates comprising an anti-OX40 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-OX40 antibodies provided herein is useful for detecting the presence of OX40 in a biological sample. The term "detecting" as used herein encompasses quantitative or qualitative detection. In certain embodiments, a biological sample comprises a cell or tissue, such as a sample of a tumor (e.g., NSCLC or breast tumor).

In one embodiment, an anti-OX40 antibody for use in a method of diagnosis or detection is provided. In a further aspect, a method of detecting the presence of OX40 in a biological sample is provided. In certain embodiments, the method comprises contacting the biological sample with an anti-OX40 antibody as described herein under conditions permissive for binding of the anti-OX40 antibody to OX40, and detecting whether a complex is formed between the anti-OX40 antibody and OX40. Such method may be an in vitro or in vivo method. In one embodiment, an anti-OX40 antibody is used to select subjects eligible for therapy with an anti-OX40 antibody, e.g. where OX40 is a biomarker for selection of patients.

In some embodiments, the anti-OX40 antibody for use in a method of diagnosis or detection is an anti-human OX40 antibody comprising at least one, two, three, four, five, or six HVRs selected from (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising the amino acid sequence of SEQ ID NO:7. In some embodiments, the anti-OX40 antibody comprises (a) a VH domain comprising at least one, at least two, or all three VH HVR sequences selected from (i) HVR-H1 comprising the amino acid sequence of SEQ ID NO:2, (ii) HVR-H2 comprising the amino acid sequence of SEQ ID NO:3, and (iii) HVR-H3 comprising an amino acid sequence selected from SEQ ID NO:4; and (b) a VL domain comprising at least one, at least two, or all three VL HVR sequences selected from (i) HVR-L1 comprising the amino acid sequence of SEQ ID NO:5, (ii) HVR-L2 comprising the amino acid sequence of SEQ ID NO:6, and (c) HVR-L3 comprising the amino acid sequence of SEQ ID NO:7. In some embodiments, the OX40 antibody comprises (a) HVR-H1 comprising the amino acid sequence of SEQ ID NO:2; (b) HVR-H2 comprising the amino acid sequence of SEQ ID NO:3; (c) HVR-H3 comprising the amino acid sequence of SEQ ID NO:4; (d) HVR-L1 comprising the amino acid sequence of SEQ ID NO:5; (e) HVR-L2 comprising the amino acid sequence of SEQ ID NO:6; and (f) HVR-L3 comprising an amino acid sequence selected from SEQ ID NO:7. In some embodiments, the antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 180. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 180. In certain embodiments, substitutions, insertions, or deletions occur in regions outside the HVRs (i.e., in the FRs). Optionally, the anti-human OX40 agonist antibody comprises the VH sequence in SEQ ID NO: 180, including post-translational modifications of that sequence. In a particular embodiment, the VH comprises one, two or three HVRs selected from: (a) HVR-H1 comprising the amino acid sequence of SEQ ID NO:2, (b) HVR-H2 comprising the amino acid sequence of SEQ ID NO:3, and (c) HVR-H3 comprising the amino acid sequence of SEQ ID NO:4. In some embodiments, the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 179. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 179. In certain embodiments, the substitutions, insertions, or deletions occur in regions outside the HVRs (i.e., in the FRs). Optionally, the anti-human OX40 agonist antibody comprises the VL sequence in SEQ ID NO: 179, including post-translational modifications of that sequence. In a particular embodiment, the VL comprises one, two or three HVRs selected from (a) HVR-L1 comprising the amino acid sequence of SEQ ID NO:5; (b) HVR-L2 comprising the amino acid sequence of SEQ ID NO:6; and (c) HVR-L3 comprising the amino acid sequence of SEQ ID NO:7.

In some embodiments, the anti-OX40 antibody used in the method of diagnosis or detection is an anti-human OX40 antibody comprising at least one, two, three, four, five, or six HVRs selected from (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:31; (d) HVR-L1 comprising the amino acid sequence of SEQ ID NO:37; (e) HVR-L2 comprising the amino acid sequence of SEQ ID NO:39; and (f) HVR-L3 comprising the amino acid sequence of SEQ ID NO:42. In some embodiments, the anti-OX40 antibody comprises (a) a VH domain comprising at least one, at least two, or all three VH HVR sequences selected from (i) HVR-H1 comprising the amino acid sequence of SEQ ID NO:29, (ii) HVR-H2 comprising the amino acid sequence of SEQ ID NO:30, and (iii) HVR-H3 comprising an amino acid sequence selected from SEQ ID NO:31; and (b) a VL domain comprising at least one, at least two, or all three VL HVR sequences selected from (i) HVR-L1 comprising the amino acid sequence of SEQ ID NO:37, (ii) HVR-L2 comprising the amino acid sequence of SEQ ID NO:39, and (c) HVR-L3 comprising the amino acid sequence of SEQ ID NO:42. In some embodiments, the anti-OX40 antibody comprises (a) HVR-H1 comprising the amino acid sequence of SEQ ID NO:29; (b) HVR-H2 comprising the amino acid sequence of SEQ ID NO:30; (c) HVR-H3 comprising the amino acid sequence of SEQ ID NO:31; (d) HVR-L1 comprising the amino acid sequence of SEQ ID NO:37; (e) HVR-L2 comprising the amino acid sequence of SEQ ID NO:39; and (f) HVR-L3 comprising an amino acid sequence selected from SEQ ID NO:42. In some embodiment, the anti-OX40 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 182. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 182. In certain embodiments, substitutions, insertions, or deletions occur in regions outside the HVRs (i.e., in the FRs). Optionally, the anti-human OX40 agonist antibody comprises the VH sequence in SEQ ID NO: 182, including post-translational modifications of that sequence. In a particular embodiment, the VH comprises one, two or three HVRs selected from: (a) HVR-H1 comprising the amino acid sequence of SEQ ID NO:29, (b) HVR-H2 comprising the amino acid sequence of SEQ ID NO:30, and (c) HVR-H3 comprising the amino acid sequence of SEQ ID NO:31. In some embodiments, the anti-OX40 antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 181. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-human OX40 agonist antibody comprising that sequence retains the ability to bind to OX40. In certain embodiments, a total of 1 to 10 amino acids have been substituted, inserted and/or deleted in SEQ ID NO: 181. In certain embodiments, the substitutions, insertions, or deletions occur in regions outside the HVRs (i.e., in the FRs). Optionally, the anti-human OX40 agonist antibody comprises the VL sequence in SEQ ID NO: 181, including post-translational modifications of that sequence. In a particular embodiment, the VL comprises one, two or three HVRs selected from (a) HVR-L1 comprising the amino acid sequence of SEQ ID NO:37; (b) HVR-L2 comprising the amino acid sequence of SEQ ID NO:39; and (c) HVR-L3 comprising the amino acid sequence of SEQ ID NO:42.

In some embodiments, the anti-OX40 antibody comprises a VH sequence of SEQ ID NO: 180. In some embodiments, the anti-OX40 antibody comprises a VL sequence of SEQ ID NO: 179. In some embodiments, the anti-OX40 antibody comprises a VH sequence of SEQ ID NO: 180 and a VL sequence of SEQ ID NO: 179. In some embodiments, the anti-OX40 antibody comprises a VH sequence of SEQ ID NO: 182. In some embodiments, the anti-OX40 antibody comprises a VL sequence of SEQ ID NO: 181. In some embodiments, the anti-OX40 antibody comprises a VH sequence of SEQ ID NO: 182 and a VL sequence of SEQ ID NO: 181.

Exemplary disorders that may be diagnosed using an antibody of the invention include cancer.

In certain embodiments, labeled anti-OX40 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, 3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In one aspect, the invention provides diagnostic methods, e.g. for identifying a cancer patient who is likely to respond to treatment with an anti-human OX40 agonist antibody.

In some embodiments, methods are provided for identifying patients who are likely to respond to treatment with anti-human OX40 agonist antibody, the methods comprising (i) determining presence or absence or amount (e.g., number per given sample size) of cells expressing FcR in a sample of cancer from the patient, and (ii) identifying the patient as likely to respond if the sample comprises cells expressing FcR (e.g., high number of cells expressing FcR). Methods for detecting cells that express FcR are well known in the art, including, e.g., by IHC. In some embodiments, FcR is FcγR. In some embodiments, FcR is an activating FcγR. In some embodiments, the cancer is any cancer described herein. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma. In some embodiments, the method is an in vitro method. In some embodiments, the methods further comprise (iii) recommending treatment with the anti-human OX40 agonist antibody (e.g., any of the anti-human OX40 agonist antibodies described herein). In some embodiments, the methods further comprise (iv) treating the patient with the anti-human OX40 agonist antibody.

In some embodiments, methods are provided for identifying patients who are likely to respond to treatment with anti-human OX40 agonist antibody, the methods comprising (i) determining presence or absence or amount (e.g., number per given sample size) of human effector cells (e.g., infiltrating effector cells) in a sample of cancer from the patient, and (ii) identifying the patient as likely to respond if the sample comprises effector cells (e.g., high number of effector cells). Methods for detecting infiltrating human effector cells are well known in the art, including, e.g., by IHC. In some embodiments, human effector cells are one or more of NK cells, macrophages, monocytes. In some embodiments, the effector cells express activating FcγR. In some embodiments, the method is an in vitro method. In some embodiments, the cancer is any cancer described herein. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma. In some embodiments, the methods further comprise (iii) recommending treatment with the anti-human OX40 agonist antibody (e.g., any of the anti-human OX40 agonist antibodies described herein). In some embodiments, the methods further comprise (iv) treating the patient with the anti-human OX40 agonist antibody.

Provided are methods of providing a cancer diagnosis comprising: (i) measuring FcR expressing cells (e.g., the level or presence or absence of or prevalence (e.g., percentage of cells expressing FcR, e.g., by IHC) of FcR) in a sample from the patient; (ii) diagnosing the patient as having cancer comprising FcR biomarker (e.g., high FcR biomarker) when the sample has FcR biomarker expression. In some embodiments, the method further comprises (iii) selecting a therapy comprising (a) anti-human OX40 agonist antibody or (b) recommending a therapy comprising anti-human OX40 agonist antibody for the patient. In some embodiments, the method is an in vitro method.

Provided are methods of providing a cancer diagnosis comprising: (i) measuring human effector cells (e.g., the level or presence or absence of or prevalence (e.g., percentage of human effector cells) of human effector cells) in a sample from the patient; (ii) diagnosing the patient as having cancer comprising human effector cells (e.g., high human effector cells) when the sample has human effector cell biomarker. In some embodiments, the method further comprises (iii) selecting a therapy comprising (a) anti-human OX40 agonist antibody or (b) recommending a therapy comprising anti-human OX40 agonist antibody for the patient. In some embodiments, the method is an in vitro method.

Provided are methods of recommending a treatment to a cancer patient comprising: (i) measuring FcR expressing cells (e.g., the level or presence or absence of or prevalence (e.g., percentage of cells expressing FcR) of FcR) in a sample from the patient; (ii) recommending treatment with an anti-human OX40 agonist antibody when the sample has FcR expressing cells (in some embodiments, high FcR expressing cells). In some embodiments, the method further comprises (iii) selecting a therapy comprising anti-human OX40 agonist antibody for the patient. In some embodiments, the method is an in vitro method.

Provided are methods of recommending a treatment to a cancer patient comprising: (i) measuring human effector cells (e.g., the level or presence or absence of or prevalence (e.g., percentage of human effector cells) of human effector cells) in a sample from the patient; (ii) recommending treatment with an anti-human OX40 agonist antibody when the sample has human effector cells (in some embodiments, high human effector cells). In some embodiments, the method further comprises (iii) selecting a therapy comprising anti-human OX40 agonist antibody for the patient. In some embodiments, the method is an in vitro method.

In some embodiments of any of the inventions provided herein, the sample is obtained prior to treatment with anti-human OX40 agonist antibody. In some embodiments, the sample is obtained prior to treatment with a cancer medicament. In some embodiments, the sample is obtained after the cancer has metastasized. In some embodiments, the sample is formalin fixed and paraffin embedded (FFPE). In some embodiments, the sample is of a biopsy (e.g., a core biopsy), a surgical specimen (e.g., a specimen from a surgical resection), or a fine needle aspirate.

F. Pharmaceutical Formulations

Pharmaceutical formulations of an anti-OX40 antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

In some embodiments, a "histidine buffer" is a buffer comprising histidine ions. Examples of histidine buffers include histidine chloride, histidine acetate, histidine phosphate, histidine sulfate. The preferred histidine buffer identified in the examples herein was found to be histidine acetate. In the preferred embodiment, the histidine acetate buffer is prepared by titrating L-histidine (free base, solid) with acetic acid (liquid). In some embodiments, the histidine buffer or histidine-acetate buffer is at pH 5.0 to 6.0, in some embodiments, pH 5.3 to 5.8.

In some embodiments, a "saccharide" herein comprises the general composition $(CH_2O)_n$ and derivatives thereof, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, iso-maltulose, etc. In some embodiments, the saccharide is a nonreducing disaccharide, such as trehalose or sucrose.

In some embodiments herein, a "surfactant" refers to a surface-active agent, preferably a nonionic surfactant. Examples of surfactants herein include polysorbate (for example, polysorbate 20 and polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. In some embodiments, the surfactant is polysorbate 20. In some embodiments, the surfactant is polysorbate 80.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an additional medicament (examples of which are provided herein). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

In some embodiments, provided herein are pharmaceutical formulations comprising: (a) any of the anti-human OX40 agonist antibodies described herein; (b) a histidine buffer at pH 5.0-6.0.

In some embodiments, provided herein are pharmaceutical formulations comprising: (a) any of the anti-human OX40 agonist antibodies described herein; (b) a histidine buffer at pH 5.0-6.0; (c) a saccharide; and (d) a surfactant.

In some embodiments of any of the formulations, the anti-human OX40 agonist antibody is present at a concentration between about 10 mg/mL and about 100 mg/mL (e.g. about 15 mg/mL, 18 mg/mL, 20 mg/mL, 60 mg/mL, and 75 mg/mL). In some embodiments, the anti-human OX40 agonist antibody is present at a concentration of about 20 mg/mL. In some embodiments, the anti-human OX40 agonist antibody is present at a concentration of about 50 mg/mL. In some embodiments, the anti-human OX40 agonist antibody is present at a concentration of about 60 mg/mL. In some embodiments, the anti-human OX40 agonist antibody is present at a concentration of about 70 mg/mL.

In some embodiments of any of the formulations, the saccharide is present at a concentration of about 75 mM to about 360 mM (e.g., about 100 mM, about 120 mM, about 240 mM, about 320 mM to about 360 mM). In some embodiments, the saccharide is present at a concentration of about 120 mM. In some embodiments, the saccharide is present at a concentration of about 240 mM. In some embodiments, the saccharide is present at a concentration of about 320 mM. In some embodiments, the saccharide is a disaccharide. In some embodiments, the disaccharide is trehalose. In some embodiments, the disaccharide is sucrose.

In some embodiments of any of the formulations, the histidine buffer is at a concentration of about 1 mM to about 50 mM (e.g. about 1 mM to about 25 mM). In some embodiments, the histidine buffer is at a concentration of about 10 mM. In some embodiments, the histidine buffer is at a concentration of about 20 mM. In some embodiments, the histidine buffer is at a concentration of about 30 mM. In some embodiments, the histidine buffer is histidine acetate.

In some embodiments of any of the formulations, the surfactant is polysorbate (e.g., polysorbate 20 or polysorbate 40), poloxamer (e.g. poloxamer 188); Triton; sodium dodecyl sulfate (SDS); sodium laurel sulfate; or sodium octyl glycoside.

In some embodiments of any of the formulations, the surfactant is polysorbate. In some embodiments, the polysorbate is present at a concentration of about 0.005% to about 0.1%. In some embodiments, the polysorbate is present at a concentration of about 0.005%. In some embodiments, the polysorbate is present at a concentration of about 0.02%. In some embodiments, the polysorbate is present at a concentration of about 0.04%. In some embodiments, the polysorbate is present at a concentration of about 0.06%. In some embodiments, the polysorbate is polysorbate 20. In some embodiments, the polysorbate is polysorbate 80.

In some embodiments of any of the formulations, the formulation is diluted with a diluent (e.g., 0.9% NaCl). In some embodiments, the anti-human OX40 agonist antibody is present at a concentration of about 1 mg/mL.

In particular, provided herein are pharmaceutical formulations comprising (a) any of the anti-human OX40 agonist antibodies described herein, (b) a polysorbate, wherein the polysorbate concentration is about 0.005% to about 0.1%; and (c) a histidine buffer (e.g., a histidine buffer at a pH between 5.0 and 6.0).

In some embodiments, the pharmaceutical formulation comprises (a) any of the anti-human OX40 agonist antibodies described herein (e.g., at a concentration between about 10 mg/mL and about 100 mg/mL), (b) a polysorbate, wherein the polysorbate concentration is about 0.02% to about 0.06%; (c) a histidine buffer (e.g., a histidine buffer at pH 5.0 to 6.0); and a saccharide, wherein the saccharide concentration is about 120 mM to about 320 mM. In some embodiments, the saccharide is sucrose.

In some embodiments, the pharmaceutical formulation comprises (a) any of the anti-human OX40 agonist antibodies described herein at a concentration between about 10 mg/mL and about 100 mg/mL, (b) a polysorbate, wherein the polysorbate concentration is about 0.02% to about 0.06%, wherein the polysorbate is polysorbate 20 or polysorbate 40; (c) a histidine acetate buffer at pH 5.0 to 6.0; and a saccharide (e.g., sucrose) at a concentration of about 120 mM to about 320 mM.

In some embodiments, the pharmaceutical formulation comprises (a) any of the anti-human OX40 agonist antibodies described herein, (b) polysorbate 20, wherein the polysorbate concentration is about 0.02% to about 0.06%; (c) a histidine acetate buffer (e.g., a histidine acetate buffer at pH 5.0 to 6.0); and (d) sucrose, wherein the sucrose concentration is about 120 mM to about 320 mM.

In some embodiments, the pharmaceutical formulation comprises (a) any of the anti-human OX40 agonist antibodies described herein, (b) polysorbate 40, wherein the polysorbate concentration is about 0.02% to about 0.06%; (c) a histidine acetate buffer (e.g., a histidine acetate buffer at a pH between 5.0 and 6.0); and sucrose, wherein the sucrose concentration is about 120 mM to about 320 mM.

In some embodiments, the pharmaceutical formulation comprises (a) any of the anti-human OX40 agonist antibodies described herein, (b) polysorbate 20, wherein the polysorbate concentration is about 0.02%; (c) a histidine acetate buffer at pH 6.0; and (d) sucrose, wherein the sucrose concentration is about 320 mM.

In some embodiments, the pharmaceutical formulation comprises (a) any of the anti-human OX40 agonist antibodies described herein, (b) polysorbate 20, wherein the polysorbate concentration is about 0.02%; (c) a histidine acetate buffer at pH 5.5; and (d) sucrose, wherein the sucrose concentration is about 240 mM.

In some embodiments, the pharmaceutical formulation comprises (a) any of the anti-human OX40 agonist antibodies described herein, (b) polysorbate 20, wherein the polysorbate concentration is about 0.04%; (c) a histidine acetate buffer at pH 6.0; and (d) sucrose, wherein the sucrose concentration is about 120 mM.

In some embodiments, the pharmaceutical formulation comprises (a) any of the anti-human OX40 agonist antibodies described herein, (b) polysorbate 40, wherein the polysorbate concentration is about 0.04%; (c) a histidine acetate buffer at pH 5.0; and (d) sucrose, wherein the sucrose concentration is about 240 mM.

In some embodiments, the pharmaceutical formulation comprises (a) any of the anti-human OX40 agonist antibodies described herein, (b) polysorbate 40, wherein the polysorbate concentration is about 0.04%; (c) a histidine acetate buffer at pH 6.0; and (d) sucrose, wherein the sucrose concentration is about 120 mM.

In some embodiments, the pharmaceutical formulation is a liquid pharmaceutical formulation. In some embodiments, the pharmaceutical formulation is a stable pharmaceutical formulation. In some embodiments, the pharmaceutical formulation is a stable liquid pharmaceutical formulation.

In some embodiments of any of the pharmaceutical formulations described herein, the anti-human OX40 agonist antibody of the pharmaceutical formulation is present at a concentration between about 10 mg/mL and about 100 mg/mL. In some embodiments, the concentration of the human OX40 agonist antibody is between about any of 10 mg/mL to 50 mg/mL, 10 mg/mL to 75 mg/mL, 25 mg/mL to 75 mg/mL, 50 mg/mL to 100 mg/mL, 50 mg/mL to 75 mg/mL, and/or 75 mg/mL to 100 mg/mL. In some embodiments, the concentration of the human OX40 agonist antibody is greater than about any of 20 mg/mL, 30 mg/mL, 40 mg/mL, 50 mg/mL, 60 mg/mL, 70 mg/mL, or 100 mg/mL.

The pharmaceutical formulation preferably comprises a polysorbate. The polysorbate is generally included in an amount which reduces aggregate formation (such as that which occurs upon shaking or shipping). Examples of polysorbate include, but are not limited to, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), and/or polysorbate 80 (polyoxyethylene (20) sorbitan monooleate). In some embodiments, the polysorbate is polysorbate 20 (polyoxyethylene (20) sorbitan monolaurate). In some embodiments of any of the pharmaceutical formulations described herein, the polysorbate concentration is sufficient to minimize aggregation and/or maintain stability upon long term storage and/or during administration (e.g., after dilution in an IV bag). In some embodiments, the polysorbate concentration is about 0.005% w/v, about 0.02% w/v, about 0.04% w/v and less than about 0.1% w/v. In some embodiments, the polysorbate concentration is greater than 0.01% w/v and less than about 0.1% w/v. In some embodiments, the polysorbate concentration is about any of 0.005% w/v, about 0.02% w/v, 0.03% w/v, 0.04% w/v, or 0.05% w/v. In some embodiments, the polysorbate is present at a concentration of about 0.04% w/v. In some embodiments, the polysorbate is present at a concentration of about 0.02% w/v.

The pharmaceutical formulation preferably comprises a saccharide. Saccharides include monosaccharides, disaccharides, trisaccharides, polysaccharides, sugar alcohols, reducing sugars, nonreducing sugars, etc. Further examples of saccharides include, but are not limited to, glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. In some embodiments, the saccharide is a disaccharide. In some embodiments, the saccharide is a nonreducing disaccharide. In some embodiments, the saccharide is trehalose.

The saccharide is generally included in an amount which reduces aggregate formation. In some embodiments of any of the pharmaceutical formulations described herein, the saccharide is present at a concentration of between about any of 50 mM to 250 mM, 75 mM to 200 mM, 75 mM to 150 mM, 100 mM to 150 mM, or 110 mM to 130 mM, or 100 mM to 320 mM, or 240 mM to 320 mM, or 240 mM to 400 mM. In some embodiments, the saccharide is present at a concentration greater than about any of 50 mM, 75 mM, 100 mM, 110 mM, or 115 mM. In some embodiments, the saccharide is present at a concentration of about any of 100 mM, 110 mM, 120 mM, 130 mM, or 140 mM. In some embodiments, the saccharide is present at a concentration of about 120 mM. In some embodiments of any of the formulations, the saccharide is present at a concentration of about 75 mM to about 360 mM (e.g., about 100 mM, about 120 mM, about 240 mM, about 320 mM to about 360 mM). In some embodiments, the saccharide is present at a concentration of about 240 mM. In some embodiments, the saccharide is present at a concentration of about 320 mM.

The pharmaceutical formulation preferably comprises a histidine buffer. Examples of histidine buffers include, but are not limited to, histidine chloride, histidine succinate, histidine acetate, histidine phosphate, histidine sulfate. In some embodiments, the histidine buffer is histidine acetate. In some embodiments of any of the pharmaceutical formulations described herein, the histidine buffer concentration is between about any of 1 mM to 50 mM, 1 mM to 35 mM, 1 mM to 25 mM, 1 mM to 20 mM, 7.5 mM to 12.5 mM, or 5 mM to 15 mM, 20 mM to 30 mM, 25 mM to 35 mM. In some embodiments, the histidine buffer concentration is about any of 5 mM, 7.5 mM, 10 mM, 12.5 mM, 15 mM, 20 mM, 25 mM, 30 mM, 35 mM or 40 mM. In some embodiments, the histidine buffer concentration is about 10 mM. In some embodiments, the histidine buffer concentration is about 20 mM. In some embodiments, the histidine buffer concentration is about 30 mM. In some embodiments, the histidine buffer concentration is about 40 mM. In some embodiments of any of the pharmaceutical formulations described herein, the histidine buffer is at a pH of between pH 5.0 and 6.0, for example, about any of pH 5.0, pH 5.1, pH 5.2, pH 5.3, pH 5.4, pH 5.5, pH 5.6, pH 5.7, pH 5.8, pH 5.9 or pH 6.0. In some embodiments, the pH is between pH 4.9 to pH 6.3.

The pharmaceutical formulation herein may also contain more than one active compound as necessary for the particular indication being treated, preferably those with complementary activities that do not adversely affect each other. Such molecules are suitably present in combination in amounts that are effective for the purpose intended.

Further, provided herein are vials and methods of filing a vial comprising a pharmaceutical formulation described herein. In some embodiments, the pharmaceutical formulation is provided inside a vial with a stopper pierceable by a syringe, preferably in aqueous form. The vial is desirably stored at about 2-8° C. as well as up to 30° C. for 24 hours until it is administered to a subject in need thereof. The vial may for example be a 15 cc vial (for example for a 200 mg dose).

The pharmaceutical formulation for administration is preferably a liquid formulation (not lyophilized) and has not been subjected to prior lyophilization. While the pharmaceutical formulation may be lyophilized, preferably it is not. In some embodiments of any of the pharmaceutical formulations, the pharmaceutical formulation, the pharmaceutical formulation is a lyophilized pharmaceutical formulation. In some embodiments, the pharmaceutical formulation is a liquid formulation. In some embodiments, the pharmaceutical formulation does not contain a tonicifying amount of a salt such as sodium chloride. In some embodiments of any of the pharmaceutical formulations, the pharmaceutical formulation is diluted.

G. Therapeutic Methods and Compositions

Any of the anti-human OX40 antibodies provided herein may be used in therapeutic methods.

In one aspect, an anti-human OX40 agonist antibody for use as a medicament is provided. In further aspects, an anti-human OX40 agonist antibody for use in treating cancer is provided. In certain embodiments, an anti-human OX40 agonist antibody for use in a method of treatment is provided. In certain embodiments, the invention provides an anti-human OX40 agonist antibody for use in a method of treating an individual having cancer comprising administering to the individual an effective amount of the anti-human agonist OX40 antibody. In one such embodiment, the method further comprises administering to the individual an effective amount of at least one additional therapeutic agent, e.g., as described below.

In one aspect, provided is an anti-human OX40 agonist antibody for use in enhancing immune function (e.g., by upregulating cell-mediated immune responses) in an individual having cancer comprising administering to the individual an effective amount of the anti-human agonist OX40 antibody. In one aspect, provided is an anti-human OX40 agonist antibody for use in enhancing T cell function in an individual having cancer comprising administering to the individual an effective amount of the anti-human agonist OX40 antibody. In one aspect, provided are an anti-human OX40 agonist antibody for use in depleting human OX40-expressing cells (e.g., OX40 expressing T cells, e.g., OX40 expressing Treg) comprising administering to the individual an effective amount of the anti-human agonist OX40 antibody. In some embodiments, depletion is by ADCC. In some embodiments, depletion is by phagocytosis. Provided is an anti-human OX40 agonist antibody for treating an individual having tumor immunity.

In further aspects, an anti-human OX40 agonist antibody for use in treating infection (e.g., with a bacteria or virus or other pathogen) is provided. In certain embodiments, the invention provides an anti-human OX40 agonist antibody for use in a method of treating an individual having an infection comprising administering to the individual an effective amount of the anti-human agonist OX40 antibody. In some embodiments, the infection is with a virus and/or a bacteria. In some embodiments, the infection is with a pathogen.

In a further aspect, the invention provides for the use of an anti-OX40 antibody in the manufacture or preparation of a medicament. In one embodiment, the medicament is for treatment of cancer. In a further embodiment, the medicament is for use in a method of treating cancer comprising administering to an individual having cancer an effective amount of the medicament. In one such embodiment, the method further comprises administering to the individual an effective amount of at least one additional therapeutic agent, e.g., as described below.

In one aspect, the medicament is for use in enhancing immune function (e.g., by upregulating cell-mediated immune responses) in an individual having cancer comprising administering to the individual an effective amount of the medicament. In one aspect, the medicament is for use in enhancing T cell function in an individual having cancer comprising administering to the individual an effective amount of the medicament. In some embodiments, the T cell dysfunctional disorder is cancer. In one aspect, the medicament is for use in depleting human OX40-expressing cells (e.g., cell expressing high OX40, e.g., OX40 expressing T cells) comprising administering to the individual an effective amount of the medicament. In some embodiments, depletion is by ADCC. In some embodiments, depletion is by phagocytosis. In one aspect, the medicament is for treating an individual having tumor immunity.

In further aspects, the medicament is for use in treating infection (e.g., with a bacteria or virus or other pathogen) is provided. In certain embodiments, the medicament is for use in a method of treating an individual having an infection comprising administering to the individual an effective amount of the medicament. In some embodiments, the infection is with virus and/or bacteria. In some embodiments, the infection is with a pathogen.

In a further aspect, the invention provides a method for treating a cancer. In one embodiment, the method comprises administering to an individual having such cancer an effective amount of an anti-OX40 antibody. In one such embodiment, the method further comprises administering to the individual an effective amount of at least one additional therapeutic agent, as described below. An "individual" according to any of the above embodiments may be a human.

In one aspect, provided is a method for enhancing immune function (e.g., by upregulating cell-mediated immune responses) in an individual having cancer comprising administering to the individual an effective amount of the anti-human agonist OX40 antibody. In one aspect, provided is a method for enhancing T cell function in an individual having cancer comprising administering to the individual an effective amount of the anti-human agonist OX40 antibody. In one aspect, provided are a method for depleting human OX40-expressing cells (e.g., cells that express high level of OX40, e.g., OX40 expressing T cells) comprising administering to the individual an effective amount of the anti-human agonist OX40 antibody. In some embodiments, depletion is by ADCC. In some embodiments, depletion is by phagocytosis. Provided is an anti-human OX40 agonist antibody for treating an individual having tumor immunity.

In some embodiments, examples of cancer further include, but are not limited to, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), B-cell proliferative disorders, and Meigs' syndrome. More specific examples include, but are not limited to, relapsed or refractory NHL, front line low grade NHL, Stage III/IV NHL, chemotherapy resistant NHL, precursor B lymphoblastic leukemia and/or lymphoma, small lymphocytic lymphoma, B-cell chronic lymphocytic leukemia and/or prolymphocytic leukemia and/or small lymphocytic lymphoma, B-cell prolymphocytic lymphoma, immunocytoma and/or lymphoplasmacytic lymphoma, lymphoplasmacytic lymphoma, marginal zone B-cell lymphoma, splenic marginal zone lymphoma, extranodal marginal zone-MALT lymphoma, nodal marginal zone lymphoma, hairy cell leukemia, plasmacytoma and/or plasma cell myeloma, low grade/follicular lymphoma, intermediate grade/follicular NHL, mantle cell lymphoma, follicle center lymphoma (follicular), intermediate grade diffuse NHL, diffuse large B-cell lymphoma, aggressive NHL (including aggressive front-line NHL and aggressive relapsed NHL), NHL relapsing after or refractory to autologous stem cell transplantation, primary mediastinal large B-cell lymphoma, primary effusion lymphoma, high grade immunoblastic NHL, high grade lymphoblastic NHL, high grade small non-cleaved cell NHL, bulky disease NHL, Burkitt's lymphoma, precursor (peripheral) large granular lymphocytic leukemia, mycosis fungoides and/or Sezary syndrome, skin (cutaneous) lymphomas, anaplastic large cell lymphoma, angiocentric lymphoma.

In some embodiments, examples of cancer further include, but are not limited to, B-cell proliferative disorders, which further include, but are not limited to, lymphomas (e.g., B-Cell Non-Hodgkin's lymphomas (NHL)) and lymphocytic leukemias. Such lymphomas and lymphocytic leukemias include e.g. a) follicular lymphomas, b) Small Non-Cleaved Cell Lymphomas/Burkitt's lymphoma (including endemic Burkitt's lymphoma, sporadic Burkitt's lymphoma and Non-Burkitt's lymphoma), c) marginal zone lymphomas (including extranodal marginal zone B-cell lymphoma (Mucosa-associated lymphatic tissue lymphomas, MALT), nodal marginal zone B-cell lymphoma and splenic marginal zone lymphoma), d) Mantle cell lymphoma (MCL), e) Large Cell Lymphoma (including B-cell diffuse large cell lymphoma (DLCL), Diffuse Mixed Cell Lymphoma, Immunoblastic Lymphoma, Primary Mediastinal B-Cell Lymphoma, Angiocentric Lymphoma-Pulmonary B-Cell Lymphoma), f) hairy cell leukemia, g) lymphocytic lymphoma, Waldenstrom's macroglobulinemia, h) acute lymphocytic leukemia (ALL), chronic lymphocytic leukemia (CLL)/small lymphocytic lymphoma (SLL), B cell prolymphocytic leukemia, i) plasma cell neoplasms, plasma cell myeloma, multiple myeloma, plasmacytoma, and/or j) Hodgkin's disease.

In some embodiments of any of the methods, the cancer is a B-cell proliferative disorder. In some embodiments, the B-cell proliferative disorder is lymphoma, non-Hodgkins lymphoma (NHL), aggressive NHL, relapsed aggressive NHL, relapsed indolent NHL, refractory NHL, refractory indolent NHL, chronic lymphocytic leukemia (CLL), small lymphocytic lymphoma, leukemia, hairy cell leukemia (HCL), acute lymphocytic leukemia (ALL), or mantle cell lymphoma. In some embodiments, the B-cell proliferative disorder is NHL, such as indolent NHL and/or aggressive NHL. In some embodiments, the B-cell proliferative disorder is indolent follicular lymphoma or diffuse large B-cell lymphoma.

In a further aspect, the invention provides pharmaceutical formulations comprising any of the anti-OX40 antibodies provided herein, e.g., for use in any of the above therapeutic methods. In one embodiment, a pharmaceutical formulation comprises any of the anti-OX40 antibodies provided herein and a pharmaceutically acceptable carrier. In another embodiment, a pharmaceutical formulation comprises any of the anti-OX40 antibodies provided herein and at least one additional therapeutic agent, e.g., as described below.

In some embodiments of any of the methods of the invention, the anti-human OX40 agonist antibodies inhibits tumor immunity by inhibiting Treg function (e.g., inhibiting the suppressive function of Tregs), killing OX40 expressing cells (e.g., cells that express high levels of OX40), increasing effector T cell function and/or increasing memory T cell function. In some embodiments of any of the methods of the invention, the anti-human OX40 agonist antibodies treat cancer by inhibiting Treg function (e.g., inhibiting the suppressive function of Tregs), killing OX40 expressing cells (e.g., cells that express high levels of OX40), increasing effector T cell function and/or increasing memory T cell function. In some embodiments of any of the methods of the invention, the anti-human OX40 agonist antibodies enhance immune function by inhibiting Treg function (e.g., inhibiting the suppressive function of Tregs), killing OX40 expressing cells (e.g., cells that express high levels of OX40), increasing effector T cell function and/or increasing memory T cell function. In some embodiments of any of the methods of the invention, the anti-human OX40 agonist antibodies enhance T cell function by inhibiting Treg function (e.g., inhibiting the suppressive function of Tregs), killing OX40 expressing cells (e.g., cells that express high levels of OX40), increasing effector T cell function and/or increasing memory T cell function.

In some embodiments of any of the methods, the anti-human OX40 agonist antibody is a depleting anti-human agonist antibody. In some embodiments, treatment with the anti-human OX40 agonist antibody results in cell depletion (e.g., depletion of OX40-expressing cells, e.g., depletion of cells that express high levels of OX40). In some embodiments, depletion is by ADCC. In some embodiments, depletion is by phagocytosis.

In some embodiments of any of the methods, the anti-human OX40 agonist antibody inhibits Treg function, e.g., by inhibiting Treg suppression of effector and/or memory T cell function (in some embodiments, effector T cell and/or memory T cell proliferation and/or cytokine secretion), relative to Treg function prior to administration of the OX40 agonist antibody. In some embodiments of any of the methods, the anti-human OX40 agonist antibody increases effector T cell proliferation, relative to effector T cell proliferation prior to administration of the OX40 agonist antibody. In some embodiments of any of the methods, the anti-human OX40 agonist antibody increases memory T cell proliferation, relative to memory T cell proliferation prior to administration of the OX40 agonist antibody. In some embodiments of any of the methods, the anti-human OX40 agonist antibody increases effector T cell cytokine production (e.g., gamma interferon production), relative to effector T cell cytokine production prior to administration of the OX40 agonist antibody. In some embodiments of any of the methods, the anti-human OX40 agonist antibody increases memory T cell cytokine production (e.g., gamma interferon production), relative to memory T cell cytokine production prior to administration of the OX40 agonist antibody. In some embodiments of any of the methods, the anti-human OX40 agonist antibody increases CD4+ effector T cell proliferation and/or CD8+ effector T cell proliferation relative to CD4+ effector T cell proliferation and/or CD8+ effector T cell proliferation prior to administration of the OX40 agonist antibody. In some embodiments of any of the methods, the anti-human OX40 agonist antibody increases memory T cell proliferation (e.g., CD4+ memory T cell proliferation), relative to memory T cell proliferation prior to administration of the OX40 agonist antibody. In some embodiments, the CD4+ effector T cells in the individual have enhanced proliferation, cytokine secretion and/or cytolytic activity relative to proliferation, cytokine secretion and/or cytolytic activity prior to the administration of the anti-human OX40 agonist antibody.

In some embodiments of any of the methods of the invention, the number of CD4+ effector T cells is elevated relative to prior to administration of the anti-human OX40 agonist antibody. In some embodiments, CD4+ effector T cell cytokine secretion is elevated relative to prior to administration of the anti-human OX40 agonist antibody. In some embodiments of any of the methods, the CD8+ effector T cells in the individual have enhanced proliferation, cytokine secretion and/or cytolytic activity relative to prior to the administration of the anti-human OX40 agonist antibody. In some embodiments, the number of CD8+ effector T cells is elevated relative to prior to administration of the anti-human OX40 agonist antibody. In some embodiments, CD8+ effector T cell cytokine secretion is elevated relative to prior to administration of the anti-human OX40 agonist antibody.

In some embodiments of any of the methods of the invention, the anti-human OX40 agonist antibody binds human effector cells, e.g., binds FcγR expressed by human effector cells. In some embodiments, the human effector cell performs ADCC effector function. In some embodiments, the human effector cell performs phagocytosis effector function.

In some embodiments of any of the methods of the invention, the anti-human OX40 agonist antibody comprising a variant IgG1 Fc polypeptide comprising a mutation that eliminates binding to human effector cells (e.g., a DANA or N297G mutation) has diminished activity (e.g., CD4+ effector T cell function, e.g., proliferation), relative to anti-human OX40 agonist antibody comprising native sequence IgG1 Fc portion. In some embodiment, the anti-human OX40 agonist antibody comprising a variant IgG1 Fc polypeptide comprising a mutation that eliminates binding to human effector cells (e.g., a DANA or N297G mutation) does not possess substantial activity (e.g., CD4+ effector T cell function, e.g., proliferation).

In some embodiments of any of the methods of the invention, antibody cross-linking is required for anti-human OX40 agonist antibody function. In some embodiments, function is stimulation of CD4+ effector T cell proliferation. In some embodiments, antibody cross-linking is determined by providing anti-human OX40 agonist antibody adhered on a solid surface (e.g., a cell culture plate). In some embodiments, antibody cross-linking is determined by introducing a mutation in the antibody's IgG1 Fc portion (e.g., a DANA or N297S mutation) and testing function of the mutant antibody.

In some embodiments of any of the methods, the memory T cells in the individual have enhanced proliferation and/or cytokine secretion relative to prior to the administration of the anti-human OX40 agonist antibody. In some embodiments, the number of memory T cells is elevated relative to prior to administration of the anti-human OX40 agonist antibody. In some embodiments, memory T cell cytokine secretion (level) is elevated relative to prior to administration of the anti-human OX40 agonist antibody. In some embodiments of any of the methods, the Treg in the individual have decreased inhibition of effector T cell function (e.g., proliferation and/or cytokine secretion) relative to prior to the administration of the anti-human OX40 agonist antibody. In some embodiments, the number of effector T cells is elevated relative to prior to administration of the anti-human OX40 agonist antibody. In some embodiments, effector T cell cytokine secretion (level) is elevated relative to prior to administration of the anti-human OX40 agonist antibody.

In some embodiments of any of the methods of the invention, the number of intratumoral (infiltrating) CD4+ effector T cells (e.g., total number of CD4+ effector T cells, or e.g., percentage of CD4+ cells in CD45+ cells) is elevated relative to prior to administration of the anti-human OX40 agonist antibody. In some embodiments of any of the methods of the invention, number of intratumoral (infiltrating) CD4+ effector T cells that express gamma interferon (e.g., total gamma interferon expressing CD4+ cells, or e.g., percentage of gamma interferon expressing CD4+ cells in total CD4+ cells) is elevated relative to prior to administration anti-human OX40 agonist antibody.

In some embodiments of any of the methods of the invention, the number of intratumoral (infiltrating) CD8+ effector T cells (e.g., total number of CD8+ effector T cells, or e.g., percentage of CD8+ in CD45+ cells) is elevated relative to prior to administration of anti-human OX40 agonist antibody. In some embodiments of any of the methods of the invention, number of intratumoral (infiltrating) CD8+ effector T cells that express gamma interferon (e.g., percentage of CD8+ cells that express gamma interferon in total CD8+ cells) is increased relative to prior to administration of anti-human OX40 agonist antibody.

In some embodiments of any of the methods of the invention, the number of intratumoral (infiltrating) Treg (e.g., total number of Treg or e.g., percentage of Fox3p+ cells in CD4+ cells) is reduced relative to prior to administration of anti-human OX40 agonist antibody.

In some embodiments of any of the methods of the invention, administration of anti-human OX40 agonist antibody is in combination with administration of a tumor antigen. In some embodiments, the tumor antigen comprises protein. In some embodiments, the tumor antigen comprises nucleic acid. In some embodiments, the tumor antigen is a tumor cell.

In some embodiments of any of the methods of the invention, the cancer displays human effector cells (e.g., is infiltrated by human effector cells). Methods for detecting human effector cells are well known in the art, including, e.g., by IHC. In some embodiments, the cancer display high levels of human effector cells. In some embodiments, human effector cells are one or more of NK cells, macrophages, monocytes. In some embodiments, the cancer is any cancer described herein. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

In some embodiments of any of the methods of the invention, the cancer displays cells expressing FcR (e.g., is infiltrated by cells expressing FcR). Methods for detecting FcR are well known in the art, including, e.g., by IHC. In some embodiments, the cancer display high levels of cells expressing FcR. In some embodiments, FcR is FcγR. In some embodiments, FcR is activating FcγR. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma.

An "individual" according to any of the above embodiments is preferably a human.

Antibodies of the invention can be used either alone or in combination with other agents in a therapy. For instance, an antibody of the invention may be co-administered with at least one additional therapeutic agent.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-OX40 antibody and administration of an additional therapeutic agent occur within about one month, or within about one, two or three weeks, or within about one, two, three, four, five, or six days, of each other. Antibodies of the invention can also be used in combination with radiation therapy.

In some embodiments, an anti-human OX40 agonist antibody may be administered in conjunction with a chemotherapy or chemotherapeutic agent. In some embodiments, an anti-human OX40 agonist antibody may be administered in conjunction with a radiation therapy or radiotherapeutic agent. In some embodiments, an anti-human OX40 agonist antibody may be administered in conjunction with a targeted therapy or targeted therapeutic agent. In some embodiments, an anti-human OX40 agonist antibody may be administered in conjunction with an immunotherapy or immunotherapeutic agent, for example a monoclonal antibody.

In some embodiments, an anti-human OX40 agonist antibody may be administered in conjunction with a PARP inhibitor (e.g., Olaparanib, Rucaparib, Niraparib, Cediranib, BMN673, Veliparib), Trabectedin, nab-paclitaxel (albumen-bound paclitaxel, ABRAXANE), Trebananib, Pazopanib, Cediranib, Palbociclib, everolimus, fluoropyrimidine (e.g., FOLFOX, FOLFIRI), IFL, regorafenib, Reolysin, Alimta, Zykadia, Sutent, Torisel (temsirolimus), Inlyta (axitinib, Pfizer), Afinitor (everolimus, Novartis), Nexavar (sorafenib, Onyx/Bayer), Votrient, Pazopanib, axitinib, IMA-901, AGS-003, cabozantinib, Vinflunine, Hsp90 inhibitor (e.g., apatorsin), Ad-GM-CSF (CT-0070), Temazolomide, IL-2, IFNa, vinblastine, Thalomid, dacarbazine, cyclophosphamide, lenalidomide, azacytidine, lenalidomide, bortezomid (VELCADE), amrubicine, carfilzomib, pralatrexate, and/or enzastaurin.

In some embodiments, an anti-human OX40 agonist antibody may be administered in conjunction with a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of MDX-1106 (nivolumab, OPDIVO), Merck 3475 (MK-3475, pembrolizumab, KEYTRUDA) and CT-011 (Pidilizumab). In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A, MEDI4736 and MDX-1105. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1106, also known as MDX-1106-04, ONO-4538, BMS-936558 or nivolumab, is an anti-PD-1 antibody described in WO2006/121168. Merck 3475, also known as MK-3475, SCH-900475 or pembrolizumab, is an anti-PD-1 antibody described in WO2009/114335. CT-011, also known as hBAT, hBAT-1 or pidilizumab, is an anti-PD-1 antibody described in WO2009/101611. AMP-224, also known as B7-DCIg, is a PD-L2-Fc fusion soluble receptor described in WO2010/027827 and WO2011/066342. In some embodiments, the anti-PD-1 antibody is MDX-1106. Alternative names for "MDX-1106" include MDX-1 106-04, ONO-4538, BMS-936558 or nivolumab. In some embodiments, the anti-PD-1 antibody is nivolumab (CAS Registry Number: 946414-94-4).

In some embodiments, an anti-human OX40 agonist antibody may be administered in conjunction with an agonist directed against an activating co-stimulatory molecule. In some embodiments, an activating co-stimulatory molecule may include CD40, CD226, CD28, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, an anti-human OX40 agonist antibody may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3 (e.g., LAG-3-IgG fusion protein (IMP321)), B7-H3, B7-H4, IDO, TIGIT, MICA/B, or arginase.

In some embodiments, an anti-human OX40 agonist antibody may be administered in conjunction with an antagonist directed against CTLA-4 (also known as CD152), e.g., a blocking antibody. In some embodiments, an anti-human OX40 agonist antibody may be administered in conjunction with ipilimumab (also known as MDX-010, MDX-101, or Yervoy®). In some embodiments, an anti-human OX40 agonist antibody may be administered in conjunction with tremelimumab (also known as ticilimumab or CP-675,206). In some embodiments, an anti-human OX40 agonist antibody may be administered in conjunction with an antagonist directed against B7-H3 (also known as CD276), e.g., a blocking antibody. In some embodiments, an anti-human OX40 agonist antibody may be administered in conjunction with MGA271. In some embodiments, an anti-human OX40 agonist antibody may be administered in conjunction with an antagonist directed against a TGF beta, e.g., metelimumab (also known as CAT-192), fresolimumab (also known as GC1008), or LY2157299.

In some embodiments, an anti-human OX40 agonist antibody may be administered in conjunction with a treatment comprising adoptive transfer of a T cell (e.g., a cytotoxic T cell or CTL) expressing a chimeric antigen receptor (CAR). In some embodiments, an anti-human OX40 agonist antibody may be administered in conjunction with UCART19. In some embodiments, an anti-human OX40 agonist antibody may be administered in conjunction with WT128z. In some embodiments, an anti-human OX40 agonist antibody may be administered in conjunction with KTE-C19 (Kite). In some embodiments, an anti-human OX40 agonist antibody may be administered in conjunction with CTL019 (Novartis). In some embodiments, an anti-human OX40 agonist antibody may be administered in conjunction with a treatment comprising adoptive transfer of a T cell comprising a dominant-negative TGF beta receptor, e.g, a dominant-negative TGF beta type II receptor. In some embodiments, an anti-human OX40 agonist antibody may be administered in conjunction with a treatment comprising a HERCREEM protocol (see, e.g., ClinicalTrials.gov Identifier NCT00889954).

In some embodiments, an anti-human OX40 agonist antibody may be administered in conjunction with an antagonist directed against CD19. In some embodiments, an anti-human OX40 agonist antibody may be administered in conjunction with MOR00208. In some embodiments, an anti-human OX40 agonist antibody may be administered in conjunction with an antagonist directed against CD38. In some embodiments, an anti-human OX40 agonist antibody may be administered in conjunction with daratumumab.

In some embodiments, an anti-human OX40 agonist antibody may be administered in conjunction with an agonist directed against CD137 (also known as TNFRSF9, 4-1BB, or ILA), e.g., an activating antibody. In some embodiments, an anti-human OX40 agonist antibody may be administered in conjunction with urelumab (also known as BMS-663513). In some embodiments, an anti-human OX40 agonist antibody may be administered in conjunction with an agonist directed against CD40, e.g., an activating antibody. In some embodiments, an anti-human OX40 agonist antibody may be administered in conjunction with CP-870893. In some embodiments, an anti-human OX40 agonist antibody may be administered in conjunction with an agonist directed against OX40 (also known as CD134), e.g., an activating antibody. In some embodiments, an anti-human OX40 agonist antibody may be administered in conjunction with a different anti-OX40 antibody (e.g., AgonOX). In some embodiments, an anti-human OX40 agonist antibody may be administered in conjunction with an agonist directed against CD27, e.g., an activating antibody. In some embodiments, an anti-human OX40 agonist antibody may be administered in conjunction with CDX-1127. In some embodiments, an anti-human OX40 agonist antibody may be administered in conjunction with an antagonist directed against indoleamine-2,3-dioxygenase (IDO). In some embodiments, with the IDO antagonist is 1-methyl-D-tryptophan (also known as 1-D-MT).

In some embodiments, an anti-human OX40 agonist antibody may be administered in conjunction with an agonist directed against CD137 (also known as TNFRSF9, 4-1BB, or ILA), e.g., an activating antibody. In some embodiments, an anti-human OX40 agonist antibody may be administered in conjunction with urelumab (also known as BMS-663513). In some embodiments, an anti-human OX40 agonist antibody may be administered in conjunction with an agonist directed against CD40, e.g., an activating antibody. In some embodiments, an anti-human OX40 agonist antibody may be administered in conjunction with CP-870893 or RO7009789. In some embodiments, an anti-human OX40 agonist antibody may be administered in conjunction with an agonist directed against OX40 (also known as CD134), e.g., an activating antibody.). In some embodiments, an anti-human OX40 agonist antibody may be administered in conjunction with an agonist directed against CD27, e.g., an activating antibody. In some embodiments, an anti-human OX40 agonist antibody may be administered in conjunction with CDX-1127 (also known as varlilumab). In some embodiments, an anti-human OX40 agonist antibody may be administered in conjunction with an antagonist directed against indoleamine-2,3-dioxygenase (IDO). In some embodiments, with the IDO antagonist is 1-methyl-D-tryptophan (also known as 1-D-MT). In some embodiments, the IDO antagonist is an IDO antagonist shown in WO2010/005958 (the contents of which are expressly incorporated by record herein). In some embodiments the IDO antagonist is 4-({2-[(Aminosulfonyl)amino]ethyl}amino)-N-(3-bromo-4-fluorophenyl)-N'-hydroxy-1,2,5-oxadiazole-3-carboximidamide (e.g., as described in Example 23 of WO2010/005958). In some embodiments the IDO antagonist is

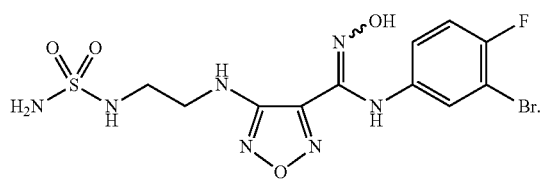 [SMILES: NS(=O)(=O)NCCNc1nonc1C(=NO)Nc1ccc(F)c(Br)c1]

In some embodiments, the IDO antagonist is INCB24360. In some embodiments, the IDO antagonist is Indoximod (the D isomer of 1-methyl-tryptophan). In some embodiments, an anti-human OX40 agonist antibody may be administered in conjunction with an antibody-drug conjugate. In some embodiments, the antibody-drug conjugate comprises mertansine or monomethyl auristatin E (MMAE). In some embodiments, an anti-human OX40 agonist antibody may be administered in conjunction with an anti-NaPi2b antibody-MMAE conjugate (also known as DNIB0600A, RG7599 or lifastuzumab vedotin). In some embodiments, an anti-human OX40 agonist antibody may be administered in conjunction with trastuzumab emtansine (also known as T-DM1, ado-trastuzumab emtansine, or KADCYLA®, Genentech). In some embodiments, an anti-human OX40 agonist antibody may be administered in conjunction with an anti-MUC16 antibody-MMAE conjugate, DMUC5754A. In some embodiments, an anti-human OX40 agonist antibody may be administered in conjunction with an anti-MUC16 antibody-MMAE conjugate, DMUC4064A. In some embodiments, an anti-human OX40 agonist antibody may be administered in conjunction with an antibody-drug conjugate targeting the endothelin B receptor (EDNBR), e.g., an antibody directed against EDNBR conjugated with MMAE. In some embodiments, an anti-human OX40 agonist antibody may be administered in conjunction with an antibody-drug conjugate targeting the lymphocyte antigen 6 complex, locus E (Ly6E), e.g., an antibody directed against Ly6E conjugated with MMAE, (also known as DLYE5953A). In some embodiments, an anti-human OX40 agonist antibody may be administered in conjunction with polatuzumab vedotin. In some embodiments, an anti-human OX40 agonist antibody may be administered in conjunction with an antibody-drug conjugate targeting CD30. In some embodiments, an anti-human OX40 agonist antibody may be administered in conjunction with ADCETRIS (also known as brentuximab vedotin). In some embodiments, an anti-human OX40 agonist antibody may be administered in conjunction with polatuzumab vedotin.

In some embodiments, an anti-human OX40 agonist antibody may be administered in conjunction with an angiogenesis inhibitor. In some embodiments, an anti-human OX40 agonist antibody may be administered in conjunction with an antibody directed against a VEGF, e.g., VEGF-A. In some embodiments, an anti-human OX40 agonist antibody may be administered in conjunction with bevacizumab (also known as AVASTIN®, Genentech). In some embodiments, an anti-human OX40 agonist antibody may be administered in conjunction with an antibody directed against angiopoietin 2 (also known as Ang2). In some embodiments, an anti-human OX40 agonist antibody may be administered in conjunction with MEDI3617. In some embodiments, an anti-human OX40 agonist antibody may be administered in conjunction with an antibody directed against VEGFR2. In some embodiments, an anti-human OX40 agonist antibody may be administered in conjunction with ramucirumab. In some embodiments, an anti-human OX40 agonist antibody may be administered in conjunction with a VEGF Receptor fusion protein. In some embodiments, an anti-human OX40 agonist antibody may be administered in conjunction with aflibercept. In some embodiments, an anti-human OX40 agonist antibody may be administered in conjunction with ziv-aflibercept (also known as VEGF Trap or Zaltrap®). In some embodiments, an anti-human OX40 agonist antibody may be administered in conjunction with a bispecific antibody directed against VEGF and Ang2. In some embodiments, an anti-human OX40 agonist antibody may be administered in conjunction with RG7221 (also known as vanucizumab). In some embodiments, an anti-human OX40 agonist antibody may be administered in conjunction with an angiogenesis inhibitor and in conjunction with a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an anti-human OX40 agonist antibody may be administered in conjunction with bevacizumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody). In some embodiments, an anti-human OX40 agonist antibody may be administered in conjunction with bevacizumab and MDX-1106 (nivolumab, OPDIVO). In some embodiments, an anti-human OX40 agonist antibody may be administered in conjunction with bevacizumab and Merck 3475 (MK-3475, pembrolizumab, KEYTRUDA). In some embodiments, an anti-human OX40 agonist antibody may be administered in conjunction with bevacizumab and CT-011 (Pidilizumab). In some embodiments, an anti-human OX40 agonist antibody may be administered in conjunction with bevacizumab and YW243.55.S70. In some embodiments, an anti-human OX40 agonist antibody may be administered in conjunction with bevacizumab and MPDL3280A. In some embodiments, an anti-human OX40 agonist antibody may be administered in conjunction with bevacizumab and MEDI4736. In some embodiments, an anti-human OX40 agonist antibody may be administered in conjunction with bevacizumab and MDX-1105.

In some embodiments, an anti-human OX40 agonist antibody may be administered in conjunction with an antineoplastic agent. In some embodiments, an anti-human OX40 agonist antibody may be administered in conjunction with an agent targeting CSF-1R (also known as M-CSFR or CD115). In some embodiments, an anti-human OX40 agonist antibody may be administered in conjunction with anti-CSF-1R antibody (also known as IMC-CS4 or LY3022855) In some embodiments, an anti-human OX40 agonist antibody may be administered in conjunction with anti-CSF-1R antibody, RG7155 (also known as RO5509554 or emactuzumab). In some embodiments, an anti-human OX40 agonist antibody may be administered in conjunction with an interferon, for example interferon alpha or interferon gamma. In some embodiments, an anti-human OX40 agonist antibody may be administered in conjunction with Roferon-A (also known as recombinant Interferon alpha-2a). In some embodiments, an anti-human OX40 agonist antibody may be administered in conjunction with GM-CSF (also known as recombinant human granulocyte macrophage colony stimulating factor, rhu GM-CSF, sargramostim, or Leukine®). In some embodiments, an anti-human OX40 agonist antibody may be administered in conjunction with IL-2 (also known as aldesleukin or Proleukin®). In some embodiments, an anti-human OX40 agonist antibody may be administered in conjunction with IL-12. In some embodiments, an anti-human OX40 agonist antibody may be administered in conjunction with IL27. In some embodiments, an anti-human OX40 agonist antibody may be administered in conjunction with IL-15. In some embodiments, an anti-human OX40 agonist antibody may be administered in conjunction with ALT-803. In some embodiments, an anti-human OX40 agonist antibody may be administered in conjunction with an antibody targeting CD20. In some embodiments, the antibody targeting CD20 is obinutuzumab (also known as GA101 or Gazyva®) or rituximab. In some embodiments, an anti-human OX40 agonist antibody may be administered in conjunction with an antibody targeting GITR. In some embodiments, the antibody targeting GITR is TRX518. In some embodiments, the antibody targeting GITR is MK04166 (Merck).

In some embodiments, an anti-human OX40 agonist antibody may be administered in conjunction with an inhibitor of Bruton's tyrosine kinase (BTK). In some embodiments, an anti-human OX40 agonist antibody may be administered in conjunction with ibrutinib. In some embodiments, an anti-human OX40 agonist antibody may be administered in conjunction with an inhibitor of Isocitrate dehydrogenase 1 (IDH1) and/or Isocitrate dehydrogenase 2 (IDH2). In some embodiments, an anti-human OX40 agonist antibody may be administered in conjunction with AG-120 (Agios).

In some embodiments, an anti-human OX40 agonist antibody may be administered in conjunction with obinutuzumab and a PD-1 axis binding antagonist (e.g., a PD-1 binding antagonist such as an anti-PD-1 antibody, a PD-L1 binding antagonist such as an anti-PD-L1 antibody, and a PD-L2 binding antagonist such as an anti-PD-L2 antibody).

In some embodiments, an anti-human OX40 agonist antibody may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., *Cancer Sci*, 104:14-21, 2013). In some embodiments, an anti-human OX40 agonist antibody may be administered in conjunction with an adjuvant. In some embodiments, an anti-human OX40 agonist antibody may be administered in conjunction with a treatment comprising a TLR agonist, e.g., Poly-ICLC (also known as Hiltonol®), LPS, MPL, or CpG ODN. In some embodiments, an anti-human OX40 agonist antibody may be administered in conjunction with tumor necrosis factor (TNF) alpha. In some embodiments, an anti-human OX40 agonist antibody may be administered in conjunction with IL-1. In some embodiments, an anti-human OX40 agonist antibody may be administered in conjunction with HMGB1. In some embodiments, an anti-human OX40 agonist antibody may be administered in conjunction with an IL-10 antagonist. In some embodiments, an anti-human OX40 agonist antibody may be administered in conjunction with an IL-4 antagonist. In some embodiments, an anti-human OX40 agonist antibody may be administered in conjunction with an IL-13 antagonist. In some embodiments, an anti-human OX40 agonist antibody may be administered in conjunction with an IL-17 antagonist. In some embodiments, an anti-human OX40 agonist antibody may be administered in conjunction with an HVEM antagonist. In some embodiments, an anti-human OX40 agonist antibody may be administered in conjunction with an ICOS agonist, e.g., by administration of ICOS-L, or an agonistic antibody directed against ICOS. In some embodiments, an anti-human OX40 agonist antibody may be administered in conjunction with a treatment targeting CX3CL1. In some embodiments, an anti-human OX40 agonist antibody may be administered in conjunction with a treatment targeting CXCL9. In some embodiments, an anti-human OX40 agonist antibody may be administered in conjunction with a treatment targeting CXCL10. In some embodiments, an anti-human OX40 agonist antibody may be administered in conjunction with a treatment targeting CCL5. In some embodiments, an anti-human OX40 agonist antibody may be administered in conjunction with an LFA-1 or ICAM1 agonist. In some embodiments, an anti-human OX40 agonist antibody may be administered in conjunction with a Selectin agonist.

In some embodiments, an anti-human OX40 agonist antibody may be administered in conjunction with an inhibitor of B-Raf. In some embodiments, an anti-human OX40 agonist antibody may be administered in conjunction with vemurafenib (also known as Zelboraf®). In some embodiments, an anti-human OX40 agonist antibody may be administered in conjunction with dabrafenib (also known as Tafinlar®). In some embodiments, an anti-human OX40 agonist antibody may be administered in conjunction with encorafenib (LGX818).

In some embodiments, an anti-human OX40 agonist antibody may be administered in conjunction with an EGFR inhibitor. In some embodiments, an anti-human OX40 agonist antibody may be administered in conjunction with erlotinib (also known as Tarceva®). In some embodiments, an anti-human OX40 agonist antibody may be administered in conjunction with an inhibitor of EGFR-T790M. In some embodiments, an anti-human OX40 agonist antibody may be administered in conjunction with gefitinib. In some embodiments, an anti-human OX40 agonist antibody may be administered in conjunction with afatinib. In some embodiments, an anti-human OX40 agonist antibody may be administered in conjunction with cetuximab (also known as Erbitux®). In some embodiments, an anti-human OX40 agonist antibody may be administered in conjunction with panitumumab (also known as Vectibix®). In some embodiments, an anti-human OX40 agonist antibody may be administered in conjunction with rociletinib. In some embodiments, an anti-human OX40 agonist antibody may be administered in conjunction with AZD9291. In some embodiments, an anti-human OX40 agonist antibody may be administered in conjunction with an inhibitor of a MEK, such as MEK1 (also known as MAP2K1) and/or MEK2 (also known as MAP2K2). In some embodiments, an anti-human OX40 agonist antibody may be administered in conjunction with cobimetinib (also known as GDC-0973 or XL-518). In some embodiments, an anti-human OX40 agonist antibody may be administered in conjunction with trametinib (also known as Mekinist®). In some embodiments, an anti-human OX40 agonist antibody may be administered in conjunction with binimetinib.

In some embodiments, an anti-human OX40 agonist antibody may be administered in conjunction an inhibitor of B-Raf (e.g., vemurafenib or dabrafenib) and an inhibitor of MEK (e.g., MEK1 and/or MEK2 (e.g., cobimetinib or trametinib). In some embodiments, an anti-human OX40 agonist antibody may be administered in conjunction with an inhibitor of ERK (e.g., ERK1/2). In some embodiments, an anti-human OX40 agonist antibody may be administered in conjunction with GDC-0994). In some embodiments, an anti-human OX40 agonist antibody may be administered in conjunction with an inhibitor of B-Raf, an inhibitor of MEK, and an inhibitor of ERK1/2. In some embodiments, an anti-human OX40 agonist antibody may be administered in conjunction with an inhibitor of EGFR, an inhibitor of MEK, and an inhibitor of ERK1/2. In some embodiments, an anti-human OX40 agonist antibody may be administered in conjunction with one or more MAP kinase pathway inhibitor. In some embodiments, an anti-human OX40 agonist antibody may be administered in conjunction with CK127. In some embodiments, an anti-human OX40 agonist antibody may be administered in conjunction with an inhibitor of K-Ras.

In some embodiments, an anti-human OX40 agonist antibody may be administered in conjunction with an inhibitor of c-Met. In some embodiments, an anti-human OX40 agonist antibody may be administered in conjunction with onartuzumab (also known as MetMAb). In some embodiments, an anti-human OX40 agonist antibody may be administered in conjunction with an inhibitor of anaplatic lymphoma kinase (ALK). In some embodiments, an anti-human OX40 agonist antibody may be administered in conjunction with AF802 (also known as CH5424802 or alectinib). In some embodiments, an anti-human OX40 agonist antibody may be administered in conjunction with crizotinib. In some embodiments, an anti-human OX40 agonist antibody may be administered in conjunction with ceritinib. In some embodiments, an anti-human OX40 agonist antibody may be administered in conjunction with an inhibitor of a phosphatidylinositol 3-kinase (PI3K). In some embodiments, an anti-human OX40 agonist antibody may be administered in conjuction with buparlisib (BKM-120). In some embodiments, an anti-human OX40 agonist antibody may be administered in conjunction with pictilisib (also known as GDC-0941). In some embodiments, an anti-human OX40 agonist antibody may be administered in conjunction with buparlisib (also known as BKM-120). In some embodiments, an anti-human OX40 agonist antibody may be administered in conjunction with perifosine (also known as KRX-0401). In some embodiments, an anti-human OX40 agonist antibody may be administered in conjunction with a delta-selective inhibitor of a phosphatidylinositol 3-kinase (PI3K). In some embodiments, an anti-human OX40 agonist antibody may be administered in conjunction with idelalisib (also known as GS-1101 or CAL-101). In some embodiments, an anti-human OX40 agonist antibody may be administered in conjunction with taselisib (also known as GDC-0032). In some embodiments, an anti-human OX40 agonist antibody may be administered in conjunction with BYL-719. In some embodiments, an anti-human OX40 agonist antibody may be administered in conjunction with an inhibitor of an Akt. In some embodiments, an anti-human OX40 agonist antibody may be administered in conjunction with MK2206. In some embodiments, an anti-human OX40 agonist antibody may be administered in conjunction with GSK690693. In some embodiments, an anti-human OX40 agonist antibody may be administered in conjunction with ipatasertib (also known as GDC-0068). In some embodiments, an anti-human OX40 agonist antibody may be administered in conjunction with an inhibitor of mTOR. In some embodiments, an anti-human OX40 agonist antibody may be administered in conjunction with sirolimus (also known as rapamycin). In some embodiments, an anti-human OX40 agonist antibody may be administered in conjunction with temsirolimus (also known as CCI-779 or Torisel®). In some embodiments, an anti-human OX40 agonist antibody may be administered in conjunction with everolimus (also known as RAD001). In some embodiments, an anti-human OX40 agonist antibody may be administered in conjunction with ridaforolimus (also known as AP-23573, MK-8669, or deforolimus). In some embodiments, an anti-human OX40 agonist antibody may be administered in conjunction with OSI-027. In some embodiments, an anti-human OX40 agonist antibody may be administered in conjunction with AZD8055. In some embodiments, an anti-human OX40 agonist antibody may be administered in conjunction with INK128. In some embodiments, an anti-human OX40 agonist antibody may be administered in conjunction with a dual PI3K/mTOR inhibitor. In some embodiments, an anti-human OX40 agonist antibody may be administered in conjunction with XL765. In some embodiments, an anti-human OX40 agonist antibody may be administered in conjunction with GDC-0980. In some embodiments, an anti-human OX40 agonist antibody may be administered in conjunction with BEZ235 (also known as NVP-BEZ235). In some embodiments, an anti-human OX40 agonist antibody may be administered in conjunction with BGT226. In some embodiments, an anti-human OX40 agonist antibody may be administered in conjunction with GSK2126458. In some embodiments, an anti-human OX40 agonist antibody may be administered in conjunction with PF-04691502. In some embodiments, an anti-human OX40 agonist antibody may be administered in conjunction with PF-05212384 (also known as PKI-587).

In some embodiments, an anti-human OX40 agonist antibody may be administered in conjunction with an agent that selectively degrades the estrogen receptor. In some embodiments, an anti-human OX40 agonist antibody may be administered in conjunction with GDC-0927. In some embodiments, an anti-human OX40 agonist antibody may be administered in conjunction with an inhibitor of HER3. In some embodiments, an anti-human OX40 agonist antibody may be administered in conjunction with duligotuzumab. In some embodiments, an anti-human OX40 agonist antibody may be administered in conjunction with an inhibitor of LSD1. In some embodiments, an anti-human OX40 agonist antibody may be administered in conjunction with an inhibitor of MDM2. In some embodiments, an anti-human OX40 agonist antibody may be administered in conjunction with an inhibitor of BCL2. In some embodiments, an anti-human OX40 agonist antibody may be administered in conjunction with venetoclax. In some embodiments, an anti-human OX40 agonist antibody may be administered in conjunction with an inhibitor of CHK1. In some embodiments, an anti-human OX40 agonist antibody may be administered in conjunction with GDC-0575. In some embodiments, an anti-human OX40 agonist antibody may be administered in conjunction with an inhibitor of activated hedgehog signaling pathway. In some embodiments, an anti-human OX40 agonist antibody may be administered in conjunction with ERIVEDGE.

In some embodiments, an anti-human OX40 agonist antibody may be administered in conjunction with radiation therapy. In some embodiments, an anti-human OX40 agonist antibody may be administered in conjunction with gemcitabine. In some embodiments, an anti-human OX40 agonist antibody may be administered in conjunction with nab-paclitaxel (ABRAXANE). In some embodiments, an anti-human OX40 agonist antibody may be administered in conjunction with trastuzumab. In some embodiments, an anti-human OX40 agonist antibody may be administered in conjunction with TVEC. In some embodiments, an anti-human OX40 agonist antibody may be administered in conjunction with IL27. In some embodiments, an anti-human OX40 agonist antibody may be administered in conjunction with cyclophosphamide. In some embodiments, an anti-human OX40 agonist antibody may be administered in conjunction with an agent that recruits T cells to the tumor. In some embodiments, an anti-human OX40 agonist antibody may be administered in conjunction with lirilumab (IPH2102/BMS-986015). In some embodiments, an anti-human OX40 agonist antibody may be administered in conjunction with Idelalisib. In some embodiments, an anti-human OX40 agonist antibody may be administered in conjunction with an antibody that targets CD3 and CD20. In some embodiments, an anti-human OX40 agonist antibody may be administered in conjunction with REGN1979. In some embodiments, an anti-human OX40 agonist antibody may be administered in conjunction with an antibody that targets CD3 and CD19. In some embodiments, an anti-human OX40 agonist antibody may be administered in conjunction with blinatumomab.

In some embodiments, an anti-human OX40 agonist antibody may be administered in conjunction with an oncolytic virus. In some embodiments, an anti-human OX40 agonist antibody may be administered in conjunction with carboplatin and nab-paclitaxel. In some embodiments, an anti-human OX40 agonist antibody may be administered in conjunction with carboplatin and paclitaxel. In some embodiments, an anti-human OX40 agonist antibody may be administered in conjunction with cisplatin and pemetrexed. In some embodiments, an anti-human OX40 agonist antibody may be administered in conjunction with cisplatin and gemcitabine. In some embodiments, an anti-human OX40 agonist antibody may be administered in conjunction with FOLFOX. In some embodiments, an anti-human OX40 agonist antibody may be administered in conjunction with FOLFIRI.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 40 mg/kg of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-OX40 antibody.

III. Combination Therapy Comprising Anti-Angiogenesis Agents and OX40 Binding Agonists Also provided herein are methods treating or delaying progression of cancer in an individual comprising administering to the individual an effective amount of an anti-angiogenesis agent and an OX40 binding agonist.

In some embodiments, "sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

In some embodiments, the terms "cancer" and "cancerous" further include but are not limited to, carcinoma, lymphoma, blastoma, sarcoma, and leukemia, More particular examples of such cancers include epithelial ovarian cancer, fallopian tube cancer, primary peritoneal cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer (including platinum sensitive and platinum resistant ovarian cancer), liver cancer, bladder cancer, hepatoma, neuroblastoma, melanoma, breast cancer, colon cancer, colorectal cancer, fallopian tube, peritoneal, endometrial or uterine carcinoma, gynecologic cancers (e.g., ovarian, peritoneal, fallopian tube, cervical, endometrial, vaginal, and vulvar cancer), salivary gland carcinoma, kidney or renal cancer, liver cancer, prostate cancer, vulval cancer, thyroid cancer, soft-tissue sarcoma, kaposi's sarcoma, carcinoid carcinoma, mesothelioma, multiple myeloma, hepatic carcinoma and various types of head and neck cancer, as well as B-cell lymphoma (including low grade/follicular non-Hodgkin's lymphoma (NHL): small lymphocytic (SL) NHL; intermediate grade/follicular NHL; intermediate grade diffuse NHL; high grade immunoblastic N-HL; high grade lymphoblastic NHL; high grade small non-cleaved cell N-HL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. In some embodiments, included in this definition are benign and malignant cancers.

In some embodiments, an "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

In some embodiments, "in conjunction with" refers to administration of one treatment modality in addition to another treatment modality. As such, "in conjunction with" refers to administration of one treatment modality before, during, or after administration of the other treatment modality to the individual. For example, an anti-angiogenesis agent may be administered in conjunction with an OX40 binding agonist. An anti-angiogenesis agent and an OX40 binding agonist may be administered in conjunction with another a chemotherapeutic agent.

In some embodiments, an "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogenesis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists antiangiogenic agents used in clinical trials).

In some embodiments, the term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246:1306 (1989), and Houck et al. Mol. Endocrin., 5:1806 (1991), together with the naturally occurring allelic and processed forms thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. Typically, VEGF refers to human VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

In some embodiments, a "chimeric VEGF receptor protein" is a VEGF receptor molecule having amino acid sequences derived from at least two different proteins, at least one of which is a VEGF receptor protein. In certain embodiments, the chimeric VEGF receptor protein is capable of binding to and inhibiting the biological activity of VEGF.

In some embodiments, a "VEGF antagonist" or "VEGF-specific antagonist" refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF-specific antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF-specific antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF-specific antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF mediated biological activities of VEGF. In certain embodiments, the VEGF antagonist reduces or inhibits, by at least 10%, 20%, 30%, 40%, 50%, 60% 70%, 80%, 90% or more, the expression level or biological activity of VEGF, In some embodiments, the VEGF inhibited by the VEGF-specific antagonist is VEGF (8-109), VEGF (1-109), or $VEGF_{165}$.

In some embodiments, as used herein, VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGFA antibodies (e.g., bevacizumab, sevacizumab) anti-VEGFB antibodies, anti-VEGFC antibodies (e.g., VGX-100), anti-VEGFD antibodies, and nonpeptide small molecule VEGF antagonists (e.g., pazopanib, axitinib, vandetanib, stivarga, cabozantinib, lenvatinib, nintedanib, orantinib, orantinib, telatinib, dovitinig, cediranib, motesanib, sulfatinib, apatinib, foretinib, famitinib, and tivozanib).

In some embodiments, an "anti-VEGF antibody" is an antibody that binds to VEGF with sufficient affinity and specificity. In certain embodiments, the antibody will have a sufficiently high binding affinity for VEGF, for example, the antibody may bind hVEGF with a $K_d$ value of between 100 nM-1 µM. Antibody affinities may be determined, e.g., by a surface plasmon resonance based assay (such as the BIAcore assay as described in PCT Application Publication No. WO2005/012359); enzyme-linked immunoabsorbent assay (ELISA); and competition assays (e.g. RIA's). In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF, or bFGF. In one embodiment, anti-VEGF antibody is a monoclonal antibody that binds to the same epitope as the monoclonal anti-VEGF antibody A46.61 produced by hybridoma ATCC HB 10709. In another embodiment, the anti-VEGF antibody is a recombinant humanized anti-VEGF monoclonal antibody generated according to Presta et al. (1997) Cancer Res. 57:4593-4599, including but not limited to the antibody known as bevacizumab (BV; AVASTIN®).

In some embodiments, the anti-VEGF antibody "Bevacizumab (BV)," also known as "rhuMAb VEGF" or "AVASTIN'®," is a recombinant humanized anti-VEGF monoclonal antibody generated according to Presta et al. (1997) Cancer Res. 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A.4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference. Additional preferred antibodies include the G6 or B20 series antibodies (e.g., G6-31, B20-4.1), as described in PCT Application Publication No. WO 2005/012359. For additional preferred antibodies see U.S. Pat. Nos. 7,060,269, 6,582,959, 6,703,020; 6,054,297; WO98/45332; WO 96/30046; WO94/10202: EP 0666868B1; U.S. Patent Application Publication Nos. 2006009360, 20050186208, 20030206899, 20030190317, 20030203409, and 2005012126; and Popkov et al., Journal of Immunological Methods 288:149-164 (2004). Other preferred antibodies include those that bind to a functional epitope on human VEGF comprising of residues F17, M18, D19, Y21, Y25, Q89, 191, K101, E103, and (104 or, alternatively, comprising residues F17, Y21, Q22, Y25, D63, 183, and Q89.

In some embodiments, the "epitope A4.6.1" refers to the epitope recognized by the anti-VEGF antibody bevacizumab (AVASTIN®) (see Muller Y et al., Structure 15 Sep. 1998, 6:1153-1167). In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599.

In some embodiments, by "standard of care" herein is intended the anti-tumor agent or agents that are routinely used to treat a particular form of cancer. For example, for platinum-resistant ovarian cancer, a standard of care is topotecan or liposomal doxorubicin.

In some embodiments, by "platinum-based chemotherapeutic agent" or "platin" is meant an antineoplastic drug that is a coordination complex of platinum. Examples of platinum-based chemotherapeutic agents include carboplatin, cisplatin, and oxaliplatinum.

In some embodiments, by "platinum-based chemotherapy" is meant therapy with one or more platinum-based chemotherapeutic agent, optionally in combination with one or more other chemotherapeutic agents.

In some embodiments, by "chemotherapy-resistant" cancer is meant cancer in a patient that has progressed while the patient is receiving a chemotherapy regimen (i.e., the patient is "chemotherapy refractory"), or the patient has progressed within 12 months (for instance, within 6 months) after completing a chemotherapy regimen.

In some embodiments, by "platinum-resistant" cancer is meant cancer in a patient that has progressed while receiving platinum-based chemotherapy (i.e., the patient is "platinum refractory"), or the patient has progressed within 12 months (for instance, within 6 months) after completing a platinum-based chemotherapy regimen.

In some embodiments, by "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

A. Anti-Angiogenesis Agents

Provided herein are methods treating or delaying progression of cancer in an individual comprising administering to the individual an effective amount of an anti-angiogenesis agent and an OX40 binding agonist.

As described supra, an anti-angiogenesis agent may include a compound such as a small molecular weight substance, a polynucleotide, a polypeptide, an isolated protein, a recombinant protein, an antibody, or conjugates or fusion proteins thereof. In some embodiments, the anti-angiogenesis agent is an anti-VEGFR2 antibody; an anti-VEGFR1 antibody; a VEGF-trap; a bispecific VEGF antibody; a bispecific antibody comprising a combination of two arms selected from an anti-VEGF arm, an anti-VEGFR1 arm, and an anti-VEGFR2 arm; an anti-VEGF-A antibody (e.g., an anti-KDR receptor or anti-Flt-1 receptor antibody); an anti-VEGFB antibody; an anti-VEGFC antibody; an anti-VEGFD antibody; a nonpeptide small molecule VEGF antagonist; an anti-PDGFR inhibitor; or a native angiogenesis inhibitor. In certain embodiments, the anti-angiogenesis agent is ramucirumab, tanibirumab, aflibercept (e.g., VEGF Trap-Eye; EYLEA®), icrucumab, ziv-aflibercept (e.g., VEGF Trap; ZALTRAP®), MP-0250, vanucizumab, sevacizumab, VGX-100, pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, imatinib (e.g., Imatinib Mesylate; Gleevec™), and tivozanib.

In some embodiments, the anti-angiogenesis agent is an anti-angiogenesis antibody. Descriptions of antibodies and methods for generating antibodies are further provided infra. In some embodiments, the anti-angiogenesis antibody is a monoclonal antibody. In some embodiments, the anti-angiogenesis antibody is a human or humanized antibody (described in more detail below).

In some embodiments, the anti-angiogenesis agent is a VEGF antagonist. For example, VEGF antagonists of the present disclosure may include without limitation polypeptides that specifically bind to VEGF, anti-VEGF antibodies and antigen-binding fragments thereof, receptor molecules and derivatives which bind specifically to VEGF, thereby sequestering its binding to one or more receptors; fusion proteins (e.g., VEGF-Trap (Regeneron)), $VEGF_{121}$-gelonin (Peregrine), antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide (e.g., an RNAi, siRNA, shRNA, or miRNA); ribozymes that target VEGF; peptibodies to VEGF; VEGF aptamers; polypeptides that bind to VEGFR; anti-VEGFR antibodies and antigen-binding fragments thereof, derivatives which bind to VEGFR thereby blocking, inhibiting, abrogating, reducing, or interfering with VEGF biological activities (e.g., VEGF signaling); fusion proteins and non-peptide small molecules that bind to VEGF or VEGFR and are capable of blocking, inhibiting, abrogating, reducing, or interfering with VEGF biological activities.

In certain embodiments, the VEGF antagonist reduces or inhibits, by at least 10%, 20%, 30%, 40%, 50%, 60%, 70%, 80%, 90% or more, the expression level or biological activity of VEGF. For example, in some embodiments, the VEGF antagonist may reduce or inhibit the expression level or biological activity of VEGF by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the VEGF inhibited by the VEGF-specific antagonist is VEGF (8-109), VEGF (1-109), or $VEGF_{165}$.

Certain aspects of the methods, uses, and kits of the present disclosure are based, at least in part, on the surprising discovery that anti-VEGF treatment can improve the functional phenotype of tumoral dendritic cells (e.g., by leading to increased expression of MHC Class II and/or OX40L). Without wishing to be bound to theory, this property, inter alia, may make combination therapies including an anti-angiogenesis agent and an OX40 binding agonist particularly advantageous for the treatment of cancer, e.g., by resulting in enhanced anti-tumor responses such as anti-tumoral T cell responses.

Therefore, in some embodiments, the VEGF antagonist increases MHC class II expression on intratumoral dendritic cells, e.g., as compared to MHC class II expression on dendritic cells from a tumor treated with a control antibody (e.g., an isotype control). MHC class II is known as a family of related molecules (typically heterodimers containing alpha and beta chains) that present antigen to T cells. As used herein, MHC class II expression may refer to expression of any MHC class II molecule or chain, including without limitation a polypeptide encoded by the human genes HLA-DM alpha (e.g., NCBI Gene ID No. 3108), HLA-DM beta (e.g., NCBI Gene ID No. 3109), HLA-DO alpha (e.g., NCBI Gene ID No. 3111), HLA-DO beta (e.g., NCBI Gene ID No. 3112), HLA-DP alpha 1 (e.g., NCBI Gene ID No. 3113), HLA-DP beta 1 (e.g., NCBI Gene ID No. 3115), HLA-DQ alpha 1 (e.g., NCBI Gene ID No. 3117), HLA-DQ alpha 2 (e.g., NCBI Gene ID No. 3118), HLA-DQ beta 1 (e.g., NCBI Gene ID No. 3119), HLA-DQ beta 2 (e.g., NCBI Gene ID No. 3120), HLA-DR alpha (e.g., NCBI Gene ID No. 3122), HLA-DR beta 1 (e.g., NCBI Gene ID No. 3123), HLA-DR beta 3 (e.g., NCBI Gene ID No. 3125), HLA-DR beta 4 (e.g., NCBI Gene ID No. 3126), or HLA-DR beta 5 (e.g., NCBI Gene ID No. 3127). It will be appreciated by one of skill in the art that MHC genes are highly variable across populations, and thus the specific genes and sequences listed are merely exemplary and in no way intended to be limiting.

In some embodiments, the VEGF antagonist increases OX40L expression on intratumoral dendritic cells, e.g., as compared to OX40L expression on dendritic cells from a tumor treated with a control antibody (e.g., an isotype control). OX40L (also known as tumor necrosis factor ligand superfamily member 4 or CD252) is known as the binding partner or ligand of OX40. Examples of OX40L polypeptides including without limitation polypeptides having the amino acid sequence represented by UniProt Accession No. P43488 and/or a polypeptide encoded by gene TNFSF4 (e.g., NCBI Gene ID No. 7292).

Methods for measuring MHC class II or OX40L expression are known in the art and may include without limitation FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometery, HPLC, qPCR, RT-qPCR, multiplex qPCR or RT-qPCR, RNA-seq, microarray analysis, SAGE, MassARRAY technique, and FISH, and combinations thereof.

In some embodiments, the dendritic cells are myeloid dendritic cells. In other embodiments, the dendritic cells are non-myeloid dendritic cells (e.g., lymphoid or plasmacytoid dendritic cells). The cell-surface antigens expressed by dendritic cells, and those that distinguish myeloid and non-myeloid dendritic cells, are known in the art. For example, dendritic cells may be identified by expression of CD45, CD11c, and MHC class II. They may be distinguished from other cell types (e.g., macrophages, neutrophils, and granulocytic myeloid cells) by their lack of significant F4/80 and Gr1 expression. In some embodiments, myeloid dendritic cells are dendritic cells that express CD11b, and non-myeloid dendritic cells are dendritic cells that lack significant CD1 b expression. For further descriptions of myeloid and non-myeloid dendritic cells, see, e.g., Steinman, R. M. and Inaba, K. (1999) *J. Leukoc. Biol.* 66:205-8.

1. VEGF Receptor Molecules

In some embodiments, the anti-angiogenesis agent is a VEGF antagonist. In some embodiments, the VEGF antagonist comprises a soluble VEGF receptor or a soluble VEGF receptor fragment that specifically binds to VEGF. The two best characterized VEGF receptors are VEGFR1 (also known as Flt-1) and VEGFR2 (also known as KDR and FLK-1 for the murine homolog). The specificity of each receptor for each VEGF family member varies but VEGF-A binds to both Flt-1 and KDR. Both Flt-I and KDR belong to the family of receptor tyrosine kinases (RTKs). The RTKs comprise a large family of transmembrane receptors with diverse biological activities. At least nineteen (19) distinct RTK subfamilies have been identified. The receptor tyrosine kinase (RTK) family includes receptors that are crucial for the growth and differentiation of a variety of cell types (Yarden and Ullrich (1988) Ann. Rev. Biochem. 57:433-478; Ullrich and Schlessinger (1990) Cell 61:243-254). The intrinsic function of RTKs is activated upon ligand binding, which results in phosphorylation of the receptor and multiple cellular substrates, and subsequently in a variety of cellular responses (Ullrich & Schlessinger (1990) Cell 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see, Schlessinger and Ullrich (1992) Neuron 9:1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) PNAS USA 88:9026-9030; Terman et al. (1991) Oncogene 6:1677-1683. The extracellular domain is involved in the binding of VEGF and the intracellular domain is involved in signal transduction.

VEGF receptor molecules, or fragments thereof, that specifically bind to VEGF can be used in the methods of the invention to bind to and sequester the VEGF protein, thereby preventing it from signaling. In certain embodiments, the VEGF receptor molecule, or VEGF binding fragment thereof, is a soluble form, such as sFlt-1. A soluble form of the receptor exerts an inhibitory effect on the biological activity of the VEGF protein by binding to VEGF, thereby preventing it from binding to its natural receptors present on the surface of target cells. Also included are VEGF receptor fusion proteins, examples of which are described below.

In some embodiments, the VEGF antagonist is a chimeric VEGF receptor protein. A chimeric VEGF receptor protein is a receptor molecule having amino acid sequences derived from at least two different proteins, at least one of which is a VEGF receptor protein (e.g., the flt-1 or KDR receptor), that is capable of binding to and inhibiting the biological activity of VEGF. In certain embodiments, the chimeric VEGF receptor proteins of the invention consist of amino acid sequences derived from only two different VEGF receptor molecules; however, amino acid sequences comprising one, two, three, four, five, six, or all seven Ig-like domains from the extracellular ligand-binding region of the flt-1 and/or KDR receptor can be linked to amino acid sequences from other unrelated proteins, for example, immunoglobulin sequences. Other amino acid sequences to which Ig-like domains are combined will be readily apparent to those of ordinary skill in the art. Examples of chimeric VEGF receptor proteins include, e.g., soluble Flt-1/Fc, KDR/Fc, or FLt-1/KDR/Fc (also known as VEGF Trap). (See for example PCT Application Publication No. WO97/44453).

A soluble VEGF receptor protein or chimeric VEGF receptor proteins of the invention includes VEGF receptor proteins which are not fixed to the surface of cells via a transmembrane domain. As such, soluble forms of the VEGF receptor, including chimeric receptor proteins, while capable of binding to and inactivating VEGF, do not comprise a transmembrane domain and thus generally do not become associated with the cell membrane of cells in which the molecule is expressed.

In some embodiments, the VEGF antagonist (I, an anti-VEGF antibody, such as bevacizumnab) is administered by gene therapy. See, for example, WO 96/07321 published Mar. 14, 1996 concerning the use of gene therapy to generate intracellular antibodies. There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187), There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus. The currently preferred in vivo nucleic acid transfer techniques include transfection with viral vectors (such as adenovirus. Herpes simplex I virus, or adeno-associated virus) and lipid-based systems (useful lipids for lipid-mediated transfer of the gene are DOTMA DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J Biol. Chem.* 262: 44294432 (1987): and Wagner et al., *Proc. Natl. Acad Sc. USA* 87:3410-3414 (1990). For review of the currently known gene marking and gene therapy protocols see Anderson et al., *Science* 256:808-813 (1992). See also WO 93/25673 and the references cited therein.

2. Anti-VEGF Antibodies

In some embodiments, the anti-angiogenesis agent is a VEGF antagonist. In some embodiments, the VEGF antagonist is an anti-VEGF antibody. In some embodiments, the anti-VEGF antibody may be a human or humanized antibody. In some embodiments, the anti-VEGF antibody may be a monoclonal antibody. Exemplary descriptions, methods of making and use, and features of antibodies are described above in sections II.A1-7, B, D, and F with respect to anti-OX40 antibodies (e.g., anti-human agonist OX40 antibodies). One of skill in the art will appreciate that general descriptions, methods, and features related to antibodies may apply to anti-OX40 and anti-VEGF antibodies.

The VEGF antigen to be used for production of VEGF antibodies may be, e.g., the $VEGF_{165}$ molecule as well as other isoforms of VEGF or a fragment thereof containing the desired epitope. In one embodiment, the desired epitope is the one recognized by bevacizumab, which binds to the same epitope as the monoclonal anti-VEGF antibody A4.6.1 produced by hybridoma ATCC HB 10709 (known as "epitope A.4.6.1" defined herein). Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) Science, 246:1306. One cDNA identified thereby encodes a 165-amino acid protein having greater than 95% homology to bovine VEGF; this 165-amino acid protein is typically referred to as human VEGF (hVEGF) or $VEGF_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) Science, supra. Further efforts were undertaken to clone and express VEGF via recombinant DNA techniques. (See, e.g., Ferrara, Laboratory Investigation 72:615-618 (1995), and the references cited therein).

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact $VEGF_{165}$ homodimer.

Several molecules structurally related to VEGF have also been identified recently, including placenta growth factor (PlGF), VEGF-B, VEGF-C, VEGF-D and VEGF-E. Ferrara and Davis-Smyth (1987) Endocr. Rev., supra; Ogawa et al. J. Biological Chem. 273:31273-31281 (1998); Meyer et al. EMBO J., 18:363-374 (1999). A receptor tyrosine kinase, Flt-4 (VEGFR-3), has been identified as the receptor for VEGF-C and VEGF-D. Joukov et al. EMBO. J. 15:1751 (1996); Lee et al. PNAS USA 93:1988-1992 (1996); Achen et al. (1998) PNAS USA 95:548-553. VEGF-C has been shown to be involved in the regulation of lymphatic angiogenesis. Jeltsch et al. Science 276:1423-1425 (1997).

Two VEGF receptors have been identified, Flt-1 (also called VEGFR-1) and KDR (also called VEGFR-2). Shibuya et al. (1990) Oncogene 8:519-527; de Vries et al. (1992) Science 255:989-991; Terman et al. (1992) Biochem. Biophys. Res. Commun. 187:1579-1586. Neuropilin-1 has been shown to be a selective VEGF receptor, able to bind the heparin-binding VEGF isoforms (Soker et al. (1998) Cell 92:735-45).

Anti-VEGF antibodies that are useful in the methods of the invention include any antibody, or antigen binding fragment thereof, that bind with sufficient affinity and specificity to VEGF and can reduce or inhibit the biological activity of VEGF. An anti-VEGF antibody will usually not bind to other VEGF homologues such as VEGF-B or VEGF-C, nor other growth factors such as PlGF, PDGF, or bFGF.

In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) Cancer Res. 57:4593-4599. In one embodiment, the anti-VEGF antibody is "bevacizumab (BV)", also known as "rhuMAb VEGF" or "AVASTIN®". It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1.

Bevacizumab (AVASTIN®) was the first anti-angiogenesis therapy approved by the FDA and is approved for the treatment metastatic colorectal cancer (first- and second-line treatment in combination with intravenous 5-FU-based chemotherapy), advanced non-squamous, non-small cell lung cancer (NSCLC) (first-line treatment of unresectable, locally advanced, recurrent or metastatic NSCLC in combination with carboplatin and paclitaxel) and metastatic HER2-negative breast cancer (previously untreated, metastatic HER2-negative breast cancer in combination with paclitaxel).

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, 1191, K101, E103, and C104 or, alternatively, comprising residues F17, Y21, Q22, Y25, D63, 183 and Q89.

In one embodiment of the invention, the anti-VEGF antibody has a light chain variable region comprising the following amino acid sequence: DIQMTQSPSS LSAS-VGDRVT ITCSASQDIS NYLNWYQQKP GKAPKVLIYF TSSLHSGVPS RFSGSGSGTD FTLTISSLQP EDFATYY-CQQ YSTVPWTFGQ GTKVEIKR. (SEQ ID NO:214); and/or a heavy chain variable region comprising the following amino acid sequence: EVQLVESGGG LVQPGGSLRL SCAASGYTFT NYGMNWVRQA PGKGLEWVGW INTYTGEPTY AADFKRRFTF SLDTSKSTAY LQMNSL-RAED TAVYYCAKYP HYYGSSHWYF DVWGQGTLVT VSS (SEQ ID NO:215).

In some embodiments, the anti-VEGF antibody comprises one, two, three, four, five, or six hypervariable region (HVR) sequences of bevacizumab. In some embodiments, the anti-VEGF antibody comprises one, two, three, four, five, or six hypervariable region (HVR) sequences of selected from (a) HVR-H1 comprising the amino acid sequence of GYTFT-NYGMN (SEQ ID NO:216); (b) HVR-H2 comprising the amino acid sequence of WINTYTGEPTYAADFKR (SEQ ID NO:217); (c) HVR-H3 comprising the amino acid sequence of YPHYYGSSHWYFDV (SEQ ID NO:218); (d) HVR-L1 comprising the amino acid sequence of SASQDIS- NYLN (SEQ ID NO:219); (e) HVR-L2 comprising the amino acid sequence of FTSSLHS (SEQ ID NO:220); and (f) HVR-L3 comprising the amino acid sequence of QQYSTVPWT (SEQ ID NO:221). In some embodiments, the anti-VEGF antibody comprises one, two, three, four, five, or six hypervariable region (HVR) sequences of an antibody described in U.S. Pat. No. 6,884,879. In some embodiments, the anti-VEGF antibody comprises one, two, or three hypervariable region (HVR) sequences of a light chain variable region comprising the following amino acid sequence: DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVP-WTFGQ GTKVEIKR. (SEQ ID NO:214) and/or one, two, or three hypervariable region (HVR) sequences of a heavy chain variable region comprising the following amino acid sequence: EVQLVESGGG LVQPGGSLRL SCAASGYTFT NYGMNWVRQA PGKGLEWVGW INTYTGEPTY AAD-FKRRFTF SLDTSKSTAY LQMNSLRAED TAVYY-CAKYP HYYGSSHWYF DVWGQGTLVT VSS (SEQ ID NO:215).

A "G6 series antibody" according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/044853, the entire disclosure of which is expressly incorporated herein by reference. In one embodiment, the G6 series antibody binds to a functional epitope on human VEGF comprising residues F17, Y21, Q22, Y25, D63, 183 and Q89.

A "B20 series antibody" according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope on human VEGF comprising residues F17, M18, D19, Y21, Y25, Q89, 191, K101, E103, and C104.

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50mutant VEGF/IC50wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4° C. with an Fab form of the antibody to be tested at a concentration of 2 µg/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethylbenzidine (TMB, Kirkegaard & Perry Labs, Gaithersburg, Md.) substrate for approximately 5 min, quenched with 1.0 M H3PO4, and read spectrophotometrically at 450 nm. The ratio of IC50 values (IC50,ala/IC50,wt) represents the fold of reduction in binding affinity (the relative binding affinity).

Assays for identifying anti-VEGF antibodies are known in the art. For example, antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062).

B. OX40 Binding Agonists for Use in Conjunction with Anti-Angiogenesis Agents

Provided herein are methods treating or delaying progression of cancer in an individual comprising administering to the individual an effective amount of an anti-angiogenesis agent and an OX40 binding agonist.

In some embodiments, an OX40 binding agonist for use in conjunction with an anti-angiogenesis agent may include any of the OX40 binding agonists described in section II.A above. An OX40 binding agonist includes, for example, an OX40 agonist antibody (e.g., an anti-human OX40 agonist antibody), an OX40L agonist fragment, an OX40 oligomeric receptor, and an OX40 immunoadhesin. In some embodiments, the OX40 binding agonist is a trimeric OX40L-Fc protein. In some embodiments, the OX40 binding agonist is an OX40L agonist fragment comprising one or more extracellular domains of OX40L. In some embodiments, the OX40 agonist antibody is a full-length human IgG1 antibody. Any of the OX40 binding agonists (e.g., anti-human OX40 agonist antibodies) described herein may be used in any of the methods, uses, and/or kits described herein.

In some embodiments, the anti-human OX40 agonist antibody is a human or humanized antibody. In some embodiments, the OX40 binding agonist (e.g., an OX40 agonist antibody) is not MEDI6383. In some embodiments, the OX40 binding agonist (e.g., an OX40 agonist antibody) is not MEDI0562.

In some embodiments, the OX40 agonist antibody is an anti-human OX40 agonist antibody described in U.S. Pat. No. 7,550,140, which is incorporated herein by reference in its entirety. In some embodiments, the anti-human OX40 agonist antibody comprises a heavy chain comprising the sequence of EVQLVESGGGLVQPGGSLRLSCAASGFTF-SNYTMNWVRQAPGKGLEWVSAISGSGGSTYYADSV KGRFTISRDNSKNTLYLQMNSLRAEDTAVYY-CAKDRYSQVHYALDYWGQGTLVTVSSASTKGPS VFPLAPSSKSTSGGTAALGCLVKDYFPEPVTVSWNS-GALTSGVHTFPAVLQSSGLYSLSSVVTVPSS SLGTQ-TYICNVNHKPSNTKVDKRVEPKSCDKTHTCPPCPA-PELLGGPSVFLFPPKPKDTLMISRTPE VTCVVVDVSHEDPEVKFNWYVDGVEVHNAKTK-PREEQYNSTYRVVSVLTVLHQDWLNGKEYKC KVSNKALPAPIEKTISKAK-
GQPREPQVYTLPPSREEMTKNQVSLTCLVKGFYPS-
DIAVEWESNGQP ENNYKTTPPVLDSDGSFFLYSKLT-
VDKSRWQQGNVFSCSVMHEALHNHYTQKSLSLSPGK
(SEQ ID NO: 183) and/or a light chain comprising the sequence of DIVMTQSPDSLPVTPGEPASIS-
CRSSQSLLHSNGYNYLDWYLQKAGQSPQLLIYLG-
SNRASGVPDRF SGSGSGTDFTLKISRVEAEDVGVYY-
CQQYYNHPTTFGQGTKLEIKRTVAAPSVFIFPPSD
EQLKSGT ASVVCLLNNFYPREAKVQWKVDNALQS-
GNSQESVTEQDSKDSTYSLSSTLTLSKADYEKHK-
VYA CEVTHQGLSSPVTKSFNRGEC (SEQ ID NO: 184). In some embodiments, the antibody comprises at least one, two, three, four, five, or six hypervariable region (HVR) sequences of antibody 008 as described in U.S. Pat. No. 7,550,140. In some embodiments, the antibody comprises a heavy chain variable region sequence and/or a light chain variable region sequence of antibody 008 as described in U.S. Pat. No. 7,550,140.

In some embodiments, the OX40 agonist antibody is an anti-human OX40 agonist antibody described in U.S. Pat. No. 7,550,140. In some embodiments, the anti-human OX40 agonist antibody comprises the sequence of DIQMTQSPD-
SLPVTPGEPASISCRSSQSLLHSNGYNYLDWYLQK-
AGQSPQLLIYLGSNRASGVPDRF SGSGSGTDFTLKIS-
RVEAEDVGVYYCQQYYNHPTTFGQGTKLEIKR
TVAAPSVFIFPPSDEQLKSGT ASVVCLLNNFYPREAK-
VQWKVDNALQSGNSQESVTEQDSKD-
STYSLSSTLTLSKADYEKHKVYA
CEVTHQGLSSPVTKSFNRGEC (SEQ ID NO: 185). In some embodiments, the antibody comprises at least one, two, three, four, five, or six hypervariable region (HVR) sequences of antibody SC02008 as described in U.S. Pat. No. 7,550,140. In some embodiments, the antibody comprises a heavy chain variable region sequence and/or a light chain variable region sequence of antibody SC02008 as described in U.S. Pat. No. 7,550,140.

In some embodiments, the OX40 agonist antibody is an anti-human OX40 agonist antibody described in U.S. Pat. No. 7,550,140. In some embodiments, the anti-human OX40 agonist antibody comprises a heavy chain comprising the sequence of EVQLVESGGGLVHPGGSLRLSCAGSGFTF-
SSYAMHWVRQAPGKGLEWVSAIGTGGGTYY-
ADSVM GRFTISRDNSKNTLYLQMNSLRAEDTAVYY-
CARYDNVMGLYWFDYWGQGTLVTVSSASTKGPS
VFPLAPSSKSTSGGTAALGCLVKDYFPEPVTVSWNS-
GALTSGVHTFPAVLQSSGLYSLSSVVTVPSS SLGTQ-
TYICNVNHKPSNTKVDKRVEPKSCDKTHTCPPCPA-
PELLGGPSVFLFPPKPKDTLMISRTPE
VTCVVVDVSHEDPEVKFNWYVDGVEVHNAKTK-
PREEQYNSTYRVVSVLTVLHQDWLNGKEYKC
KVSNKALPAPIEKTISKAK-
GQPREPQVYTLPPSREEMTKNQVSLTCLVKGFYPS-
DIAVEWESNGQP ENNYKTTPPVLDSDGSFFLYSKLT-
VDKSRWQQGNVFSCSVMHEALHNHYTQKSLSLSPGK
(SEQ ID NO: 186) and/or a light chain comprising the sequence of EIVLTQSPATLSLSPGERATLSCRASQSVS-
SYLAWYQQKPGQAPRLLIYDASNRATGIPARFSGSGS
GTDFTLTISSLEPEDFAVYYCQQRSNWPPAFGGGTK-
VEIKRTVAAPSVFIFPPSDEQLKSGTASVVC LLNNFY-
PREAKVQWKVDNALQSGNSQESVTEQDSKD-
STYSLSSTLTLSKADYEKHKVYACEVTH
QGLSSPVTKSFNRGEC (SEQ ID NO: 187). In some embodiments, the antibody comprises at least one, two, three, four, five, or six hypervariable region (HVR) sequences of antibody 023 as described in U.S. Pat. No. 7,550,140. In some embodiments, the antibody comprises a heavy chain variable region sequence and/or a light chain variable region sequence of antibody 023 as described in U.S. Pat. No. 7,550,140.

In some embodiments, the OX40 agonist antibody is an anti-human OX40 agonist antibody described in U.S. Pat. No. 7,960,515, which is incorporated herein by reference in its entirety. In some embodiments, the anti-human OX40 agonist antibody comprises a heavy chain variable region comprising the sequence of EVQLVESGGGLVQPGGSL-
RLSCAASGFTFSSYSMNWVRQAPGK-
GLEWVSYISSSSSTIDYADSVKG RFTISRD-
NAKNSLYLQMNSLRDEDTAVYYCARESGW
YLFDYWGQGTLVTVSS (SEQ ID NO: 188) and/or a light chain variable region comprising the sequence of DIQMTQSPSSLSASVGDRVTITCRASQGISSWLAWY-
QQKPEKAPKSLIYAASSLQSGVPSRFSGSGS GTD-
FTLTISSLQPEDFATYYCQQYNSYPPTFGGGTKVEIK
(SEQ ID NO: 189). In some embodiments, the antibody comprises at least one, two, three, four, five, or six hypervariable region (HVR) sequences of antibody 11D4 as described in U.S. Pat. No. 7,960,515. In some embodiments, the antibody comprises a heavy chain variable region sequence and/or a light chain variable region sequence of antibody 11D4 as described in U.S. Pat. No. 7,960,515.

In some embodiments, the OX40 agonist antibody is an anti-human OX40 agonist antibody described in U.S. Pat. No. 7,960,515. In some embodiments, the anti-human OX40 agonist antibody comprises a heavy chain variable region comprising the sequence of EVQLVESGGGLVQPGRSL-
RLSCAASGFTFDDYAMHWVRQAPGKGLEWVS-
GISWNSGSIGYADSV KGRFTISRD-
NAKNSLYLQMNSLRAEDTALYYCAKDQSTA
DYYFYYGMDVWGQGTTVTVSS (SEQ ID NO: 190) and/or a light chain variable region comprising the sequence of EIVVTQSPATLSLSPGERATLSCRASQSVSSYLAWY-
QQKPGQAPRLLIYDASNRATGIPARFSGSGS GTD-
FTLTISSLEPEDFAVYYCQQRSNWPTFGQGTKVEIK
(SEQ ID NO: 191). In some embodiments, the antibody comprises at least one, two, three, four, five, or six hypervariable region (HVR) sequences of antibody 18D8 as described in U.S. Pat. No. 7,960,515. In some embodiments, the antibody comprises a heavy chain variable region sequence and/or a light chain variable region sequence of antibody 18D8 as described in U.S. Pat. No. 7,960,515.

In some embodiments, the OX40 agonist antibody is an anti-human OX40 agonist antibody described in WO 2012/027328, which is incorporated herein by reference in its entirety. In some embodiments, the anti-human OX40 agonist antibody comprises a heavy chain variable region comprising the sequence of QVQLVQSGSELKKPGASVK-
VSCKASGYTFTDYSMHWVRQAPGQGLK
WMGWINTETGEPTYADD FKGRFVFSLDTSVSTAY-
LQISSLKAEDTAVYYCANPYYDYVSYYAMDY-
WGQGTTVTVSS (SEQ ID NO: 192) and/or a light chain variable region comprising the sequence of DIQMTQSPSSLSASVGDRVTITCKASQDVSTAVAWY-
QQKPGKAPKLLIYSASYLYTGVPSRFSGSG SGTDFT-
FTISSLQPEDIATYYCQQHYSTPRTFGQGTKLEIK
(SEQ ID NO: 193). In some embodiments, the antibody comprises at least one, two, three, four, five, or six hypervariable region (HVR) sequences of antibody hu106-222 as described in WO 2012/027328. In some embodiments, the antibody comprises a heavy chain variable region sequence and/or a light chain variable region sequence of antibody hu106-222 as described in WO 2012/027328.

In some embodiments, the OX40 agonist antibody is an anti-human OX40 agonist antibody described in WO 2012/

027328. In some embodiments, the anti-human OX40 agonist antibody comprises a heavy chain variable region comprising the sequence of EVQLVESGGGLVQPGGSLRLSCAASEYEFPSHDM-SWVRQAPGKGLELVAAINSDGGSTYYPDTME RRFTISRDNAKNSLYLQMNSLRAEDTAVYYCAR-HYDDYYAWFAYWGQGTMVTVSS (SEQ ID NO: 194) and/or a light chain variable region comprising the sequence of EIVLTQSPATLSLSPGERATLSCRASKSVSTSGY-SYMHWYQQKPGQAPRLLIYLASNLESGVPARFS GSGSGTDFTLTISSLEPEDFAVYYCQHSRELPLTF-GGGTKVEIK (SEQ ID NO: 195). In some embodiments, the antibody comprises at least one, two, three, four, five or six hypervariable region (HVR) sequences of antibody Hu119-122 as described in WO 2012/027328. In some embodiments, the antibody comprises a heavy chain variable region sequence and/or a light chain variable region sequence of antibody Hu119-122 as described in WO 2012/027328.

In some embodiments, the OX40 agonist antibody is an anti-human OX40 agonist antibody described in WO 2013/028231, which is incorporated herein by reference in its entirety. In some embodiments, the anti-human OX40 agonist antibody comprises a heavy chain comprising the sequence of MYLGLNYVFIVFLLNGVQ-SEVKLEESGGGLVQPGGSMKLSCAASGFTFSDAWM-DWVRQSPEKGL EWVAEIRSKANNHATYYAESVNGR-FTISRDDSKSSVYLQMNSLRAEDTGIYYCT WGEVFYFDYW GQGTTLTVSSASTKGPSVF-PLAPSSKSTSGGTAALGCLVKDYFPEPVTVSWNS-GALTSGVHTFPAV LQSSGLYSLSSVVTVPSSSLGTQ-TYITCNVNHKPSNTKVDKKVEPKSCDKT HTCPPCPAPELLGGPS VFLFPPKPKDTLMISRTPE-VTCVVVDVSHEDPEVKFNWYVDGVEVHNAKTK-PREEQYNSTYRVVS VLTVLHQDWLNGKEYKCK-VSNKALPAPIEKTISKAKGQPREPQVYTLPPS RDELTKNQVSLTCLV KGFYPSDIAVEWESNGQPEN-NYKTTPPVLDSDGSFFLYSKLTVDKSRWQQGNVF-SCSVMHEALHN HYTQKSLSLSPGK (SEQ ID NO: 196) and/or a light chain comprising the sequence of MRPSIQ-FLGLLLFWLHGAQCDIQMTQSPSSLSASLGGK-VTITCKSSQDINKYIAWYQHKPGKGPRL LIHYT-STLQPGIPSRFSGSGSGRDYSFSISNLEPEDIATY YCLQYDNLLTFGAGTKLELKRTVAAPSV FIFPPSD-EQLKSGTASVVCLLNNFYPREAKVQWKVDNALQS-GNSQESVTEQDSKDSTYSLSSTLTL SKADYEKHKVY-ACEVTHQGLSSPVTKSFNRGEC (SEQ ID NO: 197). In some embodiments, the anti-human OX40 agonist antibody comprises a heavy chain variable region comprising the sequence of MYLGLNYVFIVFLLNGVQ-SEVKLEESGGGLVQPGGSMKLSCAASGFTFSDAWM-DWVRQSPEKGL EWVAEIRSKANNHATYYAESVNGR-FTISRDDSKSSVYLQ MNSLRAEDTGIYYCTWGEVFYFDYW GQGTTLTVSS (SEQ ID NO: 198) and/or a light chain variable region comprising the sequence of MRPSIQFLGLLLFWLH-GAQCDIQMTQSPSSLSASLGGKVTITCKSSQDINKY-IAWYQHKPGKGPRL LIHYTSTLQPGIPSRFSGSGS-GRDYSFSISNLEPEDIATYYCLQYDNLLTFGAGTKLELK (SEQ ID NO: 199). In some embodiments, the antibody comprises at least one, two, three, four, five, or six hypervariable region (HVR) sequences of antibody Mab CH 119-43-1 as described in WO 2013/028231. In some embodiments, the antibody comprises a heavy chain variable region sequence and/or a light chain variable region sequence of antibody Mab CH 119-43-1 as described in WO 2013/028231.

In some embodiments, the OX40 agonist antibody is an anti-human OX40 agonist antibody described in WO 2013/038191, which is incorporated herein by reference in its entirety. In some embodiments, the anti-human OX40 agonist antibody comprises a heavy chain variable region comprising the sequence of EVQLQQSGPELVKPGASVKM-SCKASGYTFTSYVMHWVKQKPGQGLEWI GYINPYNDGTKYNEKF KGKATLTS-DKSSSTAYMELSSLTSEDSAVYYCANYYGSSLSMDY-WGQGTSVTVSS (SEQ ID NO:200) and/or a light chain variable region comprising the sequence of DIQMTQTTSSLSASLGDRVTISCRASQDISNYLNWY-QQKPDGTVKLLIYYTSRLHSGVPSRFSGSGS GTDYS-LTISNLEQEDIATYFCQQGNTLPWTFGGGTKLEIKR (SEQ ID NO:201). In some embodiments, the antibody comprises at least one, two, three, four, five, or six hypervariable region (HVR) sequences of antibody clone 20E5 as described in WO 2013/038191. In some embodiments, the antibody comprises a heavy chain variable region sequence and/or a light chain variable region sequence of antibody clone 20E5 as described in WO 2013/038191.

In some embodiments, the OX40 agonist antibody is an anti-human OX40 agonist antibody described in WO 2013/038191. In some embodiments, the anti-human OX40 agonist antibody comprises a heavy chain variable region comprising the sequence of EVQLQQSGPELVKPGASVKISCKTSGYTFKDYTMH-WVKQSHGKSLEWIGGIYPNNGGSTYNQNFK DKATLTVDKSSSTAYMEFRSLTSEDSAVYYCARMGY-HGPHLDFDVWGAGTTVTVSP (SEQ ID NO:202) and/or a light chain variable region comprising the sequence of DIVMTQSHKFMSTSLGDRVSITCKASQDV-GAAVAWYQQKPGQSPKLLIYWASTRHTGVPDRFTG GGSGTDFTLTISNVQSEDLTDYFCQQYINYPLTF-GGGTKLEIKR (SEQ ID NO:203). In some embodiments, the antibody comprises at least one, two, three, four, five, or six hypervariable region (HVR) sequences of antibody clone 12H3 as described in WO 2013/038191. In some embodiments, the antibody comprises a heavy chain variable region sequence and/or a light chain variable region sequence of antibody clone 12H3 as described in WO 2013/038191.

In some embodiments, the OX40 agonist antibody is an anti-human OX40 agonist antibody described in WO 2014/148895A1, which is incorporated herein by reference in its entirety. In some embodiments, the anti-human OX40 agonist antibody comprises a heavy chain variable region comprising the sequence of QVQLVQSGAEVKKPGASVK-VSCKASGYTFTSYVMHWVRQAPGQRLEW MGYINPYNDGTKYNE KFKGRVTITSDTSAS-TAYMELSSLRSEDTAVYYCANYYGSSLSMDY-WGQGTLVTVSS (SEQ ID NO:204) and/or a light chain variable region comprising the sequence of DIQMTQSPSSLSASVGDRVTITCRASQDISNYLNWY-QQKPGKAPKLLIYYTSRLHSGVPSRFSGSGS GTDYTLTISSLQPEDFATYYCQQGNTLPWTFGQGTK-VEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGAS-VKVSCKASGYTFTSYVMHWVRQAPGQRLEWMGY-INPYNDGTKYNE KFKGRVTITSDTSASTAYMELSSL- RSEDTAVYYCANYYGSSLSMDYWGQGTLVTVSS (SEQ ID NO:204) and/or a light chain variable region comprising the sequence of DIQMTQSPSSLSAS-VGDRVTITCRASQDISNYLNWYQQKPGKAVKLLI-YYTSRLHSGVPSRFSGSGS GTDYTLTISSLQPEDFA-TYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGAS-VKVSCKASGYTFTSYVMHWVRQAPGQRLEWIGYIN-PYNDGTKYNEK FKGRATITSDTSASTAYMELSSL-RSEDTAVYYCANYYGSSLSMDYWGQGTLVTVSS (SEQ ID NO:207) and/or a light chain variable region comprising the sequence of DIQMTQSPSSLSAS-VGDRVTITCRASQDISNYLNWYQQKPGKAPKLLI-YYTSRLHSGVPSRFSGSGS GTDYTLTISSLQPEDFA-TYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGAS-VKVSCKASGYTFTSYVMHWVRQAPGQRLEWIGYIN-PYNDGTKYNEK FKGRATITSDTSASTAYMELSSL-RSEDTAVYYCANYYGSSLSMDYWGQGTLVTVSS (SEQ ID NO:207) and/or a light chain variable region comprising the sequence of DIQMTQSPSSLSAS-VGDRVTITCRASQDISNYLNWYQQKPGKAVKLLI-YYTSRLHSGVPSRFSGSGS GTDYTLTISSLQPEDFA-TYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGAS-VKVSCKASGYTFTSYVMHWVRQAPGQRLEWIGYIN-PYNDGTKYNEK FKGRATLTSDKSASTAYMELSSL-RSEDTAVYYCANYYGSSLSMDYWGQGTLVTVSS (SEQ ID NO:208) and/or a light chain variable region comprising the sequence of DIQMTQSPSSLSAS-VGDRVTITCRASQDISNYLNWYQQKPGKAPKLLI-YYTSRLHSGVPSRFSGSGS GTDYTLTISSLQPEDFA-TYYCQQGNTLPWTFGQGTKVEIKR (SEQ ID NO:205). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGAS-VKVSCKASGYTFTSYVMHWVRQAPGQRLEWIGYIN-PYNDGTKYNEK FKGRATLTSDKSASTAYMELSSL-RSEDTAVYYCANYYGSSLSMDYWGQGTLVTVSS (SEQ ID NO:208) and/or a light chain variable region comprising the sequence of DIQMTQSPSSLSAS-VGDRVTITCRASQDISNYLNWYQQKPGKAVKLLI-YYTSRLHSGVPSRFSGSGS GTDYTLTISSLQPEDFA-TYFCQQGNTLPWTFGQGTKVEIKR (SEQ ID NO:206). In some embodiments, the antibody comprises at least one, two, three, four, five, or six hypervariable region (HVR) sequences of antibody clone 20E5 as described in WO 2014/148895A1. In some embodiments, the antibody comprises a heavy chain variable region sequence and/or a light chain variable region sequence of antibody clone 20E5 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSS-VKVSCKASGYTFKDYTMHWVRQAPGQGLEWMG-GIYPNNGGSTYNQ NFKDRVTITADKSTSTAYMELSS-LRSEDTAVYYCARMGYHGPHLDFDVWGQGTTVTVSS (SEQ ID NO:209) and/or a light chain variable region comprising the sequence of DIQMTQSPSSLSAS-VGDRVTITCKASQDVGAAVAWYQQKPGKAP-KLLIYWASTRHTGVPSRFSGS GSGTDFTLTISS-LQPEDFATYYCQQYINYPLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSS-VKVSCKASGYTFKDYTMHWVRQAPGQGLEWMG-GIYPNNGGSTYNQ NFKDRVTITADKSTSTAYMELSS-LRSEDTAVYYCARMGYHGPHLDFDVWGQGTTVTVSS (SEQ ID NO:209) and/or a light chain variable region comprising the sequence of DIQMTQSPSSLSAS-VGDRVTITCKASQDVGAAVAWYQQKPGKAP-KLLIYWASTRHTGVPDRFSGG GSGTDFTLTISS-LQPEDFATYYCQQYINYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSS-VKVSCKASGYTFKDYTMHWVRQAPGQGLEWIGGI-YPNNGGSTYNQN FKDRVTLTADKSTSTAYMELSSL-RSEDTAVYYCARMGYHGPHLDFDVWGQGTTVTVSS (SEQ ID NO:212) and/or a light chain variable region comprising the sequence of DIQMTQSPSSLSAS-VGDRVTITCKASQDVGAAVAWYQQKPGKAP-KLLIYWASTRHTGVPSRFSGS GSGTDFTLTISS-LQPEDFATYYCQQYINYPLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSS-VKVSCKASGYTFKDYTMHWVRQAPGQGLEWIGGI-YPNNGGSTYNQN FKDRVTLTADKSTSTAYMELSSL-RSEDTAVYYCARMGYHGPHLDFDVWGQGTTVTVSS (SEQ ID NO:212) and/or a light chain variable region comprising the sequence of DIQMTQSPSSLSAS-VGDRVTITCKASQDVGAAVAWYQQKPGKAP-KLLIYWASTRHTGVPDRFSGG GSGTDFTLTISS-LQPEDFATYYCQQYINYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSS-VKVSCKASGYTFKDYTMHWVRQAPGQGLEWIGGI-YPNNGGSTYNQN FKDRATLTVDKSTSTAYMELSSL-RSEDTAVYYCARMGYHGPHLDFDVWGQGTTVTVSS (SEQ ID NO:213) and/or a light chain variable region comprising the sequence of DIQMTQSPSSLSAS-VGDRVTITCKASQDVGAAVAWYQQKPGKAP-KLLIYWASTRHTGVPSRFSGS GSGTDFTLTISS-LQPEDFATYYCQQYINYPLTFGGGTKVEIKR (SEQ ID NO:210). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the OX40 agonist antibody is an anti-human OX40 agonist antibody described in WO 2014/148895A1. In some embodiments, the anti-human OX40 agonist antibody comprises a heavy chain variable region comprising the sequence of QVQLVQSGAEVKKPGSS-VKVSCKASGYTFKDYTMHWVRQAPGQGLEWIGGI-YPNNGGSTYNQN FKDRATLTVDKSTSTAYMELSSL-RSEDTAVYYCARMGYHGPHLDFDVWGQGTTVTVSS (SEQ ID NO:213) and/or a light chain variable region comprising the sequence of DIQMTQSPSSLSAS-VGDRVTITCKASQDVGAAVAWYQQKPGKAP-KLLIYWASTRHTGVPDRFSGG GSGTDFTLTISS-LQPEDFATYYCQQYINYPLTFGGGTKVEIKR (SEQ ID NO:211). In some embodiments, the antibody comprises at least one, two, three, four, five, or six hypervariable region (HVR) sequences of antibody clone 12H3 as described in WO 2014/148895A1. In some embodiments, the antibody comprises a heavy chain variable region sequence and/or a light chain variable region sequence of antibody clone 12H3 as described in WO 2014/148895A1.

In some embodiments, the agonist anti-human OX40 antibody is L106 BD (Pharmingen Product #340420). In some embodiments, the antibody comprises at least one, two, three, four, five or six hypervariable region (HVR) sequences of antibody L106 (BD Pharmingen Product #340420). In some embodiments, the antibody comprises a heavy chain variable region sequence and/or a light chain variable region sequence of antibody L106 (BD Pharmingen Product #340420).

In some embodiments, the agonist anti-human OX40 antibody is ACT35 (Santa Cruz Biotechnology, Catalog #20073). In some embodiments, the antibody comprises at least one, two, three, four, five or six hypervariable region (HVR) sequences of antibody ACT35 (Santa Cruz Biotechnology, Catalog #20073). In some embodiments, the antibody comprises a heavy chain variable region sequence and/or a light chain variable region sequence of antibody ACT35 (Santa Cruz Biotechnology, Catalog #20073).

In some embodiments, the OX40 agonist antibody is MEDI6469. In some embodiments, the antibody comprises at least one, two, three, four, five, or six hypervariable region (HVR) sequences of antibody MEDI6469. In some embodiments, the antibody comprises a heavy chain variable region sequence and/or a light chain variable region sequence of antibody MEDI6469.

In some embodiments, the OX40 agonist antibody is MEDI0562. In some embodiments, the antibody comprises at least one, two, three, four, five, or six hypervariable region (HVR) sequences of antibody MEDI0562. In some embodiments, the antibody comprises a heavy chain variable region sequence and/or a light chain variable region sequence of antibody MEDI0562.

In some embodiments, the OX40 agonist antibody is an agonist antibody that binds to the same epitope as any one of the OX40 agonist antibodies set forth above.

C. Methods of Treatment with an OX40 Binding Agonist and an Anti-Angiogenesis Agent Certain aspects of the present disclosure relate to method for treating or delaying progression of cancer in an individual comprising administering to the individual an effective amount of an anti-angiogenesis agent described herein and an OX40 binding agonist described herein. For example, any of the anti-angiogenesis agents (e.g., anti-VEGF antibodies) and OX40 binding agonists (e.g., anti-human OX40 antibodies) provided herein may be used in therapeutic methods. In some embodiments, the individual has cancer or has been diagnosed with cancer. In some embodiments, the treatment results in a sustained response in the individual after cessation of the treatment. In some embodiments, the individual is a human.

In some embodiments, the OX40 binding agonist is administered before the anti-angiogenesis agent, simultaneous with the anti-angiogenesis agent, or after the anti-angiogenesis agent.

Examples of various cancer types that can be treated with an anti-angiogenesis agent (e.g., a VEGF antagonist such as an anti-VEGF antibody like bevacizumab) and an OX40 binding agonist are described above. Preferred cancer types include gynecologic cancers (e.g., ovarian, peritoneal, fallopian tube, cervical, endometrial, vaginal, and vulvar cancer). Additional cancers include epithelial ovarian cancer, fallopian tube cancer, primary peritoneal cancer, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer (including platinum sensitive and platinum resistant ovarian cancer), liver cancer, bladder cancer, hepatoma, neuroblastoma, melanoma, breast cancer, colon cancer, colorectal cancer, fallopian tube, peritoneal, endometrial or uterine carcinoma, salivary gland carcinoma, kidney or renal cancer, liver cancer, prostate cancer, vulval cancer, thyroid cancer, soft-tissue sarcoma, kaposi's sarcoma, carcinoid carcinoma, mesothelioma, multiple myeloma, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. In various embodiments, the cancer that is treated is advanced, refractory, recurrent, chemotherapy-resistant, and/or platinum-resistant cancer.

In some embodiments, the anti-angiogenesis agent and/or the OX40 binding agonist are administered intravenously, intramuscularly, subcutaneously, intracerobrospinally, topically, orally, transdermally, intraperitoneally, intraorbitally, by implantation, by inhalation, intrathecally, intraventricularly, intra-articularly, intrasynovially, or intranasally. The VEGF antagonist and/or the OX40 binding agonist (e.g., an anti-VEGF antibody, such as bevacizumab), optionally in combination with one or more chemotherapeutic agents (e.g., carboplatin and/or paclitaxel), are administered to a human patient in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

In one aspect, an OX40 binding agonist (e.g., an anti-human OX40 agonist antibody) and/or anti-angiogenesis agent (e.g., an anti-VEGF antibody) for use as a medicament is provided. In some embodiments, an anti-angiogenesis agent (e.g., an anti-VEGF antibody) for use as a medicament is provided for treating or delaying progression of cancer in an individual, where the medicament comprises the anti-angiogenesis agent and an optional pharmaceutically acceptable carrier, and where the treatment comprises administration of the medicament in combination with a composition comprising an OX40 binding agonist and an optional pharmaceutically acceptable carrier. In other embodiments, an OX40 binding agonist (e.g., an anti-human OX40 agonist antibody) for use as a medicament is provided for treating or delaying progression of cancer in an individual, where the medicament comprises the anti-angiogenesis agent and an optional pharmaceutically acceptable carrier, and where the treatment comprises administration of the medicament in combination with a composition comprising an anti-angiogenesis agent and an optional pharmaceutically acceptable carrier. In some embodiments, the method further comprises administering to the individual an effective amount of at least one additional therapeutic agent, e.g., as described herein.

Exemplary doses for anti-VEGF antibodies are provided below. It will be appreciated by one of skill in the art that these doses are merely exemplary and are based on dosing of anti-VEGF antibody alone. Dosing and/or administration practices described herein for anti-VEGF antibody treatment alone may of course be modified when combined with OX40 binding agonist treatment. In some embodiments, the OX40 binding agonist is administered before the anti-angiogenesis agent (e.g., anti-VEGF antibody), simultaneous with the anti-angiogenesis agent, or after the anti-angiogenesis agent.

For the prevention or treatment of cancer, the dose of VEGF antagonist (e.g., an anti-VEGF antibody, such as bevacizumab), anti-human OX40 agonist antibody, and/or chemotherapeutic agent will depend on the type of cancer to be treated, as defined above, the severity and course of the cancer, whether the antibody is administered for preventive or therapeutic purposes, previous therapy, the patients clinical history and response to the drug, and the discretion of the attending physician. In one embodiment, VEGF antagonist (e.g., bevacizumab) is administered at 5 mg/kg of body weight given once every 2 weeks, 10 mg/kg of body weight given once every 2 weeks, 7.5 mg/kg of body weight given once every 3 weeks, or 15 mg/kg of body weight given once every 3 weeks.

With respect to bevacizumab for the treatment of colorectal cancer, the preferred dosages according to the EMEA are 5 mg/kg or 10 mg/kg of body weight given once every 2 weeks or 7.5 mg/kg or 15 mg/kg of body weight given once every 3 weeks. For the treatment of NSCLC, the preferred dosage is 15 mg/kg given once every 3 weeks by infusion in combination with carboplatin and paclitaxel. For the treatment of renal cell carcinoma, the preferred dosage is 10 mg/kg given once every 2 weeks by infusion with interferon α-2a or as a monotherapy. For the treatment of cervical cancer, the preferred dosage is 15 mg/kg given once every three weeks by infusion and administered in combination with one of the following chemotherapy regimens: paclitaxel and cisplatin or paclitaxel and topotecan. For the treatment of glioblastoma, the preferred dosage is 10 mg/kg given once every two weeks by infusion.

In one embodiment, a fixed dose of the VEGF antagonist is administered. A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/nm dose, but rather as an absolute amount of the therapeutic agent. The fixed dose may suitably be administered to the patient at one time or over a series of treatments. Where a fixed dose is administered, preferably it is in the range from about 20 mg to about 2000 mg of the inhibitor. For example, the fixed dose may be approximately 420 mg, approximately 525 mg, approximately 840 mg, or approximately 1050 mg of the inhibitor (e.g., an anti-VEGF antibody, such as bevacizumab). Where a series of doses are administered, these may, for example, be administered approximately every week, approximately every 2 weeks, approximately every 3 weeks, or approximately every 4 weeks, but preferably approximately every 3 weeks. The fixed doses may, for example, continue to be administered until disease progression, adverse event, or other time as determined by the physician. For example, from about two, three, or four, up to about 17 or more fixed doses may be administered.

Administration of an angiogenesis inhibitor, e.g., an anti-VEGF antibody, such as bevacizumab, and/or a pharmaceutical composition/treatment regimen comprising an angiogenesis inhibitor, e.g., an anti-VEGF antibody, such as bevacizumab, to a patient in need of such treatment or medical intervention may be by any suitable means known in the art for administration of a therapeutic antibody. Nonlimiting routes of administration include by oral, intravenous, intraperitoneal, subcutaneous, intramuscular, topical, intradermal, intranasal or intrabronchial administration (for example as effected by inhalation). Particularly preferred in context of this invention is parenteral administration, e.g., intravenous administration. Where a VEGF antagonist is administered as a "single anti-tumor agent" it is the only anti-tumor agent administered to treat the cancer, i.e., it is not administered in combination with another anti-tumor agent, such as chemotherapy or an OX40 binding agonist.

In one embodiment, one or more loading dose(s) of the VEGF antagonist (e.g., an anti-VEGF antibody, such as bevacizumab) are administered, followed by one or more maintenance dose(s). A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s). A "maintenance" dose or "extended" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks. In another embodiment, a plurality of the same dose is administered to the patient. According to one preferred embodiment of the invention, a fixed dose of a VEGF antagonist (e.g., an anti-VEGF antibody, such as bevacizumab) of approximately 840 mg (loading dose) is administered, followed by one or more doses of approximately 420 mg (maintenance dose(s)) of the antagonist. The maintenance doses are preferably administered about every 3 weeks, for a total of at least two doses, up to 17 or more doses.

According to another preferred embodiment of the invention, one or more fixed dose(s) of approximately 1050 mg of the VEGF antagonist (e.g., an anti-VEGF antibody, such as bevacizumab) are administered, for example every 3 weeks. According to this embodiment, one, two or more of the fixed doses are administered, e.g., for up to one year (17 cycles), and longer as desired.

In another embodiment, a fixed dose of approximately 1050 mg of the VEGF antagonist (e.g., an anti-VEGF antibody, such as bevacizumab) is administered as a loading dose, followed by one or more maintenance dose(s) of approximately 525 mg. About one, two, or more maintenance doses may be administered to the patient every 3 weeks according to this embodiment.

While the VEGF antagonist (e.g., an anti-VEGF antibody, such as bevacizumab) and/or anti-human OX40 agonist antibody or chemotherapeutic agent may be administered in conjunction, the patient is optionally treated with a combination of the inhibitor (or chemotherapeutic agent), and one or more (additional) chemotherapeutic agent(s). Exemplary chemotherapeutic agents herein include: gemcitabine, carboplatin, oxaliplatin, irinotecan, fluoropyrimidine (e.g., 5-FU), paclitaxel (e.g., nab-paclitaxel), docetaxel, topotecan, capecitabine, temozolomide, interferon-alpha, and/or liposomal doxorubicin (e.g., pegylated liposomal doxorubicin), In some embodiments, at least one of the chemotherapeutic agents is carboplatin or paclitaxel. In some embodiments, at least one of the chemotherapeutic agents is carboplatin or gemcitabine. The combined administration includes co-administration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the VEGF antagonist (e.g., an anti-VEGF antibody, such as bevacizumab). In this embodiment, the timing between at least one administration of the chemotherapeutic agent and at least one administration of the VEGF antagonist (e.g., an anti-VEGF antibody, such as bevacizumab) is preferably approximately 1 month or less, and most preferably approximately 2 weeks or less. Alternatively, the chemotherapeutic agent and the inhibitor are administered concurrently to the patient, in a single formulation or separate formulations. Treatment with the combination of the chemotherapeutic agent (e.g., carboplatin and/or paclitaxel) and the VEGF antagonist (e.g., an anti-VEGF antibody, such as bevacizumab) may result in a synergistic, or greater than additive, therapeutic benefit to the patient.

Particularly desired chemotherapeutic agents for combining with the VEGF antagonist (e.g., an anti-VEGF antibody, such as bevacizumab) and/or anti-human OX40 agonist antibody, e.g. for therapy of ovarian cancer, include: a chemotherapeutic agent such as a platinum compound (e.g., carboplatin), a taxol such as paclitaxel or docetaxel, topotecan, or liposomal doxorubicin.

Particularly desired chemotherapeutic agents for combining with the VEGF antagonist (e.g., an anti-VEGF antibody, such as bevacizumab) and/or anti-human OX40 agonist antibody, e.g., for therapy of advanced stage epithelial ovarian cancer, fallopian tube cancer, or primary peritoneal cancer include: chemotherapeutic agents such as carboplatin, paclitaxel, and/or gemcitabine.

Particularly desired chemotherapeutic agents for combining with the VEGF antagonist (e.g., an anti-VEGF antibody such as bevacizumab) and/or anti-human OX40 agonist antibody, e.g., for therapy of platinum-sensitive epithelial ovarian cancer, fallopian tube cancer, or primary peritoneal cancer include: chemotherapeutic agents such as carboplatin and gemcitabine.

Particularly desired chemotherapeutic agents for combining with the VEGF antagonist (e.g., an anti-VEGF antibody such as bevacizumab) and/or anti-human OX40 agonist antibody, e.g., for therapy of platinum-resistant recurrent epithelial ovarian cancer, fallopian tube cancer, or primary peritoneal cancer include: a chemotherapeutic agent such as paclitaxel, topotecan, or pegylated liposomal doxorubicin.

Particularly desired chemotherapeutic agents for combining with the VEGF antagonist (e.g., an anti-VEGF antibody, such as bevacizumab) and/or anti-human OX40 agonist antibody, e.g., for therapy of breast cancer, include: chemotherapeutic agents such as capecitabine, and a taxol such as paclitaxel (e.g., nab-paclitaxel) or docetaxel.

Particularly desired chemotherapeutic agents for combining with the VEGF antagonist (e.g., an anti-VEGF antibody, such as bevacizumab) and/or anti-human OX40 agonist antibody, e.g., for therapy of glioblastoma, include: chemotherapeutic agents such as temozolomide, optionally in combination with radiotherapy.

Particularly desired chemotherapeutic agents for combining with the VEGF antagonist (e.g., an anti-VEGF antibody, such as bevacizumab) and/or anti-human OX40 agonist antibody, e.g., for therapy of colorectal cancer, include: chemotherapeutic agents such as a fluoropyrimidine (e.g., 5-FU), paclitaxel, cisplatin, topotecan, irinotecan, fluoropyrimidine-oxaliplatin, fluoropyrimidine-irinotecan, FOLFOX4 (5-FU, lecovorin, oxaliplatin), and IFL (ironotecan, 5-FU, leucovorin).

Particularly desired chemotherapeutic agents for combining with the VEGF antagonist (e.g., an anti-VEGF antibody, such as bevacizumab) and/or anti-human OX40 agonist antibody, e.g., for therapy of renal cell carcinoma, include: chemotherapeutic agents such as interferon-alpha2a.

Particularly desired chemotherapeutic agents for combining with the VEGF antagonist (e.g., an anti-VEGF antibody, such as bevacizumab) and/or anti-human OX40 agonist antibody, e.g., for therapy of cervical cancer, include: chemotherapeutic agents such as paclitaxel, cisplatin, topotecan, paclitaxel in combination with cisplatin, and paclitaxel in combination with topotecan.

A chemotherapeutic agent, if administered, is usually administered at dosages known therefore, or optionally lowered due to combined action of the drugs or negative side effects attributable to administration of the chemotherapeutic agent. Preparation and dosing schedules for such chemotheraputic agents may be used according to manufacturers' instructions or as determined empirically by the skilled practitioner. Where the chemotherapeutic agent is paclitaxel, preferably, it is administered at a dose between about 130 mg/m$^2$ to 200 mg/m$^2$ (for example approximately 175 mg/m$^2$), for instance, over 3 hours, once every 3 weeks. Where the chemotherapeutic agent is carboplatin, preferably it is administered by calculating the dose of carboplatin using the Calvert formula which is based on a patient's preexisting renal function or renal function and desired platelet nadir. Renal excretion is the major route of elimination for carboplatin. The use of this dosing formula, as compared to empirical dose calculation based on body surface area, allows compensation for patient variations in pretreatment renal function that might otherwise result in either underdosing (in patients with above average renal function) or overdosing (in patients with impaired renal function). The target AUC of 4-6 mg/mL/min using single agent carboplatin appears to provide the most appropriate dose range in previously treated patients.

Aside from the VEGF antagonist (e.g., an anti-VEGF antibody, such as bevacizumab), anti-human OX40 agonist antibody, and chemotherapeutic agent, other therapeutic regimens may be combined therewith. For example, a second (third, fourth, etc.) chemotherapeutic agent(s) may be administered, wherein the second chemotherapeutic agent is an antimetabolite chemotherapeutic agent, or a chemotherapeutic agent that is not an antimetabolite. For example, the second chemotherapeutic agent may be a taxane (such as paclitaxel or docetaxel), capecitabine, or platinum-based chemotherapeutic agent (such as carboplatin, cisplatin, or oxaliplatin), anthracycline (such as doxorubicin, including, liposomal doxorubicin), topotecan, pemetrexed, vinca alkaloid (such as vinorelbine), and TLK 286. "Cocktails" of different chemotherapeutic agents may be administered.

Suitable dosages for any of the above-noted co-administered agents are those presently used and may be lowered due to the combined action (synergy) of the agent and inhibitor. In addition to the above therapeutic regimes, the patient may be subjected to surgical removal of tumors and/or cancer cells, and/or radiation therapy.

Where the VEGF antagonist is an antibody (e.g., bevacizumab), preferably the administered antibody is a naked antibody. The VEGF antagonist (e.g., an anti-VEGF antibody, such as bevacizumab) administered may be conjugated with a cytotoxic agent. Preferably, the conjugated and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases, and DNA endonucleases.

IV. Articles of Manufacture and Kits

In another aspect of the invention, an article of manufacture or kit containing materials useful for the treatment, prevention and/or diagnosis of the disorders described above is provided. The article of manufacture or kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention (e.g., an anti-human OX40 agonist antibody of the present disclosure or an anti-angiogenic antibody of the present disclosure, such as an anti-VEGF antibody). The label or package insert indicates that the composition is used for treating the condition of choice. Moreover, the article of manufacture or kit may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments, provided herein is a kit comprising a medicament comprising an anti-human OX40 agonist antibody described herein and an optional pharmaceutically acceptable carrier. In some embodiments, the kit further comprises instructions for administration of the medicament for treatment of cancer.

It is understood that any of the above articles of manufacture or kits may include an immunoconjugate of the invention in place of or in addition to an anti-OX40 antibody.

In some embodiments, provided herein is a kit comprising a medicament comprising an anti-angiogenesis agent and an optional pharmaceutically acceptable carrier, and a package insert comprising instructions for administration of the medicament in combination with a composition comprising an OX40 binding agonist and an optional pharmaceutically acceptable carrier for treating or delaying progression of cancer in an individual. Further provided here is a kit comprising a first medicament comprising an anti-angiogenesis agent and an optional pharmaceutically acceptable carrier, and a second medicament comprising an OX40 binding agonist and an optional pharmaceutically acceptable carrier. In some embodiments, the kit further comprises a package insert comprising instructions for administration of the first medicament and the second medicament for treating or delaying progression of cancer in an individual. Still further provided herein is a kit comprising a medicament comprising an OX40 binding agonist and an optional pharmaceutically acceptable carrier, and a package insert comprising instructions for administration of the medicament in combination with a composition comprising an anti-angiogenesis agent and an optional pharmaceutically acceptable carrier for treating or delaying progression of cancer in an individual.

It is understood that any of the above articles of manufacture or kits may include an immunoconjugate of the invention in place of or in addition to an anti-OX40 antibody and/or anti-angiogenesis agent.

Sequences

| Name | SEQUENCE | SEQ ID NO: |
|---|---|---|
| Human OX40 (lacking the signal peptide) | LHCVGDTYPSNDRCCHECRPGNGMVSRCSRSQNTVCRPCGPGFYNDVVSSKPCK PCTWCNLRSGSERKQLCTATQDTVCRCRAGTQPLDSYKPGVDCAPCPPGHFSPG DNQACKPWTNCTLAGKHTLQPASNSSDAICEDRDPPATQPQETQGPPARPITVQ PTEAWPRTSQGPSTRPVEVPGGRAVAAILGLGLVLGLLGPLAILLALYLLRRDQ RLPPDAHKPPGGGSFRTPIQEEQADAHSTLAKI | 1 |
| HVR-H1-1A7.gr.1 1A7.gr.2 1A7.gr.3 1A7.gr.4 1A7.gr.5 1A7.gr.5' 1A7.gr.6 1A7.gr.7 1A7.gr.7' 1A7.gr.NADS 1A7.gr.NADA 1A7.gr.NGDA 1A7.gr.SGDS 1A7.gr.NGSS 1A7.Ala.1 1A7.Ala.2 1A7.Ala.3 1A7.Ala.4 1A7.Ala.5 1A7.Ala.6 1A7.Ala.7 1A7.Ala.8 1A7.Ala.9 1A7.Ala.10 1A7.Ala.11 1A7.Ala.12 1A7.Ala.13 1A7.Ala.14 1A7.Ala.15 1A7.Ala.16 | DSYMS | 2 |
| HVR-H2-1A7.gr.1 1A7.gr.2 1A7.gr.3 1A7.gr.4 1A7.gr.5 1A7.gr.5' 1A7.gr.6 1A7.gr.7 1A7.gr.7' 1A7.gr.DA 1A7.gr.ES 1A7.Ala.1 1A7.Ala.2 1A7.Ala.3 1A7.Ala.4 | DMYPDNGDSSYNQKFRE | 3 |

-continued

| Name | SEQUENCE | SEQ ID NO: |
|---|---|---|
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |
| 1A7.Ala.15 | | |
| 1A7.Ala.16 | | |
| HVR-H3-1A7.gr.1 | APRWYFSV | 4 |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7-Ala.15 | | |
| 1A7.Ala.16 | | |
| HVR-L1-1A7.gr.1 | RASQDISNYLN | 5 |
| 1A7.gr.2 | | |
| 1A7.gr.3 | | |
| 1A7.gr.4 | | |
| 1A7.gr.5 | | |
| 1A7.gr.5' | | |
| 1A7.gr.6 | | |
| 1A7.gr.7 | | |
| 1A7.gr.7' | | |
| 1A7.gr.DA | | |
| 1A7.gr.ES | | |
| 1A7.gr.NADS | | |
| 1A7.gr.NADA | | |
| 1A7.gr.NGDA | | |
| 1A7.gr.SGDS | | |
| 1A7.gr.NGSS | | |
| 1A7.gr.DANADA | | |
| 1A7.Ala.1 | | |
| 1A7.Ala.2 | | |
| 1A7.Ala.3 | | |
| 1A7.Ala.4 | | |
| 1A7.Ala.5 | | |
| 1A7.Ala.6 | | |
| 1A7.Ala.7 | | |
| 1A7.Ala.8 | | |
| 1A7.Ala.9 | | |
| 1A7.Ala.10 | | |
| 1A7.Ala.11 | | |
| 1A7.Ala.12 | | |
| 1A7.Ala.13 | | |
| 1A7.Ala.14 | | |

Sequences

| Name | SEQUENCE | SEQ ID NO: |
|---|---|---|
| 1A7.Ala.15 | | |
| 1A7.Ala.16 | | |
| HVR-L2-1A7.gr.1<br>1A7.gr.2<br>1A7.gr.3<br>1A7.gr.4<br>1A7.gr.5<br>1A7.gr.5'<br>1A7.gr.6<br>1A7.gr.7<br>1A7.gr.7'<br>1A7.gr.DA<br>1A7.gr.ES<br>1A7.gr.NADS<br>1A7.gr.NADA<br>1A7.gr.NGDA<br>1A7.gr.SGDS<br>1A7.gr.NGSS<br>1A7.gr.DANADA<br>1A7.Ala.1<br>1A7.Ala.2<br>1A7.Ala.3<br>1A7.Ala.4<br>1A7.Ala.5<br>1A7.Ala.6<br>1A7.Ala.7<br>1A7.Ala.8<br>1A7.Ala.9<br>1A7.Ala.10<br>1A7.Ala.11<br>1A7.Ala.12<br>1A7.Ala.13<br>1A7.Ala.14<br>1A7.Ala.15<br>1A7.Ala.16 | YTSRLRS | 6 |
| HVR-L3-1A7.gr.1<br>1A7.gr.2<br>1A7.gr.3<br>1A7.gr.4<br>1A7.gr.5<br>1A7.gr.5'<br>1A7.gr.6<br>1A7.gr.7<br>1A7.gr.7'<br>1A7.gr.DA<br>1A7.gr.ES<br>1A7.gr.NADS<br>1A7.gr.NADA<br>1A7.gr.NGDA<br>1A7.gr.SGDS<br>1A7.gr.NGSS<br>1A7.gr.DANADA<br>1A7.Ala.8<br>1A7.Ala.9<br>1A7.Ala.10<br>1A7.Ala.11<br>1A7.Ala.12<br>1A7.Ala.13<br>1A7.Ala.14<br>1A7.Ala.15<br>1A7.Ala.16 | QQGHTLPPT | 7 |
| HVR-H1-1A7.gr.DA | DAYMS | 8 |
| HVR-H1-1A7.gr.ES<br>1A7.gr.DANADA | ESYMS | 9 |

-continued

| Name | SEQUENCE | SEQ ID NO: |
|---|---|---|
| HVR-H2-1A7.gr.NADS | DMYPDNADSSYNQKFRE | 10 |
| HVR-H2-1A7.gr.NADA 1A7.gr.DANADA | DMYPDNADASYNQKFRE | 11 |
| HVR-H2-1A7.gr.NGDA | DMYPDNGDASYNQKFRE | 12 |
| HVR-H2-1A7.gr.SGDS | DMYPDSGDSSYNQKFRE | 13 |
| HVR-H2-1A7.gr.NGSS | DMYPDNGSSSYNQKFRE | 14 |
| HVR-H3-1A7.Ala.8 | APRWYFSA | 15 |
| HVR-H3-1A7.Ala.9 | APRWYASV | 16 |
| HVR-H3-1A7.Ala.10 | APRWAFSV | 17 |
| HVR-H3-1A7.Ala.11 | APAWYFSV | 18 |
| HVR-H3-1A7.Ala.12 | APRWYFAV | 19 |
| HVR-H3-1A7.Ala.13 | APRAYFSV | 20 |
| HVR-H3-1A7.Ala.14 | AARWYFSV | 21 |
| HVR-L3-1A7.Ala.1 | QQGHTLPAT | 22 |
| HVR-L3-1A7.Ala.2 | QQGHTAPPT | 23 |
| HVR-L3-1A7.Ala.3 | QQGATLPPT | 24 |
| HVR-L3-1A7.Ala.4 | QQGHALPPT | 25 |
| HVR-L3-1A7.Ala.5 | QQAHTLPPT | 26 |
| HVR-L3-1A7.Ala.6 | QQGHTLAPT | 27 |
| HVR-L3-1A7.Ala.7 | QAGHTLPPT | 28 |
| HVR-H1-3C8.gr.1 3C8.gr.2 3C8.gr.3 3C8.gr.4 3C8.gr.5 3C8.gr.5.SG 3C8.gr.5.EG 3C8.gr.5.QG 3C9.gr.5.DQ 3C8.gr.5.DA 3C8.gr.6 3C8.gr.7 3C8.gr.8 3C8.gr.9 | NYLIE | 29 |

-continued

| Name | SEQUENCE | SEQ ID NO: |
|---|---|---|
| 3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | | |
| HVR-H2-<br>3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | VINPGSGDTYYSEKFKG | 30 |
| HVR-H2-<br>3C8.gr.5.DA | VINPGSGDAYYSEKFKG | 31 |
| HVR-H2-<br>3C8.gr.5.DQ | VINPGSGDQYYSEKFKG | 32 |
| HVR-H3-<br>3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7 | DRLDY | 33 |
| HVR-H3-<br>3C8.A.8 | ARLDY | 34 |
| HVR-H3-<br>3C8.A.9 | DALDY | 35 |

-continued

| Name | SEQUENCE | SEQ ID NO: |
|---|---|---|
| HVR-H3-3C8.A.10 | DRADY | 36 |
| HVR-L1-<br>3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | HASQDISSYIV | 37 |
| HVR-L2-<br>3C8.gr.1<br>3C8.gr.2<br>3C8.gr.3<br>3C8.gr.4<br>3C8.gr.5<br>3C8.gr.5.DA<br>3C8.gr.5.DQ<br>3C8.gr.6<br>3C8.gr.7<br>3C8.gr.8<br>3C8.gr.9<br>3C8.gr.10<br>3C8.gr.11<br>3C8.A.1<br>3C8.A.2<br>3C8.A.3<br>3C8.A.4<br>3C8.A.5<br>3C8.A.6<br>3C8.A.7<br>3C8.A.8<br>3C8.A.9<br>3C8.A.10 | HGTNLED | 38 |
| HVR-L2-3C8.gr5.SG | HGTNLES | 39 |
| HVR-L2-3C8.gr.5.EG | HGTNLEE | 40 |
| HVR-L2-3C8.gr.5.QG | HGTNLEQ | 41 |
| HVR-L3<br>3C8.gr.1<br>3C8.gr.2<br>3C8.gr.3<br>3C8.gr.4<br>3C8.gr.5<br>3C8.gr.5.SG<br>3C8.gr.5.EG<br>3C8.gr.5.QG | VHYAQFPYT | 42 |

-continued

| Name | SEQUENCE | SEQ ID NO: |
|---|---|---|
| 3C8.gr.5.DA | | |
| 3C8.gr.5.DQ | | |
| 3C8.gr.6 | | |
| 3C8.gr.7 | | |
| 3C8.gr.8 | | |
| 3C8.gr.9 | | |
| 3C8.gr.10 | | |
| 3C8.gr.11 | | |
| 3C8.A.8 | | |
| 3C8.A.9 | | |
| 3C8.A.10 | | |
| HVR-L3-3C8.A.1 | AHYAQFPYT | 43 |
| HVR-L3-3C8.A.2 | VAYAQFPYT | 44 |
| HVR-L3-3C8.A.3 | VHAAQFPYT | 45 |
| HVR-L3-3C8.A.4 | VHYAAFPYT | 46 |
| HVR-L3-3C8.A.5 | VHYAQAPYT | 47 |
| HVR-L3-3C8.A.6 | VHYAQFAYT | 48 |
| HVR-L3-3C8.A.7 | VHYAQFPAT | 49 |
| HVR-H1-1D2.gr.1 1D2.gr.2 1D2.gr.3 | DYGVL | 50 |
| HVR-H2-1D2.gr.1 1D2.gr.2 1D2.gr.3 | MIWSGGTTDYNAAFIS | 51 |
| HVR-H3-1D2.gr.1 1D2.gr.2 1D2.gr.3 | EEMDY | 52 |
| HVR-L1-1D2.gr.1 1D2.gr.2 1D2.gr.3 | RASQDISNFLN | 53 |
| HVR-L2-1D2.gr.1 1D2.gr.2 1D2.gr.3 | YTSRLHS | 54 |
| HVR-L3-1D2.gr.1 1D2.gr.2 1D2.gr.3 | QQGNTLPWT | 55 |
| 1A7.gr.1 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 56 |
| 1A7.gr.1 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 57 |
| 1A7.gr.2 $V_H$ | EVQLVQSGAEVKKPGASVKVSCKASGYTFTDSYMSWVRQAPGQGLEWIGDMYPD NGDSSYNQKFRERVTITVDTSTSTAYLELSSLRSEDTAVYYCVLAPRWYFSVWG QGTLVTVSS | 58 |

Sequences

| Name | SEQUENCE | SEQ ID NO: |
|---|---|---|
| 1A7.gr.2 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 59 |
| 1A7.gr.3 $V_H$ | EVQLVQSGAEVKKPGASVKVSCKASGYTFTDSYMSWVRQAPGQGLEWIGDMYPD NGDSSYNQKFRERVTLTVDTSTSTAYLELSSLRSEDTAVYYCVLAPRWYFSVWG QGTLVTVSS | 60 |
| 1A7.gr.3 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 61 |
| 1A7.gr.4 $V_H$ | EVQLVQSGAEVKKPGASVKVSCKASGYTFTDSYMSWVRQAPGQGLEWIGDMYPD NGDSSYNQKFRERVTITVDTSTSTAYLELSSLRSEDTAVYYCVLAPRWYFSVWG QGTLVTVSS | 62 |
| 1A7.gr.4 $V_L$ | DIQMTQSPSSLSASVGDRVTITCRASQDISNYLNWYQQKPGKTVKLLIYYTSRL RSGVPSRFSGSGSGTDFTLTISSLQPEDFATYYCQQGHTLPPTFGQGTKVEIK | 63 |
| 1A7.gr.5 $V_H$ | EVQLVQSGAEVKKPGASVKVSCKASGYTFTDSYMSWVRQAPGQGLEWIGDMYPD NGDSSYNQKFRERVTITVDTSTSTAYLELSSLRSEDTAVYYCVLAPRWYFSVWG QGTLVTVSS | 64 |
| 1A7.gr.5 $V_L$ | DIQMTQSPSSLSASVGDRVTITCRASQDISNYLNWYQQKPGKTVKLLIYYTSRL RSGVPSRFSGSGSGTDFTLTISSLQPEDFATYYCQQGHTLPPTFGQGTKVEIK | 65 |
| 1A7.gr.6 $V_H$ | EVQLVQSGAEVKKPGASVKVSCKASGYTFTDSYMSWVRQAPGQGLEWIGDMYPD NGDSSYNQKFRERVTITVDTSTSTAYLELSSLRSEDTAVYYCVLAPRWYFSVWG QGTLVTVSS | 66 |
| 1A7.gr.6 $V_L$ | DIQMTQSPSSLSASVGDRVTITCRASQDISNYLNWYQQKPGKTVKLLIYYTSRL RSGVPSRFSGSGSGKDYTLTISSLQPEDFATYFCQQGHTLPPTFGQGTKVEIK | 67 |
| 1A7.gr.7 $V_H$ | EVQLVQSGAEVKKPGASVKVSCKASGYTFTDSYMSWVRQAPGQGLEWIGDMYPD NGDSSYNQKFRERVTITVDTSTSTAYLELSSLRSEDTAVYYCVLAPRWYFSVWG QGTLVTVSS | 68 |
| 1A7.gr.7 $V_L$ | DIQMTQSPSSLSASVGDRVTITCRASQDISNYLNWYQQKPGKTVKLLIYYTSRL RSGVPSRFSGSGSGKDYTLTISSLQPEDFATYFCQQGHTLPPTFGQGTKVEIK | 69 |
| 1A7.gr.DA $V_H$ | EVQLVQSGAEVKKPGASVKVSCKASGYTFTDAYMSWVRQAPGQGLEWIGDMYPD NGDSSYNQKFRERVTITRDTSTSTAYLELSSLRSEDTAVYYCVLAPRWYFSVWG QGTLVTVSS | 70 |
| 1A7.gr.DA $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 71 |
| 1A7.gr.ES $V_H$ | EVQLVQSGAEVKKPGASVKVSCKASGYTFTESYMSWVRQAPGQGLEWIGDMYPD NGDSSYNQKFRERVTITRDTSTSTAYLELSSLRSEDTAVYYCVLAPRWYFSVWG QGTLVTVSS | 72 |
| 1A7.gr.ES $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 73 |
| 1A7.gr.NADS $V_H$ | EVQLVQSGAEVKKPGASVKVSCKASGYTFTDSYMSWVRQAPGQGLEWIGDMYPD NADSSYNQKFRERVTITRDTSTSTAYLELSSLRSEDTAVYYCVLAPRWYFSVWG QGTLVTVSS | 74 |
| 1A7.gr.NADS $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 75 |
| 1A7.gr.NADA $V_H$ | EVQLVQSGAEVKKPGASVKVSCKASGYTFTDSYMSWVRQAPGQGLEWIGDMYPD NADASYNQKFRERVTITRDTSTSTAYLELSSLRSEDTAVYYCVLAPRWYFSVWG QGTLVTVSS | 76 |
| 1A7.gr.NADA $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 77 |
| 1A7.gr.NGDA $V_H$ | EVQLVQSGAEVKKPGASVKVSCKASGYTFTDSYMSWVRQAPGQGLEWIGDMYPD NGDASYNQKFRERVTITRDTSTSTAYLELSSLRSEDTAVYYCVLAPRWYFSVWG QGTLVTVSS | 78 |
| 1A7.gr.NGDA $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 79 |

-continued

| Name | SEQUENCE | SEQ ID NO: |
|---|---|---|
| 1A7.gr.SGDS $V_H$ | EVQLVQSGAEVKKPGASVKVSCKASGYTFTDSYMSWVRQAPGQGLEWIGDMYPD SGDSSYNQKFRERVTITRDTSTSTAYLELSSLRSEDTAVYYCVLAPRWYFSVWG QGTLVTVSS | 80 |
| 1A7.gr.SGDS $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 81 |
| 1A7.gr.NGSS $V_H$ | EVQLVQSGAEVKKPGASVKVSCKASGYTFTDSYMSWVRQAPGQGLEWIGDMYPD NGSSSYNQKFRERVTITRDTSTSTAYLELSSLRSEDTAVYYCVLAPRWYFSVWG QGTLVTVSS | 82 |
| 1A7.gr.NGSS $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 83 |
| 1A7.gr.DANADA $V_H$ | EVQLVQSGAEVKKPGASVKVSCKASGYTFTDAYMSWVRQAPGQGLEWIGDMYPD NADASYNQKFRERVTITRDTSTSTAYLELSSLRSEDTAVYYCVLAPRWYFSVWG QGTLVTVSS | 84 |
| 1A7.gr.DANADA $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 85 |
| 1A7.Ala.1 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 86 |
| 1A7.Ala.1 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPATFGQGTKVEIK | 87 |
| 1A7.Ala.2 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 88 |
| 1A7.Ala.2 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTAPPTFGQGTKVEIK | 89 |
| 1A7.Ala.3 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 90 |
| 1A7.Ala.3 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGATLPPTFGQGTKVEIK | 91 |
| 1A7.Ala.4 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 92 |
| 1A7.Ala.4 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHALPPTFGQGTKVEIK | 93 |
| 1A7.Ala.5 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 94 |
| 1A7.Ala.5 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQAHTLPPTFGQGTKVEIK | 95 |
| 1A7.Ala.6 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 96 |
| 1A7.Ala.6 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLAPTFGQGTKVEIK | 97 |
| 1A7.Ala.7 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSVWG QGTLVTVSS | 98 |
| 1A7.Ala.7 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCAGHTLPPTFGQGTKVEIK | 99 |
| 1A7.Ala.8 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFSAWG QGTLVTVSS | 100 |

-continued

| Name | SEQUENCE | SEQ ID NO: |
|---|---|---|
| 1A7.Ala.8 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 101 |
| 1A7.Ala.9 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYASVWG QGTLVTVSS | 102 |
| 1A7.Ala.9 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 103 |
| 1A7.Ala.10 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWAFSVWG QGTLVTVSS | 104 |
| 1A7.Ala.10 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 105 |
| 1A7.Ala.11 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPAWYFSVWG QGTLVTVSS | 106 |
| 1A7.Ala.11 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 107 |
| 1A7.Ala.12 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRWYFAVWG QGTLVTVSS | 108 |
| 1A7.Ala.12 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 109 |
| 1A7.Ala.13 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAPRAYFSVWG QGTLVTVSS | 110 |
| 1A7.Ala.13 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 111 |
| 1A7.Ala.14 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVLAARWYFSVWG QGTLVTVSS | 112 |
| 1A7.Ala.14 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 113 |
| 1A7.Ala.15 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCALAPRWYFSVWG QGTLVTVSS | 114 |
| 1A7.Ala.15 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 115 |
| 1A7.Ala.16 $V_H$ | EVQLVQSGAEVKKPGASVKVSCKASGYTFTDSYMSWVRQAPGQGLEWIGDMYPD NGDSSYNQKFRERVTITRDTSTSTAYLELSSLRSEDTAVYYCVAAPRWYFSVWG QGTLVTVSS | 116 |
| 1A7.Ala.16 $V_L$ | DIQMTQSPSSLSASVGDRVTITCRASQDISNYLNWYQQKPGKAPKLLIYYTSRL RSGVPSRFSGSGSGTDFTLTISSLQPEDFATYYCQQGHTLPPTFGQGTKVEIK | 117 |
| 3C8.gr.1 $V_H$ | EVQLVQSGAEVKKPGASVKVSCKASGYAFTNYLIEWVRQAPGQGLEWIGVINPG SGDTYYSEKFKGRVTITRDTSTSTAYLELSSLRSEDTAVYYCARDLDYWGQGT LVTVSS | 118 |
| 3C8.gr.1 $V_L$ | DIQMTQSPSSLSASVGDRVTITCHASQDISSYIVWYQQKPGKAPKLLIYHGTNL EDGVPSRFSGSGSGTDFTLTISSLQPEDFATYYCVHYAQFPYTFGQGTKVEIK | 119 |
| 3C8.gr.2 $V_H$ | EVQLVQSGAEVKKPGASVKVSCKASGYAFTNYLIEWVRQAPGQGLEWIGVINPG SGDTYYSEKFKGRVTITADTSTSTAYLELSSLRSEDTAVYYCARDLDYWGQGT LVTVSS | 120 |
| 3C8.gr.2 $V_L$ | DIQMTQSPSSLSASVGDRVTITCHASQDISSYIVWYQQKPGKAPKLLIYHGTNL EDGVPSRFSGSGSGTDFTLTISSLQPEDFATYYCVHYAQFPYTFGQGTKVEIK | 121 |

-continued

| Name | SEQUENCE | SEQ ID NO: |
|---|---|---|
| 3C8.gr.3 V_H | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 122 |
| 3C8.gr.3 V_L | DIQMTQSPSSLSASVGDRVTITCHASQDISSYIVWYQQKPGKAPKLLIYHGTNL EDGVPSRFSGSGSGTDFTLTISSLQPEDFATYYCVHYAQFPYTFGQGTKVEIK | 123 |
| 3C8.gr.4 V_H | EVQLVQSGAEVKKPGASVKVSCKASGYAFTNYLIEWVRQAPGQGLEWIGVINPG SGDTYYSEKFKGRVTITADTSTSTAYLELSSLRSEDTAVYYCARDRLDYWGQGT LVTVSS | 124 |
| 3C8.gr.4 V_L | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPYTFGQGTKVEIK | 125 |
| 3C8.gr.5 V_H | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 126 |
| 3C8.gr.5 V_L | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPYTFGQGTKVEIK | 127 |
| 3C8.gr.5.SG V_H | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 128 |
| 3C8.gr.5.SG V_L | DIQMTQSPSSLSASVGDRVTITCHASQDISSYIVWYQQKPGKSFKGLIYHGTNL ESGVPSRFSGSGSGTDFTLTISSLQPEDFATYYCVHYAQFPYTFGQGTKVEIK | 129 |
| 3C8.gr.5.EG V_H | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 130 |
| 3C8.gr.5.EG V_L | DIQMTQSPSSLSASVGDRVTITCHASQDISSYIVWYQQKPGKSFKGLIYHGTNL EEGVPSRFSGSGSGTDFTLTISSLQPEDFATYYCVHYAQFPYTFGQGTKVEIK | 131 |
| 3C8.gr.5.QG V_H | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 132 |
| 3C8.gr.5.QG V_L | DIQMTQSPSSLSASVGDRVTITCHASQDISSYIVWYQQKPGKSFKGLIYHGTNL EQGVPSRFSGSGSGTDFTLTISSLQPEDFATYYCVHYAQFPYTFGQGTKVEIK | 133 |
| 3C8.gr.6 V_H | EVQLVQSGAEVKKPGASVKVSCKASGYAFTNYLIEWVRQAPGQGLEWIGVINPG SGDTYYSEKFKGRVTITADTSTSTAYLELSSLRSEDTAVYYCARDRLDYWGQGT LVTVSS | 134 |
| 3C8.gr.6 V_L | DIQMTQSPSSLSASVGDRVTITCHASQDISSYIVWYQQKPGKSFKGLIYHGTNL EDGVPSRFSGSGSGADYTLTISSLQPEDFATYYCVHYAQFPYTFGQGTKVEIK | 135 |
| 3C8.gr.7 V_H | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 136 |
| 3C8.gr.7 V_L | DIQMTQSPSSLSASVGDRVTITCHASQDISSYIVWYQQKPGKSFKGLIYHGTNL EDGVPSRFSGSGSGADYTLTISSLQPEDFATYYCVHYAQFPYTFGQGTKVEIK | 137 |
| 3C8.gr.8 V_H | EVQLVQSGAEVKKPGASVKVSCKASGYAFTNYLIEWVRQAPGQGLEWIGVINPG SGDTYYSEKFKGRVTLTRDTSTSTAYLELSSLRSEDTAVYYCARDRLDYWGQGT LVTVSS | 138 |
| 3C8.gr.8 V_L | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPYTFGQGTKVEIK | 139 |
| 3C8.gr.9 V_H | EVQLVQSGAEVKKPGASVKVSCKASGYAFTNYLIEWVRQAPGQGLEWIGVINPG SGDTYYSEKFKGRVTLTRDTSTSTAYLELSSLRSEDTAVYYCARDRLDYWGQGT LVTVSS | 140 |
| 3C8.gr.9 V_L | DIQMTQSPSSLSASVGDRVTITCHASQDISSYIVWYQQKPGKSPKLLIYHGTNL EDGVPSRFSGSGSGTDFTLTISSLQPEDFATYYCVHYAQFPYTFGQGTKVEIK | 141 |
| 3C8.gr.10 V_H | EVQLVQSGAEVKKPGASVKVSCKASGYAFTNYLIEWVRQAPGQGLEWIGVINPG SGDTYYSEKFKGRVTLTRDTSTSTAYLELSSLRSEDTAVYYCARDRLDYWGQGT LVTVSS | 142 |

-continued

| Name | SEQUENCE | SEQ ID NO: |
|---|---|---|
| 3C8.gr.10 $V_L$ | DIQMTQSPSSLSASVGDRVTITCHASQDISSYIVWYQQKPGKAFKLLIYHGTNL EDGVPSRFSGSGSGTDFTLTISSLQPEDFATYYCVHYAQFPYTFGQGTKVEIK | 143 |
| 3C8.gr.11 $V_H$ | EVQLVQSGAEVKKPGASVKVSCKASGYAFTNYLIEWVRQAPGQGLEWIGVINPG SGDTYYSEKFKGRVTLTRDTSTSTAYLELSSLRSEDTAVYYCARDRLDYWGQGT LVTVSS | 144 |
| 3C8.gr.11 $V_L$ | DIQMTQSPSSLSASVGDRVTITCHASQDISSYIVWYQQKPGKAPKGLIYHGTNL EDGVPSRFSGSGSGTDFTLTISSLQPEDFATYYCVHYAQFPYTFGQGTKVEIK | 145 |
| 3C8.A.1 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 146 |
| 3C8.A.1 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCAHYAQFPYTFGQGTKVEIK | 147 |
| 3C8.A.2 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 148 |
| 3C8.A.2 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVAYAQFPYTFGQGTKVEIK | 149 |
| 3C8.A.3 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 150 |
| 3C8.A.3 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHAAQFPYTFGQGTKVEIK | 151 |
| 3C8.A.4 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 152 |
| 3C8.A.4 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAAFPYTFGQGTKVEIK | 153 |
| 3C8.A.5 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 154 |
| 3C8.A.5 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAQAPYTFGQGTKVEIK | 155 |
| 3C8.A.6 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 156 |
| 3C8.A.6 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAQFAYTFGQGTKVEIK | 157 |
| 3C8.A.7 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRLDYWGQGT LVTVSS | 158 |
| 3C8.A.7 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPATFGQGTKVEIK | 159 |
| 3C8.A.8 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARARLDYWGQGT LVTVSS | 160 |
| 3C8.A.8 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPYTFGQGTKVEIK | 161 |
| 3C8.A.9 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDALDYWGQGT LVTVSS | 162 |
| 3C8.A.9 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPYTFGQGTKVEIK | 163 |

-continued

| Sequences | | |
|---|---|---|
| Name | SEQUENCE | SEQ ID NO: |
| 3C8.A.10 $V_H$ | EVQLVQSGAEVKKPGASVKVSCKASGYAFTNYLIEWVRQAPGQGLEWIGVINPG SGDTYYSEKFKGRVTLTADTSTSTAYLELSSLRSEDTAVYYCARDRADYWGQGT LVTVSS | 164 |
| 3C8.A.10 $V_L$ | DIQMTQSPSSLSASVGDRVTITCHASQDISSYIVWYQQKPGKSFKGLIYHGTNL EDGVPSRFSGSGSGTDFTLTISSLQPEDFATYYCVHYAQFPYTFGQGTKVEIK | 165 |
| 1D2.gr.1 $V_H$ | EVQLVESGPGLVKPSETLSLTCTVSGFSLTDYGVLWIRQPPGKGLEWIGMIWSG GTTDYNAAFISRVTISVDTSKNQFSLKLSSVTAADTAVYYCVREEMDYWGQGTL VTVSS | 166 |
| 1D2.gr.1 $V_L$ | DIQMTQSPSSLSASVGDRVTITCRASQDISNFLNWYQQKPGKAPKLLIYYTSRL HSGVPSRFSGSGSGTDFTLTISSLQPEDFATYYCQQGNTLPWTFGQGTKVEIK | 167 |
| 1D2.gr.2 $V_H$ | EVQLVESGPGLVKPSETLSLTCTVSGFSLTDYGVLWIRQPPGKGLEWIGMIWSG GTTDYNAAFISRVTISKDTSKNQVSLKLSSVTAADTAVYYCVREEMDYWGQGTL VTVSS | 168 |
| 1D2.gr.2 $_L$L | DIQMTQSPSSLSASVGDRVTITCRASQDISNFLNWYQQKPGKAPKLLIYYTSRL HSGVPSRFSGSGSGTDFTLTISSLQPEDFATYYCQQGNTLPWTFGQGTKVEIK | 169 |
| 1D2.gr.3 $V_H$ | EVQLVESGPGLVKPSETLSLTCTVSGFSLTDYGVLWVRQPPGKGLEWLGMIWSG GTTDYNAAFISRLTISKDTSKNQVSLKLSSVTAADTAVYYCVREEMDYWGQGTL VTVSS | 170 |
| 1D2.gr.3 $V_L$ | DIQMTQSPSSLSASVGDRVTITCRASQDISNFLNWYQQKPGKAPKLLIYYTSRL HSGVPSRFSGSGSGTDFTLTISSLQPEDFATYYCQQGNTLPWTFGQGTKVEIK | 171 |
| CON1 (1A7)HVR-H1 | $X_1X_2$YMS, wherein $X_1$, is D or E, and $X_2$ is S or A | 172 |
| CON1 (A7) HVR-H2 | DMYPD$X_1X_2X_3X_4$SYNQKFRE, wherein $X_1$ is N or S, $X_1$ is A or G, $X_3$ is D or S, and $X_4$ is A or S | 173 |
| CON1 (1A7) HVR-H3 | APRW$X_1X_2X_3X_4$, wherein $X_1$ is Y or A, $X_2$ is A or F, $X_3$ is S or A, $X_4$ is A or V. | 174 |
| CON1 (1A7) HVR-L3 | Q$X_1X_2X_3X_4X_5X_6X_7$T, wherein $X_1$ is A or Q, $X_2$ is A or G, $X_3$ is A or H, $X_4$ is A or T, $X_5$ is A or L, $X_6$ is A or P, and $X_7$ is A or P. | 175 |
| CON2 (3C8) HVR-H2 | VINPGSGD$X_1$YYSEKFKG, wherein $X_1$ is T, A, or Q. | 176 |
| CON2 (3C8) HVR-L2 | HGTNLE$X_1$, wherein $X_1$ is S, E, or Q. | 177 |
| CON2 (3C8) HVR-L3 | $X_1X_2$YAQFPY$X_3$, wherein $X_1$ is V or A, $X_2$ is H or A, and $X_3$ is Y or A. | 178 |
| 1A7 $V_L$ | DIQMTQTTSSLSASLGDRVTISCRADQDISNYLNWYQQKPDGTVKLLIYYTSRL RSGVPSRFSGSGSGKDYFLTISNLEQEDVAAYFCQQGHTLPPTFGGGTKLEIK | 179 |
| 1A7 $V_H$ | EVQLQQSGPELVKPGASVKISCKASGYTFTDSYMSWVKQSHGKTLEWIGDMYPD NGDSSYNQKFREKVTLTVDKSSTTAYMEFRSLTSEDSAVYYCVLAPRWYFSVWG TGTTVTVSS | 180 |
| 3C8 $V_L$ | DILMTQSPSSMSVSLGDTVSITCHASQDISSYIVWLQQKPGKSFRGLIYHGTNL EDGIPSRFSGSGSGADYSLTISSLESEDFADYYCVHYAQFPYTFGGGTKLEIK | 181 |
| 3C8 $V_H$ | QVQLQQSGAELVRPGTSVKVSCKASGYAFTNYLIEWVKQRPGQGLEWIGVINPG SGDTYYSEKFKGKVTLTADKSSSTAYMQLSSTSEDSAVYFCARDRLDYWGQGTT LTVSS | 182 |
| 1A7.gr.5' $V_H$ | EVQLVQSGAEVKKPGASVKVSCKASGYTFTDWYMSWVRQAPGQGLEWIGDMYPD NGDSSYNQKFRERVTLTVDTSTSTAYLELSSLRSEDTAVYYCVLARPRWYFSVW GQGTLVTVSS | 233 |
| 1A7.gr.7' $V_H$ | EVQLVQSGAEVKKPGASVKVSCKASGYTFTDSYMSWVRQAPGQGLEWIGDMYPD NGDSSYNQKFRERVTLTVDTSTSTAYLELSSLRSEDTAVYYCVLAPRWYFSVWG QGTLVTVSS | 234 |

EXAMPLES

Materials and Methods

Surface Plasmon Resonance:

The binding kinetics of the anti-OX40 antibodies was measured using surface plasmon resonance (SPR) on a Biacore 3000 instrument (GE Healthcare). Anti-human Fc (GE Healthcare) was immobilized on a CM5 sensor chip via amine-based coupling using manufacturer provided protocol. Anti-OX40 antibody was captured at a level of 300-400 resonance units (RU). Antibody binding was measured to human OX40 (Sino Biological Inc). Two-fold concentration series of huOX40 with a range of either 18.75 to 300 nM or 6.25 to 200 nM were used for the experiments. Sensorgrams for binding of OX40 were recorded using an injection time of 2 minutes with a flow rate of 30 µl/min, at a temperature of 25° C., and with a running buffer of 10 mM HEPES, pH 7.4, 150 mM NaCl, and 0.005% Tween 20. After injection, disassociation of the ligand from the antibody was monitored for 600 seconds in running buffer. The surface was regenerated between binding cycles with a 40 g 1 injection of 3 M Magnesium Chloride. After subtraction of a blank which contained running buffer only, sensorgrams observed for OX40 binding to anti-OX40 antibodies were analyzed using a 1:1 *Langmuir* binding model with software supplied by the manufacturer to calculate the kinetics and binding constants.

Cross-Blocking:

Cross-blocking experiments were performed using surface plasmon resonance (SPR) on a Biacore 3000 instrument (GE Healthcare) as described above. Two formats were used for analysis. For the first, the hybridoma derived parent antibodies 1A7, 3C8 and 1D2 were captured using an Anti-murine Fc (GE Healthcare) on different flow cells. Human OX40 (Sino Biological Inc) was then flowed across the antibodies for 2 minutes allowing it to bind. This was followed by a 2.5 minute injection of anti-OX40 antibody clones 1A7.gr. 1, 3C8.gr.5, and 1D2.chimera. An increase in resonance units (RUs) indicates no cross-blocking and no change in RU indicates competition. For the second format, the antibody format was reversed and the humanized variants were captured using anti-human Fc (GE Healthcare). This was followed by a 2 minute injection of huOX40 and then the murine antibodies. Each of the clones was able to bind in the presence of the other two clones and was only competed from binding by itself.

Generation of Antibody Variants:

Variants of humanized anti-OX40 agonist antibody clones 1A7, 3C8 and 1D2 were generated using Kunkel mutagenesis. Variant antibodies were expressed transiently in 293 cells and then tested for binding and function.

FACS Analysis:

The human T cell line Hut78 was stably transfected with human OX40, and humanized anti-OX40 antibody clones were tested by FACS using the Hut78-OX40 cells to assess whether variants retained binding cell-surface expressed OX40. After blocking with FACS Blocking Buffer (1×PBS, 0.5% BSA, 0.05% Na Azide), cells were stained for 30 minutes on ice with either 0.1, 1.0, or 10.0 g/ml of antibody. After staining, cells were washed 2× with cold FACS Buffer (1×PBS, 0.5% BSA, 0.05% Na Azide). Cells were then stained with Anti-huFc phycoerythrin (PE) or Anti-muFc PE for 30 minutes on ice. Stained cells were washed 3× with cold FACS Buffer before reading on a FACSCalibur, followed by analysis using Flowjo software.

Stability Testing:

anti-OX40 agonist antibodies were subjected to stability analysis, including heat stress testing and chemical stress testing. For heat testing, samples of formulated antibody were treated at 40° C. for two weeks, then subjected to analysis, e.g., for presence of isomerized or deaminated amino acid residues in CDR residues as determined using tryptic mapping using LC-MS/MS. For chemical testing, samples of formulated antibody were subjected to oxidizing conditions (e.g., using AAPH as an oxidizing agent), then analyzed for presence of oxidized residues (e.g., M or W) in CDRs using tryptic mapping using LC-MS/MS.

Equilibrium binding analysis of OX40 agonist antibody 1A7.gr.1 to recombinant human OX40 Protein expressed on transfected BT-474 Cells: Mab 1A7.gr. 1 was iodinated using the Iodogen method (Fraker and Speck 1978). The radiolabeled mab 1A7.gr.1 was purified from free $^{125}$I-Na by gel filtration using a NAP-5 column; the purified antibody had a specific activity of 24.3 µCi/µg. Competition reaction mixtures of 50 µL volume containing a fixed concentration of iodinated mab 1A7.gr.1 and decreasing concentrations of serially diluted, unlabeled mab 1A7.gr.1 were placed into 96-well plates. Stably transfected BT-474 cells expressing human OX40 were cultured at 37° C. in 5% CO2. Cells were detached from the flask using Cell Dissociation Solution (Sigma-Aldrich; St. Louis, Mo.) and were washed with binding buffer (DMEM with 2% FBS, 50 mM HEPES, pH 7.2, 2 mM sodium azide). The washed cells were added at an approximate density of 5×104 cells in 0.2 mL of binding buffer to the 96-well plates containing the 50 µL competition reaction mixtures. The final concentration of the iodinated antibody in each competition reaction with cells was approximately 100 µM (approximately 16.0×104 cpm per 0.25 mL) and the final concentration of the unlabeled antibody in the competition reaction with cells varied, starting at 500 nM and decreasing in 3-fold steps for 10 concentrations, followed by a no-added unlabeled antibody step using binding buffer only. Competition reactions with cells were incubated for 2 hours at room temperature. The competition reaction with cells at each concentration of unlabeled antibody was assayed in triplicate. After 2 hours of incubation, the competition reactions were transferred to a Millipore Multiscreen® filter plate (Millipore; Billerica, Mass.) and washed four times with binding buffer to separate the free from bound iodinated antibody. The filters were counted on a Wallac Wizard 1470 gamma counter (PerkinElmer Life and Analytical Sciences Inc.; Wellesley, Mass.). The binding data were evaluated using NewLigand software (Genentech), which uses the fitting algorithm of Munson and Rodbard to determine the binding affinity of the antibody (Munson and Rodbard 1980).

Binding of OX40 agonist antibody 1A7.gr.1 to cell surface-expressed OX40 on human, cynomolgus monkey, rat and mouse T cells through flow cytometry: Peripheral white blood cells (PBMC) were obtained from human, Mauritius cynomolgus monkey, rat or mouse whole blood by lysis of red blood cells using erythrocyte lysis buffer (BD Bioscience; San Jose, Calif.). Cells were blocked with 10% human, cynomolgus monkey, rat or mouse serum respectively in PBS for 15 minutes at 4° C. and plated in a 96 well plate at the equivalent of 100 µL of whole blood per reaction.

Mab 1A7.gr. 1 labeled with Alexa Fluor® 647 (or trastuzumab antibody control labeled with Alexa Fluor® 647) was titrated and bound to cells starting at 9 µg/mL in 3-fold serial dilutions for human, rat and mouse samples, and 8 µg/mL in 2-fold serial dilutions for Mauritius cynomolgus monkey samples. PBMCs were co-stained for 30 minutes in the dark at 4° C. to identify T cell subset populations as follows: Human, anti-CD3-PE-Cy7, anti-PerCDP-Cy5.5, anti-CD8-BV510 (BD Biosciences); Cynomolgus monkey, anti-CD3-PE-Cy7, anti-CD4-PerCP-Cy5.5, anti-CD8-APC-H7 (BD Biosciences); Rat, anti-CD3-PE, anti-CD4-FITC (BD Biosciences); Mouse, anti-CD3-FITC, anti-CD4-PE (eBioscience, San Diego, Calif.).

Cells were then washed twice with FACS Stain Buffer (BD Bioscience), and fixed with 1% paraformaldehyde (EMS) in PBS prior to sample acquisition on a flow cytometer.

All samples were run on a BD Biosciences FACSCanto II. Background staining from trastuzumab control antibody on T cells was used to set the analysis gate and normalize the mab 1A7.gr.1-Alexa 647 staining. Acquired data were analyzed using BD FACSDiva software.

Anti-OX40 Agonist Antibody 1A7.Gr.1 Mediated Effector T Cell Costimulation:

Peripheral white blood cells (PBMC) were recovered from human whole blood using a Trima Accel apheresis device and further enriched by Ficoll-Hypaque gradient centrifugation. (GE healthcare). CD4+ memory T cells were isolated from PBMC using Miltenyi CD4+ memory T cell isolation kit (Miltenyi) according to the manufacturer's instructions. L cells that express CD32 and CD80 were irradiated at 5000 Rads and employed as antigen presenting cells.

Irradiated CD32+CD80+ L cells (5000 cells/well) were mixed with CD4+ memory T cells (50000 cells/well) and cultured at 37° C. in 5% C02 in a 96-well plate. Culture media consisted of RPMI 1640 with 10% FBS, Gluta-MAX, sodium pyruvate, penicillin/streptomycin, non-essential amino acids, and beta-mercaptoethanol.

CD4+ Memory T cells were activated in CD32+CD80+ L cell-cocultures by adding 40 ng/mL of anti-CD3 (clone SP34) and (BD Biosciences) and variable amounts of mab 1A7.gr.1 or isotype control (anti-HSV glycoprotein D, anti-gD) (serially diluted two-fold from 320 ng/mL to 0.16 ng/mL). IFN-gamma levels in the supernatant were assessed by Luminex (Bio-Rad) at day 5 of culture, and T cell proliferation was measured by Cell Titer-Glo luminescence (Promega) and read on EnVision Multilabel Reader (Perkin Elmer) at day 7 of culture.

Results:

OX40 agonist antibodies bound human OX40 with sub-nanomolar affinity. Surface plasmon resonance analysis was used to measure the binding kinetics of anti-OX40 antibodies binding to human OX40. Variants of humanized antibody 1A7 showed high affinity binding to human OX40 as measured by Biacore. The results of this analysis are shown in Table 2.

TABLE 2

Kinetics Constants for Humanized Anti-OX40 antibody 1A7 Variants Binding to Human OX40

| | ka (1/Ms) | kd (1/s) | KD (nM) |
|---|---|---|---|
| 1A7.gr.1 | 4.38e5 | 1.52e−4 | 0.529 |
| 1A7.gr.2 | 4.44e5 | 2.33e−4 | 0.524 |
| 1A7.gr.3 | 4.62e5 | 2.43e−4 | 0.525 |
| 1A7.gr.4 | 3.45e5 | 1.63e−4 | 0.472 |
| 1A7.gr.5' | 2.78e5 | 4.92e−4 | 1.77 |
| 1A7.gr.6 | 3.91e5 | 6.93e−5 | 0.177 |
| 1A7.gr.7' | 4.01e5 | 1.45e−4 | 0.360 |

Variants of humanized antibody 3C8 showed high affinity to huOX40. The results of this analysis are shown in Table 3.

TABLE 3

Kinetics Constants for Humanized Anti-OX40 antibody 3C8 Variants Binding to human OX40

| | ka (1/Ms) | kd (1/s) | KD (nM) |
|---|---|---|---|
| 3C8.gr.1 | 4.12e5 | 2.67e−3 | 6.49 |
| 3C8.gr.2 | 4.66e5 | 2.55e−3 | 5.48 |
| 3C8.gr.3 | 4.98e5 | 1.96e−3 | 3.94 |
| 3C8.gr.4 | 4.2e5 | 9.23e−4 | 2.20 |
| 3C8.gr.5 | 4.57e5 | 6.19e−4 | 1.35 |
| 3C8.gr.6 | 3.95e5 | 1.22e−3 | 3.08 |
| 3C8.gr.7 | 4.86e5 | 6.85e−4 | 1.41 |
| 3C8.gr.8 | 3.29e5 | 7.09e−4 | 2.16 |
| 3C8.gr.9 | 4.04e5 | 1.73e−3 | 4.28 |
| 3C8.gr.10 | 3.82e5 | 1.08e−3 | 2.84 |
| 3C8.gr.11 | 3.21e5 | 9.17e−4 | 2.86 |
| 3C8.gr.12 | 5.5e5 | 1.58e−3 | 2.87 |
| 3C8.gr.13 | 4.65e5 | 9.17e−4 | 1.97 |
| 3C8.gr.14 | 5.12e5 | 8.58e−4 | 1.68 |
| 3C8.gr.15 | 5.2e5 | 7.83e−4 | 1.50 |

Humanized variants of antibody 1D2 showed reduced binding to huOX40 as compared to the parent hybridoma antibody. The results of this analysis are shown in Table 4.

TABLE 4

Kinetics Constants for Humanized Anti-OX40 antibody 1D2 Variants Binding to human OX40

| | ka (1/Ms) | kd (1/s) | KD (nM) |
|---|---|---|---|
| 1D2.gr.1 | Fast on | Fast off | |
| 1D2.gr.2 | 3.19e5 | 1.78e−2 | 55.9 |
| 1D2.gr.3 | 2.73e5 | 1.63e−2 | 59.5 |

FACs Analysis:

Humanized OX40 antibody variants were analyzed by FACS to evaluate antibody binding to huOX40 expressed on the surface of Hut78 cells. The results of this analysis are shown in FIG. 1. Humanized anti-OX40 agonist antibodies 1A7.gr.1, 1A7.gr.2, 1A7.gr.3, 3C8.gr.1, 3C8.gr.2, and 3C8.gr.3 bound well to human OX40 expressed on the cell surface.

Cross-Blocking Experiments:

Each of the antibody clones were able to bind in the presence of the other two clones, and was only competed for binding to human OX40 by itself, suggesting that antibodies 1A7, 3C8 and 1D2 do not compete for binding to human OX40 with each other.

Generation and Characterization of Variant OX40 Antibodies:

Variants of anti-OX40 clones 1A7.gr.1 and 3C8.gr.5 were generated by kunkel mutagenesis to mutate CDR residue motifs that were potentially labile (e.g., under heat stress conditions). For antibody 1A7.gr1, sequences DS (D is in CDRH1; DS is potentially subject to increased isomerization) and NGDS (in CDR H2; NG is potentially subject to increased isomerization) were identified as potentially unstable residues, and were mutated to as shown in Table 5. Variants were tested by Biacore as described above to evaluate binding kinetics and in co-stimulation assays to determine biological activity.

TABLE 5

Mutations introduced into variants of mab 1A7.gr.1

| Antibody | Sequence change (original sequence → mutated sequence) |
|---|---|
| 1A7.gr.DA | CDR H1 DS→DA |
| 1A7.gr.ES | CDR H1 DS→ES |
| 1A7.gr.NADS | CDR H2 NGDS→NADS |
| 1A7.gr.NADA | CDR H2 NGDS→NADA |
| 1A7.gr.NGDA | CDR H2 NGDS→NGDA |
| 1A7.gr.SGDS | CDR H2 NGDS→SGDS |
| 1A7.gr.NGSS | CDR H2 NGDS→NGSS |

Mutation of residues DS (D is in CDR H1) to either DA or ES did not significantly alter binding affinity for huOX40 (Table 6). Mutation of residues NGDS in CDR H2 to NADS, NADA, NGDA, and NGSS also did not significantly alter binding affinity for human OX40. Mutation of NGDS (in CDR H2) to SGDS resulted in two fold loss of binding affinity (Table 6). Variant antibodies were analyzed using a T cell co-stimulation assay and level of co-stimulation of T effector cells was not significantly altered in the variants as compared to the 1A7.gr1 antibody (data not shown).

TABLE 6

Kinetics Constants for Anti-OX40 1A7 variants binding to human OX40

| | | ka (1/Ms) | kd (1/s) | KD (nM) |
|---|---|---|---|---|
| 1A7.gr.1 | | 3.23e5 | 1.29e−4 | 0.398 |
| 1A7.gr.DA | CDR H1 DS→DA | 3.21e5 | 8.32e−5 | 0.259 |
| 1A7.gr.ES | CDR H1 DS→ES | 3.41e5 | 1.09e−4 | 0.319 |
| 1A7.gr.NADS | CDR H2 NGDS→NADS | 2.75e5 | 1.21e−4 | 0.442 |
| 1A7.gr.NADA | CDR H2 NGDS→NADA | 3.04e5 | 1.08e−4 | 0.355 |
| 1A7.gr.NGDA | CDR H2 NGDS→NGDA | 3.37e5 | 1.09e−4 | 0.322 |
| 1A7.gr.SGDS | CDR H2 NGDS→SGDS | 2.30e5 | 2.28e−4 | 0.993 |
| 1A7.gr.NGSS | CDR H2 NGDS→NGSS | 3.49e5 | 1.08e−4 | 0.311 |
| 1A7.gr.DANADA | CDR H2 NGDS→NADA CDR H1 DS→DA | 3.87e5 | 2.15e−4 | 0.557 |

For antibody 3C8.gr5, sequences DT (in CDRH2) and DG (in CDR L2) (both potential isomerization sites) were identified as potentially unstable residues in antibody 3C8.gr.5. Mutations were made in each of these sequences, as shown in Table 7.

TABLE 7

Mutations introduced into variants of mab 3C8.gr.5

| Antibody clone | Sequence change (original sequence →mutated sequence) |
|---|---|
| 3C8.gr.DA | CDR H2 DT→DA |
| 3C8.gr.DQ | CDR H2 DT→DQ |
| 3C8.gr.5.EG | CDR L2 DG→EG |
| 3C8.gr.5.QG | CDR L2 DG→QG |
| 3C8.gr.5.SG | CDR L2 DG→SG |

Mutation of residues DT in CDR H2 to either DA or DQ resulted in a loss in affinity for human OX40 (as compared to affinity of the parent antibody) (Table 8). Mutation of residues DG in CDR L2 to either EG, QG, or SG did not significantly alter binding affinity (Table 8).

TABLE 8

Kinetics Constants for Anti-OX40 3C8 Stability Variants Binding to human OX40

| | | ka (1/Ms) | kd (1/s) | KD (nM) |
|---|---|---|---|---|
| 3C8.gr.5 | | 4.29e5 | 6.13e−4 | 1.43 |
| 3C8.gr.DA | CDR H2 DT→DA | 3.88e5 | 5.02e−3 | 12.9 |
| 3C8.gr.DQ | CDR H2 DT→DQ | 3.81e5 | 3.09e−3 | 8.12 |
| 3C8.gr.5.EG | CDR L2 DG→EG | 5.80e5 | 5.69e−4 | 0.98 |
| 3C8.gr.5.QG | CDR L2 DG→QG | 4.57e5 | 5.34e−4 | 1.17 |
| 3C8.gr.5.SG | CDR L2 DG→SG | 4.50e5 | 6.82e−4 | 1.51 |

Stability Testing:

Antibody 1A7.gr. 1 was subjected to stability testing as described above, and sequences DS (D is in CDRH1) and NGDS (in CDR H2) were stable under thermal stress testing conditions. In addition, M and W residues (in CDR-H1, -H2 and -H3) did not show unacceptable levels of oxidation during chemical stress testing.

Antibody 3C8.gr.5 was also subjected to stability testing. While residues DT were stable under thermal testing conditions, residues DG (CDR-L2) were not stable under thermal testing conditions.

Generation and Characterization of OX40 Antibody Alanine Scanning Mutants:

Alanine scan mutants of 1A7.gr.1 and 3C8.gr.5 to were generated, e.g., to examine impact of mutations on binding affinity. In addition, impact of binding affinity on antibody activity was determined. Mutants were generated using kunkel mutagenesis to change amino acid residues in the third CDR of the light chain and the heavy chain. The variant antibodies were expressed transiently in 293 cells, and tested by Biacore 3000 for binding to human OX40.

The results of this experiment are shown in Table 9. Alanine substitutions into heavy chain CDR 3 at positions 96 (1A7.Ala.14), 97 (1A7.Ala.11), 98 (1A7.Ala.13), 99 (1A7.Ala.10), and 100 (1A7.Ala.9) showed reduced binding to huOX40. These results suggest that the residues at position 96, 97, 98, 99 and 100 may be important for antibody binding to OX40. Functional characterization of Ala scan mutants 1A7.Ala9, 1A7.Ala10, 1A7.Ala11, 1A7.Ala13, and 1A7.Ala14 in an in vitro T cell co-stimulation assay showed that decreased OX40 antibody affinity correlated with reduced ability of antibodies to co-stimulation effector T cell proliferation activity.

TABLE 9

Kinetics Constants for Anti-OX40 1A7.gr.1 Alanine Scan Variants Binding to human OX40 (substituted alanine is underlined)

| | LC-CDR 3 | HC-CDR 3 | KD (nM) |
|---|---|---|---|
| 1A7.gr.1 | QQGHTLPPT (SEQ ID NO: 7) | VLAPRWYFSV (SEQ ID NO: 248) | 0.62 |
| 1A7.Ala.7 | QAGHTLPPT (SEQ ID NO: 28) | VLAPRWYFSV (SEQ ID NO: 248) | 0.91 |
| 1A7.Ala.5 | QQAHTLPPT (SEQ ID NO: 26) | VLAPRWYFSV (SEQ ID NO: 248) | 0.39 |
| 1A7.Ala.3 | QQGATLPPT (SEQ ID NO: 24) | VLAPRWYFSV (SEQ ID NO: 248) | ~0.5 |
| 1A7.Ala.4 | QQGHALPPT (SEQ ID NO: 25) | VLAPRWYFSV (SEQ ID NO: 248) | 0.67 |
| 1A7.Ala.2 | QQGHTAPPT (SEQ ID NO: 23) | VLAPRWYFSV (SEQ ID NO: 248) | ~0.5 |
| 1A7.Ala.6 | QQGHTLAPT (SEQ ID NO: 27) | VLAPRWYFSV (SEQ ID NO: 248) | 0.16 |
| 1A7.Ala.1 | QQGHTLPAT (SEQ ID NO: 22) | VLAPRWYFSV (SEQ ID NO: 248) | ~0.5 |
| 1A7.Ala.15 | QQGHTLPPT (SEQ ID NO: 7) | ALAPRWYFSV (SEQ ID NO: 235) | 0.66 |
| 1A7.Ala.16 | QQGHTLPPT (SEQ ID NO: 7) | VAAPRWYFSV (SEQ ID NO: 240) | 0.54 |
| 1A7.Ala.14 | QQGHTLPPT (SEQ ID NO: 7) | VLAARWYFSV (SEQ ID NO: 241) | 6.88 |
| 1A7.Ala.11 | QQGHTLPPT (SEQ ID NO: 7) | VLAPAWYFSV (SEQ ID NO: 242) | 16.7 |
| 1A7.Ala.13 | QQGHTLPPT (SEQ ID NO: 7) | VLAPRAYFSV (SEQ ID NO: 243) | Weak binding |
| 1A7.Ala.10 | QQGHTLPPT (SEQ ID NO: 7) | VLAPRWAFSV (SEQ ID NO: 244) | 5.94 |
| 1A7.Ala.9 | QQGHTLPPT (SEQ ID NO: 7) | VLAPRWYASV (SEQ ID NO: 245) | 5.32 |
| 1A7.Ala.12 | QQGHTLPPT (SEQ ID NO: 7) | VLAPRWYFAV (SEQ ID NO: 246) | 0.41 |
| 1A7.Ala.8 | QQGHTLPPT (SEQ ID NO: 7) | VLAPRWYFSA (SEQ ID NO: 247) | 0.41 |

Analysis of antibody 3C8.gr5 alanine scan variants is shown in Table 10. Variant antibodies comprising alanine substitutions into light chain heavy chain CDR 3 at positions 91, 93, 94, and 95 showed significantly reduced binding to huOX40. All three positions (95, 96 and 97) in heavy chain CDR3 when mutated to alanine showed reduced binding to huOX40.

TABLE 10

Kinetics Constants for Anti-OX40 3C8.gr.5 Alanine Scan Variants Binding to human OX40 (alanine substitution is underlined)

| | LC-CDR 3 | HC-CDR 3 | KD (nM) |
|---|---|---|---|
| 3C8.gr.5 | VHYAQFPYT (SEQ ID NO: 42) | ARDRLDY (SEQ ID NO: 239) | 1.28 |
| 3C8.A.1 | AHYAQFPYT (SEQ ID NO: 43) | ARDRLDY (SEQ ID NO: 239) | 2.7 |

TABLE 10-continued

Kinetics Constants for Anti-OX40 3C8.gr.5 Alanine Scan Variants Binding to human OX40 (alanine substitution is underlined)

| | LC-CDR 3 | HC-CDR 3 | KD (nM) |
|---|---|---|---|
| 3C8.A.2 | VAYAQFPYT (SEQ ID NO: 44) | ARDRLDY (SEQ ID NO: 239) | 2.6 |
| 3C8.A.3 | VHAAQFPYT (SEQ ID NO: 45) | ARDRLDY (SEQ ID NO: 239) | >100 |
| 3C8.A.4 | VHYAAFPYT (SEQ ID NO: 46) | ARDRLDY (SEQ ID NO: 239) | 1.27 |
| 3C8.A.5 | VHYAQAPYT (SEQ ID NO: 47) | ARDRLDY (SEQ ID NO: 239) | 27.9 |
| 3C8.A.6 | VHYAQFAYT (SEQ ID NO: 48) | ARDRLDY (SEQ ID NO: 239) | >100 |
| 3C8.A.7 | VHYAQFPAT (SEQ ID NO: 49) | ARDRLDY (SEQ ID NO: 239) | weak binding |
| 3C8.A.8 | VHYAQFPYT (SEQ ID NO: 42) | ARARLDY (SEQ ID NO: 236) | No binding |
| 3C8.A.9 | VHYAQFPYT (SEQ ID NO: 42) | ARDALDY (SEQ ID NO: 237) | 32.5 |
| 3C8.A.10 | VHYAQFPYT (SEQ ID NO: 42) | ARDRADY (SEQ ID NO: 238) | 15.8 |

Mab 1A7.Gr.1 Bound with High Affinity to Human OX40, Analyzed Using Radioimmunoassay Analysis:

Equilibrium binding studies were performed as described to determine the affinity of mab 1A7.gr.1 to human OX40 expressed on transfected BT-474 cells. The Kd values are summarized in Table 11. The average measured binding affinity was 0.45 nM (n=3, individual values 0.43, 0.44, 0.49).

TABLE 11

Equilibrium Binding Analysis of mab 1A7.gr.1 binding to BT-474 cells Expressing Recombinant human OX40

| Antibody | Assay | Kd (nM) | Average $K_d$ (nM) (±SD) |
|---|---|---|---|
| 1A7.gr.1 | 1 | 0.43 | 0.45 ± 0.03 |
| | 2 | 0.44 | |
| | 3 | 0.49 | |

Figure 2:
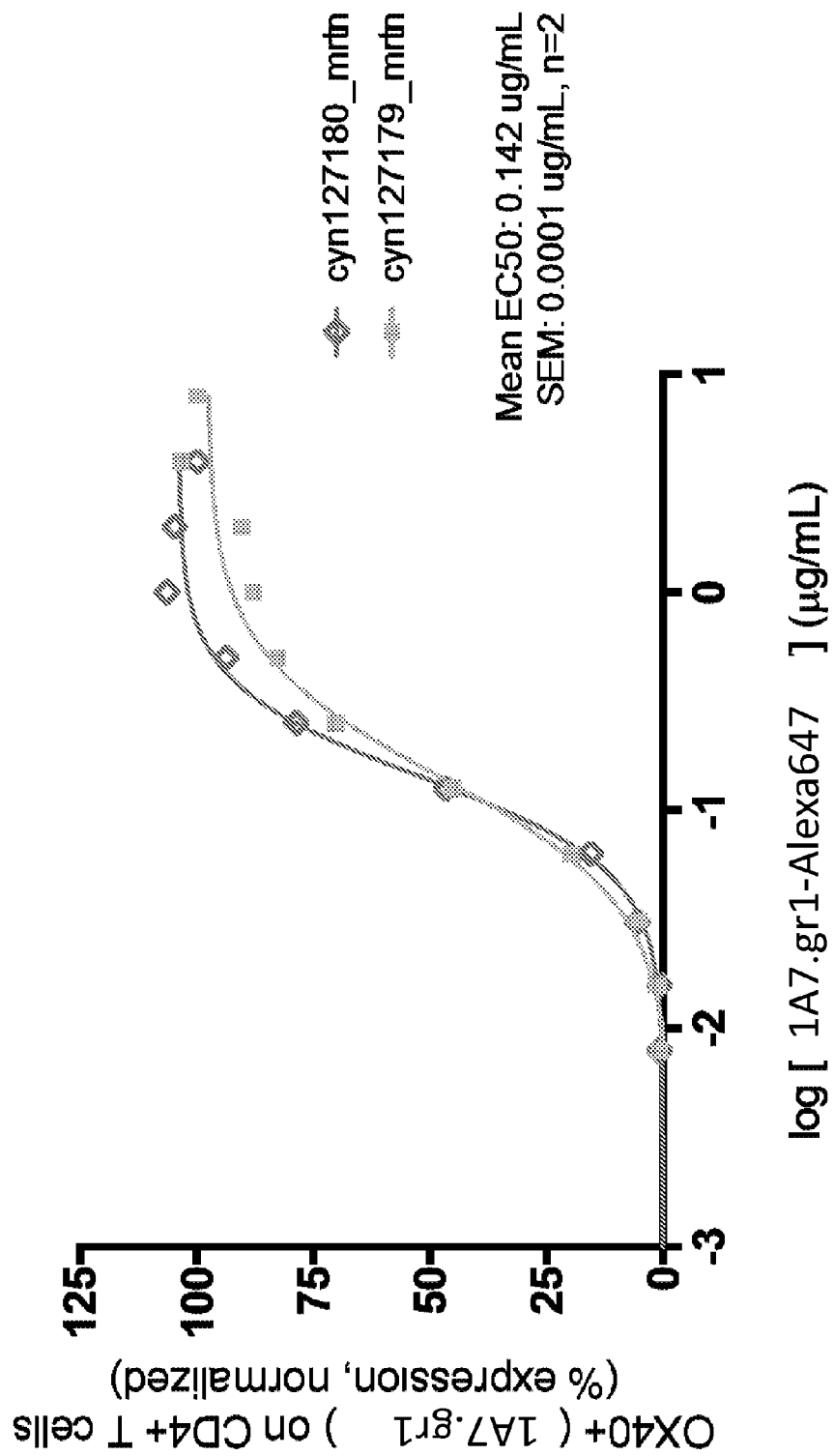
FIG. 2: OX40 agonist antibody 1A7.gr. 1 bound with high affinity to human and cynomolgus monkey T cells.

Mab 1A7.Gr.1 Bound with High Affinity to OX40 Expressed on Human, Cynomolgus Monkey, Rat and Mouse T Cells:

Binding of mab 1A7.gr.1 to OX40 expressed on human, cynomolgus monkey, rat and mouse T cells was assessed in a flow cytometry-based assay. The average EC50 values for mab 1A7.gr.1 binding to human and cynomolgus monkey T cells are summarized in Table 12, and binding curves are shown in FIG. 2. The results indicate that mab 1A7.gr.1 bound to human and cynomolgus monkey T cells with similar high affinity, with EC50 values of 0.220±0.026 (1.47 nM) and 0.142±0.0001 µg/mL (0.946 nM) for human and cynomolgus monkey T cells respectively. No measurable binding of mab1A7.gr.1 to rat or mouse T cells was detected.

TABLE 12

Mab 1A7.gr.1 Binding to Human and Cynomolgus Monkey T Cells

| | Assay | $EC_{50}$ (µg/mL) | Average $EC_{50}$ (µg/mL) (±SD) |
|---|---|---|---|
| Cynomolgus monkey | 1 | 0.143 | 0.142 ± 0.00014 |
| | 2 | 0.142 | |
| Human | 1 | 0.196 | 0.220 ± 0.053 |
| | 2 | 0.184 | |
| | 3 | 0.201 | |
| | 4 | 0.298 | |

Figure 3A:
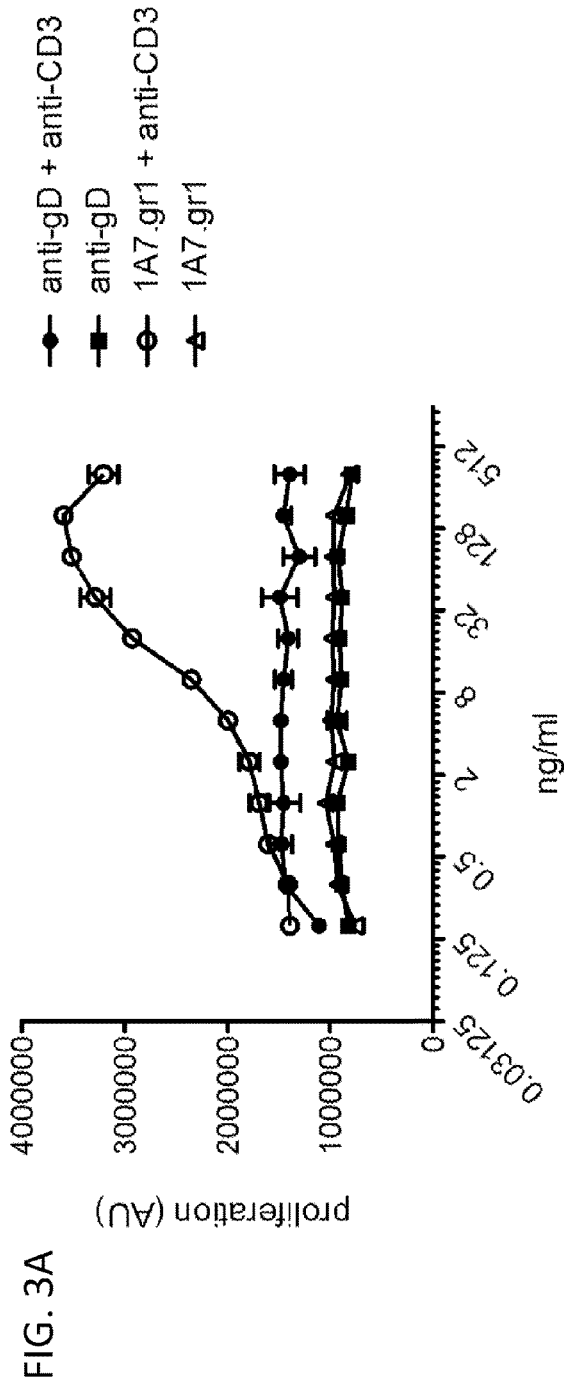
FIGS. 3A and 3B.
Figure 3B:
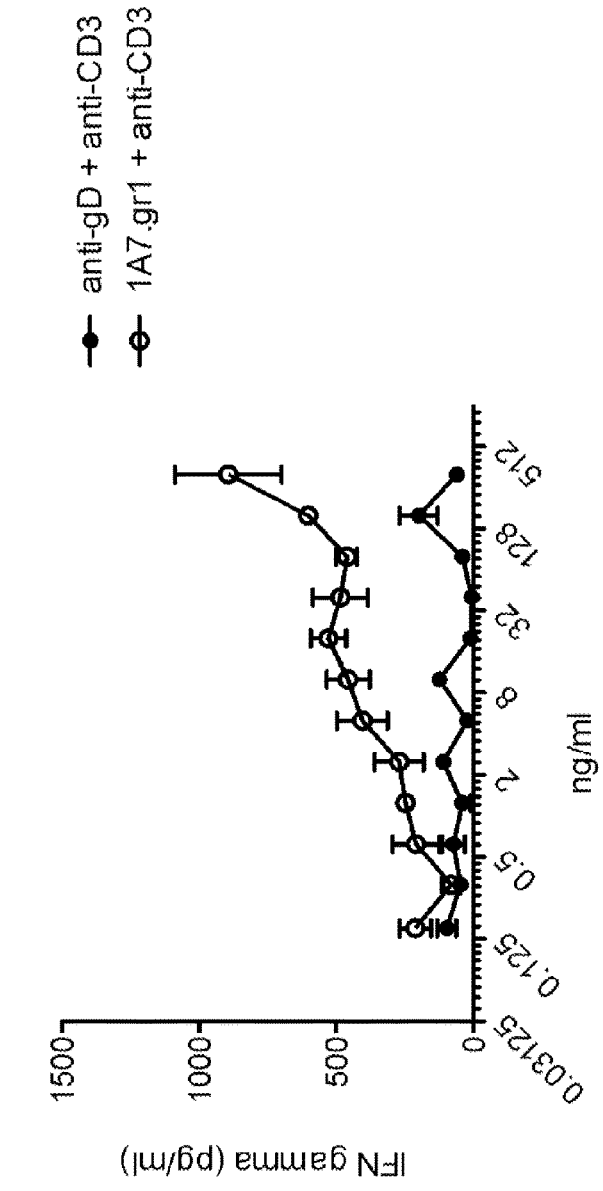

Treatment with OX40 Agonist Antibody mab1A7.Gr.1 Costimulated T Effector Cell Proliferation and Interferon Gamma Production Following T Cell Receptor Engagement in a Dose Dependent Manner:

CD4+ memory T cells were stimulated with a fixed concentration of anti-CD3 and variable concentration of anti-OX40 or control antibodies as described. In the absence of anti-CD3 crosslinking, mab 1A7.gr. 1 had no effect on T cell proliferation (FIG. 3A). Increasing concentration of mab 1A7.gr. 1 costimulated CD4+ memory T cell proliferation in response to anti-CD3 crosslinking. The calculated EC50 for the costimulatory effect of mab 1A7.gr.1 was 9.96 ng/mL (n=2, FIG. 3A). Increasing concentrations of mab 1A7.gr.1 costimulated CD4+ memory T cell production of interferon gamma in response to anti-CD3 crosslinking (FIG. 3B). These results demonstrated that agonist OX40 mab 1A7.gr.1 costimulated CD4+ memory T cell proliferation and interferon gamma production.

Materials and Methods II

1. Antibodies:

Purified anti-human OX40 (PE) (clone ACT35), mouse IgG1 (PE), anti-human CD3 (clone SP34), anti-human CD4 (FITC), anti-human CD25 (PE), anti-human CD45RA (APC), anti-human CD3-APC and purified mouse anti-human CD11b antibody were purchased from BD biosciences. Alemtuzumab (Campath) was purchased from Genzyme. Anti-human CD52 (APC) was purchased from Sigma. Goat anti-mouse IgG Alexa Fluor 647 was purchased from Invitrogen. Anti-human CD127 (eFluor 450) and rat anti-mouse OX40 (PE, clone OX86) were purchased from eBiosciences. Anti-human OX40 antibody 1A7gr1, Rituximab (chimeric anti-CD20, IgG1) and anti-HSV glycoprotein D (anti-gD antibody, human IgG1) were generated at Genentech. Anti-human IgG (PE) was purchased from BD Biosciences. Human CD4 Isolation Kit II was from Miltenyi Biotech. Human NK isolation kit was purchased from Stem Cell Technology.

2. Cells and Media a, Cell Lines:

BT474 (a human breast cancer cell line) was acquired from ATCC; 293-based Amphotropic cell line was acquired from Life Technology. BT474 and Amphotropic cells were cultured and maintained in DMEM media supplemented with 10% FBS/Pen/Strep, at 37C/5% $CO_2$ incubator. L cells expressing CD32a and CD80 were cultured and maintained in the complete RPMI media (RPMI-1640, supplemented with 10% FBS (heat-inactivated)/Pen/strep/Glutamine/Non-essential amino acids/55 µM βME), at 37C/5% $CO_2$ incubator. U937 (a human monocytic cell line) was cultured and maintained in the complete RPMI media at 37C/5% $CO_2$ incubator.

b, Generation of Human OX40-Expressing BT474 Clones:

To generate human OX40-MSCV (hOX40-MSCV) plasmid, human OX40 cDNA was cloned as a fusion protein with a 5' HSV glycoprotein D (gD) tag into MSCV IRES GFP retroviral vector (Clontech). Amphotropic Phoenix packaging cells were transfected with hOX40-MSCV plasmid via Fugene HD (Roche). BT474 cells were subsequently infected with viral supernatants from the transfected amphotropic cells. Pools of OX40-expressing BT474 cells were enriched by sorting surface gD+ and GFP+ cells. OX40-expressing clones were generated by limiting dilution analysis of OX40-expressing clones. Clones expressing high and low levels of OX40 were selected based on surface expression of the gD tag and OX40 expression levels by flow cytometry. To determine human OX40 expression levels on BT474 clones, OX40-expressing cells were stained with anti-human OX40-PE (clone ACT35, BD Biosciences), and cell fluorescence was measured on a FACS Canto II (BD Bioscience) and analyzed using Flowjo software (TreeStar).

c, Isolation of Normal Human Peripheral Blood Mononuclear Cells (PBMC), T Cells, Monocytes and NK Cells:

Normal human peripheral blood samples were donated by registered Genentech employees and provided by the Employee Health Service department. Normal human buffy coat was procured from San Francisco Blood Bank via Genentech Employee Health Service department. Peripheral white blood cells (PBMC) were recovered from human whole blood using a Trima Accel apheresis device and further enriched by Ficoll-Hypaque gradient centrifugation (GE Healthcare).

$CD4^+$ T cells were isolated from PBMC using a Miltenyi $CD4^+$ T cell isolation kit. CD4+ naïve T cells were stained with CD4-FITC, CD25-PE, and CD127-e450 (eBiosciences) to sort CD4+CD25-CD127+ cells and $CD4^+CD25^+$ $CD127^-$ T cells. Treg cells were sorted from the same donor with FACS Aria (BD Biosciences). The purity of sorted cells was confirmed by flow cytometric analysis immediately after sorting.

The PBMC of the whole blood samples isolated by Ficoll-Paque gradient centrifugation were used for isolation of monocytes. Monocytes were isolated from PBMC using human monocyte isolation kit (Miltenyi). Isolated monocytes were cultured 7 to 14 days with the complete RPMI media in the presence of 20 ng/mL GM-CSF for the generation of monocyte-derived macrophages (MDM).

Normal human NK cells were isolated from PBMC of buffy coat using the human NK cell enrichment kit (Stem Cell Technology) according to the manufacturer's instructions, and cells were used immediately for the ADCC assay.

3, Cell Labeling Reagents:

Purified CD4+ naïve T cells were labeled with CFSE using the CellTrace CFSE Cell Proliferation Kit (Life Technology) and purified Treg cells were labeled with PKH26 Red Fluorescent Cell Linker Kit (Sigma). Both kits were used according to the manufacturer's instructions.

4. Treg Suppression Assay:

L cells that express CD32 and CD80 were irradiated at 5000 rads and employed as antigen-presenting cells for the CD4+CD25+CD127-cell suppression assay.

Irradiated CD32+CD80+ L cells (5000 RAD, 10,000 cells/well) were plated on a flat bottomed 96-well tissue culture plate, and maintained at 37C/5% CO2 incubator overnight. On the following day, CD4+ naïve T cell proliferation in the presence or absence of sorted Treg cells was assessed in the following CD4+CD25+CD127-T cell suppression assay.

To monitor the proliferation of naïve CD4+ T cells, 100,000 CFSE (5 um) labeled naïve CD4+ T cells were added to each well in the assay plate, which already contained L cells seeded the day before. To test the suppressive function of Treg cells, 200,000 PKH26 (2 um)-labeled Treg cells were added to each well containing CFSE labeled CD4+ naïve T cells. To test the activity of the anti-OX40 antibody 1A7.gr1, 1A7.gr1 or the isotype control antibody anti-CD20 antibody (rituximab) (each at 200 ng/ml) was added to the co-culture of naïve CD4+ T cells, Treg cells, and irradiated $CD32^+CD80^+$ L cells. Soluble anti-CD3 was added to cells at a final concentration of 2.5 ng/mL. The assay plate was maintained at 37C/5% $CO_2$ incubator for 6 days before data acquisition. At day 6, the proliferation of naïve CD4 T cells was traced by CFSE dye dilution and cell fluorescence was measured on a FACS Canto II (BD Bioscience) and analyzed using FlowJo software (Treestar).

5. Antibody Dependent Cell-Mediated Phagocytosis (ADCP) Assay:

U937 cells were employed as phagocytic effector cells in the ADCP assay. 50,000 U937 cells labeled with PKH26 (2 um) were seeded in a 96 well tissue culture plate. Variable amounts of anti-OX40, 1A7.gr1 or anti-HER2 (trastuzumab isotype control) antibodies (2-fold serial dilutions from 1000 to 7.8 ng/ml) were added to U937 cells. Either OX40-high or -low expressing BT474 clones were utilized as target cells in the ADCP assay. 5,000 OX40+BT474 cells were added to U937 cells in the assay plate. The assay plate was incubated at 37C/5% $CO_2$ incubator for 4 hours. Cells then were harvested for cell fluorescence measurement on a FACS Canto II (BD Bioscience) and analyzed using FlowJo software (Treestar). The percentage of phagocytosis was calculated by dividing GFP+ PKH26+ events (i.e., measured U937 cells that have engulfed BT474 cells) from all $GFP^+$ events (all BT474 cells).

6, Antibody Dependent Cell-Mediate Cytotoxicity (ADCC) Assay:

To demonstrate that 1A7.gr1 induced ADCC of OX40 expressing T cells, primary NK cells were co-cultured with activated primary CD4+ T cells. CD4+ T cells and NK cells were isolated from the same PBMC donor using the human CD4 T cell isolation kit (Miltenyi kit) and human NK cell enrichment kit (Stem Cell Technology), respectively. OX40 expression on isolated CD4+ T cells was induced by activating T cells with PHA (5 ug/ml) for 48 hours in complete RPMI-1640 media. Alemtuzumab (anti-CD52 mAb) was used as positive control and anti-gD was used as negative control for the ADCC assay. Activated CD4+ cells (5,000 per well) were incubated with variable amounts of 1A7.gr1 or control antibodies (3-fold serial dilutions from 10000 to 0.01 ng/ml) for 30 minutes in a 96-well tissue culture assay plate. Subsequently, ADCC assay was initiated by adding NK cells (50,000 cells) to each well. The assay plate was then incubated for another for 20 hours in a 37C/5% $CO_2$ incubator. Co-cultures were then stained with anti-human CD4-FITC and 7AAD (BD Biosciences). After washing with PBS, data were acquired by Flow cytometry (BD FACScaliber) and analyzed by Flowjo program (TreeStar). The killing (ADCC) frequency of OX40-expressing CD4 T cells was defined by the percentage of $CD4^+7AAD^+$ cell over total CD4 T cells.

To demonstrate 1A7gr1 induced OX40-sensitive ADCC, high or low human OX40-expressing BT474 (human breast cancer cell line) clones were seeded (5,000 per well) into a black-wall 96-well tissue culture assay plate, to allow attachment and maintained for 24 hours at 37C/5% $CO_2$ incubator. Then, anti-CD20 (isotype control) or anti-OX40 agonist antibody 1A7.gr1 were added to the BT474 cells. Primary human NK cells from healthy donors were isolated from buffy coat PBMC using the human NK cell enrichment kit (Stem Cell Technology), and 50,000 purified NK cells were then added to the wells containing BT474 clones in the presence of anti-CD20 (Rituximab isotype control) or 1A7.gr1. The assay plate was incubated for 24 hours before CellTiterGlo reagent was added to capture the chemiluminescent signal. The percentage of cells undergoing anti-OX40-mediated ADCC was calculated by dividing the signal of antibody-treated cells with that of non-treated cells. The signal from NK single culture was subtracted to offset the background signal from NK cells.

Results II

Figure 6:
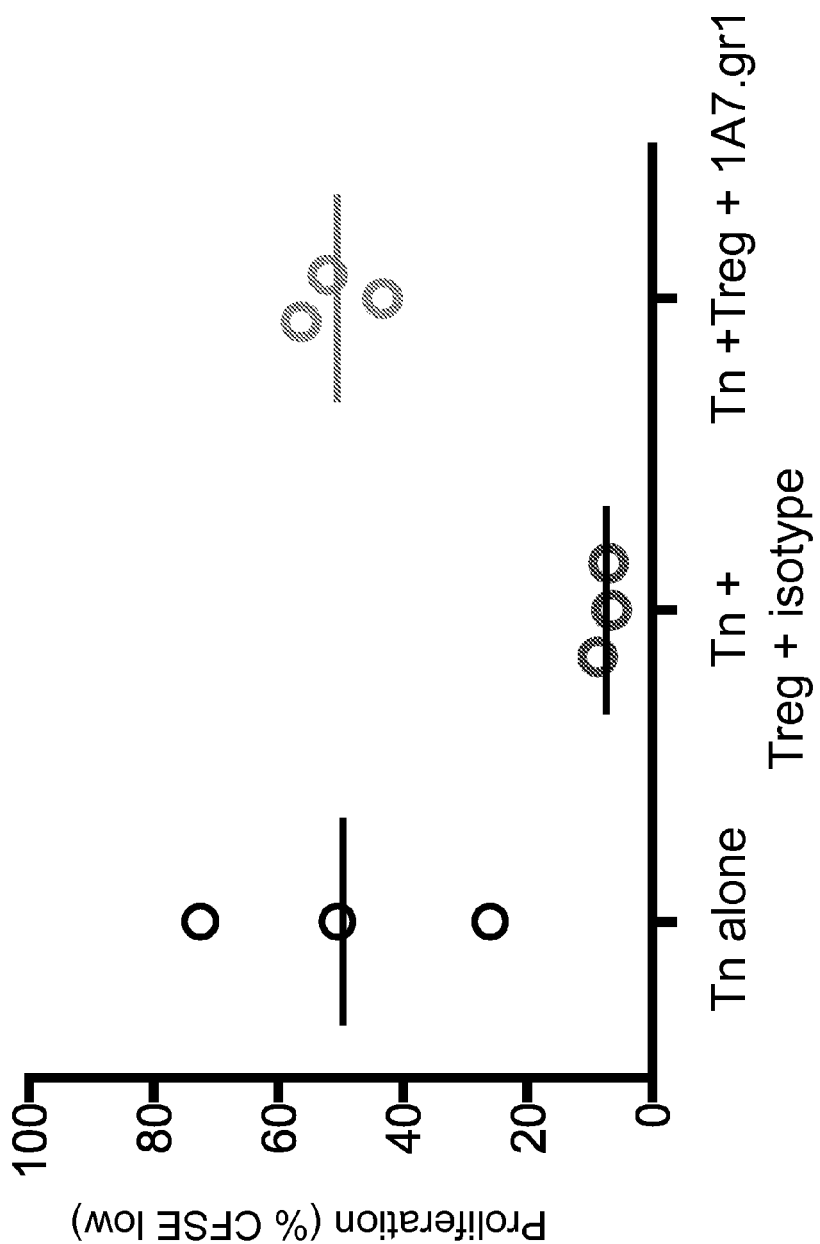
FIG. 6: Treatment with mab 1A7.gr. 1 impaired the suppressive function of Treg cells.

Mab 1A7.Gr.1 Inhibited Treg Suppression of CD4+Naïve T Cells:

We tested whether OX40 crosslinking by binding of OX40 agonist antibody to Treg cells will inhibit their capacity to inhibit naïve T cell proliferation. Naïve $CD4^+$ T cell proliferation was induced by anti-CD3 crosslinking in the absence of 1A7.gr1. The addition of Treg cells to naïve T cell cultures suppressed anti-CD3-induced naïve T cell proliferation. Treatment with mAb 1A7.gr.1 inhibited the suppressive function of regulatory T cells (n=3, FIG. 6). Naïve T cell proliferation was measured by monitoring CFSE low populations through flow cytometric analysis. This result demonstrated that mAb 1A7.gr. 1 inhibited the suppressive function of Treg cells.

Figure 8B:
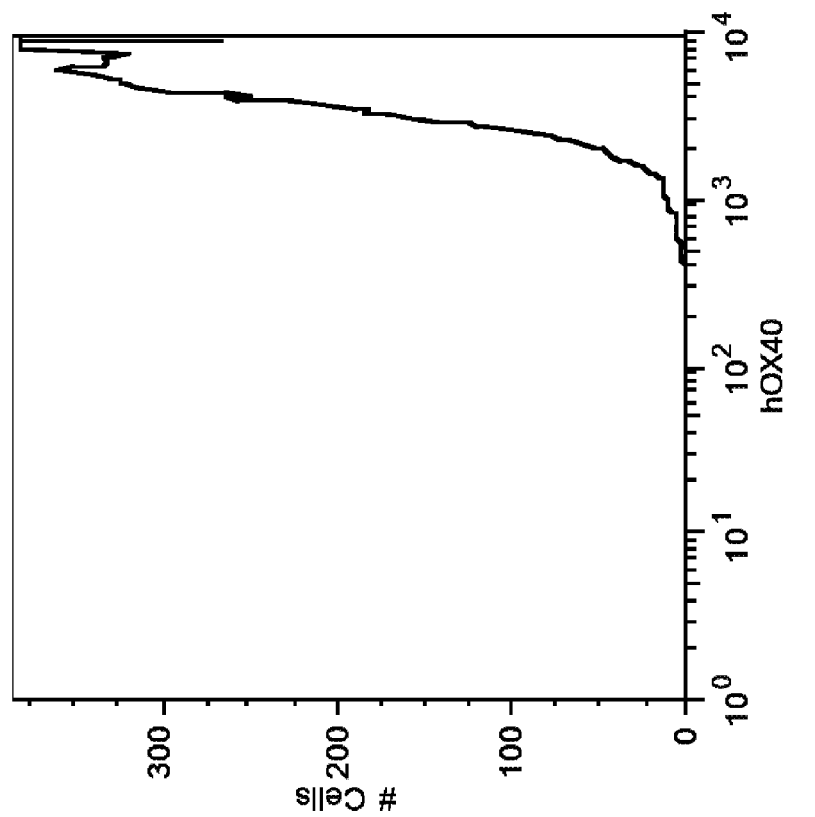
FIGS. 8A and 8B: BT474-human OX40 transgenic clones expressed different levels of human OX40.
Figure 8A:
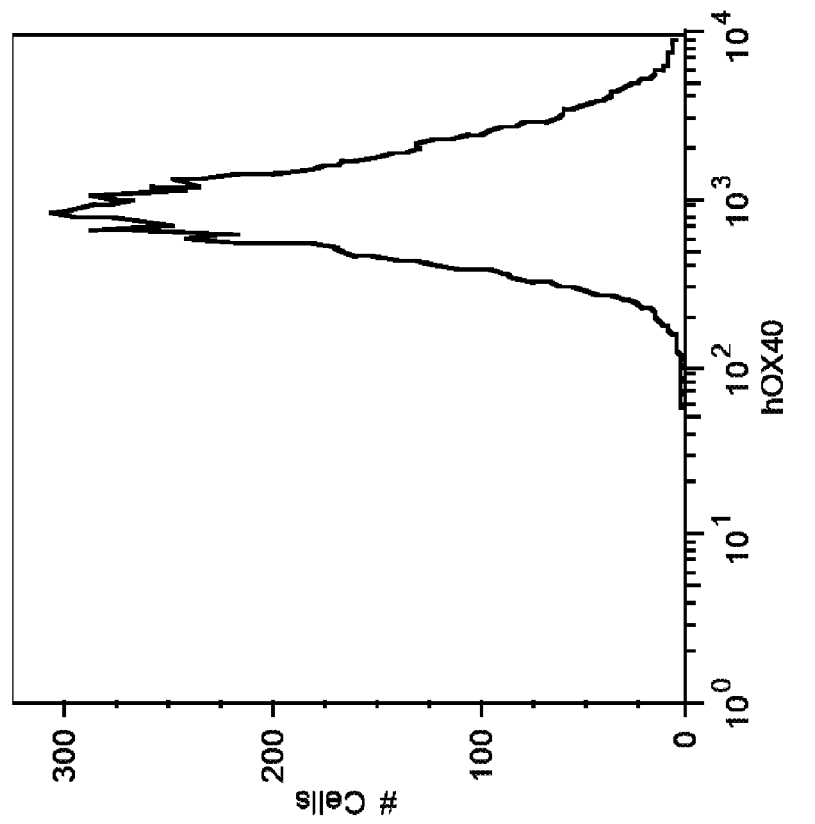

BT474-hOX40 Transgenic Clones Expressed Different Levels of hOX40:

Expression level of human OX40 was characterized in transgenic BT474 cell clones using hOX40 surface staining and mean fluorescent intensity (MFI) by flow cytometric analysis. The BT474-human OX40-high clone expressed more than 5-fold higher OX40 than BT474-human OX40 low clone, with the high-OX40 clone showing a MFI of 5243 (FIG. 8B) and the low-OX40 clone showing MFI of 994 (FIG. 8A). The isotype control antibody, trastuzumab, had an MFI of 10 (data not shown).

Figure 9:
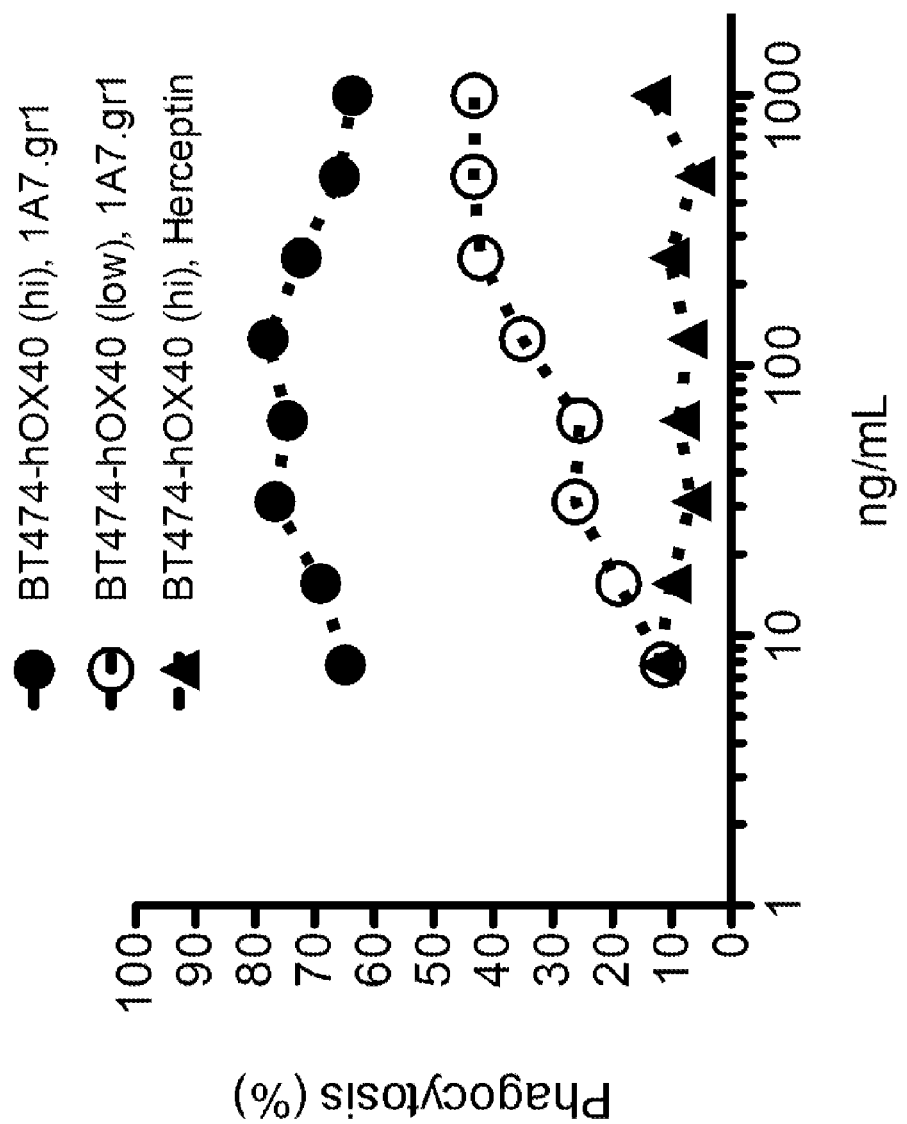
FIG. 9: Treatment with OX40 agonist antibody induced antibody dependent cell-mediated phagocytosis of cell lines expressing human OX40, and level of antibody dependent cell-mediated phagocytosis was sensitive to level of OX40 expression in the target cells.

Treatment with OX40 Agonist Antibody Induced OX40-Dependent Antibody Dependent Cell Mediated Phagocytosis (ADCP):

To determine whether anti-human OX40 mab 1A7.gr. 1, mediated ADCP, U937 myeloid cells were cultured with OX40-expressing target cells, BT474 clones that expressed high or low levels of OX40. Treatment with OX40 agonist antibody 1A7 induced phagocytosis of BT474-hOX40 clones expressing low and high levels of hOX40, in a dose-dependent manner as assayed using FACS (FIG. 9). In addition, higher level of phagocytosis was observed using the BT474-hOX40-high clone than when using the BT474-hOX4-low clone, suggesting that OX40 antibody-mediated cell-mediated phagocytosis was dependent on OX40 expression level on target cells (FIG. 9). By contrast, trastuzumab (also termed Herceptin), the isotype control antibody, only mediated 10% phagocytosis as shown with BT474-hOX40 high clone. These data demonstrated that mab 1A7.gr. 1 induced phagocytosis of OX40 expressing target cells, and that the levels of antibody dependent cell-mediated phagocytosis were correlated with OX40 levels.

Figure 10:
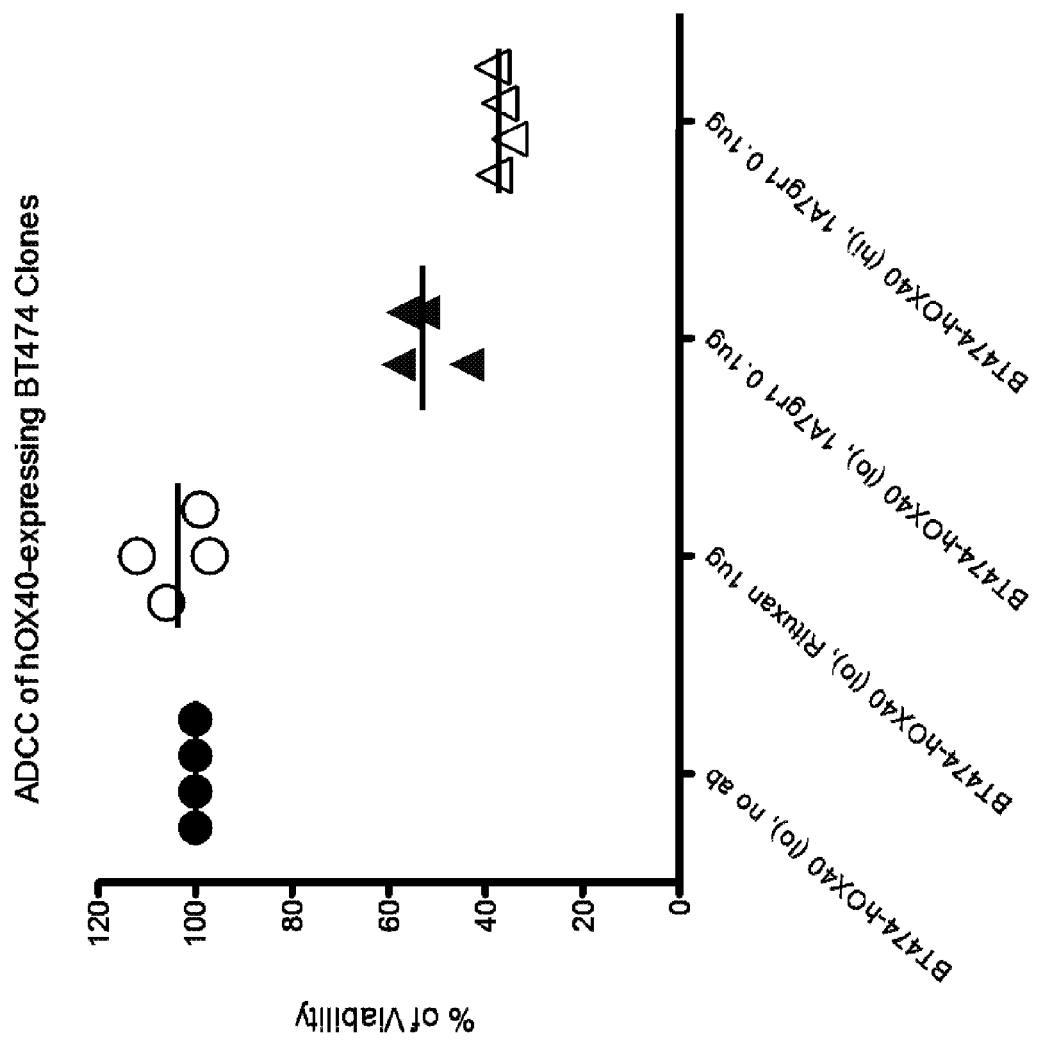
FIG. 10: Treatment with OX40 agonist antibody 1A7.gr1 induced ADCC in OX40-expressing cells.
Figure 11C:
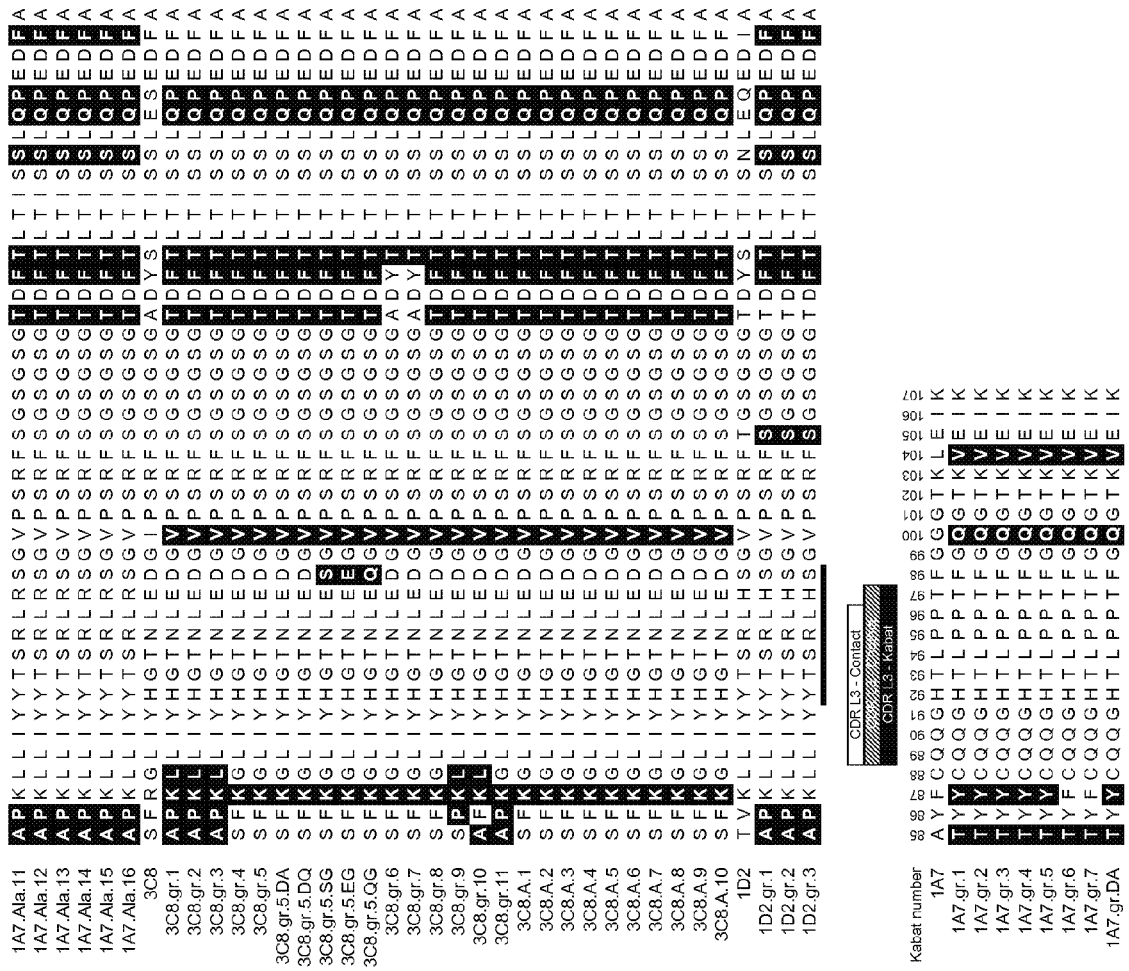
Figure 11D:
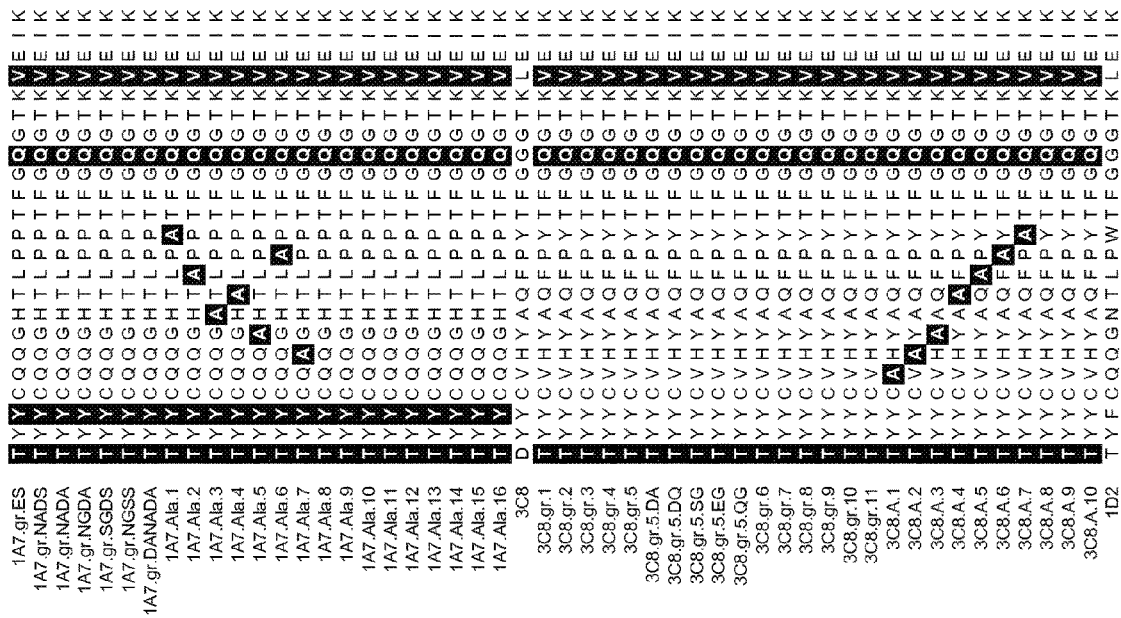
Figure 11G:
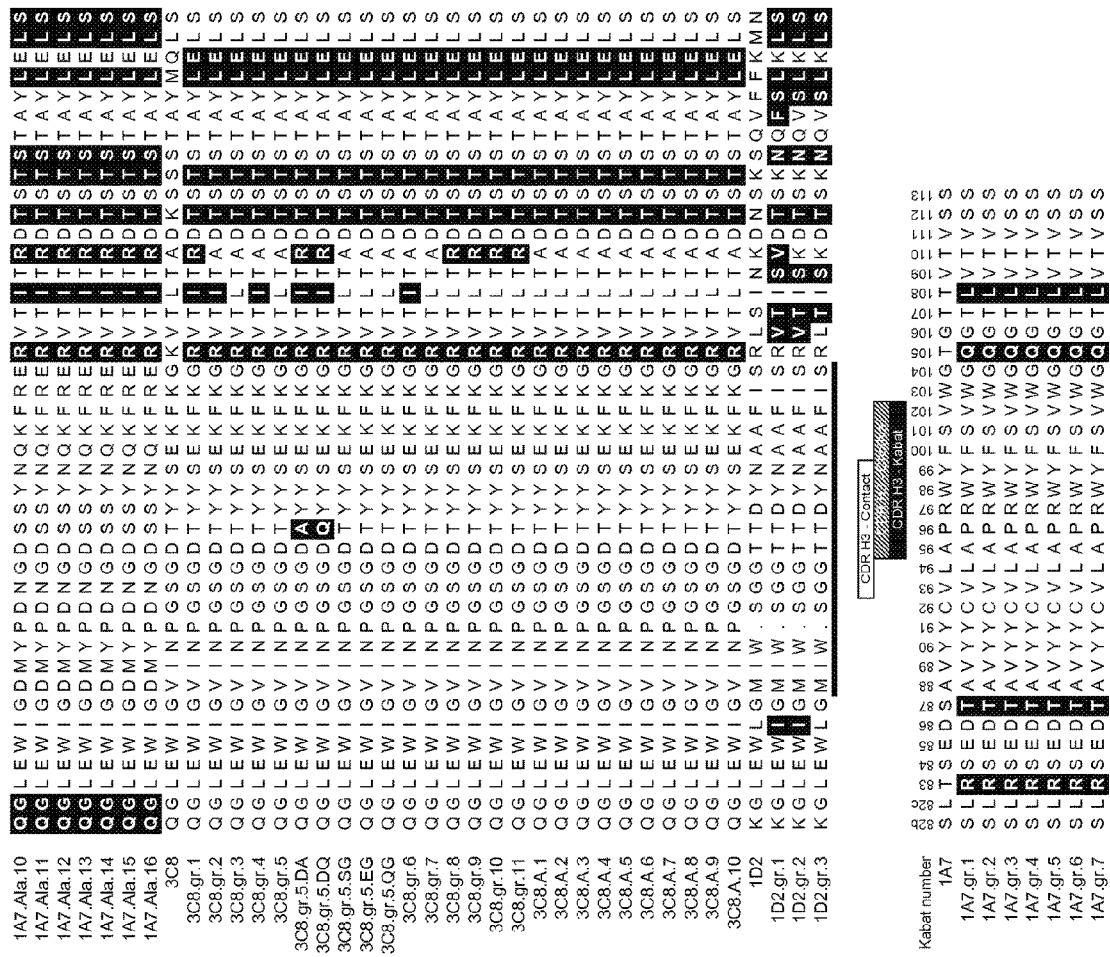

Treatment with Agonist OX40 Antibody 1A7.Gr1 Induced ADCC in BT474 Clones Expressing Human OX40, and Level of ADCC was Significantly Higher in Cells Expressing High Levels of OX40 Verses Level of ADCC in Cells Expressing Low Levels of OX40:

Treatment with OX40 agonist antibody 1A7.gr1 induced ADCC in OX40-expressing cells (FIG. 10). To detect ADCC, CellTiterGlo assay was performed. Treatment with anti-OX40 agonist antibody 1A7.gr1 at 0.1 ug/mL induced significant ADCC of hOX40-BT474-low cells as evidenced by reduced target cell viability. Treatment with OX40 agonist antibody 1A7.gr1 at 0.1 ug/ml resulted in even more extensive ADCC of hOX40-BT474 high cells. The difference of ADCC between hOX40-BT474-low and -high clones was statistically significant (p=0.0077). By contrast, treatment with rituximab (control) did not alter viability for both high and low-OX40 expressing BT474 clones. These data demonstrated that agonist OX40 antibody 1A7.gr1 was capable of mediating killing of OX40-expressing cells in vitro. In addition, level of ADCC was significantly higher in cells expressing high levels of OX40 verses level of ADCC in cells expressing low levels of OX40. OX40 is highly expressed in intratumoral T cells, and human intratumoral Treg cells express high levels of human OX40.

Figure 4A:
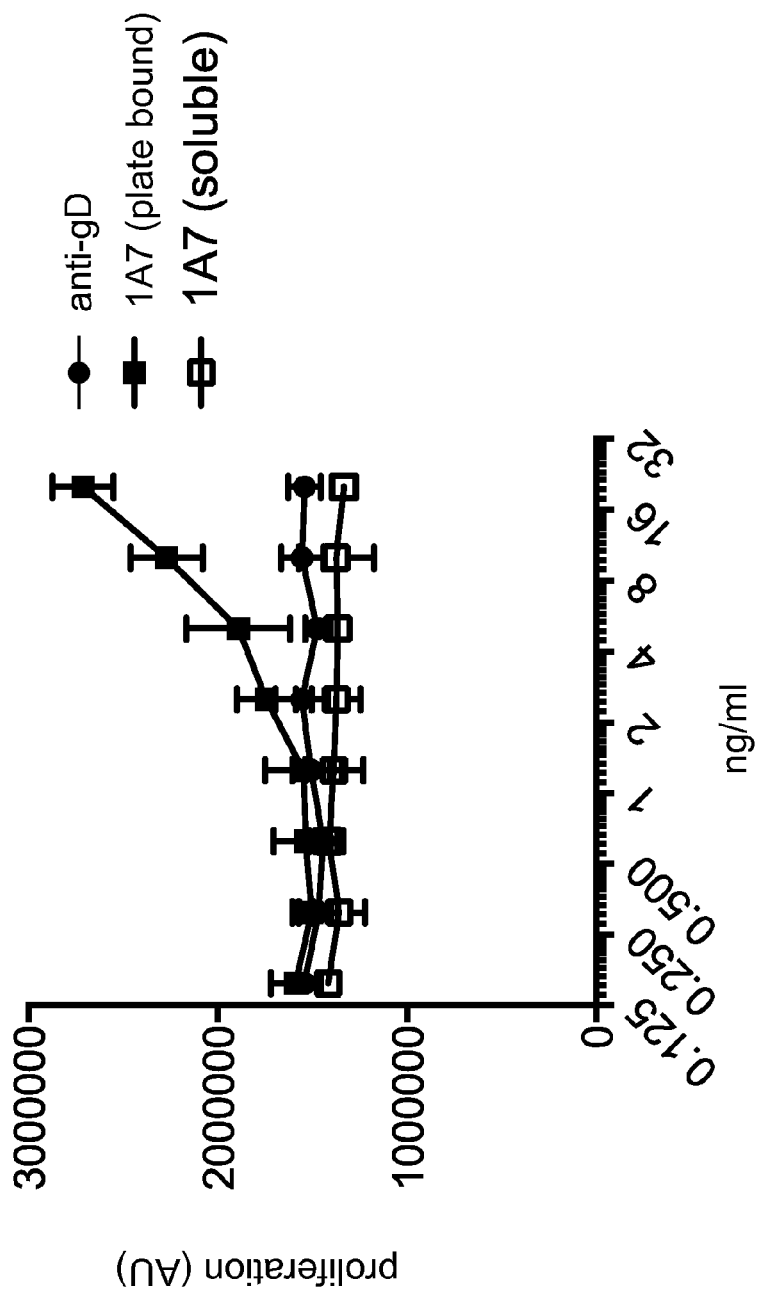
FIG. 4A: In the presence of plate-bound anti-CD3, plate-bound mab 1A7 costimulated effector T cell proliferation. By contrast, costimulatory activity was abrogated when mab 1A7 was provided in soluble form in the presence of plate-bound anti-CD3, to a similar level as that observed with a plate-bound isotype control antibody in the presence of plate-bound anti-CD3.

Activity of Agonist OX40 Antibody was Cross-Linking Dependent and Required Fc Effector Function to Costimulate Effector T Cells:

To determine whether mab 1A7 was dependent on antibody crosslinking to costimulate effector T cell proliferation, mab 1A7.gr.1 was added to the culture in plate-bound or soluble form. The results of this experiment are shown in FIG. 4A. In the presence of plate-bound anti-CD3, plate-bound mab 1A7.gr. 1 costimulated CD4+ effector T cell proliferation. In contrast, costimulatory activity was abrogated when 1A7 was provided in soluble form in the presence of plate-bound anti-CD3, to a similar level as that observed with a plate-bound isotype control antibody in the presence of plate-bound anti-CD3. These results suggest that crosslinking (e.g., provided by adhering mab 1A7.gr.1 to the plate) may be required for mab 1A7 costimulation of effector T cells.

Figure 4B:
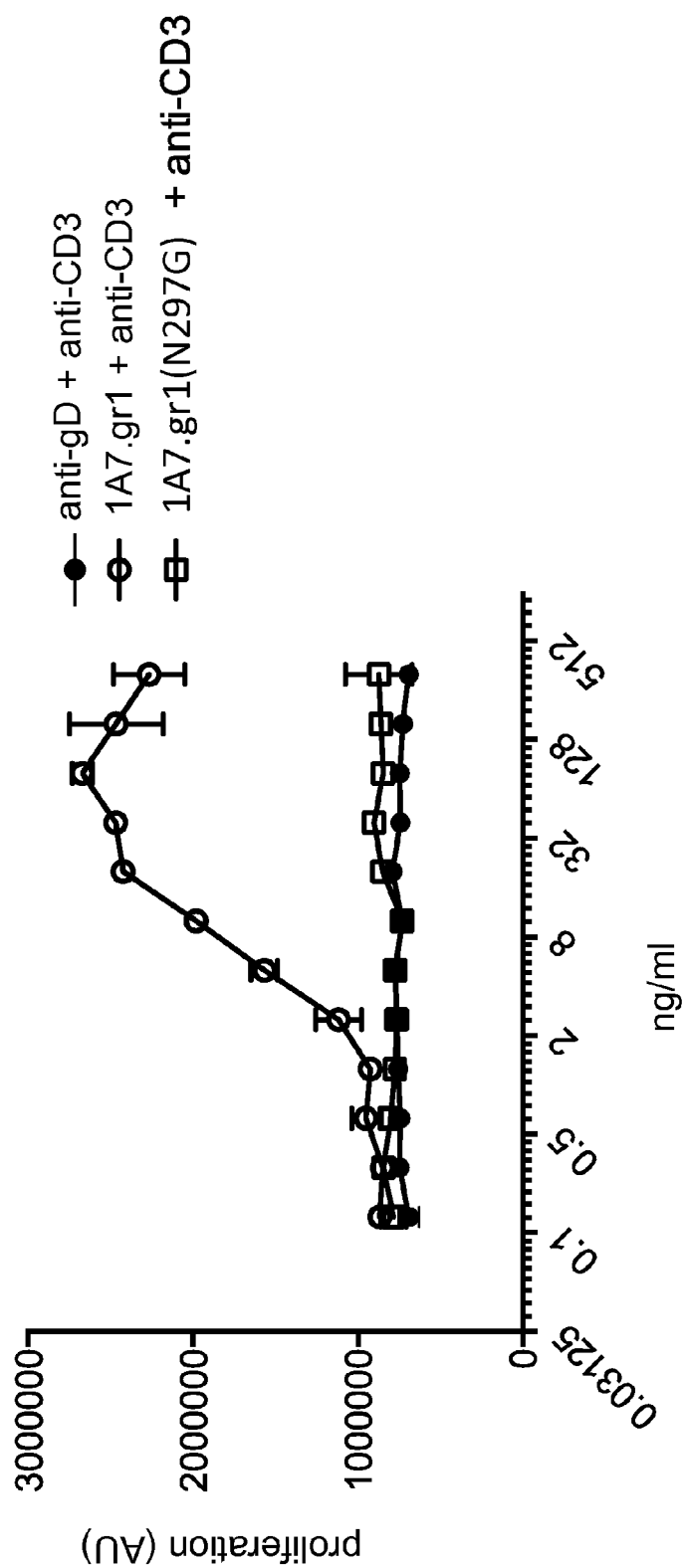
FIG. 4B: MAb 1A7 gr.1 harboring the N297G mutation failed to costimulate Teff cell proliferation. By contrast, wild type (un-mutated) mab 1A7 gr. 1 costimulated anti-CD3 induced Teff cell proliferation.

To further interrogate whether mab 1A7.gr. 1 required crosslinking for activity, mutant antibody was generated to create an antibody that was unable to bind to Fc gamma receptor presented on cells. Briefly, Fc residue asparagine 297, the site for N-linked glycosylation required for binding to Fc gamma receptors, was mutated to glycine (N297G) to prevent antibody Fc binding to Fc receptors. The results of this experiment are shown in FIG. 4B. MAb 1A7 gr. 1 (IgG1) harboring the N297G mutation failed to costimulate Teff cell proliferation. By contrast, wildtype (un-mutated) mab 1A7 gr.1 costimulated anti-CD3 induced Teff cell proliferation. Together with the results shown in FIG. 4A, these results demonstrated that activity of OX40 agonist mab 1A7 gr. 1 was cross-linking dependent, requiring Fc effector function to costimulate effector T cells.

Mab 1A7 gr.1 IgG1 Possessed More Potent Crosslinking Activity than Mab 1A7.Gr.1 IgG4.

Figure 5:
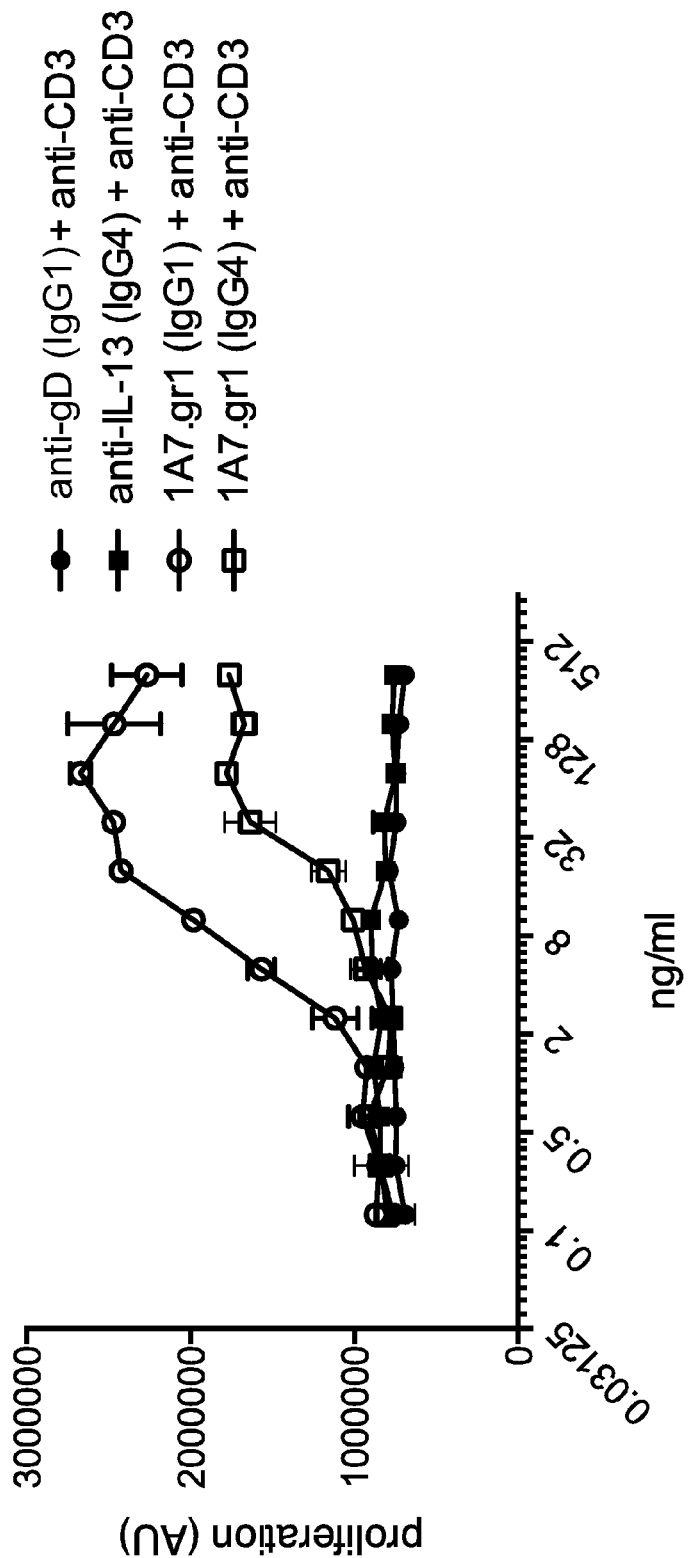
FIG. 5: Treatment with OX40 agonist antibody inhibited Treg cell-mediated suppression of naïve CD4+ T cells. Naïve CD4+ T cell (Tn) when cultured alone were inhibited by the addition of Treg cells and an isotype control antibody. Treg cell mediated inhibition of native CD4+ T cell proliferation was abrogated in cultures containing anti-OX40 antibody, mab 1A7.gr1. The data represented the average of 3 independent experiments.

Antibody isotypes have differential binding to Fc gamma receptors. To identify the isotype that permitted the most potent effector T cell costimulation activity, activity of mab 1A7.gr. 1 having a human IgG1 Fc was compared to activity of mab 1A7 gr.1 on a human IgG4 backbone. The results of this experiment are shown in FIG. 5. Mab 1A7 gr. 1-IgG1 costimulated anti-CD3 induced effector T cell proliferation more potently than did mab 1A7 gr.1-IgG4. This result indicated that mab1A7 gr.1 comprising a human IgG1 Fc possessed more potent crosslinking activity than did mab 1A7.gr1 comprising a human IgG4 Fc.

Treatment with Mab 1A7.Gr.1 Induced ADCC of OX40-Expressing T Cells.

Figure 7A:
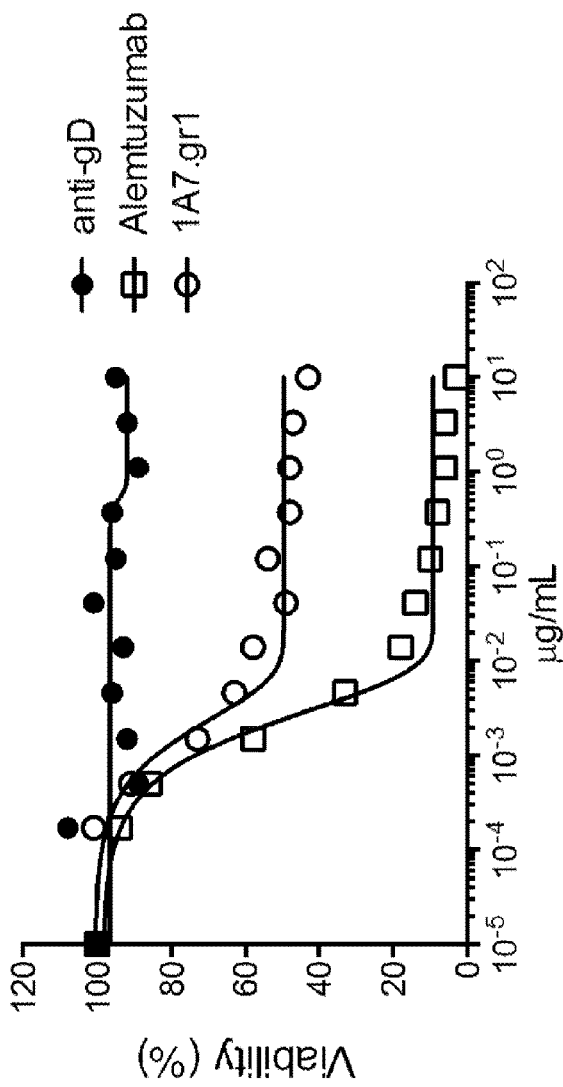
FIGS. 7A and 7B.

Antibodies that recognize cell surface antigens have the potential to mediate target cell depletion through antibody dependent cellular cytotoxicity (ADCC). To determine whether mab1A7.gr1 induced ADCC, target cells that express high levels of OX40 were generated by stimulating peripheral blood CD4+ T cells with PHA and contacted with mab 1A7.gr. 1 in the presence of human effector cells. The results of this experiment are shown in FIG. 7A. Treatment with mab 1A7.gr. 1 induced ADCC of OX40-expressing T cells when NK cells were cultured with stimulated CD4+ T cells (at a ratio of 10 NK cells:1 activated T cell). This result demonstrated that 1A7.gr1 induced ADCC on T cells that express high levels of OX40. Depletion induced by mab. 1A7.gr. 1 was less extensive than that induced by treatment with the positive control antibody, Alemtuzumab (anti-CD52 mab). By contrast, treatment with negative control mab anti-gD (isotype control) did not result in induction of ADCC.

Figure 7B:
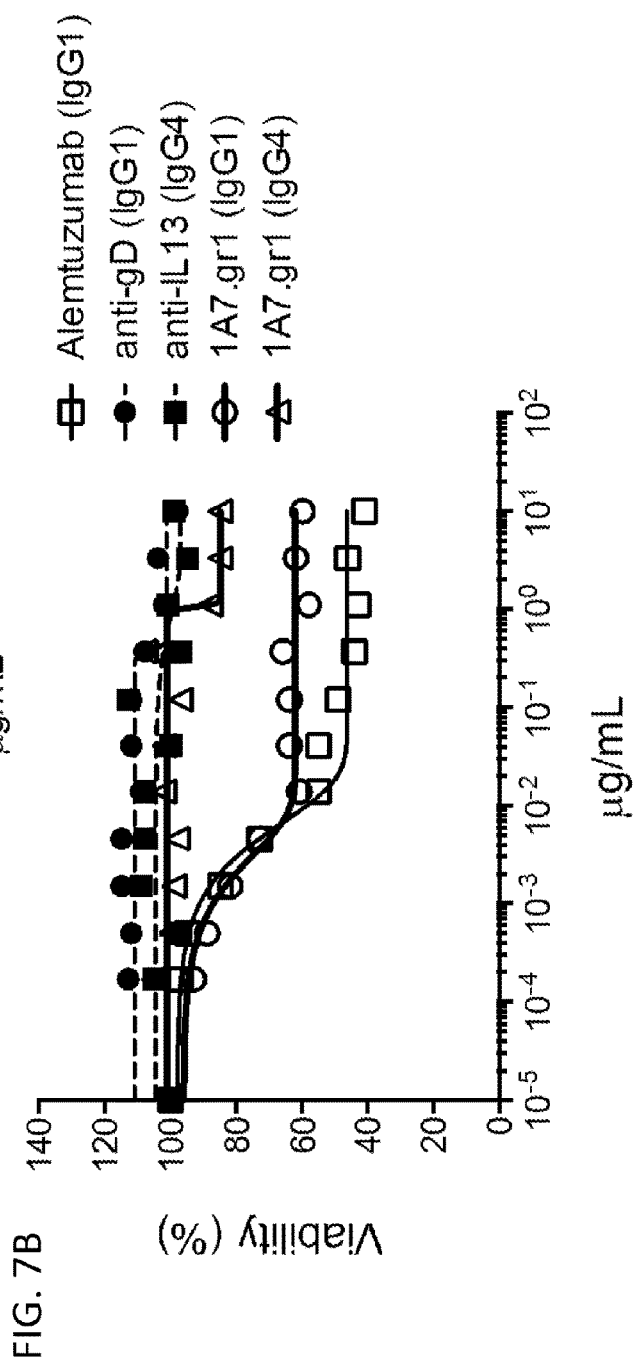

To determine whether mab 1A7.gr. 1 antibodies with different Fc isotypes demonstrated differential ADCC activity in vitro, activity of mab 1A7.gr1 with the IgG1 isotype was compared to activity of mab 1A7.gr1 with the IgG4 isotype. The results of this experiment are shown in FIG. 7B. Treatment with mab A7.gr1 (IgG1) induced greater ADCC of OX40-expressing CD4+ T cells compared to level of ADCC induced by mab 1A7.gr1 (IgG4).

Materials and Methods III

OX40L and Anti-OX40 Binding Competition Assay.

Anti-human OX40 antibody 1A7gr1 was conjugated to Alexa Fluor647. Human OX40L-flag and human DR5-flag proteins were generated at Genentech. Anti-flag antibody conjugated to Alexa Fluor 555 was purchased from Cell Signaling (Cat #3768). Transgenic Hut78-hOX40 cells (Hut78-hOX40, a human T cell line, retroviral transduced for human OX40 expression) were cultured and maintained in the complete RPMI media (RPMI-1640, supplemented with 10% FBS (heat-inactivated)/Pen/strep/Glutamine/Non-essential amino acids/55 uM (3ME) at 37C/5% $CO_2$ incubator.

First, titration of mab 1A7gr1 binding to OX40 was performed. $1 \times 10^6$ Hut78-hOX40 cells were used and the concentration of mab1A7gr1 was titrated 2 fold down starting from 10 ug/mL. After 30 min of incubation at 4C, cells were washed twice in Wash Buffer (PBS/0.5% FBS/2 mM EDTA), followed by data acquisition on FACSCantoII flow cytometer (BD). Data were then analyzed by Flowjo program (TreeStar) and the mean fluorescent intensity (MFI) was captured. The amount of mab 1A7.gr.1 (200 ng/mL) that generated around 70% of maximum MFI was chosen for use in the competition assay. A titration of OX40L-flag binding was carried out in a similar fashion, except that OX40L-flag was titrated 3 fold down starting from 10 ug/mL.

The OX40L and anti-OX40 mab binding competition assay was performed as follows: OX40L-flag or control DR5-flag was added at concentrations of 10 ug/ml to 10 ng/mL to $1 \times 10^6$ Hut78-hOX40 cells. After 30 min of incubation at 4C, cells were washed twice in Wash Buffer, and then 10 ug/mL of anti-flag-Alexa Fluor 555 and 200 ng/mL mab 1A7.gr.1-AlexaFluor647 were added to test competition between OX40L and anti-hOX40 mab 1A7.gr.1. After 30 min of incubation at 4C, cells were washed twice in Wash Buffer, followed by data acquisition on FACSCantoII flow cytometer (BD). Data were then analyzed by Flowjo program (TreeStar) to capture MFI of 1A7gr1 binding.

Results III

Figure 12A:
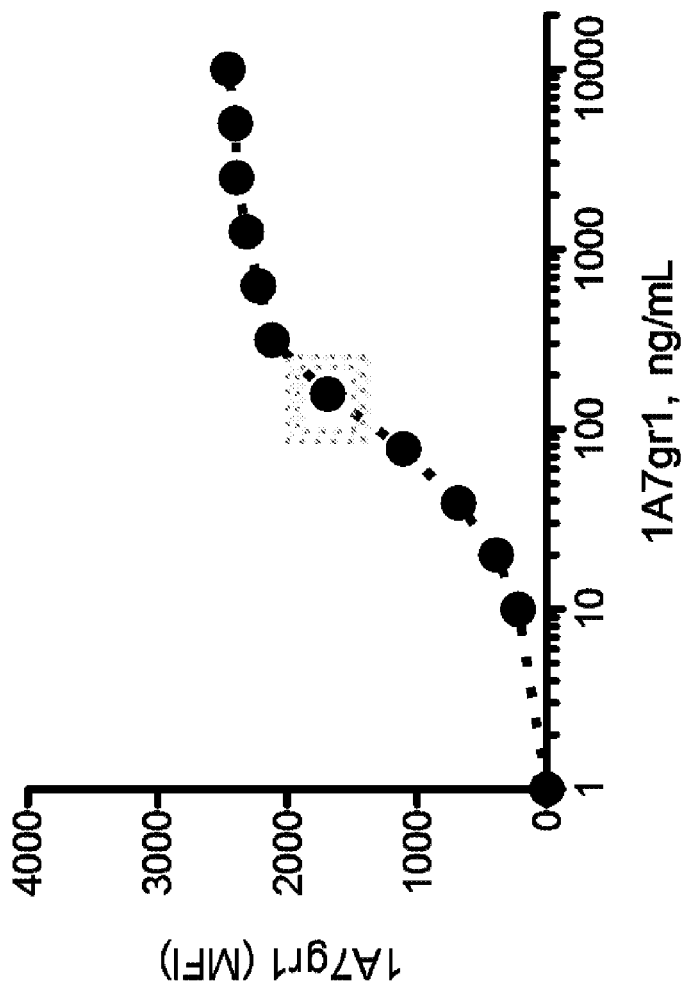
FIG. 12A: Anti-human OX40 mab 1A7gr1 bound to Hut78-hOX40 cells in a dose dependent fashion, with 70% of maximum binding observed at about 200 ng/mL of antibody (indicated by the dotted square).
Figure 12B:
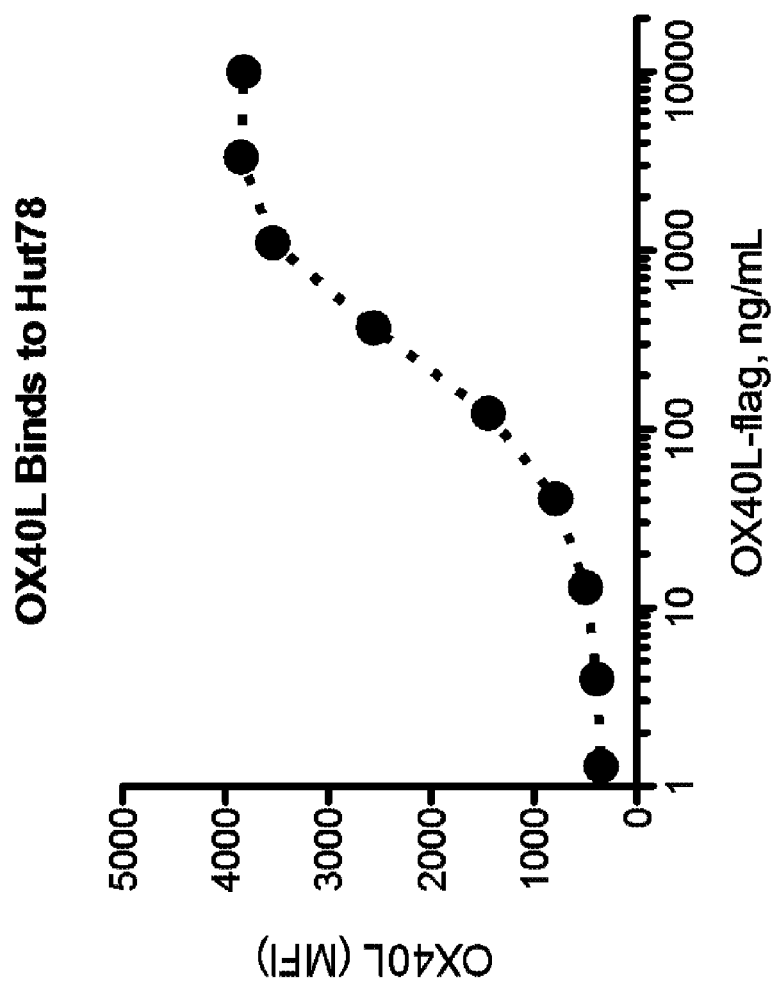
FIG. 12B: OX40L-flag demonstrated dose dependent binding to Hut78-hOX40 cells.

The titration experiment demonstrated that anti-human OX40 mab 1A7gr1 bound to Hut78-hOX40 cells in a dose dependent fashion, with 70% of maximum binding observed at about 200 ng/mL of antibody (FIG. 12A). This concentration was chosen for competition experiments. OX40L-flag also demonstrated a dose dependent binding to Hut78-hOX40 cells (FIG. 12B).

Figure 12C:
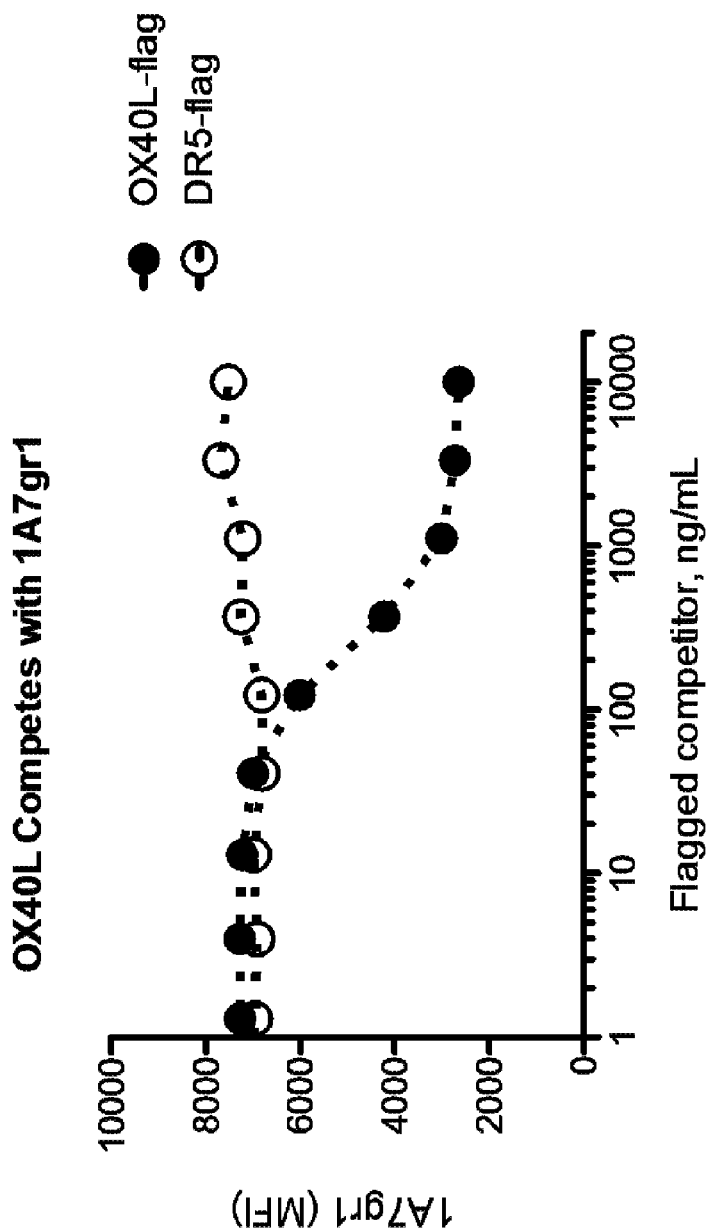
FIG. 12C: Binding of anti-human OX40 mab 1A7.gr. 1 to Hut78-hOX40 cells decreased as the concentration of OX40L-flag increased.
Figure 12D:
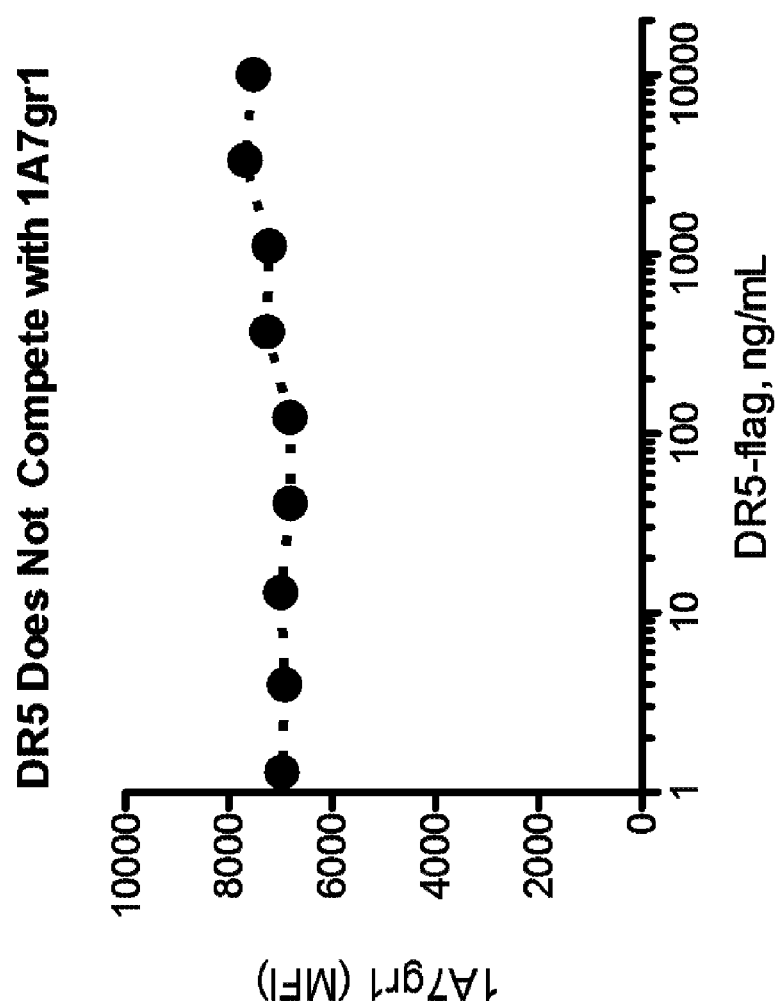
FIG. 12D: Presence of control DR5-flag had no impact on mab 1A7.gr.1 binding.

In the competition assay, binding of anti-human OX40 mab 1A7.gr.1 to Hut78-hOX40 cells decreased as the concentration of OX40L-flag increased (FIG. 12C). By contrast, presence of control DR5-flag had no impact on mab 1A7.gr. 1 binding (FIG. 12D), indicating that OX40L binding to Hut78-OX40 cells was specific. These data demonstrated that OX40L competes with anti-human OX40 mab 1A7gr1 for binding to hOX40 on Hut78-OX40 cells. In similar experiments, 3C8.gr5 was also observed to compete for binding with OX40L.

Materials and Methods IV

Pharmacokinetic (PK) Evaluation of Anti-OX40 in Mice.

Female B6.CB17-Prkdc$^{scid}$/SzJ mice (n=12 animals/group) were given a single IV injection of 1A7.gr1 IgG1 (MOXR0916) at 1 mg/kg or 10 mg/kg on Day 0. Each mouse was given a dose volume of 5 mL/kg (1 mg/kg dose was at a concentration of 0.2 mg/mL; 10 mg/kg dose was at a concentration of 2 mg/mL). Blood samples (125-150 µL) were collected from each animal via cardiac puncture (3 timepoints per animal; 3 animals per timepoint) at 5 minutes; 1, 3, 8, and 24 hours; and 2, 4, 7, 10, 14, 21, and 28 days post-dose. No predose samples were collected for the study. The samples were collected into tubes containing serum separator tubes and were processed as described below.

The samples were allowed to clot at ambient temperature for at least 20 minutes prior to centrifugation. Centrifugation began within 1 hour of collection at a relative centrifugal force of 11,000 revolutions per minute for 5 minutes in a centrifuge set to maintain 2° C.–8° C. Serum separated from the blood was transferred into pre-labeled, 0.5-mL tubes with caps. Samples were stored in a freezer set to maintain −80° C. until analysis.

1A7.gr1 IgG1 was analyzed with a generic ELISA using sheep anti-human IgG as the capturing reagent and goat anti-human IgG horseradish peroxidase (HRP) as the detection reagent. The effective limit of detection (LOD) for this assay was 0.08 µg/mL.

The serum concentration versus time data from each animal were analyzed using the IV bolus input model and sparse sampling (Model 201), WinNonlin Pro, version 5.2.1, (Pharsight Corporation; Mountain View, Calif.). All PK analysis was based on naïve pool of individual animal data. The following methods were used to estimate specific PK parameters: Cmax (Maximum concentration), $AUC_{last}$ (Area under the serum concentration versus time curve from time=0 to time of the last measurable concentration was calculated using the linear trapezoidal rule), $AUC_{inf}$ (Area under the serum concentration versus time curve extrapolated to infinity), Cmax/D (Dose normalized Cmax), $AUC_{inf}/D$ (Dose normalized $AUC_{inf}$), CL (Clearance; Dose/$AUC_{inf}$), Vss (Volume of distribution at steady state), and $t_{1/2},\lambda_z$ (Terminal half-life).

Results IV

Figure 13:
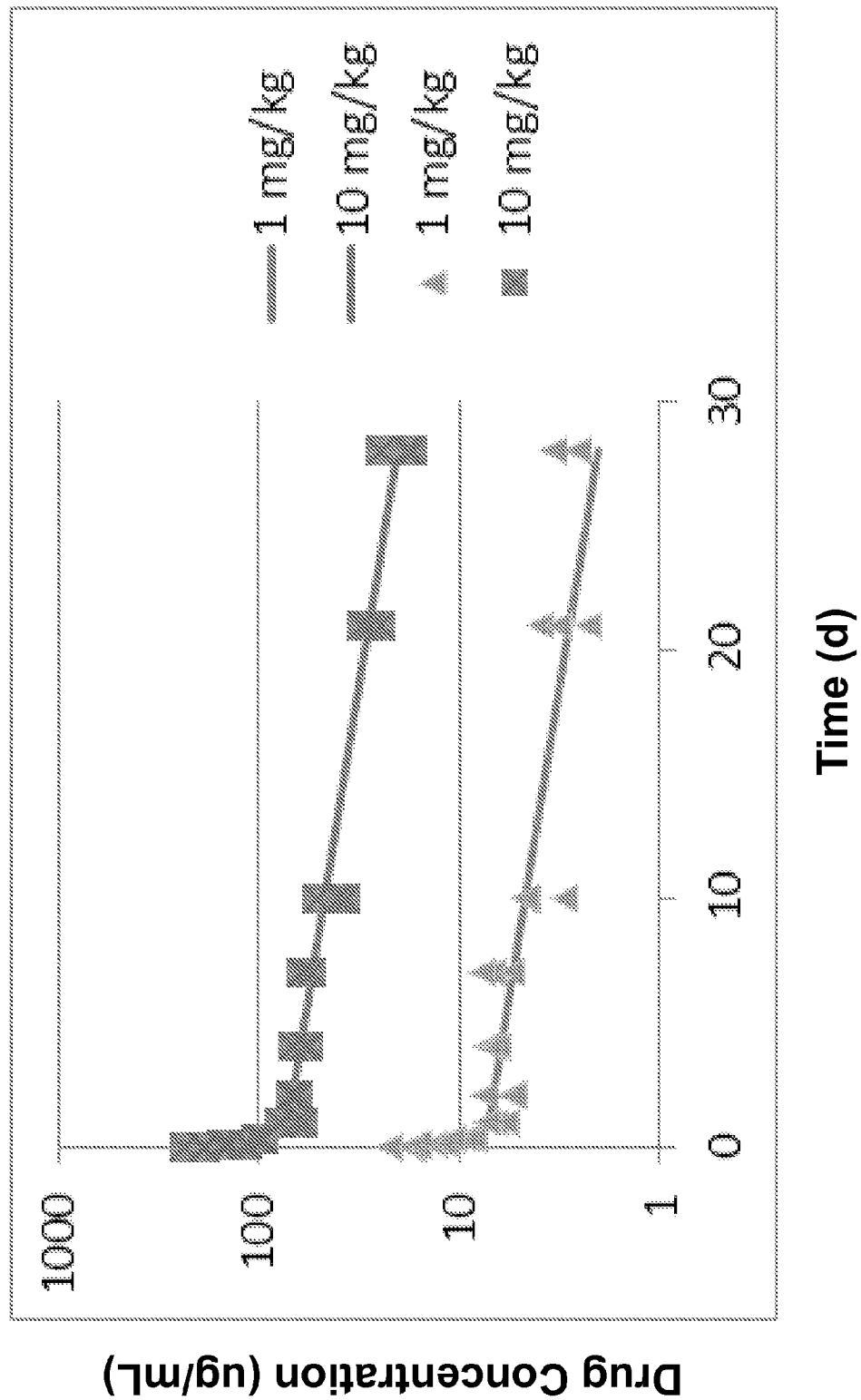
FIG. 13: Pharmacokinetics (PK) of 1A7.gr1 dosed at 1 mg/kg or 10 mg/kg in SCID mice.

Following the administration of 1 and 10 mg/kg, PK was observed to be dose-proportional for 1A7.gr1 IgG1 (FIG. 13). PK parameters are summarized in Table 13 below.

TABLE 13

PK parameters

| Parameter | Estimate | Standard Error |
|---|---|---|
| CL (ml/kg/day) | 6.1 | 0.2 |
| Vc (ml/kg) | 54.5 | 2.2 |
| Vp (ml/kg) | 76.4 | 4.5 |
| CLD (ml/kg/day) | 188 | 26.8 |

Linear, dose-proportional PK was observed for 1A7.gr1 in non-tumor bearing SCID mice. These data suggest that the pharmacokinetics of 1A7.gr1 IgG1 at the dose levels tested was as expected for a non-cross-reactive human IgG1 monoclonal antibody in mice and similar to that of typical IgG1 monoclonal antibodies.

Materials and Methods V

Pilot 4-Week Toxicity Study in Cynomolgus Monkeys.

Vehicle (10 mM histidine acetate, 6% sucrose, 0.02% Tween 20, pH 5.8) or 1A7.gr1 IgG1 was administered intravenously at 0.01, 0.3, or 10 mg/kg/dose in male cynomolgus monkeys. Dosing regimen was once every 2 weeks for three doses (administered on Days 1, 15, and 29). Terminal necropsy was performed three days after last dose. Safety endpoints included: clinical and daily observations, clinical pathology, coagulation, urinalysis, macroscopic and microscopic analysis, toxicokinetic (TK), and anti-therapeutic antibody (ATA) titers. Pharmacodynamic (PD) analyses included serum cytokines, T cell activation/proliferation/depletion, and OX40 receptor occupancy.

Blood was collected by venipuncture. Additional blood samples were obtained (e.g., due to clotting of non-serum samples) when permissible sampling frequency and blood volume were not exceeded. When other samples types were being collected at the same time as FACS and PD samples, those samples were collected first after venipuncture followed by FACS and PD samples. Urine was collected by drainage from special stainless steel cage pans. After collection, samples were transferred to the appropriate laboratory for processing. Blood samples were processed for serum, and the serum was analyzed for various clinical chemistry parameters.

Individual clinical chemistry values were analyzed with an OLYMPUS® au640e analyzer. C-reactive protein (CRP) was measured by immunoturbidimetry.

Blood samples with K2-EDTA anticoagulant were collected for cytokine analysis at the indicated timepoints. After centrifugation, plasma was collected and stored at −80° C. until analysis. Cytokine levels were determined using the LUMINEX® xMAP® assay technology (Luminex, Austin, Tex.), a bead-based multiplexing technology that enables simultaneous quantitation of multiple cytokines. Samples were analyzed using the MILLIPLEX® MAP Non-Human Primate Cytokine Magnetic Bead Panel Kit (EMD Millipore, Billerica, Mass.) according to manufacturer's protocol. The standard contained a mixture of recombinant GCSF, GMCSF, IFNγ, IL1beta, IL1ra, IL2, IL4, IL5, IL6, IL8, IL10, IL12/23p40, IL13, IL15, IL17A, IL18, MCP1, MIP1alpha, MIP1beta, sCD40, TGFalpha, TNFalpha, and VEGF. The standard curve ranges were 4.6-3000 pg/mL for IL4; 11.6-7500 pg/mL for IL10 and IL18; and 2.3-1500 pg/mL for all other cytokines. The plasma samples were diluted 1:3 followed by three serial 1:2 dilutions in 96-well plates, and a cocktail of antibody-conjugated fluorescent beads specific for each cytokine was added. The plates were incubated for 30 minutes at room temperature, followed by an overnight incubation at 4° C. The next day, a mixture of biotinylated detection antibodies was added to the samples, and the plates were incubated for 1 hour at room temperature, followed by a 30-minute incubation with streptavidin-phycoerythrin. Fluorescence signals were then assessed using a LUMINEX® FLEXMAP 3D® instrument, with the intensity of the phycoerythrin signal corresponding to the amount of cytokine present. The serum cytokine concentrations were determined from five-parameter fits of the standard curves for each protein.

The concentration of 1A7.gr1 IgG1 in monkey serum was analyzed using a generic ELISA. Sheep anti-human IgG (H+L) (monkey absorbed) was used as the capturing reagent, and goat anti-human IgG (H+L) (monkey absorbed) conjugated to horseradish peroxidase (HRP) was used as the detecting reagent.

Blood samples were collected throughout the study for receptor occupancy analyses using flow cytometry. For flow cytometry assay of staining surface markers (e.g., OX40 receptor), antibody cocktails were prepared for each staining panel on each study day. An appropriate aliquot of the cocktail was dispensed into the designated wells of a 96 deep-well plate. For each animal, 100 μL whole blood sample were transferred and mixed into the appropriate wells containing the staining cocktail. Stained blood was incubated in the dark at ambient temperature for a minimum of 30 minutes. Red blood cells were lysed with 1.8 mL of 1×BD FACS Lyse (BD Biosciences) for at least 6 minutes at room temperature. The samples were centrifuged, and the supernatant was aspirated and discarded. Cell pellets were washed twice with 1.8 mL HBSS. Following the second wash, each sample was resuspended in 300 μL of 1% paraformaldehyde. Each sample (200 μL) was transferred to the appropriate wells of a 96-well U-bottom plate for acquisition on a BD FACS Canto II flow cytometer. Data analysis was performed using FACS Diva software (BD Biosciences). Lymphocytes were identified based on their FSC/SSC profile, and T cells were gated as CD3+/SSC$^{low}$. Subsequent hierarchical gating of CD3+ T cells was used to identify and enumerate each of the T-cell subsets. Occupancy of OX40 on CD3+CD4+CD8-Th lymphocytes was evaluated using fluorescently labeled test article (anti-OX40 antibody) that does not bind to OX40 in the presence of the administered test article. An unrelated humanized IgG1 antibody was used as an isotype control for 1A7.gr1. The fraction of Th cells that were positive above the isotype gate was classified as % OX40+ cells.

The study design is summarized in Table 14 below.

TABLE 14

Pilot toxicity study design.

| Group | # of male cynos | Test Article | Dose (mg/kg) | Projected $C_{max}$ (% occupancy) | Projected $C_{trough}$ (% occupancy) |
|---|---|---|---|---|---|
| 1 | 4 | Vehicle | 0 | — | — |
| 2 | 4 | 1A7.gr1 | 0.01 | 0.2 µg/mL (80%) | 0.05 µg/mL (50%) |
| 3 | 4 | | 0.3 | 6 µg/mL (99%) | 1.5 µg/mL (96%) |
| 4 | 4 | | 10 | 200 µg/mL (100%) | 60 µg/mL (100%) |

Good Laboratory Practice (GLP) Toxicity Study.

Vehicle (20 mM histidine acetate, 240 mM sucrose, 0.02% polysorbate 20, pH 5.5) or 1A7.gr1 IgG1 was administered via intravenous bolus at 0.5, 5, or 30 mg/kg/dose in male and female cynomolgus monkeys (five males and five females per group). Dosing regimen was once every 2 weeks for six weeks, for a total of four doses (administered on Days 1, 15, 29, and 43). Main study animals were designated for terminal necropsy at Day 45. Animals designated for recovery necropsy underwent 6 weeks of recovery after the last dose and were necropsied on Day 85. Safety endpoints included: clinical and daily observations, clinical pathology, coagulation, urinalysis, macroscopic and microscopic analysis, toxicokinetic (TK), anti-therapeutic antibody (ATA) titers, CV safety pharmacology, and neurological evaluations. Pharmacodynamic (PD) analyses included serum cytokines, T cell activation/proliferation/depletion, and OX40 receptor occupancy (peripheral and tissue).

Blood was collected by venipuncture. Urine was collected from/by drainage from special stainless steel cage pans overnight on wet ice prior to blood collection. After collection, samples were transferred to the appropriate laboratory for processing. Animals were fasted prior to clinical chemistry blood collections.

The concentration of 1A7.gr1 IgG1 in monkey serum was analyzed using a generic ELISA.

Receptor occupancy was assessed by evaluation of binding of AF647-labeled 1A7.gr1 on CD3+CD4+T-helper lymphocytes by flow cytometry. Briefly, 100 µL of whole blood or single cell suspensions were added to the appropriate wells of a 2.2 ml/well 96 well plate along with 1.8 mL of freshly prepared Pharm Lyse. The samples were mixed well and incubated for 20 minutes at room temperature. After lysing, the samples were centrifuged, the supernatants discarded, and the samples washed once with 1.8 mL HBSS. After the washing, the cells were blocked in 100 µL of 10% cynomolgus monkey serum and incubated for a minimum of 15 minutes in the dark in a refrigerator set to maintain 2-8° C. After the blocking step, the appropriate volumes of antibody cocktail were added to the appropriate wells on the plate, the plate was mixed, and then incubated for a minimum of 30 minutes in the dark in a refrigerator set to maintain 2-8° C. After the incubation, the plate was washed twice with 1.8 mL HBSS and the samples were resuspended in 300 µL of 1% parafolrmaldehyde and incubated for 10-15 minutes in the dark in a refrigerator set to maintain 2-8° C. After the incubation, 200 µL of each sample was transferred to a 96-well v-bottom plate and analyzed on the cytometer. The flow cytometry instrument yielded data on the relative abundance of the various cell-types with the marker antigens. Samples were analyzed utilizing the FACSCanto™ II Flow Cytometer and DIVA® 6.0 software. Data generated for each animal at each post dose time point were compared to the corresponding prestudy value as well as the range of control values. The magnitude of increase or decrease was evaluated secondarily to determine the potential biological significance of any observed change.

MCP-1 levels were measured by validated LUMINEX®-based methods. The bead-based multiplex sandwich immunoassay is a solid phase protein assay which uses spectrally encoded beads conjugated to analyte specific capture antibodies as the solid support. Standards and samples were added to the wells, and the analyte (cytokine) present bound the specific capture antibody conjugated to a color-coded bead (each color bead is specific to 1 cytokine). The detection system in the assay was streptavidin conjugated to the fluorescent protein, R-phycoerythrin or streptavidin-phycoerythrin (streptavidin-RPE) mixed with analyte-specific biotinylated detection antibodies. The contents of each microplate well were drawn in the Luminex instrument. By monitoring the spectral properties of the beads and the amount of associated RPE fluorescence, the concentrations of several analytes were determined simultaneously. Samples were centrifuged to pellet debris. Wells of a 96-well multi-screen filter plate were washed with 200 µL of wash buffer. Standards, quality control (QC) samples, and samples were then transferred (25 µL) to appropriate wells containing 25 µL of assay buffer and followed by the addition of 25 µL of the appropriate antibody bead working solution. The plate was incubated in the dark at room temperature on a plate shaker set to vigorously shake for 2 hours (+5 minutes), then washed twice with 200 µL of wash buffer, followed by the addition of 25 µL of detection antibodies to each well. The plate was incubated in the dark at room temperature for 1 hour (+2 minutes) on a plate shaker set to shake vigorously. Then, 25 L of working streptavidin-RPE working solution was added to each well and the plate was incubated in the dark at room temperature, for 30 minutes (+1 minute) on a plate shaker set to shake vigorously. After the plate was washed twice with 200 µL of wash buffer, 150 µL of sheath fluid was added to each well and the plate was incubated at room temperature for at least 5 minutes in the dark, on a plate shaker set to shake vigorously. The plate was read on the Luminex system. Standards of monkey MCP-1 were prepared in assay diluent covering the concentration range of 37.500 to 6000 pg/mL. The LLOQ and ULOQ of the assay were 75.00 to 6000 pg/mL. QC samples of monkey MCP-1 were prepared in assay diluent at theoretical concentrations of 200, 1000, and 3200 pg/mL. In addition, an endogenous QC (EQC) was Plated Neat and was in the range of the curve.

The study design is summarized in Table 15 below.

TABLE 15

GLP toxicity study design.

| Group | # of cynos | Test Article | Dose (mg/kg) | # of animals terminal necropsy (Day 45) | # of animals recovery necropsy (Day 85) |
|---|---|---|---|---|---|
| 1 | 5F/5M | Vehicle | 0 | 3F/3M | 2F/2M |
| 2 | 5F/5M | 1A7.gr1 | 0.5 | 3F/3M | 2F/2M |
| 3 | 5F/5M |  | 5 | 3F/3M | 2F/2M |
| 4 | 5F/5M |  | 30 | 3F/3M | 2F/2M |

Results V
Pilot Toxicity Study

The objective of this study was to evaluate the toxicity, toxicokinetic profile, and pharmacodynamics of anti-OX40 (1A7.gr1 IgG1) when administered via intravenous injection to cynomolgus monkeys once every 2 weeks (Days 1, 15, and 29) for a total of 3 doses.

Figure 14A:
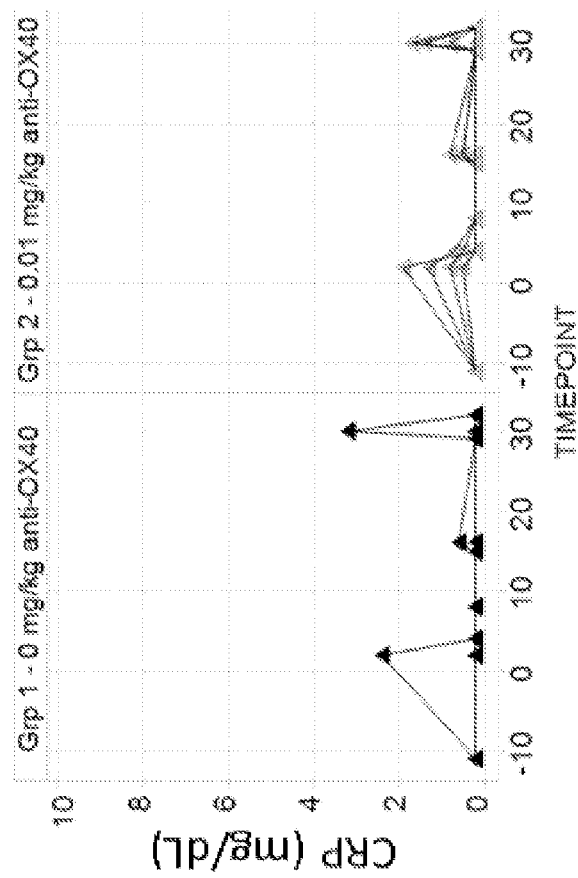
FIGS. 14A and 14B: Administration of 1A7.gr1 in cynomolgus monkeys resulted in minimal or transient increases in c-reactive protein (CRP).
Figure 14B:
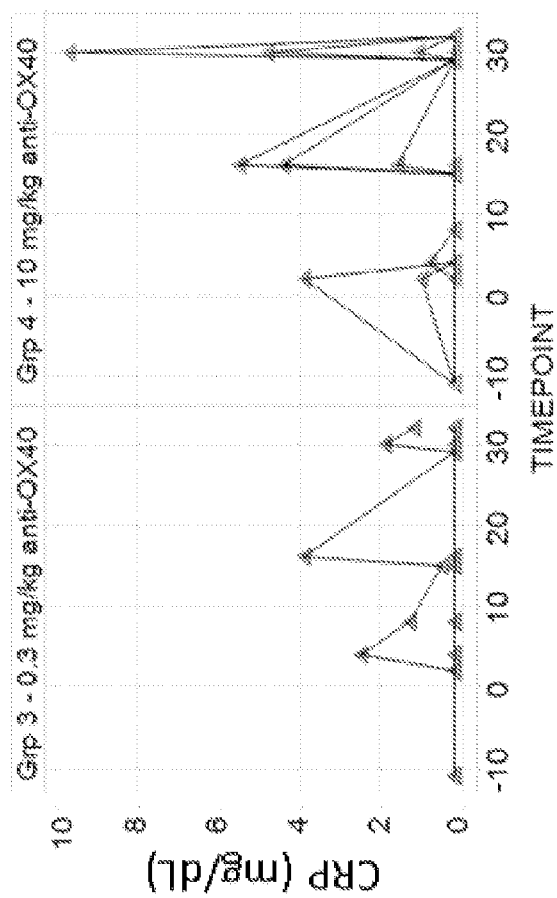
Figure 15A:
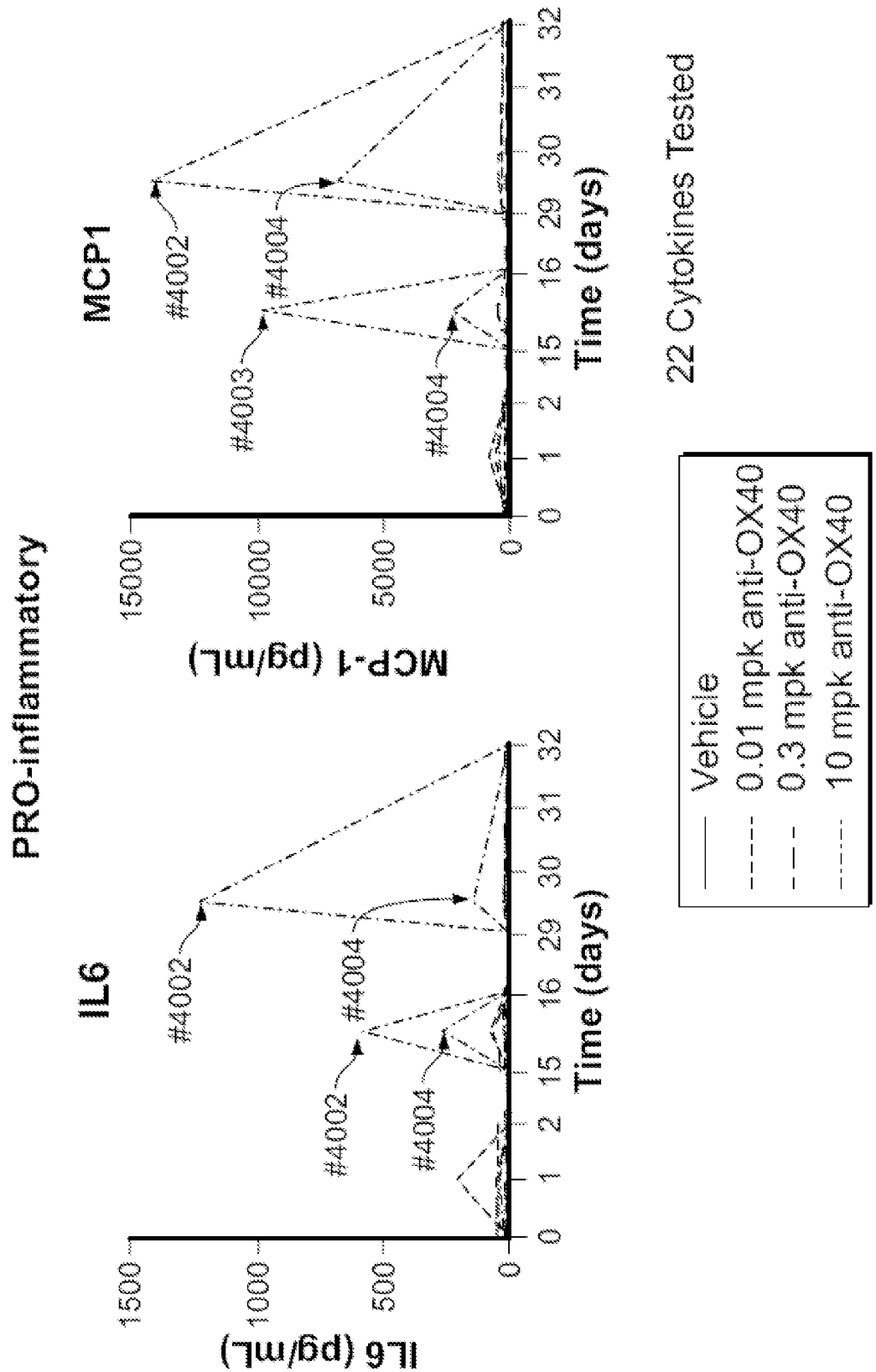
FIGS. 15A and 15B: Administration of 1A7.gr1 in cynomolgus monkeys resulted in minimal or transient increases in a mixed subset of cytokines.
Figure 15B:
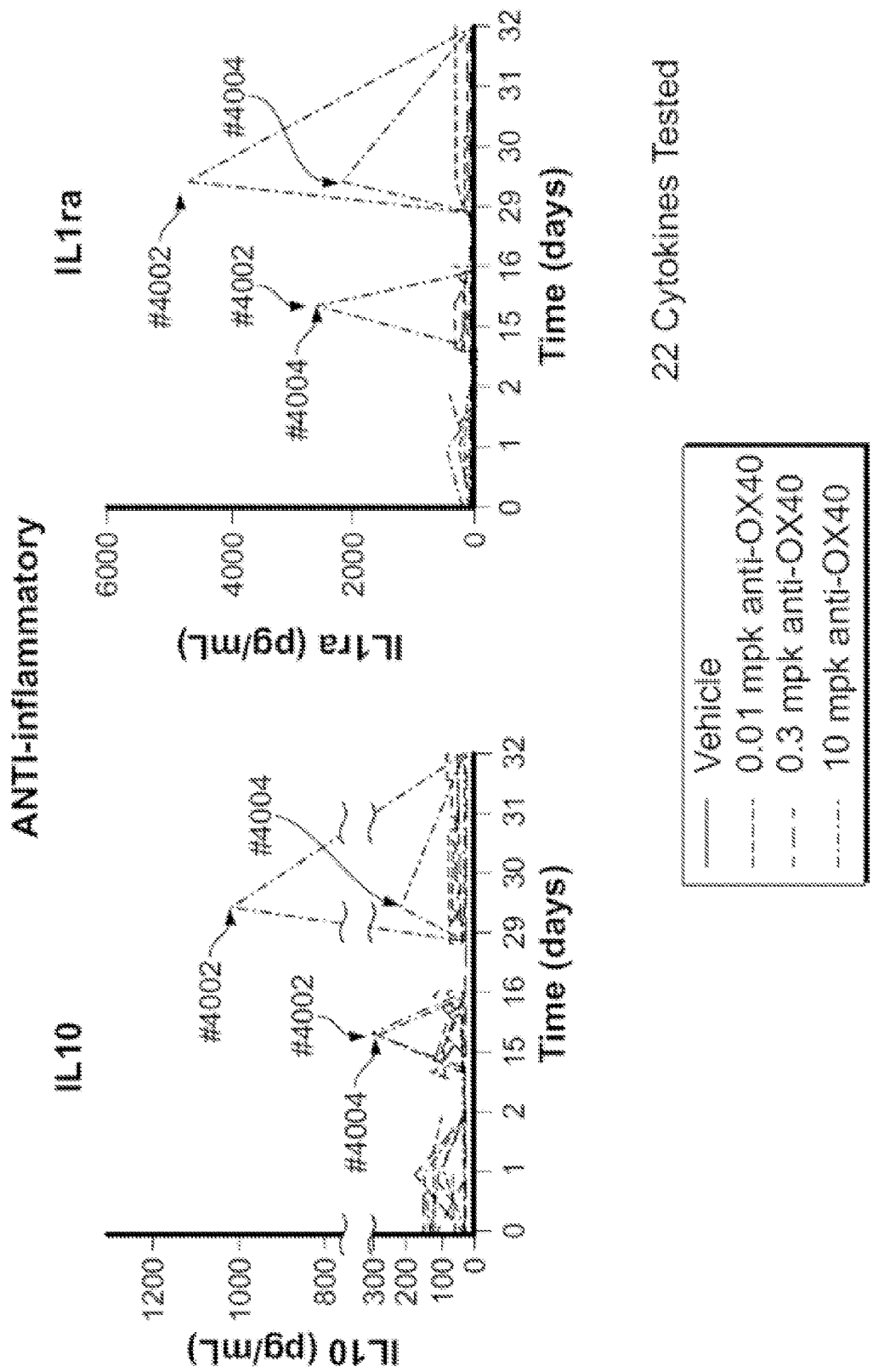

Intravenous administration of 1A7.gr1 IgG1 was well tolerated in cynomolgus monkeys up to 10 mg/kg once every 2 weeks for 4 weeks, and all animals survived until the scheduled necropsy. Minimal increases in c-reactive protein (CRP) (FIGS. 14A and B) were observed, with transient increases in CRP limited to three ATA+ monkeys primarily in the high dose group (10 mg/kg). Similarly, transient increases in a mixed subset of cytokines (FIGS. 15A and B) were limited to the three ATA+ monkeys primarily in the high dose (10 mg/kg) group. No clinical pathology changes or cytokine elevations were observed in the remaining ATA+ or ATA-animals. No IFNγ increase was observed, as was expected in the absence of antigen challenge.

Figure 16A:
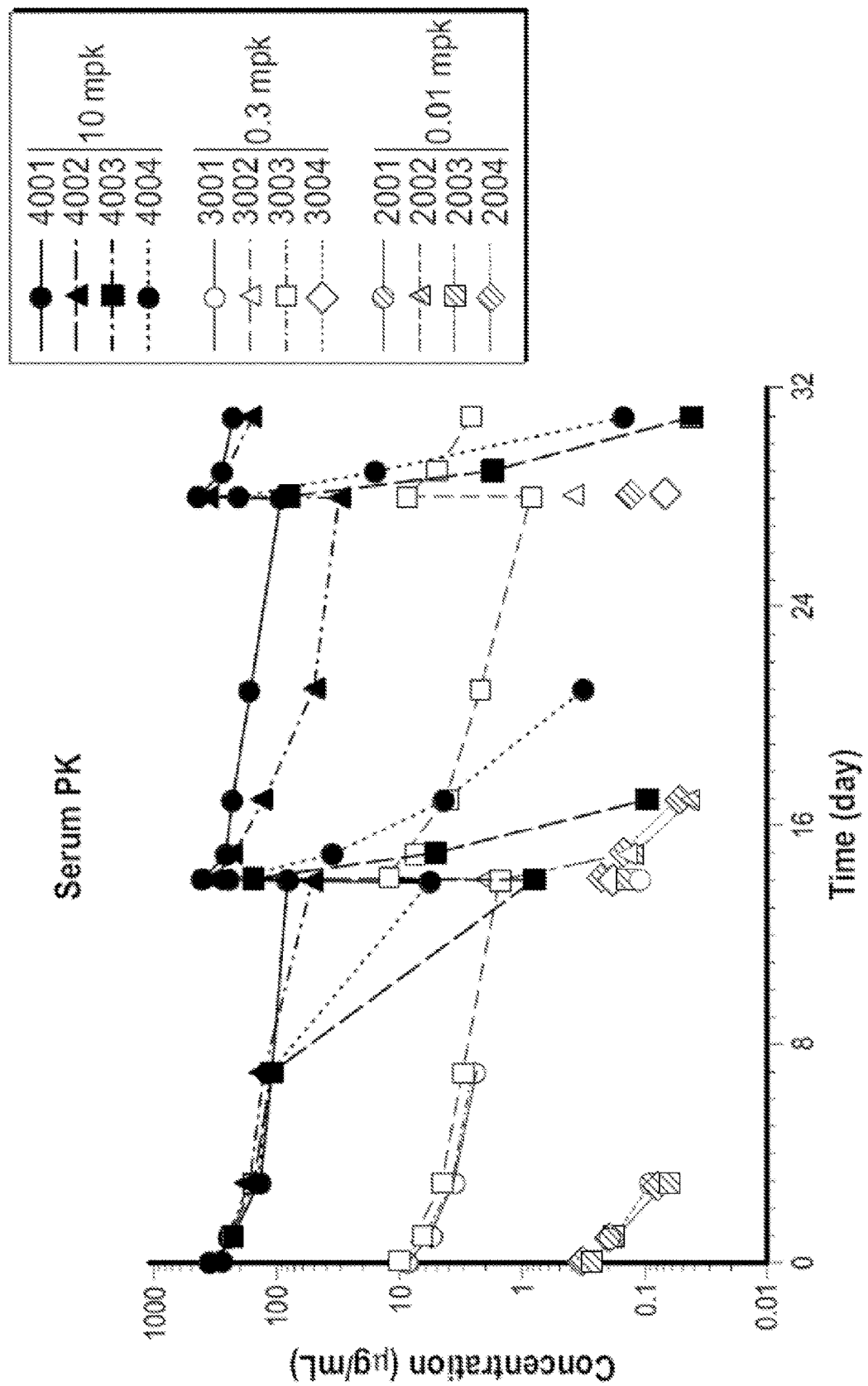
FIGS. 16A and 16B: Exposure of cynomolgus monkeys to 1A7.gr1 was confirmed by serum PK and peripheral receptor occupancy.
Figure 16B:
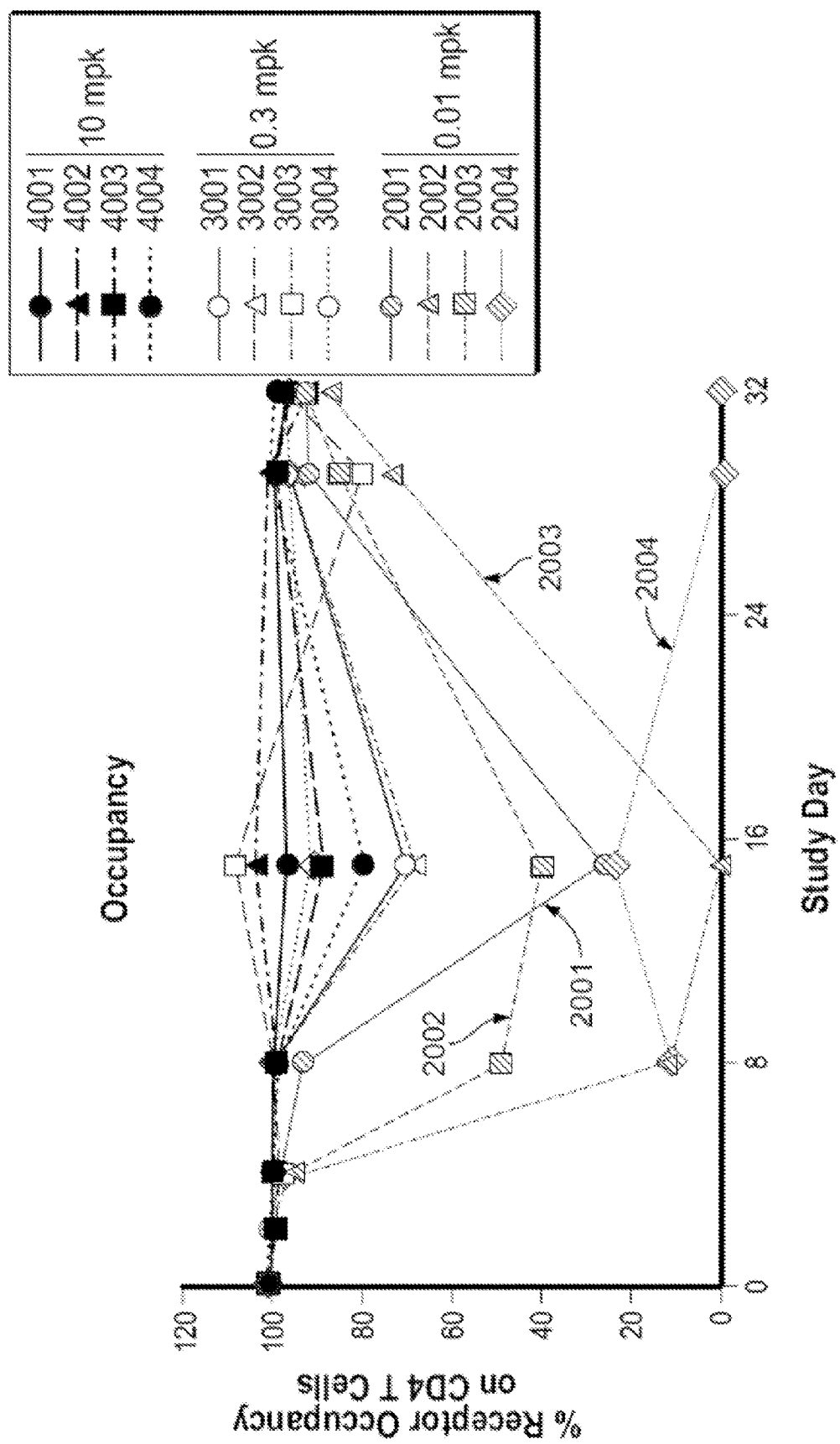

Exposure was confirmed in all animals by measurements of serum PK (FIG. 16A) and peripheral receptor occupancy (FIG. 16B). The first cycle $C_{max}$ dose was proportional for all three groups. PK was as expected for an IgG1 antibody based on $AUC_{0-14}$ at 10 mg/kg. A high frequency of ATAs was observed: 3 out of 4 animals in 0.01 and 0.3 mg/kg groups; and 2 out of 4 animals in the 10 mg/kg group. The impact was decreased serum concentration and receptor occupancy. These results demonstrate that IV administration of 1A7.gr1 was well-tolerated in cynomolgus monkeys at the indicated dosing schedule.

GLP Toxicity Study

The objective of the GLP toxicity study was to determine the toxicity of 1A7.gr1 in cynomolgus monkeys dosed intravenously at 0, 0.5, 5, and 30 mg/kg/dose on study days 1, 15, 29, and 43, followed by 42 days without dosing (recovery period).

Figure 17:
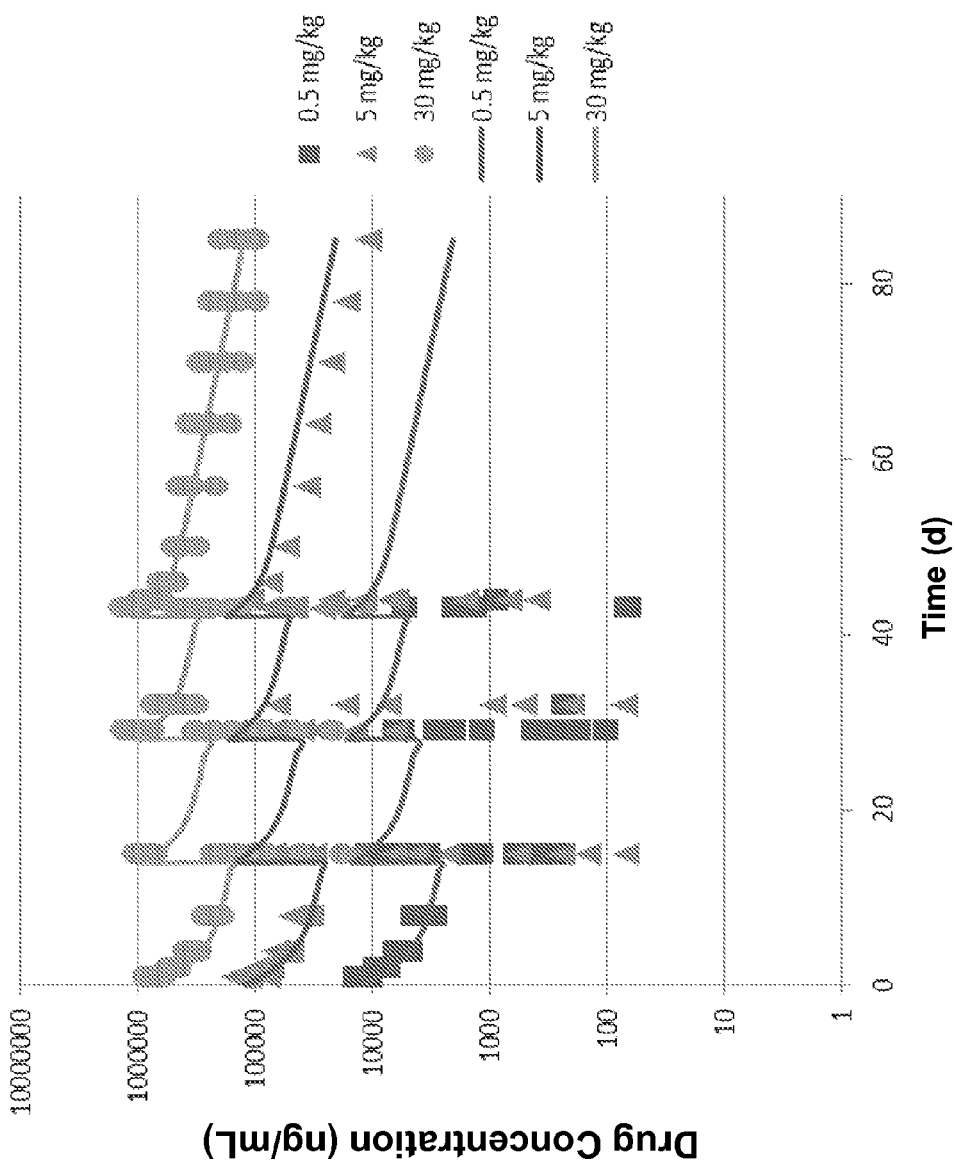
FIG. 17: Pharmacokinetics (PK) of 1A7.gr1 dosed at 0.5, 5, or 30 mg/kg in cynomolgus monkeys.
Figure 18:
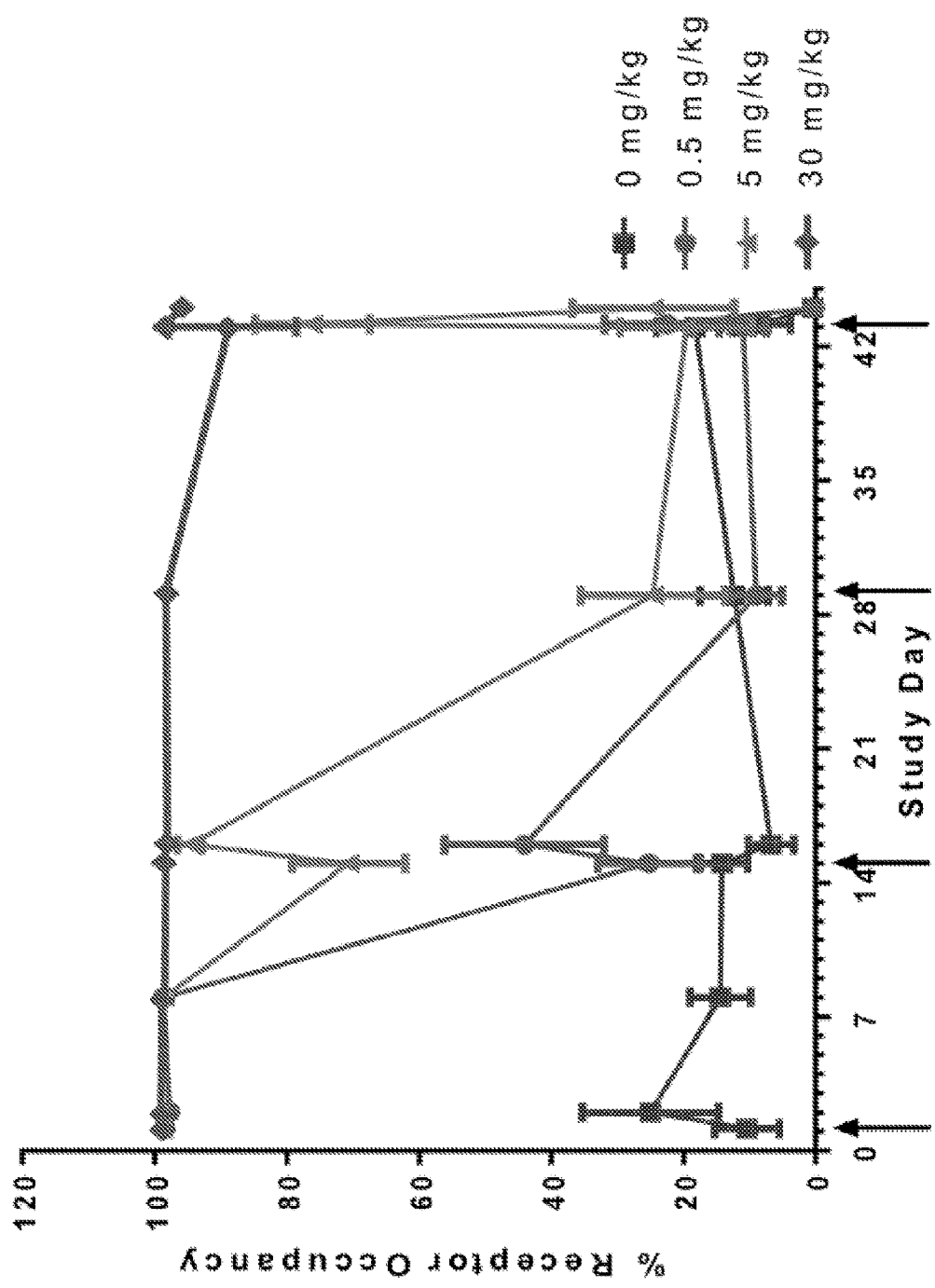
FIG. 18: OX40 receptor occupancy over time in monkeys administered 0, 0.5, 5, or 30 mg/kg of 1A7.gr1. Arrows indicate days on which samples were obtained.
Figure 19:
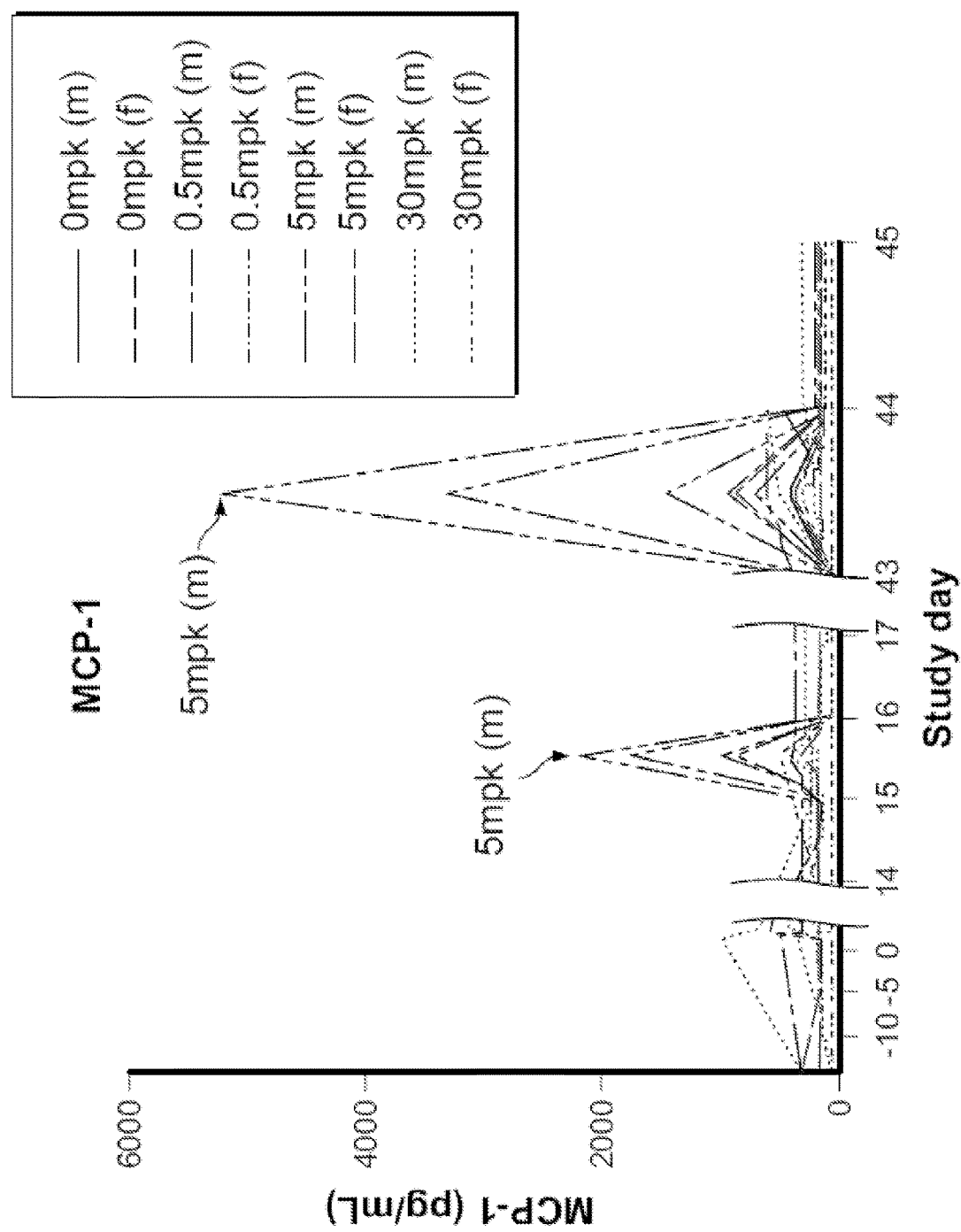
FIG. 19: MCP-1 levels overtime in monkeys administered 0, 0.5, 5, or 30 mg/kg of 1A7.gr1.
Figure 20:
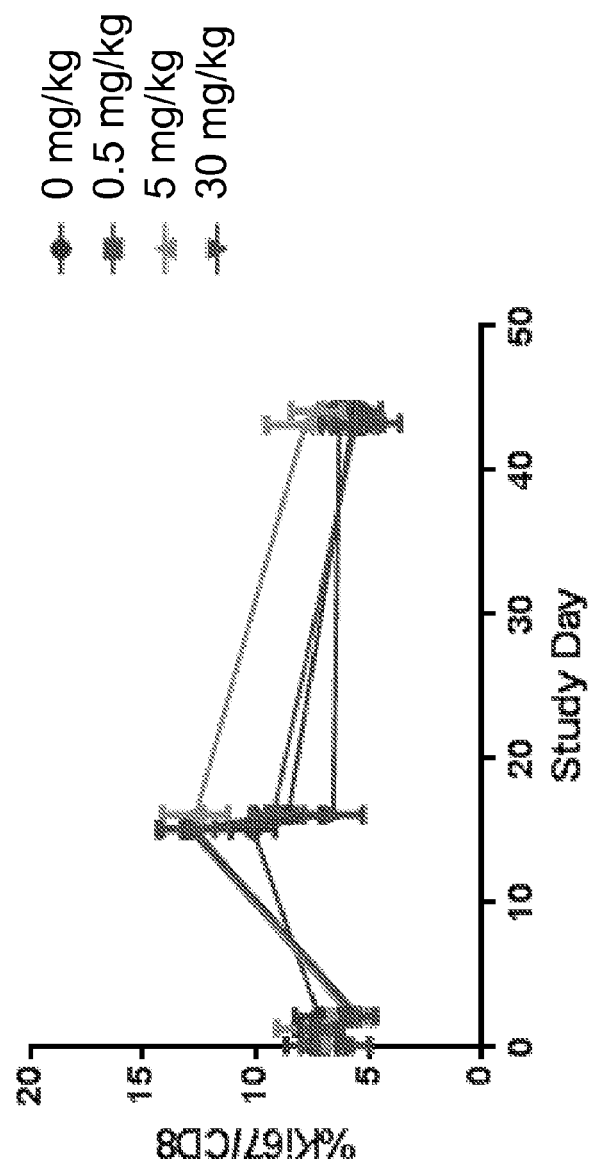
FIG. 20: No significant activation or proliferation of peripheral T cells was observed in monkeys administered 0, 0.5, 5, or 30 mg/kg of 1A7.gr1.

Intravenous administration of 1A7.gr1 IgG1 was well tolerated in cynomolgus monkeys up to 30 mg/kg once every 2 weeks for 6 weeks, and all animals survived until their scheduled necropsy timepoints on Study Days 45 and 85. The expected, dose-proportional PK for an IgG1 antibody was observed (FIG. 17). Exposure and receptor occupancy maintained at the 30 mg/kg dose level (FIG. 18). ATAs were detected in all animals in the 0.5 and 5 mg/kg dose levels, but not the 30 mg/kg dose level, with loss of exposure and receptor occupancy. Transient elevation of MCP-1 was observed in mid-dose animals (FIG. 19). No significant activation or proliferation of peripheral T cells was observed (FIG. 20), nor was any significant reduction in absolute peripheral T counts observed.

In summary, no clinical observations or changes in clinical pathology parameters after the first dose were observed. Acute post dose reactions, and transient increases in acute phase proteins and cytokines were observed beginning after $2^{nd}$ dose, potentially due to ATA (consistent in both studies). No drug-related organ weight changes, macroscopic, or microscopic findings were noted. ATAs were detected in all animals in the 0.5 mg/kg and 5 mg/kg (but not 30 mg/kg) dose groups, with loss of exposure and receptor occupancy. 1A7.gr1 was found to bind human OX40 with high affinity (~0.45 nM), and PK was as expected for a typical IgG1 and dose-proportional. These project to a human CL=2.5 mL/d/kg and $t_{1/2}$~3 weeks. No significant PD effects were observed on T cell number or activation status in tissues or the periphery. Lack of significant activation or proliferation of peripheral T cells and lack of significant changes in absolute peripheral T cell counts was not surprising since OX40 is transiently expressed only on activated T cells and healthy cynos will have negligible activated T cells.

Materials and Methods VI

CT26 Mouse Tumor Model.

6 week old female Balb/C mice were inoculated subcutaneously in the right hind flank with 100 μl of HBSS+matrigel (according to manufacturer's specifications) containing $1\times10^5$ CT26 tumor cells. Tumors were allowed to grow for ~2 weeks. Mice were grouped into four different experimental arms of 10 mice per arm. Groups were selected to have similar tumor volume averages with a tumor volume range from 100-300 mm³.

Mice received 0.1 mg/kg of anti-OX40 or isotype control anti-GP120 (negative control). The anti-OX40 antibody was clone OX-86 mouse-IgG2a (generated by cloning rat anti-mouse OX40 agonist antibody OX-86 onto a murine IgG2a backbone). Antibody was administered intravenously on day 1 followed by 0.1 mg/kg of the same antibody intraperitoneally (i.p.) 3 times a week for a total treatment duration of three weeks. These same treatment groups also received 5 mg/kg of anti-VEGFA (B20) or isotype control anti-GP120 (negative control) i.p. twice a week for three weeks starting on day 1.

Antibodies were diluted to the desired concentration with sterile PBS and administered in volumes of 100 or 200 μl. Tumor volume was measured by calipers periodically over the duration of the experiment. Mice were euthanized and removed from the experiment when: 1) Mice became moribund, 2) Tumor became ulcerated, or 3) Tumor volume exceeded 2000 mm³.

Flow Cytometry.

CT26 tumors harvested from mice treated with anti-VEGF or anti-GP120 (control) were subjected to enzymatic digestion for retrieval of a suspension of single cells. Subsequently, these cells were stained for flow cytometry using a cocktail of antibodies against CD45, CD11b, CD11c, F4/80 (used for exclusion of macrophages), Gr1 (used for exclusion of neutrophils and granulocytic myeloid cells), MHC-II, OX40L, and PD-L1. Fixable Viability Dye eFluor® 780 was used for exclusion of dead cells from flow cytometric analysis. Myeloid dendritic cells were defined and gated as CD45⁺CD11b⁺Gr1⁻ F4/80⁻CD11c⁺MHCII⁺. Non-myeloid dendritic cells were defined and gated as CD45⁺CD11b⁻Gr1⁻ F4/80⁻CD11c⁺MHCII⁺. Expression of the functional markers MHCII, PD-L1, and OX40L was quantified by means of flow cytometric Mean Fluorescence Intensity using the following antibodies: PeCy7-conjugated anti-MHC-II (Biolegend), BV421-conjugated anti-PD-L1 (Biolegend), and PE-conjugated OX-40L.

Results VI

Combining different modalities for cancer treatment may result in beneficial effects on tumor growth. As described below, anti-VEGF treatment resulted in reduced tumor growth when compared to anti-GP120 (control) treated mice. Anti-OX40 treatment exhibited little activity alone. Surprisingly, despite little anti-tumor activity on its own, anti-OX40 treatment in combination with anti-VEGF treatment demonstrated superior tumor growth inhibition when compared to single agent administration or anti-GP120 treatment. Without wishing to be bound to theory, it is hypothesized that the synergistic enhancement of activity observed with combinatorial anti-VEGF+anti-OX40 treatment may be due to increased intratumoral dendritic cell activation induced by anti-VEGF treatment.

The results described herein suggest that sequencing anti-OX40 treatment with anti-VEGF administration may augment therapy. For instance, without wishing to be bound to theory, administering anti-VEGF first (thereby enhancing dendritic cell activation), followed by anti-OX40 therapy, may be more effective than co-administration of treatments. However, it is possible that the anti-angiogenic effects of anti-VEGF treatment may deplete vasculature, thereby limiting leukocyte infiltration. Therefore, without wishing to be bound to theory, it may be more beneficial to administer anti-OX40 prior to anti-VEGF treatment.

Figure 21:
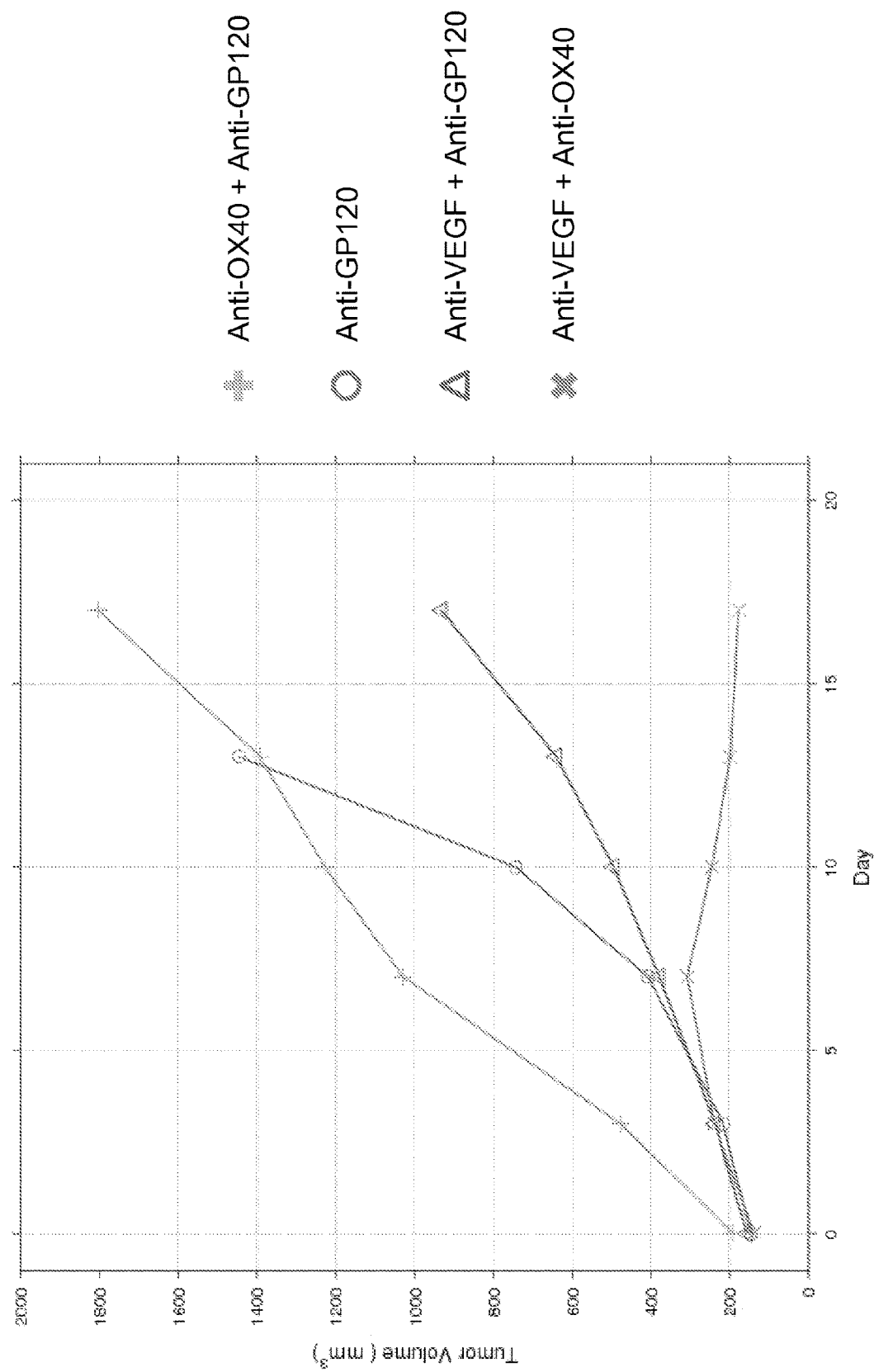
FIG. 21 shows the efficacy of different treatments on inhibiting tumor growth in a CT26 tumor model. Average tumor volumes (y-axis) over time (x-axis) are plotted for each experimental group. Experimental groups were anti-OX40 and anti-GP120 treatment (pluses), anti-GP120 treatment (circles), anti-VEGF and anti-GP120 treatment (triangles), and anti-VEGF and anti-OX40 treatment (X's).

To determine the effect of combination treatment with anti-OX40 and anti-VEGF on tumor growth, a mouse CT26 tumor model was used. FIG. 21 shows that anti-VEGF treatment plus isotype control inhibited tumor growth when compared to anti-GP120 negative control administration. In contrast, anti-OX40 plus isotype control afforded no inhibition of tumor growth when compared to anti-GP120 negative control administration this experiment. This is inconsistent with other experiments utilizing the same antibody and experimental tumor model where tumor growth inhibition was observed. Without wishing to be bound to theory, an explanation for why anti-OX40 treatment did not work in this experiment is that the average starting tumor volume was larger in this group and anti-OX40 efficacy in the CT26 tumor model is dramatically affected by tumor size especially when tumors are larger than 200 mm$^3$. It is thought that anti-OX40 efficacy in the CT26 tumor model may be negatively affected by tumor size. FIG. 21 also shows that combinatorial anti-VEGF and anti-OX40 treatment showed superior efficacy over anti-VEGF or anti-OX40 alone.

FIGS. 22A-22D provide tumor volume measurements for individual mice. These data further demonstrate the superior efficacy of combinatorial anti-VEGF and anti-OX40 treatment over anti-VEGF or anti-OX40 alone. Compared to tumor growth in mice receiving control treatment, mice receiving VEGF treatment experienced 53% tumor growth inhibition. Anti-OX40 treatment alone resulted in tumor growth 30% above control treatment. In contrast, combination anti-VEGF plus anti-OX40 treatment resulted in a remarkable 94% tumor growth inhibition compared to control treatment. In this treatment group, 9 out of 10 mice exhibited tumor stasis or regression. These results demonstrate the superior and synergistic effects of combination anti-VEGF and anti-OX40 treatment, as compared to each single treatment or control treatment.

Figure 23A:
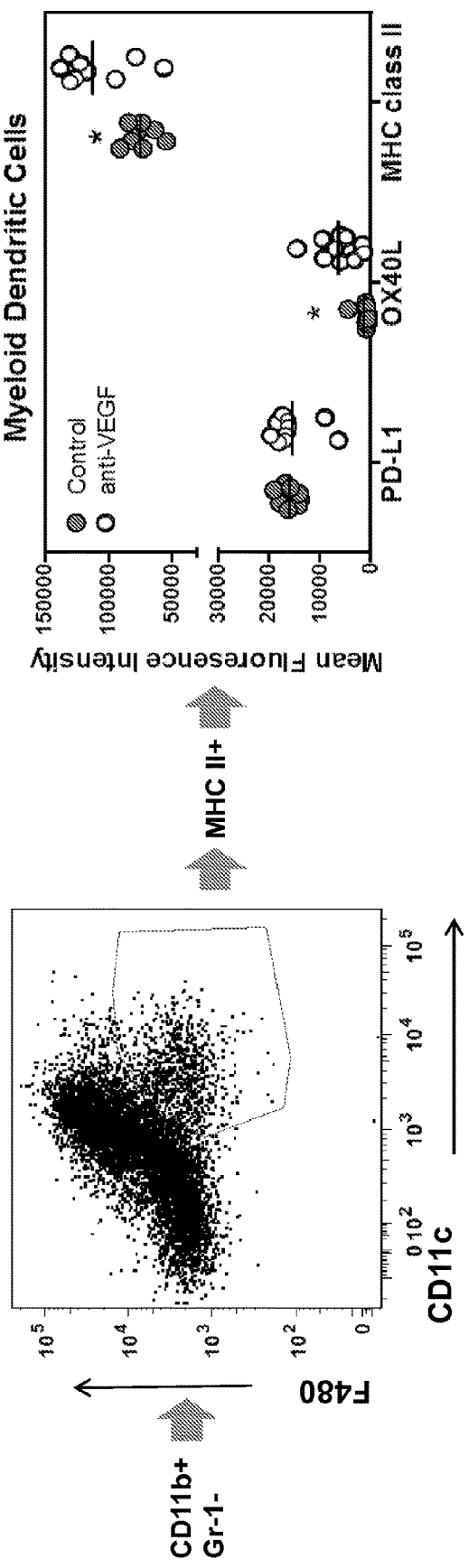
FIGS. 23A and 23B show increased intratumoral dendritic cell activation following anti-VEGF treatment in a CT26 tumor model.

Next, the effect of anti-VEGF treatment on intratumoral dendritic cell activation was tested in the CT26 tumor model. First, in FIG. 23A, intratumoral myeloid dendritic cells were assayed. Among $CD45^+CD11b^+Gr1^-F4/80^-CD11c^+MHCII^+$myeloid dendritic cells, abundance of expression of MHC class II, OX40L, and PD-L1 was determined by quantifying the mean fluorescence intensity of each molecule. Myeloid dendritic cells from anti-VEGF-treated mice were found to have higher MHC II (p=0.002) and OX40L (p=0.003) expression, as compared to cells from anti-GP120 (control)-treated mice. PD-L1 expression, a negative regulator of T cell responses, was statistically undistinguishable between the two groups (p=0.81). These results suggest that treatment with anti-VEGF promoted maturation of tumoral dendritic cells as opposed to control treatment. Improved expression of MHC Class II and OX40L enables dendritic cells to present antigens and prime T cells more effectively.

Figure 23B:
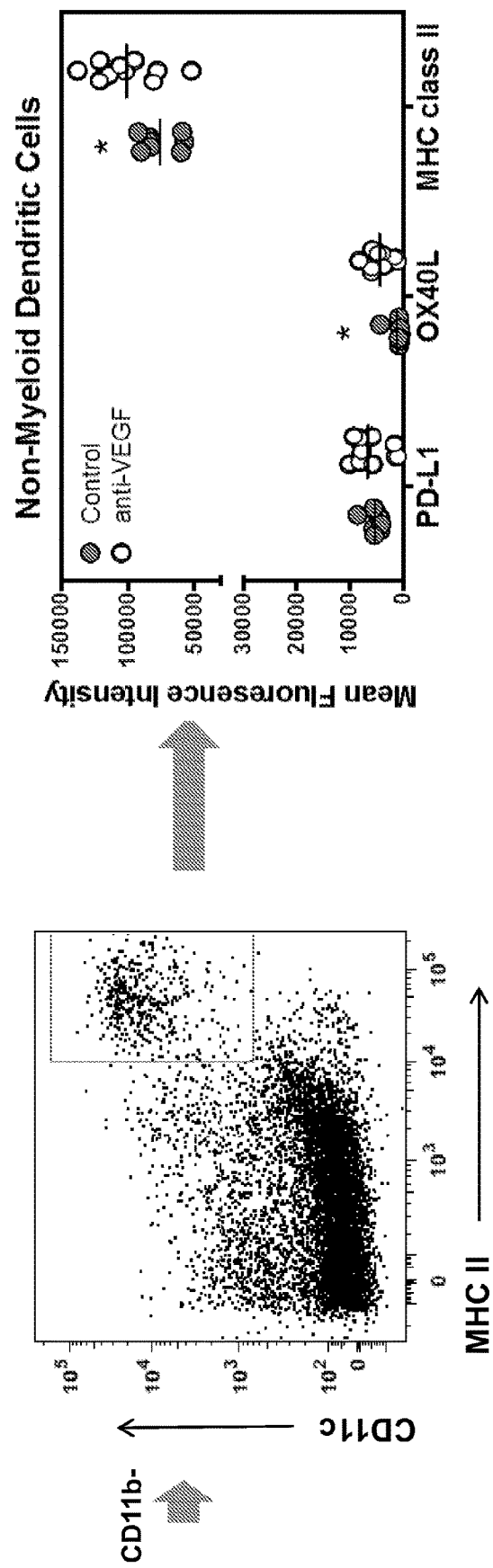

FIG. 23B shows the effect of anti-VEGF treatment on non-myeloid intratumoral dendritic cell activation. Among $CD45^+CD11b^-Gr1^-$ $F4/80^-CD11c^+MHCII^+$non-myeloid dendritic cells, expression of MHC class II, as well as PD-L1 and OX40L was determined by quantifying the mean fluorescence intensity of each molecule. Similar to myeloid dendritic cells, non-myeloid dendritic cells also expressed significantly higher levels of MHC II (p=0.03) and OX40L (p=0.002) when treated with anti-VEGF, as compared to control treatment.

These results suggest that anti-VEGF treatment can improve the functional phenotype of tumoral dendritic cells, a phenomenon that can result in enhanced anti-tumoral T cell responses. Hence, combining anti-VEGF treatment with immunotherapeutics targeting T cells (e.g., anti-OX40) may synergistically potentiate anti-tumor responses.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated nucleic acid encoding an anti-human OX40 agonist antibody, wherein the antibody comprises:
   (1) a heavy chain variable domain (VH) comprising (a) an HVR-H1 comprising the amino acid sequence of DSYMS (SEQ ID NO:2); (b) an HVR-H2 comprising the amino acid sequence of DMYPDNGDSSYNQK-FRE (SEQ ID NO:3); and (c) an HVR-H3 comprising the amino acid sequence of APRWYFSV (SEQ ID NO:4); and
   (2) a light chain variable domain (VL) comprising (d) an HVR-L1 comprising the amino acid sequence of RASQDISNYLN (SEQ ID NO:5); (e) an HVR-L2 comprising the amino acid sequence of YTSRLRS (SEQ ID NO:6); and (f) an HVR-L3 comprising the amino acid sequence of QQGHTLPPT (SEQ ID NO:7).

2. The isolated nucleic acid of claim 1, wherein the antibody is a humanized antibody.

3. The isolated nucleic acid of claim 1, wherein the antibody comprises:
   (1) a heavy chain variable domain (VH) comprising the amino acid sequence of EVQLVQSGAEVKKPGAS-VKVSCKASGYTFTDSYMSWVRQAPGQ-GLEWIGDMYPDNG DSSYNQK-FRERVTITRDTSTSTAYLELSSLRSEDTAVY YCVLAPRWYFSVWGQGTLVTV SS (SEQ ID NO:56); and
   (2) a light chain variable domain (VL) comprising the amino acid sequence of DIQMTQSPSSLSAS- VGDRVTITCRASQDISNYLNWYQQKPGKAP-KLLIYYTSRLRSGVPS RFSGSGSGTDFTLTISS-LQPEDFATYYCQQGHTLPPTFGQGTKVEIK (SEQ ID NO:57).

4. The isolated nucleic acid of claim 3, wherein the antibody further comprises a human IgG1 Fc region.

5. An isolated host cell comprising the nucleic acid of claim 1.

6. A method of producing an antibody comprising culturing the host cell of claim 5 so that the antibody is produced.

7. The method of claim 6, further comprising recovering the antibody from the host cell.

* * * * *